(12) United States Patent
Rajendran et al.

(10) Patent No.: US 11,939,601 B2
(45) Date of Patent: Mar. 26, 2024

(54) POLYNUCLEOTIDES ENCODING PHENYLALANINE HYDROXYLASE FOR THE TREATMENT OF PHENYLKETONURIA

(71) Applicant: ModernaTX, Inc., Cambridge, MA (US)

(72) Inventors: Raj Rajendran, Sharon, MA (US); Patrick Finn, Franklin, MA (US); Paolo G. V. Martini, Boston, MA (US); Ding An, Waban, MA (US); Athanasios Dousis, Boston, MA (US); Kanchana Ravichandran, Cambridge, MA (US)

(73) Assignee: ModernaTX, Inc., Cambridge, MA (US)

(*) Notice: Subject to any disclaimer, the term of this patent is extended or adjusted under 35 U.S.C. 154(b) by 449 days.

(21) Appl. No.: 16/765,656

(22) PCT Filed: Nov. 21, 2018

(86) PCT No.: PCT/US2018/062237
§ 371 (c)(1),
(2) Date: May 20, 2020

(87) PCT Pub. No.: WO2019/104160
PCT Pub. Date: May 31, 2019

(65) Prior Publication Data
US 2021/0040456 A1 Feb. 11, 2021

Related U.S. Application Data

(60) Provisional application No. 62/590,128, filed on Nov. 22, 2017, provisional application No. 62/679,081, filed on Jun. 1, 2018.

(51) Int. Cl.
| | | |
|---|---|---|
| *A61P 3/00* | (2006.01) | |
| *A61K 9/00* | (2006.01) | |
| *A61K 9/51* | (2006.01) | |
| *A61K 48/00* | (2006.01) | |
| *C12N 9/02* | (2006.01) | |

(52) U.S. Cl.
CPC .......... *C12N 9/0071* (2013.01); *A61K 9/0019* (2013.01); *A61K 9/5123* (2013.01); *A61K 48/0075* (2013.01); *A61P 3/00* (2018.01); *C12Y 114/16001* (2013.01)

(58) Field of Classification Search
CPC .......................... C12Y 114/16001; A61P 3/00
See application file for complete search history.

(56) References Cited

U.S. PATENT DOCUMENTS

| | | | |
|---|---|---|---|
| 8,691,966 | B2 | 4/2014 | Kariko et al. |
| 9,522,176 | B2 | 12/2016 | DeRosa et al. |
| 10,208,295 | B2 | 2/2019 | DeRosa et al. |
| 11,377,642 | B2 | 7/2022 | DeRosa et al. |
| 11,382,941 | B2 | 7/2022 | Wilson et al. |
| 2010/0047261 | A1 | 2/2010 | Hoerr et al. |
| 2018/0126003 | A1 | 5/2018 | Hoerr et al. |
| 2019/0167808 | A1 | 6/2019 | Fotin-Mleczek et al. |
| 2023/0235298 | A1 | 7/2023 | Rice et al. |

FOREIGN PATENT DOCUMENTS

| | | |
|---|---|---|
| WO | WO199527512 | 10/1995 |
| WO | WO2009127230 | 10/2009 |
| WO | WO2013086373 | 6/2013 |
| WO | WO2013151666 | 10/2013 |
| WO | WO2014152513 | 9/2014 |
| WO | WO2015061467 | 4/2015 |
| WO | WO2015061491 | 4/2015 |
| WO | WO2015199952 | 12/2015 |
| WO | WO2016004318 | 1/2016 |
| WO | WO2016070166 | 5/2016 |
| WO | WO2016118697 | 7/2016 |
| WO | 3143153 | 3/2017 |
| WO | WO2017049245 | 3/2017 |
| WO | WO2017062513 | 4/2017 |
| WO | WO2017100551 | 6/2017 |
| WO | WO2017153936 | 9/2017 |
| WO | WO2017167866 | 10/2017 |
| WO | WO2017177169 | 10/2017 |
| WO | WO2017191274 | 11/2017 |
| WO | WO2017201349 | 11/2017 |
| WO | WO2018089801 | 5/2018 |
| WO | WO2018089846 | 5/2018 |
| WO | WO2018126112 | 7/2018 |
| WO | WO2018167621 | 9/2018 |
| WO | WO2018222925 | 12/2018 |
| WO | WO2019217513 | 11/2019 |

(Continued)

OTHER PUBLICATIONS

Robin Lachmann, Sapropterin hydrochloride: enzyme enhancement therapy for phenylketonuria. Therapeutic Advances in Endocrinology and Metabolism, Review, vol. 2(3), pp. 127-133 (Year: 2011).*
Fusetti et al., "Structure of Tetrameric Human Phenylalanine Hydroxylase and Its Implications for Phenylketonuria", Journal of Biological Chemistry, Jul. 1998, 273(27):16926-16967.

(Continued)

*Primary Examiner* — Barbara P Badio
(74) *Attorney, Agent, or Firm* — Fish & Richardson P.C.

(57) ABSTRACT

This disclosure relates to mRNA therapy for the treatment of hyperphenylalaninemias such as phenylketonuria (PKU). mRNAs for use in the invention, when administered in vivo, encode human phenylalanine hydroxylase (PAH), functional fragments thereof (e.g., those comprising the catalytic domain or the catalytic domain and the tetramerization domains), and fusion proteins comprising PAH. mRNAs of the invention are preferably encapsulated in lipid nanoparticles (LNPs) to effect efficient delivery to cells and/or tissues in subjects, when administered thereto. mRNA therapies of the invention increase and/or restore deficient levels of PAH expression and/or activity in subjects. mRNA therapies of the invention further decrease abnormal accumulation of phenylalanine associated with deficient PAH activity in subjects.

19 Claims, 33 Drawing Sheets

Specification includes a Sequence Listing.

(56) References Cited

FOREIGN PATENT DOCUMENTS

| WO | WO2020077250 | 4/2020 |
|----|--------------|--------|
| WO | WO2020118239 | 6/2020 |
| WO | WO2020198641 | 10/2020 |
| WO | WO2020243717 | 12/2020 |
| WO | WO2021247507 | 12/2021 |

OTHER PUBLICATIONS

Hanson et al., "Codon optimality, bias and usage in translation and mRNA decay", Nat. Rev. Mol. Cell Biol., Oct. 2017, 19(1):20-30.
International Preliminary Report on Patentability in International Application No. PCT/US2018/062237, dated Jun. 4, 2020, 17 pages.
International Search Report and Written Opinion in International Application No. PCT/US2018/062237, dated May 21, 2019, 29 pages.
Kochhar et al., "Clinical therapeutics for phenylketonuria", Drug Delivery and Translational Research, May 2012, 2(4): 223-237.
Tavernier et al., "mRNA as gene therapeutic: How to control protein expression", Journal of Controlled Release, Oct. 2010, 150(3):238-247.
Yamamoto et al., "Current Prospects for mRNA gene delivery", European Journal of Pharmaceutics and Biopharmaceutics, Oct. 2008, 71(3):484-489.
Youn et al., "Modified mRNA as an alternative to plasmid DNA (pDNA) for transcript replacement and vaccination therapy", Expert Opinion on Biological Therapy, Jun. 2015, 15(9): 1337-1348.
International Preliminary Report on Patentability in International Application No. PCT/US2021/035154, dated Dec. 15, 2022, 13 pages.
International Search Report and Written Opinion in International Application No. PCT/US2021/035154, dated Nov. 24, 2021, 23 pages.
Uniprot Accession No. A0A2K6G6V1, dated Mar. 28, 2018, 2 pages.
Uniprot Accession No. A0A337S7G7, dated Oct. 10, 2018, 2 pages.
Uniprot Accession No. A0A485PIR0, dated Jun. 5, 2019, 2 pages.
Daubner et al., "Expression and Characterization of the Catalytic Domain of Human Phenylalanine Hydroxylase," Archives of Biochemistry and Biophysics, Dec. 1997, 348(2):295-302.

* cited by examiner

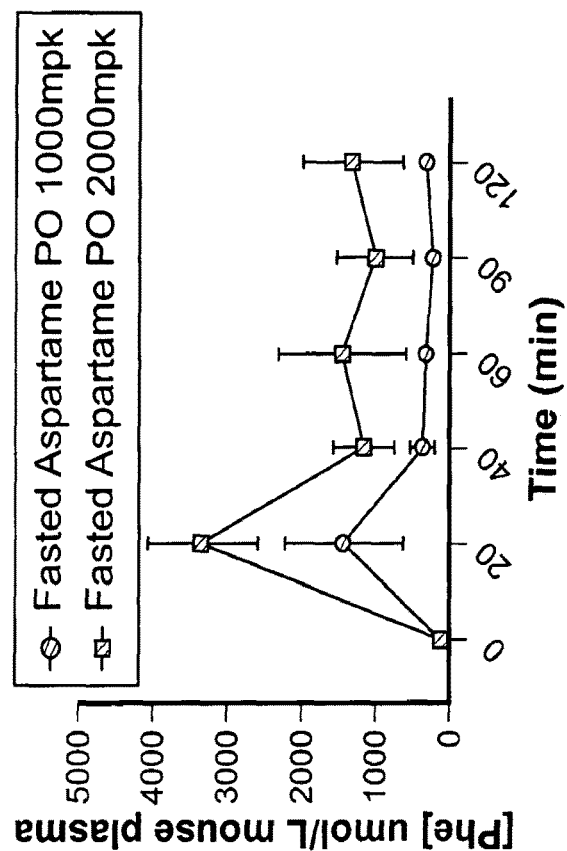
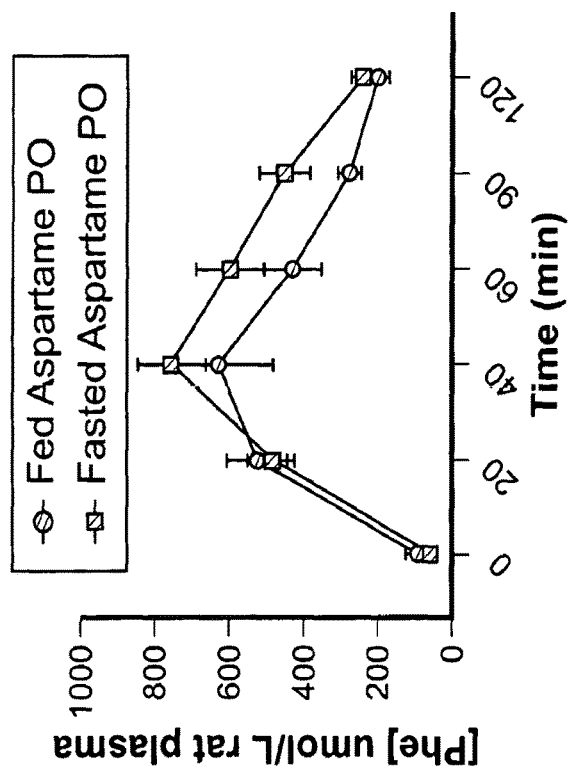
FIGURE 7B
FIGURE 7A

SEQUENCE LISTING

<160> NUMBER OF SEQ ID NOS: 226

<210> SEQ ID NO 1
<211> LENGTH: 452
<212> TYPE: PRT
<213> ORGANISM: Homo sapiens

<400> SEQUENCE: 1

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

```
Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gly Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 2
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
auguccaccg ccgugcucga gaaccccggc cuggggcgga aacugagcga cuuuggccag      60
gaaaccagcu auauugagga caacugcaac cagaacggcg ccaucagccu gaucuucuca     120
cugaaggagg aggugggcgc ccuggccaag gugcucaggc uguucgagga gaacgacgug     180
aaccugacuc auaucgagag cagaccaucu cggcugaaga aagacgagua cgaguucuuc     240
acccaucucg auaagagaag ccugcccgca cugaccaaca ucauaaagau ucugaggcac     300
gacaucgggg ccaccgugca cgaacugagu cgggacaaga agaaggacac uguuccuugg     360
uucccacgga cuauucagga gcuggacaga uucgcuaacc agauccuguc cuacggcgcc     420
gagcucgacg cugaccaccc aggcuucaag gaccccgugu accgggcuag aagaaagcaa     480
uucgccgaca ucgccuacaa uuauaggcac ggccagccca uuccuagagu ggaguacaug     540
gaggaagaga agaagaccug gggcaccgug uucaagaccu uaaagagccu guauaagaca     600
cacgcuugcu acgaguacaa ucacauuuuc ccacugcugg agaaguacug uggcuuucac     660
gaggauaaua uaccucagcu ggaagacguu ucccaguucc ugcagacuug caccggcuuc     720
agacuuaggc cuguggcggg ccuccugucu ucgagagauu ccugggagg gcuggccuuc     780 cgcguguucc acugcaccca guauauccgc cacgggagca agcccaugua cacacccgag     840
cccgacauuu gccacgagcu guuaggccac gugccuuugu ucucugacag gagcuuugcg     900
caguucaguc aggaaaucgg acuggccagc cugggugccc cugacgagua caucgagaag     960
cuggccacca ucuacugguu cacugucgag uucggucugu gcaagcaggg cgauagcauc    1020
aaggcuuacg gagccggccu ucugagcagc uucggcgagc ugcaauacug ccugagcgag    1080
aagccuaagc uguugccuuu ggaacucgag aagacagcua ccagaacua caccguuacc     1140 gaguuccagc cucuguacua cguggccgag agcuucaacg acgccaagga gaaggugaga    1200
aacuucgcgg caacaauucc caggccuuuu agcgugagau acgacccccua cacucaacga    1260 aucgaagugc uggauaacac ccagcagcug aagauccugg ccgacaguau caacagcgaa    1320
auuggcauuc ugugcucagc ccugcagaag auuaaa                               1356
```

```
<210> SEQ ID NO 3
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gggaauuaag agagaaaaga agaguaagaa gaaauauaag agccacc                47

<210> SEQ ID NO 4
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
ugauaauagg cuggagccuc gguggccuag cuucuugccc cuugggccuc cccccagccc    60 cuccucccu uccugcaccc guacccccuc cauaaaguag gaaacacuac aguggucuuu    120
gaauaaaguc ugagugggcg gc                                            142

<210> SEQ ID NO 5
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
augucaaccg cuguucugga gaacccggc cugggccgga agcuguccga uuucggccag     60
gagacuagcu acaucgagga uaacugcaac cagaacggcg ccaucagccu gauauuuagc   120
cucaaggaag aagugggugc ucuggccaag guccugagac uguucgaaga gaacgacgug   180
aaccugaccc auaucgaaag ccggcccagc cggcugaaga aggacgagua cgaguucuuu   240
acgcaccugg acaaacggag ccuccccgca cugacuaaca uuauuaagau ccugaggcac   300
gauaucggug ccacugugca cgaacugagc cgggacaaga agaaagacac uguuccuugg   360
uuucccagga cgauucagga acuggacaga uucgccaauc agauccucag cuacggcgcc   420
gagcuggacg cugaccaucc cggcuuuaag gacccggugu aucgggccag acgcaagcag   480
uucgccgaua uugccuauaa cuacagacac ggccagccua ucccuagggu ggaguacaug   540
gaggaggaga agaagacuug gggcaccguu ucaagacccu gaaaucccu cuacaagacc   600 cacgcgugcu acgaguauaa ccauaucuuu ccucuccugg agaaguacug cggcuuccac   660
gaggacaaua ucccacagcu cgaggacgug agccaguucu ugcagaccug cacagggguuc   720 agacugcgcc ccgguggccgg ucugcucagc aguagggacu uccucggcgg acuggcauuc   780
cggguguucc acuguaccca guacauuaga cacggcucca agcccauguca cccccagaa    840 ccagacaucu gccacgagcu gcugggccac gugcccuugu uucagauag gagcuucgcc    900 caguucagcc aggaaaucgg gcuggccagu cugggcgccc cugacgagua uaucgagaaa   960
cuggccacca ucuacugguu caccgugag uucggcucu gcaagcaggg ugacagcauc   1020
aaggcauacg gcgcagggcu gcugagcagc uucggcgagc uccaguauug ccugucggag   1080
```

| aagcccaagc ugcugccacu ggagcuggag aagaccgcca uccagaauua uaccgucaca | 1140 |
| gaguuucagc cucuguauua cguggcugag uccuuuaacg acgccaaaga gaaggugagg | 1200 |
| aacuucgcag cgacuauucc uagacccuuc uccgúccggu acgauccuua cacccagagg | 1260 |
| aucgaggugc uggacaacac ccagcagcuc aagauucugg ccgauuccau aauagcgag | 1320 |
| auaggcauuc ugugcagcgc acugcagaag aucaag | 1356 |

<210> SEQ ID NO 6
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

| augagcaccg ccgugcucga gaaccccggc cugguagga agcugagcga cuucggccag | 60 |
| gaaacaagcu acaucgaaga uaacugcaac cagaacggug ccaucucccu gaucuuuuca | 120 |
| cuuaaggaag aggucggagc cuuagccaag gugcuuaggc uguucgagga aacgacguc | 180 |
| aaccuuaccc acauugaguc cagacccagc aggcugaaga aggacgagua cgaguucuuc | 240 |
| acacaucugg acaagagaag cuuacccgcc cugaccaaca uuauuaagau ccugcgacac | 300 |
| gacaucgggg ccaccgugca cgaacugagc agagacaaga agaaggauac ugugcccugg | 360 |
| uucccuagga caauccagga guuggaucgu uucgccaacc agauccuguc cuacggagcc | 420 |
| gaacuggacg cugaccaccc cggauuuaag gauccugugu aucgggcccg aagaaagcag | 480 |
| uucgcagaua uugccuauaa uuacaggcac ggccagccua uccccagagu cgaguacaug | 540 |
| gaagaggaga agaagaccug ggguacagug uucaagaccc ucaagagccu guacaagacc | 600 |
| cacgcuugcu acgaauacaa ccacaucuuc cccuugcuug agaaauacug cgguuuccac | 660 |
| gaggacaaua uuccgcaacu ggaggacgug ucgcaguuuc ugcagaccug uaccggcuuu | 720 |
| cggcucaggc cuguggccgg ucuguugucu agcagagauu uucugggcgg gcuggccuuc | 780 |
| agagucuucc acugcaccca guacaucagg cacggaagca agccaugua cacacccgag | 840 |
| cccgacaucu gucacgagcu ccucggccac gugcccccugu cagcgacag aagcuucgcc | 900 |
| caguuuaguc aggaaaucgg ccuggccagu cugggcgccc cugacgagua uaucgagaag | 960 |
| cuggcuacca uauauugguu uaccguggag uucgacugu gcaagcaggg cgacuccauc | 1020 |
| aaggcuuacg gugccgggcu gcugagcagc uucggcgagc uccaguauug ccugagcgag | 1080 |
| aagcccaagc ugcugccgcu ggagcuggag aagaccgcca uccagaacua uaccgucacc | 1140 |
| gaguuccagc cccuguacua cguggcugag agcuuuaacg acgccaagga gaaggucaga | 1200 |
| aacuucgccg cuaccauucc cagacccuuc agcgugagau acgacccuua cacacagagg | 1260 |
| auagagguuu uggacaacac ccagcaacug aagaucuugg cugauagcau uaacucagag | 1320 |
| aucggcauuc ugugcagcgc ccugcagaag aucaag | 1356 |

<210> SEQ ID NO 7
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

```
augagcacug ccguguugga gaaccccggg cugggcagaa agcucagcga cuucggccag    60
gaaaccaguu auauugagga caacugcaac cagaacggcg caauuagucu uaucuuuagc   120
cugaaggagg agguaggcgc ccuggccaaa gugcugagac uguucgaaga gaacgacgug   180
aaucugacac acaucgaguc ccgccccagc cggcucaaga aggacgagua cgaguucuuu   240
acccaccugg auaagcgcag ccuuccugcc cugaccaaca ucauaaagau ucucagacac   300
gacauuggcg ccaccguuca cgaacugagc agagacaaga agaaagacac cgucccucug   360
uuccccagga ccauccagga acuggaccgg uucgcuaacc agauccuguc cuacggcgcc   420
gagcuggacg ccgaccaccc uggcuuuaag gaccccgugu auagggccag aaggaagcag   480
uucgcggaua ucgcuuacaa cuaccgucac ggccaaccga ucccaagggu cgaguacaug   540
gaggaggaga agaagaccug ggguacagug uucaagacuc ucaagagucu gaacaagaca   600
cacgccugcu acgaguacaa ccacaucuuc ccauugcugg agaaguauug cggcuuccac   660
gaagacaaca uuccccagcu ggaggacgug agccaguuuc ugcagaccug caccggcuuc   720
cggcugaggc ccguggcggg gcugcugucu ucaagagacu uccugggcgg acuggccuuc   780
agggucuucc acugcacaca guacaucaga cacggaagca aacccaugua caccccugag   840
cccgacaucu gccacgagcu gcugggccac gugccucugu cagcgaccg cagcuucgcc   900
caguucucgc aggaaaucgg ccuggccagc cugggcgcuc cugacgaaua cauugagaaa   960
cucgccacaa uuuacugguu cacguggag uucggacugu gcaagcaggg cgauuccauc  1020
aaagcguacg gcgcaggccu gcugagcucg ucggcgaac ugcaauacug ccugcccgag  1080
aagccgaaac ugcugccucu ggagcucgag aagacagcca uccagaauua cacagugaca  1140
gaauuccagc ccuuauacua cgguggcuaa ucuuucaacg acgcaaagga gaaggugcgc  1200
aacuuugcag ccaccaucc acgacccuuc agcgugcggu acgacccgua cacccagaga  1260
aucgaggugc uggacaauac ccaacagcuc aagauccucg ccgauucaau caauuccgag  1320
aucgggaucc ugugcagcgc acugcagaag auaaag                            1356
```

<210> SEQ ID NO 8
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
augagcaccg ccgugcugga gaaccccggc cugggccgga agcugagcga cuucggccag    60
gagacaagcu acaucgagga caacugcaac cagaacggcg ccaucagccu gaucuucucc   120
cugaaggagg aggugggcgc ccuggccaag gugcugcggc uguucgagga gaacgacgug   180
aaccugaccc acaucgagag ccggcccagc cggcugaaga aggacgagua cgaguucuuc   240
acccaccugg acaagcggag ccugcccgcc cugaccaaca ucaucaagau ccugcggcac   300
gacaucggcg ccaccgugca cgagcugagc cgggacaaga agaaggauac cgugcccugg   360
uucccacgga ccauccagga gcuggaccgg uucgccaacc agauccugag cuacggcgcc   420
gagcuggacg ccgaccaccc cggcuucaag gaccccgugu accgggcccg gcggaagcag   480
uucgccgaca ucgccuacaa cuaccggcac ggccagccca uuccucgggu ggaguacaug   540
gaggaggaga agaagaccug ggcaccgug uucaagaccc ucaagagcu guacaagacc   600
```

| | |
|---|---|
| cacgccugcu acgaguacaa ccacaucuuc ccacugcugg agaaguacug cggcuuccac | 660 |
| gaggauaaca ucccacagcu ggaggacgug agccaguucc ugcagaccug caccggcuuc | 720 |
| agacugcggc cuguggccgg ccugcugagc uccagagacu uccugggcgg ccuggccuuc | 780 |
| cggguguucc acugcaccca guacaucaga cacggcagca agcccaugua cacaccugag | 840 |
| cccgacaucu gccacgaacu ccugggccac gugcccugu ucagcgaccg gagcuucgcc | 900 |
| caguucuccc aggagaucgg acuggccagc cuuggagcuc ccgacgaaua cauugagaag | 960 |
| cuggccacca ucuacugguu caccguggag uucggccugu gcaagcaggg cgacagcauc | 1020 |
| aaggccuacg cgccggccu ucugagcagc uucggcgagc ugcaguacug ccugagcgag | 1080 |
| aagcccaagc ugcugccccu ggagcuagag aagaccgcca uccagaacua caccgugacc | 1140 |
| gaguuccagc cccuguacua cguggccgag agcuucaacg acgccaagga gaaggugcgg | 1200 |
| aacuucgccg ccacaauccc uagacccuuc agcgugcggu acgaccccua cacccagcgg | 1260 |
| aucgaggugc uggacaauac ccagcagcug aagauucugg ccgacuccau caacagcgaa | 1320 |
| aucggcaucc ugugcagcgc ccugcagaag aucaag | 1356 |

<210> SEQ ID NO 9
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 9

| | |
|---|---|
| augagcaccg ccgugcugga aaccccggc cugggccgga agcugagcga cuucggccag | 60 |
| gagacaagcu acaucgagga caacugcaac cagaacggcg ccaucagccu gaucuuuucu | 120 |
| cugaaggagg aggugggcgc ccuggccaag gugcugcggc uguucgagga aacgacgug | 180 |
| aaccugaccc acaucgagag ccggccagc cggcugaaga aggacgagua cgaguucuuc | 240 |
| acccaccugg acaagcggag ccugcccgcc cugaccaaca ucaucaagau ccugcggcac | 300 |
| gacaucggcg ccaccgugca cgagcugagc cgggacaaga agaaggacac cgugcccugg | 360 |
| uucccucgga ccauccagga gcuggaccgg uucgccaacc agauccugag cuacggcgcc | 420 |
| gagcuggacg ccgaccaccc cggcuucaag acccccgugu accgggcccg gcggaagcag | 480 |
| uucgccgaca ucgccuacaa cuaccggcac ggccagccca uccucgggu ggaguacaug | 540 |
| gaggaggaga agaagaccug gggcaccgug uucaagaccc ugaagcucuc guacaagacc | 600 |
| cacgccugcu acgaguacaa ccacaucuuu ccucuccugg agaaguacug cggcuuccac | 660 |
| gaggacaaua ucccucagcu ggaggacgug agccaguucc ugcagaccug caccggcuuc | 720 |
| cggcugaggc cuguggccgg gcugcugagc agcagagacu uccugggcgg ccuggccuuc | 780 |
| cggguguucc acugcaccca guacaucaga cacgggagca agcccaugua cacucccgag | 840 |
| cccgacaucu gccacgaguu acuggccac gugcccugu ucagcgaccg gagcuucgcc | 900 |
| caguucucac aggagaucgg gcuggcaagc cuggcgcuc ccgacgagua uauagagaag | 960 |
| cuggccacca ucuacugguu caccguggag uucggccugu gcaagcaggg cgacagcauc | 1020 |
| aaggcuuacg gagcugggcu gcuuagcucc uucggcgagc ugcaguacug ccugagcgag | 1080 |
| aagcccaagc ugcugccccu ugagcucgag aagaccgcca uccagaacua caccgugacc | 1140 |
| gaguuccagc cccuguacua cguggccgag agcuucaacg acgccaagga gaaggugcgg | 1200 |
| aacuucgccg caaccauccc uaggcccuuc agcgugcggu acgaccccua cacccagcgg | 1260 |

| | |
|---|---|
| aucgaggugc uggacaauac ccagcagcug aagaucuuag cugacucaau caacagcgag | 1320 |
| auuggcaucc ugugcagcgc ccugcagaag aucaag | 1356 |

<210> SEQ ID NO 10
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10

| | |
|---|---|
| augagcaccg ccgugcugga gaccccggc cugggccgga agcugagcga cuucggccag | 60 |
| gagacauccu acaucgagga caacugcaac cagaacggcg ccaucucccu caucuucagc | 120 |
| cugaaggagg aggucggcgc ccucgccaag guccuccgcc ucuucgagga gaacgacguc | 180 |
| aaccucaccc acaucgaguc ccgcccccuc cgccucaaga aggacgagua cgaguucuuc | 240 |
| acccaccucg acaagcgcuc ccuccccgcc cucaccaaca ucaucaagau ucuuaggcac | 300 |
| gacaucggcg ccaccgucca cgagcucucc cgcgacaaga agaaggacac cguccccugg | 360 |
| uucccucgca ccauccagga gcucgaccgc uucgccaacc agauccucuc cuacggcgcc | 420 |
| gaguuagacg ccgaccaccc cggcuucaag gaccccgucu accgcgcccg ccgcaagcag | 480 |
| uucgccgaca ucgccuacaa cuaccgccac ggccagccca ucccacgcgu cgaguacaug | 540 |
| gaggaggaga agaagaccug gggcaccguc uucaagaccc ucaagucccu cuacaagacc | 600 |
| cacgccugcu acgaguacaa ccacaucuuu ccacuccucg agaaguacug cggcuuccac | 660 |
| gaggauaaca ucccucagcu cgaggacguc ucccaguucc uccagaccug caccggcuuu | 720 |
| cgccugcgcc ggguggcagg ccugcugagc ucucgggacu uccucggcgg ccucgccuuc | 780 |
| cgcgucuucc acugcacccca guacaucagg cacggguccaa agcccaugua caccccagag | 840 |
| cccgacaucu gccacgaacu ccucggccac gugcccucu ucuccgaccg cuccuucgcc | 900 |
| caguucuccc aggagauugg ccuggccagc uugggagcac ccgacgagua cauagagaag | 960 |
| cucgccacca ucuacugguu caccgucgag uucggccucu gcaagcaggg cgacuccauc | 1020 |
| aaggccuacg gggccggcuu gcugaguucu uucggcgagc uccaguacug ccucuccgag | 1080 |
| aagcccaagc ucuuaccacu ggagcuggag aagaccgcca uccagaacua caccgucacc | 1140 |
| gaguuccagc cccucuacua cgucgccgag uccuucaacg acgccaagga aaggguccgc | 1200 |
| aacuucgcgg caacaauccc uagacccuuc uccguccgcu acgaccccua cacccagcgc | 1260 |
| aucgaggugc uggacaacac ucagcagcug aagauccugg cugauagcau uaacuccgaa | 1320 |
| auugggaucc ucugcuccgc ccuccagaag aucaag | 1356 |

<210> SEQ ID NO 11
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

| | |
|---|---|
| augagcaccg ccguccucga gaaccccggc cugggcagaa agcugagcga cuucggccag | 60 |
| gaaaccagcu acaucgagga caacugcaac cagaacggcg ccaucagccu gaucuucagc | 120 |
| cugaaggagg aggugggcgc ccuggccaag gugcugagac uguucgagga gaacgacgug | 180 |

| | |
|---|---|
| aaccugaccc acaucgagag cagacccucc agacugaaga aggacgagua cgaguucuuc | 240 |
| acccaccugg acaagagaag ccugcccgcc cugaccaaca ucaucaagau ccugagacac | 300 |
| gacaucggag ccaccgugca cgagcugagc agagacaaga agaaggacac cgugcccugg | 360 |
| uuccccagaa ccauccagga gcuggacaga uucgccaacc agauccugag cuacggugcc | 420 |
| gagcuagacg ccgaccaccc cggcuucaag daccccgugu acagagccag aagaaagcag | 480 |
| uucgccgaca ucgccuacaa cuacagacac gggcagccga uccccagagu ggaguacaug | 540 |
| gaggaggaga agaagaccug gggcaccgug uucaagaccc ucaagagccu guacaagacc | 600 |
| cacgccugcu acgaguacaa cccacaucuuc ccucugcugg agaaguacug cggcuuccac | 660 |
| gaggacaaca ucccacagcu ggaggacgug agccaguucc ugcagaccug caccggcuuc | 720 |
| agacucaggc ccguugccgg acugcugagc agcagagacu uccugggcgg ccuggccuuc | 780 |
| agaguguucc acugcaccca guacaucaga cacggcagca agcccaugua cacacccgag | 840 |
| cccgacaucu gccacgaacu gcugggccac gugccccugu ucagcgacag aagcuucgcc | 900 |
| caguucagcc aggagaucgg ucuggcuagc uugggagccc cagacgagua caucgagaag | 960 |
| cuggccacca ucuacugguu caccguggag uucggccugu gcaagcaggg agacagcauc | 1020 |
| aaggccuacg gagccggccu acugagcagc uucggcgagc ugcaguacug ccugagcgag | 1080 |
| aagcccaagc uguugccucu ggagcuggag aagaccgcca uccagaacua caccgugacc | 1140 |
| gaguccagc cccuguacua cguggccgag agcuucaacg acgccaagga gaaggugaga | 1200 |
| aacuucgccg ccacuauccc cagacccuuc agcgugagau acgaccccua cacccagaga | 1260 |
| aucgaggugc uggacaacac ccagcagcug aagauucugg ccgauagcau caacagcgag | 1320 |
| aucggcaucc ugugcagcgc ccugcagaag aucaag | 1356 |

<210> SEQ ID NO 12
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

| | |
|---|---|
| augagcaccg ccguccucga gaaccccggc cugggcagaa agcugagcga cuucggccag | 60 |
| gaaaccagcu acaucgagga caacugcaac cagaacggcg ccaucagccu gaucuucuca | 120 |
| cucaaagaag aaguuggugc auuggccaaa guauugcgcu uauuugagga gaacgacgug | 180 |
| aaccugaccc acaucgagag cagacccucc agacugaaga aggacgagua cgaguucuuc | 240 |
| acccaccugg acaagagaag ccugcccgcc cugaccaaca ucaucaagau ccugagacac | 300 |
| gacaucggag ccaccgugca cgagcugagc agagacaaga agaaggacac cgugcccugg | 360 |
| uuccccagaa ccauccagga gcuggacaga uucgccaacc agauccugag cuacggugcc | 420 |
| gagcuagacg ccgaccaccc cggcuucaag daccccgugu acagagccag aagaaagcag | 480 |
| uucgccgaca ucgccuacaa cuacagacac gggcagccga uccccagagu ggaguacaug | 540 |
| gaggaggaga agaagaccug gggcaccgug uucaagaccc ucaagagccu guacaagacc | 600 |
| cacgccugcu acgaguacaa cccacaucuuc ccucugcugg agaaguacug cggcuuccac | 660 |
| gaggacaaca ucccacagcu ggaggacgug agccaguucc ugcagaccug caccggcuuc | 720 |
| agacucaggc ccguugccgg acugcugagc agcagagacu uccugggcgg ccuggccuuc | 780 |
| agaguguucc acugcaccca guacaucaga cacggcagca agcccaugua cacacccgag | 840 |

| | | |
|---|---|---|
| cccgacaucu gccacgaacu gcugggccac gugcccugu ucagcgacag aagcuucgcc | | 900 |
| caguucagcc aggagaucgg ucuggcuagc uugggagccc cagacgagua caucgagaag | | 960 |
| cuggccacca ucuacugguu caccguggag uucggccugu gcaagcaggg agacagcauc | | 1020 |
| aaggccuacg gagccggccu acugagcagc uucggcgagc ugcaguacug ccugagcgag | | 1080 |
| aagcccaagc uguugccucu ggagcuggag aagaccgcca uccagaacua caccgugacc | | 1140 |
| gaguuccagc cccuguacua cguggccgag agcuucaacg acgccaagga aaggugaga | | 1200 |
| aacuucgccg ccacuauccc cagacccuuc agcgugagau acgacccua cacccagaga | | 1260 |
| aucgaggugc uggacaacac ccagcagcug aagauucugg ccgauagcau caacagcgag | | 1320 |
| aucggcaucc ugugcagcgc ccugcagaag aucaag | | 1356 |

<210> SEQ ID NO 13
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

| | | |
|---|---|---|
| augagcaccg ccgugcugga aaccccggc cugggccgga agcugagcga cuucggccag | | 60 |
| gagaccagcu acaucgagga caacugcaac cagaacggcg ccaucagccu gaucuucagc | | 120 |
| cugaaggagg aggugggcgc ccuggccaag gugcugcggc uguucgagga gaacgacgug | | 180 |
| aaccugaccc acaucgagag ccggcccagc cggcugaaga aggacgagua cgaguucuuc | | 240 |
| acccaccugg acaagcggag ccugcccgcc cugaccaaca ucaucaagau ccugcggcac | | 300 |
| gacaucggcg ccaccgugca cgagcugagc cgggacaaga gaaggacac cgugcccugg | | 360 |
| uucccgcgga ccauccagga gcuggaccgg uucgccaacc agauccugag cuacggcgcc | | 420 |
| gagcuggacg ccgaccaccc cggcuucaag gaccccgugu accgggcccg gcggaagcag | | 480 |
| uucgccgaca ucgccuacaa cuaccggcac ggccagccca uccgcgggu ggaguacaug | | 540 |
| gaggaggaga agaagaccug gggcaccgug uucaagaccc ugaagagccu guacaagacc | | 600 |
| cacgccugcu acgaguacaa ccacaucuuc ccacugcugg agaaguacug cggcuuccac | | 660 |
| gaggacaaca ucccacagcu ggaggacgug agccaguucc ugcagaccug caccggcuuc | | 720 |
| cggcugcggc ccguggccgg ccugcugagc agcgggacu ccugggcgg ccuggccuuc | | 780 |
| cggguguucc acugcaccca guacauccgg cacggcagca agcccaugua cacgcccgag | | 840 |
| cccgacaucu gccacgagcu gcugggccac gugcccugu ucagcgaccg gagcuucgcc | | 900 |
| caguucagcc aggagaucgg ccuggccagc cuggcgcgc ccgacgagua caucgagaag | | 960 |
| cuggccacca ucuacugguu caccguggag uucggccugu gcaagcaggg cgacagcauc | | 1020 |
| aaggccuacg gcgccggccu gcugagcagc uucggcgagc ugcaguacug ccugagcgag | | 1080 |
| aagcccaagc ugcugcccu ggagcuggag aagaccgcca uccagaacua caccgugacc | | 1140 |
| gaguuccagc cccuguacua cguggccgag agcuucaacg acgccaagga aaggugcgg | | 1200 |
| aacuucgccg ccaccauccc acggcccuuc agcgugcggu acgacccua cacccagcgg | | 1260 |
| aucgaggugc uggacaacac ccagcagcug aagauccugg ccgacagcau caacagcgag | | 1320 |
| aucggcaucc ugugcagcgc ccugcagaag aucaag | | 1356 |

-continued

```
<210> SEQ ID NO 14
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
augagcaccg ccgugcugga gaaccccgga cugggaagaa agcugugccga uuucgggcag    60 gagacuuccu acaucgagga caacugcaac cagaacgggg ccaucucccu gaucuucagc   120
cugaaggagg aggugggcgc ccuggcgaag gugcuccggc uguucgagga gaacgacgug   180
aaccugacgc acaucgaaag ccggcccagc cggcugaaga aggacgagua cgaguucuuc   240
acgcaccugg acaaggagga cuugcccgcc cucaccaaca ucaucaagau ccugcggcac   300
gacaucggcg ccacggugca cgagcugagc cgcgacaaga agaaggauac cgugcccugg   360
uuccccagga ccauccagga gcuggacaga uucgccaacc agauccugag cuacggcgcc   420
gaacuggacg ccgaccaccc cggcuuuaag gaccccgugu acagggccag gcggaaacag   480
uucgccgaca ucgccuauaa cuacaggcac gggcaaccca ucccuagggu cgaguacaug   540
gaggaggaga agaagaccug gggcacagug uucaagaccc ucaaaucccu guacaagaca   600
cacgccugcu acgaguauaa ccacaucuuc ccucuccugg agaaguauug cggcuuucac   660
gaagacaaca ucccgcagcu ggaagacgug ucccaguucc ugcagaccug uaccggauuc   720
agguuaagac cuguggccgg ccugcugagc agcagggauu ccuaggcgg gcucgccuuc   780 aggguguucc auugcaccca guacaucaga cacggcucca agccgaugua acgccugag   840 cccgacaucu gccacgagcu gcugggccac gugccgcugu ucagcgauag aagcuucgcc   900
caguucagcc aggagaucgg ccuggccagc cuggagcgc cugacgaaua uaucgagaag   960
cucgccacca ucuacugguu uaccguggaa ucggccugu gcaagcaggg agacuccauc  1020
aaggccuacg gggcugggcu gcuguccucc uucggggagc uccaguacug ucucucccgag 1080 aagcccaagc ugcugccccu cgagcuggag aagaccgcga uccagaacua uaccgucacc  1140
gaauuccagc cccuguauua cguggccgag uccuuuaacg acgccaagga gaaggucgg  1200 aauuucgcug ccaccauucc caggcccuuc agcgugcggu acgaucccua cacccagcgc  1260 auagagugc uggauaauac acagcagcug aagauccugg ccgacagcau caauagcgaa  1320
auaggcaucc ugugcagcgc ccugcagaag aucaag                            1356

<210> SEQ ID NO 15
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
auguccaccg ccgugcucga gaaccccuggc cugggcagga agcugagcga cuucgggcaa    60
gagacaagcu acaucgagga uaacugcaau cagaacggcg ccaucagccu gaucuucucc   120
cugaaggagg aggugggcgc ccuggcuaag gugcugaggc uauucgaaga gaacgacgug   180
aaucugaccc auaucgagag ccgccccagc cggcucaaga aggacgagua cgaguucuuu   240
acucaccugg acaagcgguc ccugcccgcc cugacaaaca ucaucaagau ccucaggcac   300
```

```
gauaucggag ccaccgucca cgagcugagc cgcgacaaga agaaagacac cgugcccugg      360
uuucccagga ccauccagga gcuggaucgg uuugccaacc agauccugag cuacggggcc      420
gaacuugacg ccgaccaucc cgguucaag  gacccggugu accgggcuag gcgaaagcaa      480
uucgccgaca uugccuacaa cuaccgucac ggccagccca ucccacgggu ggaauacaug      540
gaggaggaga agaagaccug gggaacaguc uucaagaccc ugaagucacu guacaagacc      600
cacgccugcu acgaguauaa ccacaucuuc ccacuccucg agaaguacug cggcuuccac      660
gaggacaaca ucccucagcu ggaggacgug agccaguucc ugcagaccug caccggcuuu      720
cgucugcguc ccguggcggg acugcugagc agcagggacu ccuggggcgg acuggccuuc      780 cgggguguucc acugcacaca guacauccga cacggcagca agccgaugua uacaccggag      840
ccggacauuu gccacgagcu ccugggccac gugccccugu cagcgacag  gagcuucgcc      900 caguucagcc aggagaucgg ccuggccagc cugggugccc cagacgagua cauagagaag      960
cuggcgacca ucuacugguu cacgucgag  uucggccugu gcaaacaggg cgacagcauu      1020
aaggccuacg gcgccggccu gcucagcucc uucggcgagc uccaguauug ccugagcgag      1080
aagcccaagc ugcugccccu ggagcucgag aagacugcca ucagaacua  cacugugacc      1140 gaguuccagc cccuguacua cguggcggag agcuucaacg acgccaagga gaaggugagg      1200
aacuucgccg ccaccauccc ucggcccuuc uccguuaggu acgaccccua cacccagagg      1260
aucgaggugc uggauaauac ccagcagcug aagauccugg cggacagcau caacagcgaa      1320
aucggcaucc ugugcagcgc cuuacagaag aucaag                                1356
```

<210> SEQ ID NO 16
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
augagcaccg ccgugcugga gaaccccggc cugggccgga agcugagcga cuucggccag       60
gagacgucau acaucgagga uaacugcaac cagaacggug ccaucucccu gaucuucagc      120
cugaaggaag  agguggGcgc ccuggccaag gucGugagac uguucgagga gaacgacgug      180
aaccugaccc acaucgaaag cagacccagc aggcugaaga agacgagua  cgaauucuuc      240 acccaccugg acaagcggag ccugcccgcc cucacuaaca ucaucaagau ccuuagacac      300
gacauaggcg ccaccgucca cgaacucagc agggacaaga agaaggacac cgugcccugg      360
uuccccagga ccauccagga gcuggaccgc uucgccaacc agauucuguc cuacggagcu      420
gaacucgacg ccgaccaucc cggauucaaa  gaccccgugu acagagccag aagaaagcag      480
uucgccgaca ucgcguacaa cuauaggcac ggccagccga uccccagagu cgaguacaug      540
gaggaggaga agaagaccug gggcaccgug uucaagaccc ugaagucccu guacaagacc      600
cacgcuugcu acgaguauaa ccacaucuuc ccacuccugg agaaguacug cggcuuccac      660
gaagacaaca ucccccagcu cgaggacgug agccaauucc ugcagaccug caccggcuuc      720
cgccugaggc ccguugccgg ccugcugagc ccagagauu  ccucggcgg  ccuggccuuc      780 agaguguuc  acugcacccca guacauccgc cacggcucca agccaaugua cacccccggag      840 cccgauaucu gcacgagcu  gcuggccccac gugccccucu cagcgaccg  aagcuucgcc      900 caguuuuccc aagagauagg acuugccucc cucggugccc cggacgaaua uauugagaaa       960
```

| cucgccacca ucuacugguu uacgguggaa uucggacugu gcaagcaggg cgacagcauc | 1020 |
| aaagccuacg gggcagggcu gcugucuagc uucggggagc uccaauacug ccugagcgag | 1080 |
| aaacccaagc uccugccucu cgagcuggag aagaccgcua uccagaauua caccgugacu | 1140 |
| gaauuccagc cccuguacua cgucgccgag agcuuuaacg acgccaagga gaaaguacga | 1200 |
| aacuucgccg cuaccauucc ccgcccuuc agcgugaggu acgacccuua caccagcgu | 1260 |
| aucgaggugc uggauaauac ccaacagcug aagauacucg ccgacuccau caacagcgag | 1320 |
| aucggcaucc uguguuccgc ccuccagaag aucaag | 1356 |

<210> SEQ ID NO 17
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

| auguccacgg ccguccugga gaauccgggc cuggggagga aacugagcga cuucgggcag | 60 |
| gagacauccu acaucgagga caacugcaac cagaacggag ccaucagccu gaucuucagc | 120 |
| cucaaagagg agguggggcgc ucucgccaag gugcugagac uguucgagga gaacgacguc | 180 |
| aaccucacgc acaucgaauc ccgacccagc cgucugaaga aggacgagua cgaguucuuc | 240 |
| acccaucucg acaagcgguc ccugcccgcc cucacaaaca ucaucaagau ccugcggcac | 300 |
| gacaucggcg ccaccgugca cgagcugucc agggacaaga agaaagauac cgugccgugg | 360 |
| uuccccagga cgauccagga gcucgaccgg uucgccaacc agauccugag cuacggcgcc | 420 |
| gaacucgacg ccgaccaccc cggcuuuaag gaucccgugu acagagccag gaggaagcag | 480 |
| uuugccgaca ucgcguacaa cuacagacac gggcagccca uccccagggu ggaguacaug | 540 |
| gaggaggaga agaagaccug gggcaccguc uucaagacac ugaaguccu guacaagacc | 600 |
| cacgccugcu acgaguacaa ccacauuuuc ccucugcugg agaaguacug cggcuuccac | 660 |
| gaagacaaca uaccgcagcu cgaggacgug agccaauuuc ugcagaccug caccgguuuu | 720 |
| agacugaggc ccguggccgg ccugcugagc agcagggauu uucucggugg acuggccuuc | 780 |
| agaguguucc acugcacccca guauauaaga cacggcucca agcccaugua caccccagag | 840 |
| ccugacaucu gccacgaacu gcugggucac gugccccucu cagcgacag guccuucgcc | 900 |
| caguucagcc aggaaaucgg ccuggccucc cucggcgcuc ccgacgaaua caucgagaag | 960 |
| cuggccacaa ucuacugguu caccgucgag uucggccugu gcaagcaggg cgacuccauc | 1020 |
| aaggccuacg gcgcggggcu gcuauccucc uucggggagc uccaguacug ccuguccgag | 1080 |
| aagcccaagc uccugcccu ggaacuggag aagaccgcca uccagaacua caccgugacc | 1140 |
| gaguuccagc cacuguacua cgucgccgag aguuucaacg acgccaaaga gaagugcgg | 1200 |
| aacuucgccg ccaccauccc uagaccuuuc uccgucagau acgacccaua cacgcagcgg | 1260 |
| aucgagguce uggacaacac ucagcaacuc aagauucugg cugacaguau caauagcgag | 1320 |
| aucgggauce uguguagcgc ccuucagaag aucaag | 1356 |

<210> SEQ ID NO 18
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18

| augagcaccg ccgugcugga gaccccggc cugggccgga agcugagcga cuucggccag | 60 |
| gagacgagcu acaucgagga caacugcaac cagaacggcg ccaucagccu gaucuucucc | 120 |
| cugaaggagg aggugggcgc ccuggccaag gugcugcggc uguucgagga gaacgacgug | 180 |
| aaccugaccc acaucgagag ccggcccagc cggcugaaga aggacgagua cgaguucuuc | 240 |
| acccaccugg acaagcggag ccugcccgcc cugaccaaca ucaucaagau ccugcggcac | 300 |
| gacaucggcg ccaccgugca cgagcugagc cgggacaaga agaaagacac cgugcccugg | 360 |
| uucccacgga ccauccagga gcuggaccgg uucgccaacc agauccugag cuacggcgcc | 420 |
| gagcuggacg ccgaccaccc cggcuucaag gaccccgugu accgggcccg gcggaagcag | 480 |
| uucgccgaca ucgccuacaa cuaccggcac ggccagccca ucccacgggu ggaguacaug | 540 |
| gaggaggaga agaagaccug gggcaccgug uucaagaccc ugaaguccu guacaagacc | 600 |
| cacgccugcu acgaguacaa ccacaucuuu ccccuucugg agaaguacug cggcuuccac | 660 |
| gaggacaaua ucccucagcu ggaggacgug agccaguucc ugcagaccug caccggcuuc | 720 |
| cgccugaggc ccguggccgg ccugcugagc ccaggacu ccugggcgg ccuggccuuc | 780 |
| cggguguucc acugcaccca guacauccga cacggcagca agcccaugua cacgcccgag | 840 |
| cccgacaucu gccacgagcu ccuggccac gugcccugu cagcaccg gagcuucgcc | 900 |
| caguucuccc aggagaucgg acuggccagc cuggagcac ccgacgaaua caucgagaag | 960 |
| cuggccacca ucuacugguu caccguggag uucggccugu gcaagcaggg cgacagcauc | 1020 |
| aaggccuacg gcgccggucu gcuguccagc uucgcgagc ugcaguacug ccugagcgag | 1080 |
| aagcccaagc ugcugccccu ggaacuggag aagaccgcca uccagaacua caccgugacc | 1140 |
| gaguuccagc cccuguacua cguggccgag agcuucaacg acgccaagga aaggugcgg | 1200 |
| aacuucgccg ccaccauacc ccgccccuuc agcgugcggu acgacccccua cacccagcgg | 1260 |
| aucgaggugc uggacaacac ccaacagcug aagauccugg ccgauagcau caacagcgag | 1320 |
| aucggcaucc ugugcagcgc ccugcagaag aucaag | 1356 |

<210> SEQ ID NO 19
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

| augagcaccg ccgugcugga gaccccggc cugggccgga agcugagcga cuucggccag | 60 |
| gaaaccagcu acaucgagga caacugcaac cagaacggcg ccaucagccu gaucuucagc | 120 |
| cucaaggagg aggugggcgc ccuggccaag gugcugcggc uguucgagga gaacgacgug | 180 |
| aaccugaccc acaucgagag ccggcccagc cggcugaaga aggacgagua cgaguucuuc | 240 |
| acccaccugg acaagcggag ccugcccgcc cugaccaaca ucaucaagau ccugcggcac | 300 |
| gacaucggcg ccaccgugca cgagcugagc cgggacaaga agaaggauac cgugcccugg | 360 |
| uucccgcgga ccauccagga gcuggaccgg uucgccaacc agauccugag cuacggcgcc | 420 |

| | |
|---|---|
| gagcuggacg ccgaccaccc cggcuucaag daccccgugu accgggcccg gcggaagcag | 480 |
| uucgccgaca cgccuacaa cuaccggcac ggccagccca ucccgcgggu ggaguacaug | 540 |
| gaggaggaga agaagaccug ggcaccgug uucaagaccc ugaagucucu guacaagacc | 600 |
| cacgccugcu acgaguacaa ccacaucuuu ccccugcucg agaaguacug cggcuuccac | 660 |
| gaggauaaca uaccgcagcu ggaggacgug agccaguucc ugcagaccug caccggcuuc | 720 |
| agauugaggc ccgucgcugg ucugcugagc ccaggacu uccugggcgg ccuggccuuc | 780 |
| cgggguguucc acugcaccca guacaucagg cacggcagca agcccaugua cacgcccgag | 840 |
| cccgacaucu gccacgagcu ccugggccac gugcccugu ucagcgaccg gagcuucgcc | 900 |
| caguucagcc aagagaucgg acuggcuagc cucgcgccc cggacgagua uaucgagaag | 960 |
| cuggccacca ucuacggguu caccguggag uucggccugu gcaagcaggg cgacagcauc | 1020 |
| aaggccuacg gcgccggccu ccucagcucu uucggcgagc ugcaguacug ccugagcgag | 1080 |
| aagcccaagc ugcugcccu cgaacuggag aagaccgcca uccagaacua caccgugacc | 1140 |
| gaguccagc cccuguacua cguggccgag agcuucaacg acgccaagga gaaggugcgg | 1200 |
| aacuucgccg cgaccauccc uaggcccuuc agcgugcggu acgacccua cacccagcgg | 1260 |
| aucgaggugc uggacaauac ccagcagcug aagauucucg ccgacucgau caacagcgag | 1320 |
| aucgggaucc ugugcagcgc ccugcagaag aucaag | 1356 |

<210> SEQ ID NO 20
<211> LENGTH: 1356
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

| | |
|---|---|
| augagcaccg ccgugcugga gaaccccggc cugggccgga agcugagcga cuucggccag | 60 |
| gagacguccu acaucgagga caacugcaac cagaacggcg ccaucucccu caucuucagc | 120 |
| cugaaggagg aggucggcgc ccucgccaag gucuccgcc ucuucgagga gaacgacguc | 180 |
| aaccucaccc acaucgaguc ccgcccccuc cgccucaaga aggacgagua cgaguucuuc | 240 |
| acccaccucg acaagcgcuc ccuccccgcc cucaccaaca ucaucaagau ccugagacac | 300 |
| gacaucggcg ccaccgucca cgagcucucc cgcgacaaga agaaggauac cguccccugg | 360 |
| uucccacgca ccauccagga gcucgaccgc uucgccaacc agauccucuc cuacggcgcc | 420 |
| gagcuggacg ccgaccaccc cggcuucaag daccccgucu accgcgcccg ccgcaagcag | 480 |
| uucgccgaca cgccuacaa cuaccggcac ggccagccca ucccgcgu cgaguacaug | 540 |
| gaggaggaga agaagaccug ggcaccgucu ucaagaccc ucaagcccu cuacaagacc | 600 |
| cacgccugcu acgaguacaa ccacaucuuu ccccuccucg agaaguacug cggcuuccac | 660 |
| gaggacaaua ucccucagcu cgaggacguc ucccaguucc ucagaccug caccggcuuu | 720 |
| cggcugcgcc cggucgccgg ccugcugucc agcaggacu uccucggcgg ccucgccuuc | 780 |
| cgcgucuucc acugcaccca guacauucgg cacggcucca agcccaugua cacacccgag | 840 |
| cccgacaucu gccacgagcu gcucggccac gugcccucu ucuccgaccg cucuuucgcc | 900 |
| caguucuccc aggagauugg gcuggccucc cugggagcgc ccgacgagua cauugagaag | 960 |
| cucgccacca ucuacggguu caccgucgag uucggccucu gcaagcaggg cgacuccauc | 1020 |
| aaggcuuacg gggcggggcu ccucuccagc uucggcgagc uccaguacug ccucucccgag | 1080 |

```
aagcccaagc uccucccgcu ggaacuggag aagaccgcca uccagaacua caccgucacc   1140
gaguuccagc cccucuacua cgucgccgag uccuucaacg acgccaagga gaagguccgc   1200
aacuucgcgg cuaccauccc gcggcccuuc uccguccgcu acgaccccua cacccagcgc   1260
aucgaggugc ucgacaauac ccaacagcug aagauccugg cggacagcau uaacuccgag   1320
aucgggaucc ucugcuccgc cuccagaag aucaag                              1356
```

<210> SEQ ID NO 21
<211> LENGTH: 336
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Met Val Pro Trp Phe Pro Arg Thr Ile Gln Glu Leu Asp Arg Phe Ala
1               5                   10                  15

Asn Gln Ile Leu Ser Tyr Gly Ala Glu Leu Asp Ala Asp His Pro Gly
            20                  25                  30

Phe Lys Asp Pro Val Tyr Arg Ala Arg Arg Lys Gln Phe Ala Asp Ile
        35                  40                  45

Ala Tyr Asn Tyr Arg His Gly Gln Pro Ile Pro Arg Val Glu Tyr Met
    50                  55                  60

Glu Glu Glu Lys Lys Thr Trp Gly Thr Val Phe Lys Thr Leu Lys Ser
65                  70                  75                  80

Leu Tyr Lys Thr His Ala Cys Tyr Glu Tyr Asn His Ile Phe Pro Leu
                85                  90                  95

Leu Glu Lys Tyr Cys Gly Phe His Glu Asp Asn Ile Pro Gln Leu Glu
            100                 105                 110

Asp Val Ser Gln Phe Leu Gln Thr Cys Thr Gly Phe Arg Leu Arg Pro
        115                 120                 125

Val Ala Gly Leu Leu Ser Ser Arg Asp Phe Leu Gly Gly Leu Ala Phe
    130                 135                 140

Arg Val Phe His Cys Thr Gln Tyr Ile Arg His Gly Ser Lys Pro Met
145                 150                 155                 160

Tyr Thr Pro Glu Pro Asp Ile Cys His Glu Leu Leu Gly His Val Pro
                165                 170                 175

Leu Phe Ser Asp Arg Ser Phe Ala Gln Phe Ser Gln Glu Ile Gly Leu
            180                 185                 190

Ala Ser Leu Gly Ala Pro Asp Glu Tyr Ile Glu Lys Leu Ala Thr Ile
        195                 200                 205

Tyr Trp Phe Thr Val Glu Phe Gly Leu Cys Lys Gln Gly Asp Ser Ile
    210                 215                 220

Lys Ala Tyr Gly Ala Gly Leu Leu Ser Ser Phe Gly Glu Leu Gln Tyr
225                 230                 235                 240

Cys Leu Ser Glu Lys Pro Lys Leu Leu Pro Leu Glu Leu Glu Lys Thr
                245                 250                 255

Ala Ile Gln Asn Tyr Thr Val Thr Glu Phe Gln Pro Leu Tyr Tyr Val
            260                 265                 270

Ala Glu Ser Phe Asn Asp Ala Lys Glu Lys Val Arg Asn Phe Ala Ala
        275                 280                 285

Thr Ile Pro Arg Pro Phe Ser Val Arg Tyr Asp Pro Tyr Thr Gln Arg
    290                 295                 300
```

```
Ile Glu Val Leu Asp Asn Thr Gln Gln Leu Lys Ile Leu Ala Asp Ser
305                 310                 315                 320

Ile Asn Ser Glu Ile Gly Ile Leu Cys Ser Ala Leu Gln Lys Ile Lys
                325                 330                 335
```

<210> SEQ ID NO 22
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
auggugcccu gguuucccag aaccauccag gagcuggaca gguucgcaaa ccagauacuc      60
uccuacggcg cagagcugga cgccgaccac ccaggcuuca aggaccccgu cuacagggcc     120
aggcgcaagc aguucgcaga uauugccuac aauuaucgac acggucagcc caucccuaga     180
guggaguaca uggaggaaga aagaagacc uggggcaccg uguucaagac ucugaagagu      240
cuguacaaga cacacgcuug uuacgaguau aaucacaucu ucccucugcu ggagaaguac     300
ugcgguuucc acgaagauaa cauccccgcag cucgaggacg ugucccaguu ucugcagacu    360
ugcacuggcu uuagacugag gcccgucgcc ggacugcugu ccuccagaga cuuccugggc     420
gggcuugcuu ucagaguguu ucacuguaca caguauauuc gccacgggag caaacccaug     480
uacacccug agcccgacau uugucacgaa ugcugggac acgugccucu guuuagcgau      540
agaagcuucg cccaguucag ccaggaaauc gggcuggccu cacugggcgc cccagacgag     600
uacaucgaga agcuggccac cauauacugg uucacagugg aguucggccu gugcaagcaa     660
ggcgacucua ucaaggcuua cggugccggg cuguugagcu cauucggaga gcugcaauau     720
uguuuaucag agaaaccuaa gcugcugccc cuugagcucg agaagacagc cauacagaac     780
uacaccguga ccgaguucca gccacuguau uacguggccg aauccuucaa cgacgcaaag     840
gagaagguga gaaacuuugc cgcuaccauc ccucggcccu ucuccguuag auacgacccc    900
uacacccaac ggauugaggu gcuggacaau acccagcaau ugaagauccu ugccgacucg    960
aucaacagcg agaucggcau ucugugcagc gcguugcaga agaucaag               1008
```

<210> SEQ ID NO 23
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
auggugcccu gguucccacg uacuauccag gagcuggaua gauucgcgaa ccagauccug      60
agcuacggcg ccgagcucga cgccgaccau cccggauuua aggaucccgu guauagggcu     120
aggaggaaac aguucgccga uauugccuau aauuauagac acgggcagcc uauuccaaga     180
guggaguaua uggaggagga aagaagacc uggggcacag uguucaagac cuugaagagu      240
cuguacaaga cacacgccug uuacgaguac aaccacaucu uccccugcu ggagaaguac      300
ugcggcuucc acgaggauaa uaucccacaa cuggaggacg ugagccaguu ccugcaaacc     360
ugcacuggcu uccgucugcg acccgucgcc ggccuccuca gcagccggga uuccuuggc     420
gggcuggccu ucggguguu ucacugcacu caguacaucc ggcacgguuc uaagcccaug     480
```

```
uauaccccag agccugacau cugucacgag cugcucggcc acgugcccu guucagcgac    540 cgguccuucg cccaguucag ccaggagauc ggccuggccu cucugggcgc ucccgacgag    600
uauaucgaga agcuggcuac gauuuacugg uucaccgucg aauucggccu gugcaagcaa    660
ggggacagca uuaaagccua cggggcugga uuacugucaa gcuucgggga acugcaguau    720
ugccuguccg agaaacccaa acugcuuccg cuggagcucg agaagacugc cauccagaac    780
uacacgguga ccgaguucca gccccuguac uacgucgcug agucauucaa cgacgcuaag    840
gagaaggugc gcaauuucgc ugccaccauc cccaggcccu uuagcgugag auacgauccu    900
uacacccaga ggauugaagu gcuggauaac acucagcaac ugaagauccu ggcagacagc    960
aucaauagcg agauuggcau ccugugcagc gcccugcaga gauuaaaa             1008
```

<210> SEQ ID NO 24
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

```
auggugcccu gguucccucg gaccauccag gagcuggaca gauucgccaa ccagauucug     60
agcuacgggg ccgaauugga cgccgaccac ccaggcuuua aggacccugu uacagagcu    120 aggaggaagc aguucgccga uauugccuau aacuacagac acggccagcc uauccccaga    180
guggaguaca uggaggagga gaagaagacg uggggcaccg guucaagac ucugaagucu    240 cuuuacaaga cacacgcuug cuacgaguac aaucacaucu ucccacugcu ggagaaguac    300
uguggcuucc acgaagacaa cauucccag cuugaggacg ugagcaguu ccugcagacc    360 ugcacaggcu uccgucuccg gccugugcu gggcugcuga gcagcagaga cuuccuggga    420
ggccuggcuu ccggguguu ucauugcacg caguacauua gacacggcuc caagccaaug    480
uacacaccag agcccgacau cugccacgag cugcugggac acgugccacu cuucagcgac    540
agaucauucg cccaguucuc ucaggagauc ggacuggcuu cccuuggagc accgacgag    600 uacaucgaga aacuggccac uaucuauugg uucacagugg aauuggccu gugcaagcag    660 ggcgacucua ucaaggccua cggcgccgga cugcuguccu ccuucggcga acugcaguau    720
ugucugucag agaagcccaa gcugcugccc cuagaacucg agaagacagc cauacagaau    780
uacaccguga ccgaguuuca gccccucuac uacguggccg aaucuuucaa cgacgccaag    840
gagaagguga ggaauuucgc cgccaccauc ccucggccgu uuccgugcg auacgacccc    900 uauacccagc ggaucgaggu gcuggacaac acgcagcaac ugaagauucu ggcggacuca    960
aucaacagcg agaucggcau ccuguguagc gcacugcaga gauuaaag              1008
```

<210> SEQ ID NO 25
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

```
augguaccuu gguucccag aacaauucag gaacuggacc gguuugccaa ccagauccuu     60
aguuacggcg ccgagcucga cgccgaccac cccggcuuua aggauccugu guauagagcc    120
```

| | | |
|---|---|---|
| aggaggaagc aguucgcuga uauugccuac aauuacaggc acggucaacc caucCccagg | 180 | |
| guggaguaca uggaggagga gaagaagacc uggggcaccg ucuucaagac ccugaagucu | 240 | |
| cuauauaaga cucacgccug cuacgaguac aaucacaucu ucccacuccu ggagaaguac | 300 | |
| ugcggcuucc acgaggacaa cauuccccag cuggaggacg ugcccaguu ccugcagacc | 360 | |
| ugcaccggcu uccggcugcg uccggucgcc gggcugcugu cuucacgcga uuuucgggc | 420 | |
| ggauuggccu uuaggguCuu ccacugcacc caguacauca gacacggauc uaagcccaug | 480 | |
| uacacacccg agccugauau ugccacgaa cuguuggga cgugccucu guucucugac | 540 | |
| agaagcuucg cccaguuuuc ccaggagauc ggccuggccu cccucggagc acccgacgag | 600 | |
| uacauagaga agcuggccac uauauacugg ucacuguug aguuugggcu gugcaagcag | 660 | |
| ggcgauucua uaaaggccua cggggccgga cugcugucCu ccuuugggga gcugcaguac | 720 | |
| ugucuuucug agaagcccaa acuucugccc cuggagcuug agaagacggc cauccagaau | 780 | |
| uacaccguga cugaguucca accacuuuau uacguggcug aauccuucaa cgacgccaag | 840 | |
| gagaagguga ggaacuuugc cgccacaauu ccucgcccuu ucuccgugag auacgacccc | 900 | |
| uauacccaac ggauugaagu ucuugacaac acccagcagc ugaagauacu ggccgacuca | 960 | |
| auaaacucug agaucggaau ccugugcagu gcccugcaga agaucaag | 1008 | |

<210> SEQ ID NO 26
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

| | | |
|---|---|---|
| auggugcccu gguuuccccg gaccauccag gagcuggacc gguucgccaa ccagauccug | 60 | |
| agcuacggcg ccgagcugga cgccgaccac cccggcuuca aggaccccgu guacggggcc | 120 | |
| cggcggaagc aguucgccga caucgccuac aacuaccggc acggccagcc caucccgcgg | 180 | |
| guggaguaca uggaggagga gaagaagacc uggggcaccg uguucaagac ccuuaagagc | 240 | |
| cuguacaaga cccacgccug cuacgaguac aaccacaucu uccccugcu ggagaaguac | 300 | |
| ugcggcuucc acgaggacaa cauccacag cuggaggacg ugagccaguu ccugcagacc | 360 | |
| ugcaccggcu uccggccugcg gccugugggcc ggacugcuga gcagccggga cuuccugggc | 420 | |
| ggccuggccu ccggguguu ccacugcacc caguacaucc ggcacggcag caagcccaug | 480 | |
| uacacacccg agcccgacau cugccacgag cugcugggcc acgugcccu guucagcgac | 540 | |
| cggagcuucg cccaguucag ccaggagauc ggguuagcca gccugggcgc ucccgacgag | 600 | |
| uacaucgaga agcuggccac caucuacugg uucaccgugg aguucggccu gugcaagcag | 660 | |
| ggcgacagca ucaaggccua cggggccggg cugcucagca gcuucggcga gcugcaguac | 720 | |
| ugccugagcg agaagcccaa gcugcugccc cuggaguuga agaagaccgc cauccagaac | 780 | |
| uacaccguga ccgaguucca gcccucuuac uacguggccg agagcuucaa cgacgccaag | 840 | |
| gagaaggugc ggaacuucgc cgccacaauc ccagacccu ucagcgugcg guacgacccc | 900 | |
| uacacccagc ggaucgaggu gcuggacaac acacagcagc ugaagauccu ggccgacuca | 960 | |
| aucaacagcg aaaucggcau ccugugcagc gcccugcaga agaucaag | 1008 | |

<210> SEQ ID NO 27
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
auggugcccu gguucccccg gaccauccag gagcuggacc gguucgccaa ccagauccug      60
agcuacggcg ccgaacucga cgccgaccac cccggcuuca aggaccccgu guaccgggcc     120
cggcggaagc aguucgccga caucgccuac aacuaccggc acggccagcc cauuccccgg     180
guggaguaca uggaggagga gaagaagacc uggggcaccg uguucaagac ccucaagucc     240
cguacaaga cccacgccug cuacgaguac aaccacaucu cccgcugcu ggagaaguac      300
ugcggcuucc acgaggacaa cauuccucag cuggaggacg ugagccaguu ccugcagacc    360
ugcaccggcu ucaggcugcg acccgucgcc ggccugcuga gcagccggga cuuccugggc    420
ggccuggccu uccgggguguu ccacugcacc caguacaucc gacacggcag caagcccaug   480
uacacgcccg agcccgacau cugccacgag cugcuggggcc acgugccccu guucagcgac  540
cggagcuucg cccaguucag ccaggagauc ggacuggcua gccugggcgc uccagacgaa   600
uacaucgaga agcuggccac caucuacugg uucaccgugg aguucggccu gugcaagcag   660
ggcgacagca ucaaggccua cggagcaggc cuucugucaa gcuucggcga gcugcaguac   720
ugccugagcg agaagcccaa gcugcugccc cuggaguugg agaagaccgc cauccagaac   780
uacaccguga ccgaguucca gccccuguac uacguggccg agagcuucaa cgacgccaag   840
gagaaggugc ggaacuucgc cgcuaccauu cccggcccu ucagcgugcg guacgacccc    900
uacacccagc ggaucgaggu gcuggacaac acacagcagc ugaagauccu ggcugacucc    960
aucaacagcg agauugggau ccugugcagc gcccugcaga gaucaag                  1008
```

<210> SEQ ID NO 28
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
auggugcccu gguucccgcg gaccauccag gagcuggacc gguucgccaa ccagauccug      60
agcuacggcg ccgagcucga cgccgaccac cccggcuuca aggaccccgu cuaccgcgcc     120
cgccgcaagc aguucgccga caucgccuac aacuaccgcc acggccagcc cauuccccgc     180
gucgaguaca uggaggagga gaagaagacc uggggcaccg ucuucaagac ccucaagucc    240
cucuacaaga cccacgccug cuacgaguac aaccacaucu uccccucucu cgagaaguac    300
ugcggcuucc acgaggacaa cauccccucag cucgaggacg ucucccaguu ccuccagacc   360
ugcaccggcu uccggcugag gcccguggcu ggaucucucu ccuccgcga cuuccucggc    420
ggccucgccu uccgcgucuu ccacugcacc caguacauaa gacacggguc caagcccaug    480
uacacgcccg agcccgacau cugccacgag cuccucgggcc acgugccccu cuucccgac    540
cgcuccuucg cccaguucuc ccaggagauc ggcccuggccu cccugggagc gcccgacgag   600
uacaucgaga agcucgccac caucuacugg uucaccgucg aguucggccu cugcaagcag   660
```

| | |
|---|---|
| ggcgacucca ucaaggccua cggagcuggc cugcuguccu ccuucggcga gcuccaguac | 720 |
| ugccucuccg agaagcccaa gcuccuccca cuggaguugg agaagaccgc cauccagaac | 780 |
| uacaccguca ccgaguucca gccccucuac uacgucgccg aguccuucaa cgacgccaag | 840 |
| gagaaggucc gcaacuucgc ugcaaccauc ccacggcccu ucccguccg cuacgacccc | 900 |
| uacacccagc gcaucgaggu ccucgacaau acgcagcagc ucaagauccu cgccgacucg | 960 |
| auuaacuccg aaaucggcau ccucugcucc gcccuccaga agaucaag | 1008 |

<210> SEQ ID NO 29
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

| | |
|---|---|
| auggugcccu gguuccccag aaccauccag gagcuggaca gauucgccaa ccagauccug | 60 |
| agcuacggcg ccgagcucga cgccgaccac cccggcuuca aggaccccgu guacagagcc | 120 |
| agaagaaagc aguucgccga caucgccuac aacuacagac acggcagcc cаucсссааgа | 180 |
| guggaguaca uggaggagga gaagaagacc uggggcaccg uguucaagac ccucaagagc | 240 |
| cuguacaaga cccacgccug cuacgaguac aaccacaucu ucccccugcu ggagaaguac | 300 |
| ugcggcuucc acgaggacaa cauaccccag cuggaggacg ugagccaguu ccugcagacc | 360 |
| ugcaccggcu ucagacugag gcccguggcc ggccugcugu ccaguagaga cuuccugggc | 420 |
| ggccuggccu ucagaguguu ccacugcacc caguacauca gacacggcag caagcccaug | 480 |
| uacaccccag agcccgacau cugccacgag cugcugggac acgugccccu guucagcgac | 540 |
| agaagcuucg cccaguucuc ccaggaaauc ggccucgcca gucugggcgc cccggacgag | 600 |
| uacaucgaga gcuggccac caucuacugg uucaccgugg aguucggccu gugcaagcaa | 660 |
| ggggacucca ucaaggccua cggagccgga cugcugagca gcuucggcga gcugcaguac | 720 |
| ugccugagcg agaagcccaa gcugcugccc uuggagcugg agaagaccgc cauccagaac | 780 |
| uacaccguga ccgaguucca gccccuguac uacguggccg agagcuucaa cgacgccaag | 840 |
| gagaagguga aaacuucgc cgccaccauc cccagacccu ucagcgugag auacgacccc | 900 |
| uacacccaga gaaucgaggu gcuggacaac acccagcagc ugaagauccu ggccgacagc | 960 |
| aucaacagcg agaucggcau ccugugcagc gcccugcaga agaucaag | 1008 |

<210> SEQ ID NO 30
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

| | |
|---|---|
| auggugcccu gguuccccag aaccauccag gagcuggaca gauucgccaa ccagauccug | 60 |
| agcuacggcg ccgagcugga cgccgaccac cccggcuuca aggaccccgu guacagagcc | 120 |
| agaagaaagc aguucgccga caucgccuac aacuacagac acggcagcc cauccccaga | 180 |
| guggaguaca uggaggagga gaagaagacc uggggcaccg uguucaagac ccuuaagagc | 240 |
| cuguacaaga cccacgccug cuacgaguac aaccacaucu ucccacugcu ggagaaguac | 300 |

| | |
|---|---|
| ugcggcuucc acgaggacaa cauuccgcag cuggaggacg ugagccaguu ccugcagacc | 360 |
| ugcaccggcu ucagacuucg ccccguggcc ggccugcuga gcagcagaga cuuccgggc | 420 |
| ggccuggccu ucagagyguu ccacugcacc caguacauca gacacggcag caagcccaug | 480 |
| uacacaccug agcccgacau cugccacgag cugcugggcc acgugcccu guucagcgac | 540 |
| agaagcuucg cccaguucag ccaggagauc ggccuggcaa gucugggcgc uccugacgag | 600 |
| uacaucgaga agcuggccac caucuacugg uucaccgugg aguucggccu gugcaagcag | 660 |
| ggcgacagca ucaaggccua cggcgcuggc cugcuguucca guucggcga gcugcaguac | 720 |
| ugccugagcg agaagcccaa gcugcugccc cuggagcugg agaagaccgc caucccagaac | 780 |
| uacaccguga ccgaguucca gccccuguac uacguggccg agagcuucaa cgacgccaag | 840 |
| gagaagguga gaaacuucgc cgccaccauc cccagacccu ucagcgugag auacgacccc | 900 |
| uacacccaga gaaucgaggu gcuggacaac acccagcagc ugaagauccu ggccgauagc | 960 |
| aucaacagcg agaucggcau ccugugcagc gcccugcaga agaucaag | 1008 |

<210> SEQ ID NO 31
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

| | |
|---|---|
| auggugcccu gguucccacg gaccauccag gagcuggacc gguucgccaa ccagauccug | 60 |
| agcuacggcg ccgagcugga cgccgaccac cccggcuuca aggaccccgu guaccgggcc | 120 |
| cggcggaagc aguucgccga caucgccuac aacuaccggc acggcagcc caucccgcgg | 180 |
| guggaguaca uggaggagga gaagaagacc uggggcaccg uguucaagac ccugaagagc | 240 |
| cuguacaaga cccacgccug cuacgaguac aaccacaucu ucccucugcu ggagaaguac | 300 |
| ugcggcuucc acgaggacaa cauccgcag cuggaggacg ugagccaguu ccugcagacc | 360 |
| ugcaccggcu uccggcugcg gcccguggcc ggccugcuga gcagccggga cuuccgggc | 420 |
| ggccuggccu uccgggguguu ccacugcacc caguacaucc ggcacggcag caagcccaug | 480 |
| uacacgcccg agcccgacau cugccacgag cugcugggcc acgugcccu guucagcgac | 540 |
| cggagcuucg cccaguucag ccaggagauc ggccuggcca gccugggcgc gcccgacgag | 600 |
| uacaucgaga agcuggccac caucuacugg uucaccgugg aguucggccu gugcaagcag | 660 |
| ggcgacagca ucaaggccua cggcgccggc cugcugagca gcuucggcga gcugcaguac | 720 |
| ugccugagcg agaagcccaa gcugcugccc cuggagcugg agaagaccgc caucccagaac | 780 |
| uacaccguga ccgaguucca gccccuguac uacguggccg agagcuucaa cgacgccaag | 840 |
| gagaaggugc ggaacuucgc cgccaccauc ccucggcccu ucagcgugcg guacgacccc | 900 |
| uacacccagc ggaucgaggu gcuggacaac acccagcagc ugaagauccu ggccgacagc | 960 |
| aucaacagcg agaucggcau ccugugcagc gcccugcaga agaucaag | 1008 |

<210> SEQ ID NO 32
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

```
<400> SEQUENCE: 32
auggugcccu gguucccag gaccauucag gagcuggaca gguucgccaa ccaaauccuc    60
uccuacggcg ccgagcucga cgcugaccac cccggcuuca aggaccccgu guaccgggcc   120
aggaggaagc aguucgccga uaucgccuac aacuacaggc acggccagcc caucccgagg   180
guggaguaca uggaggagga gaagaagacc uggggaaccg guucaagac ccucaaguc     240 cguacaaga cccacgccug cuacgaguac aaccacaucu uccccugcu cgagaaguac     300 ugcgguuucc acgaggacaa cauccgcag cuggaggacg ugucgcaguu ccugcagacu    360
uguaccggau ccggcugcg gcccguggca ggacugcuga gcagccggga cuuccugggc    420
ggucuggccu uucgugugu ccacugcacc caguacaucc ggcacggcuc caagcccaug    480
uacaccccug agcccgacau cugccacgag cugcugggcc acgugcccu guuuagcgac    540 aggagcuucg cccaguuuag ccaggagauc ggcuuggcca gccugggugc cccagacgag   600
uauaucgaga gcuggccac caucuacugg uuuacggugg aguucggccu ugcaagcag     660 ggagacagca ucaaggcgua cggagccggc cugcucagcu ccuucggcga gcugcaauac   720
ugccugagcg agaagccuaa gcuccugccu cuggaacugg agaagacuugc cauccagaac  780 uacacaguca ccgaguucca gccgcucuau acguggccg agagcuucaa cgacgcgaag   840
gagaagguga gaaauuucgc ggcaaccauc cccagacccu ucagcgugcg cuacgacccc   900
uauacccagc ggaucgaggu gcuagauaac acccagcagc ugaagauccu ggccgacucg   960
auuaacucag agaucggaau ccugugcagc gcccugcaga gaucaag             1008

<210> SEQ ID NO 33
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33 auggucccu gguucccag aaccauucag gagcuggauc gguucgccaa ccaaauccuc     60
uccuacgggg ccgagcugga cgcagaccac ccaggcuuca agauccugu guaccgggcc    120 cgccgcaagc aguucgccga caucgccuac aacuacagac acggccagcc caucccgcgc   180
guggaguaca uggaggagga gaagaagacc uggggcacgg ucuucaagac ccugaagucu   240
cucuacaaga cgcacgcgug cuacgaguac aaucacaucu uccgcugcu ggagaaguac    300 ugcggcuucc acgaggacaa cauccccag cuggaggacg ugagcaguu ccuccagacc     360 uguacgggcu ucagacugcg cccaguggcu ggucugcuga gcagcggga cuuucugggc    420 gggcucgccu uccggguguu ucauugcacc caguacaucc ggcacggcag caagccuaug   480
uacacucccg agcccgacau cugccacgag cugcugggcc acgugccgcu guucuccgac   540
aggagcuucg cccaguucag ccaggagauc ggccucgcca gccucggagc accgacgag   600 uauauugaga gcuggccac caucuacugg uucaccgugg aguucggacu gucaagcag     660 ggcgacagca uaaaggccua cggcgccggc cuccuguca gcuucggcga gcuccaguac    720
ugccucuccg agaagcccaa gcugcugccc cuggagcucg agaagaccgc cauccagaau   780
uacaccguga ccgaguucca accccuguac acguggccg aguccuucaa cgacgccaag   840
gagaaggugc ggaacuuugc cgccacaauu ccucgaccau ucucggugcg cuacgacccg   900
```

```
uacacccagc gaaucgaggu acuggacaac acacagcagc ugaagauccu ggccgauucc    960
aucaacuccg aaaucggcau ccugugcagc gcccugcaga agaucaag                1008
```

<210> SEQ ID NO 34
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

```
auggugcccu gguucccgcg gacgauccaa gagcuggaca gguucgccaa ccagauccug     60
agcuacgggg ccgagcucga cgccgaccac cccggcuuca aggacccugu cuacagagcc    120
aggcggaaac aguucgccga uaucgccuau aacuacaggc acggccagcc caucccagga    180
gucgaguaca uggaggaaga gaagaagacc uggggcaccg ucuucaagac ccucaaaucg    240
cuguacaaga cccacgccug cuacgaguac aaccacaucu ucccacuccu ggagaaguac    300
uguggcuucc acgaggauaa cauuccccag cuggaagacg ugagccaauu ccugcagacc    360
ugcaccggau ucagacugcg ccccguggcc ggacugcugu cauccagaga uuccugggc    420 gggcuggccu uucgaguuuu ccacugcacc caguacaucc gcacgggag caagcccaug    480 uauacaccgg agcccgauau cugccacgag cugcucggac acgugcccu guucagugac    540 agaaguuuug cccaauuuag ccaagagauc ggccuggccu cccgggagc cccugacgag    600 uacaucgaga gcuggccac caucuacugg uucaccgugg aguucgggu ugcaagcag     660 ggcgacucca ucaaagccua cggcgccggc cugcuguccu ccuucggcga gcugcaauac    720
ugccuguccg agaagcccaa gcugcugccc cuugaacugg aagaccgc cauccagaac    780 uauaccguga ccgaguucca accccuguac uacguggccg agagcuucaa cgacgccaag    840
gagaagguuc gcaauuuugc cgccacuauc ccacggcccu ucccugugcg guacgauccc    900
uacacccagc guaucgaggu gcucgacaau acccagcaac ugaagauccu cgccgacagc    960
aucaacagcg agauaggaau ccuguguagc gcccugcaga agauuaaa               1008
```

<210> SEQ ID NO 35
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35

```
auggugcccu gguuccacg gaccauccag gagcuggaca gauucgccaa ccagauucug     60
agcuacgggg ccgagcucga cgccgaccac cccggcuuca aggaccccgu guacagggcc    120
aggaggaagc aguucgccga caucgccuau aacuaccggc acggacagcc caucccacgg    180
gugagauaua uggaggagga gaagaagacc uggggcaccg uguuaagac ccucaagagc    240 cuuuacaaga cacacgccug cuacgaguac aaccauaucu ucccccugcu agagaaguac    300
ugcgguuucc acgaagauaa uauaccccag cuggaagacg ucucccaguu ccugcagacc    360
ugcaccggcu uccgcucag acccguggcg ggucugcuga gcagccggga cuuccucggc    420
ggacuggccu uuagagguu ccauugcacc caguacaucc gccacggcuc caagcccaug    480
uacaccccgg agcccgauau cugccacgag cuccucggac acgugcccu guuuucgac     540
```

| | |
|---|---|
| cgguccuucg cccaguucag ccaggaaauc gggcuugcaa gccugggagc ucccgacgag | 600 |
| uauaucgaga agcuggccac aaucuacugg uucacggugg aguucggccu gugcaaacag | 660 |
| ggagauagca ucaaggccua cggcgccggc cugcucagca gcuuggggga gcugcaguac | 720 |
| ugccucagcg agaagcccaa gcugcugccc cucgagcugg aagaccgcc cauccagaac | 780 |
| uacaccguga ccgaguucca gccccuguau uacguugccg agagcuucaa cgacgccaag | 840 |
| gagaagg ucc gaaauuucgc cgcgaccauc cccaggcccu ucuccgugag guacgacccu | 900 |
| uacacccagc ggaucgaggu gcuggacaau acccagcagc ugaagauccu ggcggauagc | 960 |
| auaaacagcg aaaucggaau ccucugcagc gcccugcaga agaucaaa | 1008 |

<210> SEQ ID NO 36
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

| | |
|---|---|
| auggugcccu gguuccccg gaccauccag gagcuggacc gguucgccaa ccagauccug | 60 |
| agcuacggcg ccgagcugga cgccgaccac cccggcuuca aggaccccgu guaccgggcc | 120 |
| cggcggaagc aguucgccga caucgccuac aacuaccggc acggccagcc cauccc ucgg | 180 |
| guggaguaca uggaggagga gaagaagacc uggggcaccg uguucaagac ccugaagucc | 240 |
| cuguacaaga cccacgccug cuacgaguac aaccacaucu uccccugcu ggagaaguac | 300 |
| ugcggcuucc acgaggacaa cauccccgcag cuggaggacg ugagccaguu ccugcagacc | 360 |
| ugcaccggcu uccggcugcg gcccguggcc ggccugcuga cagccggga cuuccugggc | 420 |
| ggccuggccu uccggguguu ccacugcacc caguacaucc gccacggcag caagcccaug | 480 |
| uacaccccag agcccgacau cugccacgag cugcugggcc acgugcccu guucagcgac | 540 |
| cggagcuucg cccaguucag ccaggagauc ggccuggccu cucgggcgc cccugacgag | 600 |
| uauaucgaga agcuggccac caucuacugg uucaccgugg aguucggccu gugcaagcag | 660 |
| ggcgacagca ucaaggccua cggcgccggg cugcuguccu ccuucggcga gcugcaguac | 720 |
| ugccugagcg agaagcccaa gcugcugccc cuggaacucg agaaccgcc cauccagaac | 780 |
| uacaccguga ccgaguucca gccccuguac uacguggccg agagcuucaa cgacgccaag | 840 |
| gagaaggugc ggaacuucgc cgccaccaua cccaggcccu ucagcgugcg guacgacccc | 900 |
| uacacccagc ggaucgaggu gcuggacaau acccagcagc ugaagauccu ggccgacucc | 960 |
| aucaacagcg agaucggaau ccugugcagc gcccugcaga agaucaag | 1008 |

<210> SEQ ID NO 37
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

| | |
|---|---|
| auggugcccu gguuccccg gaccauccag gagcuggacc gguucgccaa ccagauccug | 60 |
| agcuacggcg ccgagcugga cgccgaccac cccggcuuca aggaccccgu guaccgggcc | 120 |
| cggcggaagc aguucgccga caucgccuac aacuaccggc acggccagcc cauccc acgg | 180 |

| | |
|---|---|
| guggaguaca uggaggagga gaagaagacc uggggcaccg uguucaagac ccugaagucu | 240 |
| cuguacaaga cccacgccug cuacgaguac aaccacaucu cccgcugcu ggagaaguac | 300 |
| ugcggcuucc acgaggacaa caucccgcag cuggaggacg ugagccaguu ccugcagacc | 360 |
| ugcaccggcu uccgccugcg acccguggcg ggcugcuga gcagccggga cuuccugggc | 420 |
| ggccuggccu uccggguguu ccacugcacc caguacaucc gccacgggag caagcccaug | 480 |
| uacaccccug agcccgacau cugccacgag cugcugggcc acgugcccu guucagcgac | 540 |
| cggagcuucg cccaguucag ccaggagauc ggccuggcca gcugggagc cccggacgag | 600 |
| uauaucgaga agcuggccac caucuacugg uucaccgugg aguucggccu gugcaagcag | 660 |
| ggcgacagca ucaaggccua cggggccggg cugcugucca gcuucggcga gcugcaguac | 720 |
| ugccugagcg agaagcccaa gcugcugccc cucgagcucg agaagaccgc cauccagaac | 780 |
| uacaccguga ccgaguucca gccccuguac uacguggccg agagcuucaa cgacgccaag | 840 |
| gagaaggugc ggaacuucgc cgccacaauc cccaggcccu ucagcugcg guacgacccc | 900 |
| uacacccagc ggaucgaggu gcuggacaau acccagcagc ugaagauccu ggcggacucc | 960 |
| aucaacagcg agaucggaau ccugugcagc gcccugcaga agaucaag | 1008 |

<210> SEQ ID NO 38
<211> LENGTH: 1008
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

| | |
|---|---|
| auggugcccu gguucccgcg gaccauccag gagcuggacc gguucgccaa ccagauccug | 60 |
| agcuacggcg ccgagcucga cgccgaccac cccggcuuca aggaccccgu cuaccgcgcc | 120 |
| cgccgcaagc aguucgccga caucgccuac aacuaccgcc acggccagcc cauccccgcg | 180 |
| gucgaguaca uggaggagga gaagaagacc uggggcaccg ucuucaagac ccucaagucc | 240 |
| cucuacaaga cccacgccug cuacgaguac aaccacaucu cccgcuccu cgagaaguac | 300 |
| ugcggcuucc acgaggacaa caucccgcag cucgaggacg ucucccaguu ccuccagacc | 360 |
| ugcaccggcu uuagacgcg gcccguggcc ggacuccucu ccuccgcga cuuccucggc | 420 |
| ggccucgccu uccgcgucuu ccacugcacc caguacauua gacacggguc caagcccaug | 480 |
| uacacgcccg agcccgacau cugccacgag cuccucggcc acgugccccu cuucuccgac | 540 |
| cgcuccuucg cccaguucuc ccaggagauc ggccuggccu cacugggcgc cccugacgaa | 600 |
| uacaucgaga agcucgccac caucuacugg uucaccgucg aguucggccu cugcaagcag | 660 |
| ggcgacucca ucaaggcaua cggcgcuggc cugcugagca gcuucggcga gcuccaguac | 720 |
| ugccucuccg agaagcccaa gcuccugccc cuagaacugg agaagaccgc cauccagaac | 780 |
| uacaccguca ccgaguucca gccccucuac uacgucgccg agccuucaa cgacgccaag | 840 |
| gagaaggucc gcaacuucgc cgccacgauc ccgcggcccu cuccguccg cuacgacccc | 900 |
| uacacccagc gcaucgaggu ccugacaau acgcagcagc ucaagauccu cgccgacucg | 960 |
| aucaacuccg agauugggau ccucugcucc gcccuccaga agaucaag | 1008 |

<210> SEQ ID NO 39
<211> LENGTH: 57
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 39
gggaaauaag agagaaaaga agaguaagaa gaaauauaag accccggcgc cgccacc          57

<210> SEQ ID NO 40
<211> LENGTH: 54
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gggaaauaag agagaaaaga agaguaagaa gaaauauaag accccggcgc cacc             54

<210> SEQ ID NO 41
<211> LENGTH: 6
<212> TYPE: RNA
<213> ORGANISM: Unknown
<220> FEATURE:
<221> NAME/KEY: source
<223> OTHER INFORMATION: /note="Description of Unknown:
      Kozak sequence"

<400> SEQUENCE: 41 gccrcc                                                                   6

<210> SEQ ID NO 42
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42 gccgcc                                                                   6

<210> SEQ ID NO 43
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ccccggcgcc                                                              10

<210> SEQ ID NO 44
<211> LENGTH: 7
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 44 ccccggc                                                              7

<210> SEQ ID NO 45
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gggaaauaag agagaaaaga agaguaagaa gaaauauaag agccaccaug uccaccgccg     60
ugcucgagaa ccccggccug gggcggaaac ugagcgacuu uggccaggaa accagcuaua    120
uugaggacaa cugcaaccag aacggcgcca ucagccugau cuucucacug aaggaggagg    180
ugggcgcccu ggccaaggug ucaggcugu ucgaggagaa cgacgugaac cugacucaua    240
ucgagagcag accaucucgg cugaagaaag acgaguacga guucuucacc caucucgaua    300
agagaagccu gccgcacug accaacauca uaaagauucu gaggcacgac aucggggcca    360
ccgugcacga acugagucgg gacaagaaga aggacacugu uccuugguuc ccacggacua    420
uucaggagcu ggacagauuc gcuaaccaga uccugcccua cggcgccgag cucgacgcug    480
accacccagg cuucaaggac cccguguacc gggcugaaag aaagcaauuc gccgacaucg    540
ccuacaauua uaggcacggc cagcccauuc cuagagugga guacauggag aagagaaga    600
agaccugggg caccguguuc aagaccuuaa agagccugua uaagacacac gcuugcuacg    660
aguacaauca cauuuuccca cugcuggaga aguacugugg cuuucacgag gauaauauac    720
cucagcugga agacguuucc caguuccugc agacuugcac cggcuucaga cuuaggccug    780
uggcgggccu ccugucuucg agagauuucc ugggagggcu ggccuuccgc uguuccacu    840
gcacccagua uauccgccac gggagcaagc ccauguacac acccgagccc gacauuugcc    900
acgagcuguu aggccacgug ccuuuguucu cugacaggag cuuugcgcag uucagucagg    960
aaaucggacu ggccagccug ggugccccug acgaguacau cgagaagcug gccaccaucu   1020
acugguucac ugucgaguuc ggucugugca agcagggcga uagcaucaag gcuuacggag   1080
ccggccuucu gagcagcuuc ggcgagcugc aauacgccu gagcgagaag ccuaagcugu   1140
ugccuuugga acucgagaag acagcuaucc agaacuacac cguuaccgag uuccagccuc   1200
uguacuacgu ggccgagagc uucaacgacg ccaaggagaa ggugagaac uucgcggcaa   1260
caauucccag gccuuuuagc gugagauacg accccuacac ucaacgaauc gaagugcugg   1320
auaacacccca gcagcugaag auccuggccg acaguaucaa cagcgaaauu ggcauucugu   1380
gcucagcccu gcagaagauu aaaugauaau aggcuggagc cucggguggcc uagcuucuug   1440
ccccuugggc cucccccag ccccuccucc ccuuccugca cccguaccc cuccauaaag    1500
uaggaaacac uacaguagguc uuugaauaaa gucugaguggg gcggc                 1545

<210> SEQ ID NO 46
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

```
gggaaauaag agagaaaaga agaguaagaa gaaauauaag agccaccaug ucaaccgcug      60
uucuggagaa ccccggccug ggccggaagc uguccgauuu cggccaggag acuagcuaca     120
ucgaggauaa cugcaaccag aacggcgcca ucagccugau auuuagccuc aaggaagaag     180
ugggugcucu ggccaagguc cugagacugu ucgaagagaa cgacgugaac cugacccaua     240
ucgaaagccg gccagccgg cugaagaagg acgaguacga guucuuuacg caccuggaca      300
aacggagccu ccccgcacug acuaacauua uuaagauccu gaggcacgau aucggugcca     360
cugugcacga acugagccgg gacaagaaga aagacacugu uccuuggcuuu cccaggacga    420
uucaggaacu ggacagauuc gccaaucaga uccucagcua cggcgccgag cuggacgcug     480
accaucccgg cuuuaaggac ccggucuauc gggccagacg caagcaguuc gccgauauug     540
ccuauaacua cagacacggc cagccuaucc cuagggugga guacauggag gaggagaaga     600
agacuugggg caccguuuuc aagacccuga aaucccucua caagacccac gcgugcuacg     660
aguauaacca uaucuuuccu cuccuggaga auacugcgg cuuccacgag gacaauaucc      720
cacagcucga ggacgugagc caguucuugc agaccugcac agggucaga cugcgccccg      780
uggccggucu gcucagcagu agggacuccc ucggcggacu ggcauccgg uguuccacu       840
guacccagua cauuagacac ggcuccaagc ccauguacac cccagaacca gacaucugcc     900
acgagcugcu gggccacgug cccuuguuuu cagauaggac cuucgcccag uucagccagg     960
aaaucgggcu ggccagucug ggcgcccug acgaguauau cgagaaacug gccaccaucu     1020
acugguucac cguggaguuc ggccucugca agcagguga cagcaucaag gcauacggcg    1080
cagggcugcu gagcagcuuc ggcgagcucc aguauugccu gucggagaag cccaagcugc    1140
ugccacugga gcuggagaag accgccaucc agaauuauac cgucacagag uuucagccuc    1200
uguauuacgu ggcugaguc uuuaacgacg ccaaagagaa ggugaggaac uucgcagcga    1260
cuauuccuag accccuucuc guccgguacg auccuuacac ccagaggauc gaggugcugg    1320
acaacaccca gcagcucaag auucuggccg auuccauuaa uagcgagaua ggcauucugu    1380
gcagcgcacu gcagaagauc aagugauaau aggcuggagc cucggguggcc uagcuucuug    1440
cccuugggc ccccccag cccuccucc ccuccugca cccguacccc cuccauaaag          1500
uaggaaacac uacaguguc uuugaauaaa gucugagugg gcggc                     1545
```

<210> SEQ ID NO 47  
<211> LENGTH: 1545  
<212> TYPE: RNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 47

```
gggaaauaag agagaaaaga agaguaagaa gaaauauaag agccaccaug agcaccgccg      60
ugcucgagaa ccccggccug gguaggaagc ugagcgacuu cggccaggaa acaagcuaca    120
ucgaagauaa cugcaaccag aacggcgucca ucucccugau cuuucacuu aaggaagagg    180
ucggagccuu agccaaggug cuuaggcugu ucgaggagaa cgacgucaac cuuacccaca    240
uugagccag acccagcagg cugaagaagg acgaguacga guucuucaca caucuggaca    300
agagaagcuu acccgcccug accaacauua uuaagauccu gcgacacgac aucggggcca    360
ccgugcacga acugagcaga gacaagaaga aggauacugu gcccuggucc ccuaggacaa    420
```

-continued

| | |
|---|---|
| uccaggaguu ggaucguuuc gccaaccaga uccugUccua cggagccgaa cuggacgcug | 480 |
| accaccccgg auuuaaggau ccuguguauc gggcccgaag aaagcaguuc gcagauauug | 540 |
| ccuauaauua caggcacggc cagccuaucc ccagagucga guacauggaa gaggagaaga | 600 |
| agaccugggg uacaguguuc aagacccuca gagccuguac aagacccac gcuugcuacg | 660 |
| aauacaacca caucuucccc uugcuugaga aauacugcgg uuccacgag gacaauauuc | 720 |
| cgcaacugga ggacgugucg caguuucugc agaccuguac cggcuuucgg ucaggccug | 780 |
| uggccggucu guugucuagc agagauuuuc ugggcgggcu ggccuucaga gucuccacu | 840 |
| gcacccagua caucaggcac ggaagcaagc cgauguacac acccgagccc gacaucuguc | 900 |
| acgagcuccu cggccacgug ccccuguuca gcgacagaag cuucgcccag uuuagucagg | 960 |
| aaaucggccu ggccagucug ggcgccccug acgaguauau cgagaagcug gcuaccauau | 1020 |
| auugguuuac cguggaguuc ggacugugca agcagggcga cuccaucaag gcuuacggug | 1080 |
| ccgggcugcu gagcagcuuc ggcgagcucc aguauugccu gagcgagaag cccaagcugc | 1140 |
| ugccgcugga gcuggagaag accgccaucc agaacuauac cgucaccgag uuccagcccc | 1200 |
| uguacuacgu ggcugagagc uuuaacgacg ccaaggagaa ggucagaaac uucgccgcua | 1260 |
| ccauucccag acccuucagc gugagaaucg acccuuacac acagaggaua gagguuuugg | 1320 |
| acaacaccca gcaacugaag aucuuggcug auagcauuaa cucagagauc ggcauucgu | 1380 |
| gcagcgcccu gcagaagauc aagugauaau aggcuggagc cucggugcc uagcuucuug | 1440 |
| cccccuugggc cucccccag ccccuccucc ccuuccugca cccguacccc cuccauaaag | 1500 |
| uaggaaacac uacaguggug uuugaauaaa gucugagugg gcggc | 1545 |

<210> SEQ ID NO 48
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 48

| | |
|---|---|
| gggaaauaag agagaaaaga agaguaagaa gaaauauaag agccaccaug agcacugccg | 60 |
| uguuggagaa ccccgggcug ggcagaaagc ucagcgacuu cggccaggaa accaguuaua | 120 |
| uugaggacaa cugcaaccag aacggcgcaa uuagucuuau cuuuagccug aaggaggagg | 180 |
| uaggcgcccu ggccaaagug cugagacugu cgaagagaa cgacgugaau cugacacaca | 240 |
| ucgaguccccg ccccagccgg cucaagaagg acgaguacga guucuuuacc caccuggaua | 300 |
| agcgcagccu uccugcccug accaacauca uaaagauucu cagacacgac auuggcgcca | 360 |
| ccguucacga acugagcaga gacaagaaga aagacaccgu ccccugguuc cccaggacca | 420 |
| uccaggaacu ggaccgguuc gcuaaccaga uccugUccua cggcgccgag cuggacgccg | 480 |
| accacccugg cuuuaaggac cccguguaua gggccagaag gaagcaguuc gcggauaucg | 540 |
| cuuacaacua ccgucacggc caaccgaucc aagggucga guacauggag gaggagaaga | 600 |
| agaccugggu uacaguguuc aagacucuca gagucuguac aagacacac gccugcuacg | 660 |
| aguacaacca caucuucccc uugcuggaga aguauugcgg cuuccacgaa gacaacauuc | 720 |
| cccagcugga ggacgugagc caguuucugc agaccugcac cggcuuccgg cugaggcccg | 780 |
| uggcggggcu gcugucuuca agagacuucc ugggcggacu ggccuucagg gucuccacu | 840 |
| gcacacagua caucagacac ggaagcaaac ccauguacac cccugagccc gacaucugcc | 900 |

-continued

| | |
|---|---|
| acgagcugcu gggccacgug ccucuguuca gcgaccgcag cuucgcccag uucucgcagg | 960 |
| aaaucggccu ggccagccug ggcgcuccug acgaauacau ugagaaacuc gccacaauuu | 1020 |
| acugguucac ugguggaguuc ggacugugca agcagggcga uuccaucaaa gcuacggcg | 1080 |
| caggccugcu gagcucguuc ggcgaacugc aauacgccu guccgagaag ccgaaacugc | 1140 |
| ugccucugga gcucgagaag acagccaucc agaauuacac agugacagaa uuccagcccu | 1200 |
| uauacuacgu ggcugaaucu uucaacgacg caaaggagaa ggugcgcaac uuugcagcca | 1260 |
| ccaucccacg acccuucagc gugcgguacg acccguacac ccagagaauc gaggugcugg | 1320 |
| acaauacccca acagcucaag auccucgccg auucaaucaa uuccgagauc gggauccugu | 1380 |
| gcagcgcacu gcagaagaua aagugauaau aggcuggagc cucgguggcc uagcuucuug | 1440 |
| cccccuuggc cucccccccag cccccuccucc ccuuccugca cccguaccccc cuccauaaag | 1500 |
| uaggaaacac acaguggguc uuugaauaaa gucugaguuugg gcggc | 1545 |

<210> SEQ ID NO 49
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49

| | |
|---|---|
| gggaaauaag agagaaaaga agaguaagaa gaaauauaag agccaccaug agcaccgccg | 60 |
| ugcuggagaa ccccggccug ggccggaagc ugagcgacuu cggccaggag acaagcuaca | 120 |
| ucgaggacaa cugcaaccag aacggcgcca ucagccugau cuucucccug aaggaggagg | 180 |
| ugggcgcccu ggccaaggug cugcggcugu ucgaggagaa cgacgugaac cugacccaca | 240 |
| ucgagagccg gccagccgg cugaagaagg acgaguacga guucuucacc caccuggaca | 300 |
| agcggagccu gccccgcccug accaacauca ucaagauccu gcggcacgac aucgcgcca | 360 |
| ccgugcacga gcugagccgg gacaagaaga aggauaccgu gcccugguuc ccacggacca | 420 |
| uccaggagcu ggaccgguuc gccaaccaga uccugagcua cggcgccgag cuggacgccg | 480 |
| accaccccgg cuucaaggac cccguguacc gggccggcg gaagcaguuc gccgacaucg | 540 |
| ccuacaacua ccggcacggc cagcccauuc ucggguggga guacauggag gaggagaaga | 600 |
| agaccugggg caccguguuc aagacccuca agagccugua caagacccac gccugcuacg | 660 |
| aguacaacca caucuucccca cugcuggaga aguacgcggg cuuccacgag gauaacauccc | 720 |
| cacagcugga ggacgugagc caguccugcc agaccugcac cggcuucaga cugcggccug | 780 |
| uggccggccu gcugagcucc agagacuucc ugggcggccu ggccuuccgg guguccacu | 840 |
| gcacccagua caucagacac ggcagcaagc ccauguacac accugagccc gacaucugcc | 900 |
| acgaacuccu gggccacgug cccccuguuca gcgaccggag cuucgcccag uucucccagg | 960 |
| agaucggacu ggccagccuu ggagcucccg acgaauacau ugagaagcug gccaccaucu | 1020 |
| acugguucac cguggaguuc ggccugugca agcagggcga cagcaucaag gccuacggcg | 1080 |
| ccggccuucu gagcagcuuc ggcgagcugc aguacgccu gagcgagaag cccaagcugc | 1140 |
| ugccccugga gcuagagaag accgccaucc agaacuacac cgugaccgag uuccagcccc | 1200 |
| uguacuacgu ggccgagagc uucaacgacg ccaaggagaa ggugcggaac uucgccgcca | 1260 |
| caauccccuag acccuucagc gugcgguacg accccuacac ccagcggauc gaggugcugg | 1320 |
| acaauacccca gcagcugaag auucuggccg acuccaucaa cagcgaaauc ggcauccugu | 1380 |

| | |
|---|---|
| gcagcgcccu gcagaagauc aagugauaau aggcuggagc cucgguggcc uagcuucuug | 1440 |
| ccccuugggc cucccccccag ccccuccucc ccuuccugca cccguacccc cuccauaaag | 1500 |
| uaggaaacac uacagugguc uuugaauaaa gucugagugg gcggc | 1545 |

<210> SEQ ID NO 50
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

| | |
|---|---|
| gggaauaag agagaaaaga agaguaagaa gaaauauaag agccaccaug agcaccgccg | 60 |
| ugcuggagaa ccccggccug ggccggaagc ugagcgacuu cggccaggag acaagcuaca | 120 |
| ucgaggacaa cugcaaccag aacggcgcca ucagccugau cuuuucucug aaggaggagg | 180 |
| ugggcgcccu ggccaaggug cugcggcugu ucgaggagaa cgacgugaac cugacccaca | 240 |
| ucgagagccg gccagccgg cugaagaagg acgaguacga guucuucacc caccuggaca | 300 |
| agcggagccu gcccgcccug accaacauca ucaagauccu gcggcacgac aucggcgcca | 360 |
| ccgugcacga gcugagccgg gacaagaaga aggacaccgu gcccugguuc ccucggacca | 420 |
| uccaggagcu ggaccgguuc gccaaccaga uccugagcua cggcgccgag cuggacgccg | 480 |
| accaccccgg cuucaaggac cccguguacc gggcccggcg gaagcaguuc gccgacaucg | 540 |
| ccuacaacua ccggcacggc cagcccaucc ucggguggga guacauggag gaggagaaga | 600 |
| agaccugggg caccguguuc aagacccuga agucucugua caagacccac gccugcuacg | 660 |
| aguacaacca caucuuuccu cuccuggaga guacagcgg cuuccacgag gacaauauccc | 720 |
| cucagcugga ggacgugagc caguccugcc agaccugcac cggcuuccgg cugaggccug | 780 |
| uggccgggcu gcugagcagc agagacuucc ugggcggccu ggccuuccgg guguuccacu | 840 |
| gcacccagua caucagacac gggagcaagc ccauguacac ucccgagccc gacaucugcc | 900 |
| acgaguuacu gggccacgug cccccuguuca gcgaccggag cuucgcccag uucucacagg | 960 |
| agaucgggcu ggcaagccug ggcgcucccg acgaguauau agagaagcug gccaccaucu | 1020 |
| acugguucac cguggaguuc ggccugugca agcagggcga cagcaucaag gcuuacggag | 1080 |
| cugggcugcu uagcuccuuc ggcgagcugc aguacugccu gagcgagaag cccaagcugc | 1140 |
| ugccccuuga gcucgagaag accgccaucc agaacuacac cgugaccgag uccagcccc | 1200 |
| uguacuacgu ggccgagagc uucaacgacg ccaaggagaa ggugcggaac uucgccgcaa | 1260 |
| ccaucccuag gccuucagc gugcgguacg accccuacac ccagcggauc gaggugcugg | 1320 |
| acaauacccca gcagcugaag aucuuuagcug acucaaucaa cagcgagauu ggcauccugu | 1380 |
| gcagcgcccu gcagaagauc aagugauaau aggcuggagc cucgguggcc uagcuucuug | 1440 |
| ccccuugggc cucccccccag ccccuccucc ccuuccugca cccguacccc cuccauaaag | 1500 |
| uaggaaacac uacagugguc uuugaauaaa gucugagugg gcggc | 1545 |

<210> SEQ ID NO 51
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

```
gggaaauaag agagaaaaga agaguaagaa gaaauauaag agccaccaug agcaccgccg    60
ugcuggagaa ccccggccug ggccggaagc ugagcgacuu cggccaggag acauccuaca   120
ucgaggacaa cugcaaccag aacggcgcca ucucccucau cuucagccug aaggaggagg   180
ucggcgcccu cgccaagguc cuccgccucu cgaggagaa cgacgucaac cucacccaca   240
ucgaguccg ccccucccgc ucaagaagg acgaguacga guucuucacc caccucgaca   300
agcgcucccu ccccgcccuc accaacauca ucaagauucu uaggcacgac aucggcgcca   360
ccguccacga gcucucccgc gacaagaaga aggacaccgu ccccugguuc ccucgcacca   420
uccaggagcu cgaccgcuuc gccaaccaga uccucuccua cggcgccgag uuagacgccg   480
accaccccgg cuucaaggac cccgucuacc gcgcccgccg caagcaguuc gccgacaucg   540
ccuacaacua ccgccacggc cagcccaucc cacgcgucga guacauggag gaggagaaga   600
agaccugggg caccgucuuc aagacccuca agucccucua caagacccac gccugcuacg   660
aguacaacca caucuuucca cuccucgaga aguacugcgg cuuccacgag gauaacaucc   720
cucagcucga ggacgucucc caguccucc agaccugcac cggcuuucgc cugcgcccgg   780
uggcaggccu gcugagcucu cgggacuucc ucggcggccu cgccuccgc gucuccacu    840
gcacccagua caucaggcac gggucccagc ccauguacac cccagagccc gacaucugcc   900
acgaacuccc cggccacgug ccccucuucu ccgaccgcuc cuucgcccag uucucccagg   960
agauuggccu ggccagcuug ggagcacccg acgaguacau agagaagcuc gccaccaucu  1020
acugguucac cgucgaguuc ggcucucgca agcagggcga cuccaucaag gccuacgggg  1080
ccggcuugcu gaguucuuuc ggcgagcucc aguacugccu cuccgagaag cccaagcucu  1140
uaccacugga gcuggagaag accgccaucc agaacuacac cgucaccgag uuccagcccc  1200
ucuacuacgu cgccgagucc uucaacgacg ccaaggagaa ggucgcaac uucgcggcaa   1260
caauccuag accccuuccc gucccgcuacg accccuacac ccagcgcauc gaggugcugg   1320
acaacacuca gcagcugaag auccuggcug auagcauuaa cuccgaaauu gggauccucu  1380
gcuccgcccu ccagaagauc aagugauaau aggcuggagc cucggugcc uagcuucuug   1440
ccccuugggc cuccccccag ccccuccucc ccuuccugca cccguacccc cuccauaaag   1500
uaggaaacac uacagugguc uuugaauaaa gucugagugg gcggc                  1545
```

<210> SEQ ID NO 52
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

```
gggaaauaag agagaaaaga agaguaagaa gaaauauaag agccaccaug agcaccgccg    60
uccucgagaa ccccggccug ggcagaaagc ugagcgacuu cggccaggaa accagcuaca   120
ucgaggacaa cugcaaccag aacggcgcca ucagccugau cuucagccug aaggaggagg   180
ugggcgcccu ggccaaggug cugagacugu cgaggagaa cgacgugaac cugacccaca   240
ucgagagcag accuccagaa cugaagaagg acgaguacga guucuucacc caccuggaca   300
agagaagccu gccgcccug accaacauca ucaagauccu gagacacgac aucggagcca   360
ccgugcacga gcugagcaga gacaagaaga aggacaccgu gcccugguuc cccagaacca   420
```

| | |
|---|---|
| uccaggagcu ggacagauuc gccaaccaga uccugagcua cggugccgag cuagacgccg | 480 |
| accaccccgg cuucaaggac cccguguaca gagccagaag aaagcaguuc gccgacaucg | 540 |
| ccuacaacua cagacacggg cagccgaucc ccagagugga guacauggag gaggagaaga | 600 |
| agaccugggg caccguguuc aagacccuca gagccuguac caagacccac gccugcuacg | 660 |
| aguacaacca caucuuccu cugcuggaga aguacugcgg cuuccacgag gacaacaucc | 720 |
| cacagcugga ggacgugagc caguccugc agaccgcac cggcuucaga cucaggcccg | 780 |
| uugccggacu gcugagcagc agagacuucc ugggcggccu ggccuucaga guguccacu | 840 |
| gcacccagua caucagacac ggcagcaagc ccauguacac acccgagccc gacaucugcc | 900 |
| acgaacugcu gggccacgug ccccuguuca gcgacagaag cuucgcccag uucagccagg | 960 |
| agaucggucu ggcuagccuug ggagcccag acgaguacau cgagaagcug gccaccaucu | 1020 |
| acugguucac cguggaguuc ggccugugca agcagggaga cagcaucaag gccuacggag | 1080 |
| ccggccuacu gagcagcuuc ggcgagcugc aguacugccu gagcgagaag cccaagcugu | 1140 |
| ugccucugga gcuggagaag accgccaucc agaacuacac cgugaccgag uuccagcccc | 1200 |
| uguacuacgu ggccgagagc uucaacgacg ccaaggagaa ggugagaaac uucgccgcca | 1260 |
| cuaucccag acccuucagc gugagauacg acccccuacc ccagagaauc gaggugcugg | 1320 |
| acaacaccca gcagcugaag auucggccg auagcaucaa cagcgagauc ggcauccugu | 1380 |
| gcagcgcccu gcagaagauc aagugauaau aggcuggagc cucggugggcc uagcuucuug | 1440 |
| ccccuugggc cucccccag ccccuccucc ccuuccugca cccguacccc cuccauaaag | 1500 |
| uaggaaacac uacagguggguc uuugaauaaa gucugagugg gcggc | 1545 |

<210> SEQ ID NO 53
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 53

| | |
|---|---|
| gggaauaag agagaaaaga agaguaagaa gaaauauaag agccaccaug agcaccgccg | 60 |
| uccucgagaa ccccggccug ggcagaaagc ugagcgacuu cggccaggaa accagcuaca | 120 |
| ucgaggacaa cugcaaccag aacggcgcca ucagccugau cuucucacuc aaagaagaag | 180 |
| uuggugcauu ggccaaagua uugcgcuuau uugaggagaa cgacgugaac cugacccaca | 240 |
| ucgagagcag acccuccaga cugaagaagg acgaguacga guucuuccacc caccuggaca | 300 |
| agagaagccu gccgccccug accaacauca ucaagaucu gagacacgac aucgagcca | 360 |
| ccgugcacga gcugagcaga gacaagaaga aggacaccgu gcccugguuc cccagaacca | 420 |
| uccaggagcu ggacagauuc gccaaccaga uccugagcua cggugccgag cuagacgccg | 480 |
| accaccccgg cuucaaggac cccguguaca gagccagaag aaagcaguuc gccgacaucg | 540 |
| ccuacaacua cagacacggg cagccgaucc ccagagugga guacauggag gaggagaaga | 600 |
| agaccugggg caccguguuc aagacccuca gagccuguac caagacccac gccugcuacg | 660 |
| aguacaacca caucuuccu cugcuggaga aguacugcgg cuuccacgag gacaacaucc | 720 |
| cacagcugga ggacgugagc caguccugc agaccgcac cggcuucaga cucaggcccg | 780 |
| uugccggacu gcugagcagc agagacuucc ugggcggccu ggccuucaga guguccacu | 840 |
| gcacccagua caucagacac ggcagcaagc ccauguacac acccgagccc gacaucugcc | 900 |

| | |
|---|---:|
| acgaacugcu gggccacgug cccuguuca gcgacagaag cuucgcccag uucagccagg | 960 |
| agaucggucu ggcuagcuug ggagccccag acgaguacau cgagaagcug gccaccaucu | 1020 |
| acugguucac cguggaguuc ggccugugca agcagggaga cagcaucaag gccuacggag | 1080 |
| ccggccuacu gagcagcuuc ggcgagcugc aguacgccu gagcgagaag cccaagcugu | 1140 |
| ugccucugga gcuggagaag accgccaucc agaacuacac cgugaccgag uuccagcccc | 1200 |
| uguacuacgu ggccgagagc uucaacgacg ccaaggagaa ggugaaaac uucgccgcca | 1260 |
| cuaucccag acccuucagc gugagaaucg accccuacac ccagagaauc gaggugcugg | 1320 |
| acaacaccca gcagcugaag auucggccg auagcaucaa cagcgagauc ggcauccugu | 1380 |
| gcagcgcccu gcagaagauc aagugauaau aggcuggagc cucgguggcc uagcuucuug | 1440 |
| ccccuugggc cucccccag ccccuccucc ccuuccugca cccguacccc cuccauaaag | 1500 |
| uaggaaacac uacagugguc uuugaauaaa gucugagugg gcggc | 1545 |

<210> SEQ ID NO 54
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

| | |
|---|---:|
| gggaauaag agagaaaaga agaguaagaa gaaauauaag agccaccaug agcaccgccg | 60 |
| ugcuggagaa ccccggccug ggccggaagc ugagcgacuu cggccaggag accagcuaca | 120 |
| ucgaggacaa cugcaaccag aacggcgcca ucagccugau cuucagccug aaggaggagg | 180 |
| ugggcgcccu ggccaaggug cugcggcugu cgaggagaa cgacgugaac cugacccaca | 240 |
| ucgagagccg gccagccgg cugaagaagg acgaguacga guucuucacc caccuggaca | 300 |
| agcggagccu gccgcccug accaacauca ucaagaucuu gcggcacgac aucgcgcca | 360 |
| ccgugcacga gcugagccgg acaagaaga aggacaccgu gcccugguuc ccgcggacca | 420 |
| uccaggagcu ggaccgguuc gccaaccaga uccugagcua cggcgccgag cuggacgccg | 480 |
| accaccccgg cuucaaggac cccguguacc gggccggcg gaagcaguuc gccgacaucg | 540 |
| ccuacaacua ccggcacggc cagcccaucc gcgggugga guacauggag gaggagaaga | 600 |
| agaccugggg caccguguuc aagacccuga agagccugua caagacccac gccugcuacg | 660 |
| aguacaacca caucuucca cugcuggaga aguacgcgg cuccacgag gacaacaucc | 720 |
| cacagcugga ggacgugagc caguccugc agaccugcac cggcuuccgg cugcggcccg | 780 |
| uggccggccu gcugagcagc cgggacuucc ugggcggccu ggccuuccgg guguccacu | 840 |
| gcacccagua caucggcac ggcagcaagc ccauguacac gcccgagccc gacaucugcc | 900 |
| acgagcugcu gggccacgug cccuguuca gcgaccggag cuucgcccag uucagccagg | 960 |
| agaucggccu ggcagccug ggcgcgcccg acgaguacau cgagaagcug gccaccaucu | 1020 |
| acugguucac cguggaguuc ggccugugca agcagggcga cagcaucaag gccuacggcg | 1080 |
| ccggccugcu gagcagcuuc ggcgagcugc aguacgccu gagcgagaag cccaagcugc | 1140 |
| ugccccugga gcuggagaag accgccaucc agaacuacac cgugaccgag uuccagcccc | 1200 |
| uguacuacgu ggccgagagc uucaacgacg ccaaggagaa ggugcgccaa uucgccgcca | 1260 |
| ccaucccacg gccuucagc gugcgguacg accccuacac ccagcggauc gaggugcugg | 1320 |
| acaacaccca gcagcugaag auccggccg acagcaucaa cagcgagauc ggcauccugu | 1380 |

```
gcagcgcccu gcagaagauc aagugauaau aggcuggagc cucgguggcc uagcuucuug    1440
ccccuugggc cucccccag ccccuccucc ccuuccugca cccguacccc cuccauaaag    1500
uaggaaacac uacagugguc uuugaauaaa gucugagugg gcggc                   1545

<210> SEQ ID NO 55
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55 gggaauaag agagaaaaga agaguaagaa gaaauauaag agccaccaug agcaccgccg     60
ugcuggagaa ccccggacug ggaagaaagc uguccgauuu cgggcaggag acuuccuaca    120
ucgaggacaa cugcaaccag aacggggcca ucucccugau cuucagccug aaggaggagg    180
ugggcgcccu ggcgaaggug cuccggcugu ucgaggagaa cgacgugaac cugacgcaca    240
ucgaaagccg gcccagccgg cugaagaagg acgaguacga guucuuacg caccuggaca    300 agaggagcuu gccgcccuc accaacauca ucaagauccu gcggcacgac aucggcgcca    360
cggugcacga gcugagccgc gacaagaaga aggauaccgu gcccugguuc cccaggacca    420
uccaggagcu ggacagauuc gccaaccaga uccugcuca cggcgccgaa cuggacgccg    480
accaccccgg cuuuaaggac cccguguaca gggccaggcg gaaacaguuc gccgacaucg    540
ccuauaacua caggcacggg caacccaucc cuagggucga guacauggag gaggagaaga    600
agaccugggg cacaguguuc aagacccuca aaucccugua caagacacac gccugcuacg    660
aguauaacca caucuucccu cuccuggaga aguauugcgg cuuucacgaa gacaacauccc    720 cgcagcugga agacguguccc caguccugc agaccuguac cggauucagg uuaagaccug    780
uggccggccu gcugagcagc agggauuucc uaggcgggcu cgccuucagg guguccauu    840 gcacccagua caucagacac ggcuccaagc cgauguauac gccugagccc gacaucugcc    900
acgagcugcu gggccacgug ccgcuguuca gcgauagaag cuucgcccag uucagccagg    960
agaucggccu ggccagccug ggagcgccug acgaauauau cgagaagcuc gccaccaucu    1020
acugguuuac cguggaauuc ggccugugca agcaggagaa cuccaucaag gccuacgggg    1080
cugggcugcu guccuccuuc ggggagcucc aguacugucu cuccgagaag cccaagcugc    1140
ugccccucga gcuggagaag accgcgaucc agaacuauac cgucaccgaa uuccagcccc    1200
uguauuacgu ggccgagucc uuuaacgacg ccaaggagaa ggucggaau uucgcugcca    1260 ccauucccag gccuucagc gugcgguacg auccccuacac ccagcgcaua gaggugcugg    1320
auaauacaca gcagcugaag auccuggccg acagcaucaa uagcgaaaua ggcauccugu    1380
gcagcgcccu gcagaagauc aagugauaau aggcuggagc cucgguggcc uagcuucuug    1440
ccccuugggc cucccccag ccccuccucc ccuuccugca cccguacccc cuccauaaag    1500
uaggaaacac uacagugguc uuugaauaaa gucugagugg gcggc                   1545

<210> SEQ ID NO 56
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 56

```
gggaaauaag agagaaaaga agaguaagaa gaaauauaag agccaccaug uccaccgccg      60
ugcucgagaa cccuggccug ggcaggaagc ugagcgacuu cgggcaagag acaagcuaca     120
ucgaggauaa cugcaaucag aacggcgcca ucagccugau cuucucccug aaggaggagg     180
ugggcgcccu ggcuaaggug cugaggcuau cgaagagaa cgacgugaau cugacccaua      240
ucgagagccg ccccagccgg ucaagaagg acgaguacga guucuuuacu caccuggaca      300
agcgguccc u gcccgcccug acaaacauca ucaagauccu caggcacgau aucggagcca    360
ccguccacga gcuagccgc gacaagaaga aagacaccgu gcccugguuu cccaggacca      420
uccaggagcu ggaucgguuu gccaaccaga uccugagcua cggggccgaa cuugacgccg     480
accaucccgg guucaaggac ccggugu acc gggcuaggcg aaagcaauuc gccgacauug     540
ccuacaacua ccgucacggc cagcccuauc cacggguga auacauggag gaggagaaga     600
agaccugggg aacagucuuc aagacccuga gucacugua caagacccac gccugcuacg     660
aguauaacca caucuuccca cuccucgaga guacugcgg cuuccacgag acaacaucc      720
cucagcugga ggacgugagc caguuccugc agaccugcac cggcuuucgu cugcgucccg     780
uggcgggacu gcugagcagc agggacuccc uggggcggacu ggccuuccgg guguccacu     840
gcacacagua caucgacac ggcagcaagc cgauguauac accggagccg acauuugcc      900
acgagcuccu gggccacgug ccccuguuca gcgacaggac cuucgcccag uucagccagg     960
agaucggccu ggccagccug ggugccccag acgaguacau agagaagcug gcgaccaucu    1020
acugguucac ggucgaguuc ggccugugca acagggcga cagcauuaag gccuacggcg     1080
ccggccugcu cagcucccuc ggcgagcucc aguauugccu gagcgagaag cccaagcugc    1140
ugccccugga gcucgagaag acugccauuc agaacuacac ugugaccgag uuccagcccc    1200
uguacuacgu ggcggagagc uucaacgacg ccaaggagaa ggugaggaac uucgccgcca    1260
ccaucccucg gccuucccc guuagguacg accccuacac ccagaggauc gaggugcugg    1320
auaauaccca gcagcugaag auccuggcgg acagcaucaa cagcgaaauc ggcauccugu    1380
gcagcgccuu acagaagauc aagugauaau aggcuggagc cucgguggcc uagcuucuug    1440
ccccuugggc cuccccccag ccccuccucc ccuuccugca cccguacccc cuccauaaag    1500
uaggaaacac uacagugguc uuugaauaaa gucugagugg gcggc                    1545
```

<210> SEQ ID NO 57
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 57

```
gggaaauaag agagaaaaga agaguaagaa gaaauauaag agccaccaug agcaccgccg     60
ugcuggagaa ccccggccug ggccggaagc ugagcgacuu cgggccaggag acgucauaca    120
ucgaggauaa cugcaaccag aacggcgugcca ucucccugau cuucagccug aaggaagagg   180
ugggcgcccu ggccaagguc cugagacugu cgaggagaa cgacgugaac cugacccaca     240
ucgaaagcag acccagcagg cugaagaaag acgaguacga auucuucacc caccuggaca     300
agcggagccu gcccgcccuc acuaacauca ucaagauccu uagacacgac auaggcgcca    360
ccguccacga acucagcagg gacaagaaga aggacaccgu gcccugguuc cccaggacca    420
```

| | |
|---|---|
| uccaggagcu ggaccgcuuc gccaaccaga uucuguccua cggagcugaa cucgacgccg | 480 |
| accaucccgg auucaaagac cccguguaca gagccagaag aaagcaguuc gccgacaucg | 540 |
| cguacaacua uaggcacggc cagccgaucc ccagagucga guacauggag gaggagaaga | 600 |
| agaccugggg caccguguuc aagacccuga aguccccugua caagacccac gcuugcuacg | 660 |
| aguauaacca caucuuccca cuccuggaga aguacugcgg cuuccacgaa gacaacauuc | 720 |
| cccagcucga ggacgugagc caauuccugc agaccgcac cggcuuccgc cugaggcccg | 780 |
| uugccggccu gcugagcucc agagauuucc ucggcggccu ggccuucaga guguuucacu | 840 |
| gcacccagua cauccgccac ggcuccaagc caauguacac cccggagccc gauaucuguc | 900 |
| acgagcugcu gggccacgug ccccucuuca gcgaccgaag cuucgcccag uuuucccaag | 960 |
| agauaggacu ugccucccuc ggugccccgg acgaauauau ugagaaacuc gccaccaucu | 1020 |
| acugguuuac gguggaauuc ggacugugca agcagggcga cagcaucaaa gccuacgggg | 1080 |
| cagggcugcu gucuagcuuc ggggagcucc aauacugccu gagcgagaaa cccaagcucc | 1140 |
| ugccucucga gcuggagaag accgcuaucc agaauuacac cgugacgaaa uuccagcccc | 1200 |
| uguacuacgu cgccgagagc uuuaacgacg ccaaggagaa aguacgaaac uucgccgcua | 1260 |
| ccauuccccg cccuucagc gugagguacg acccuuacac ccagcguauc gaggugcugg | 1320 |
| auaauaccca acagcugaag auacucgccg acuccaucaa cagcgagauc ggcauccugu | 1380 |
| guuccgcccu ccagaagauc aagugauaau aggcuggagc cucgguggcc uagcuucuug | 1440 |
| ccccuugggc cucccccag ccccuccucc ccuuccugca cccguacccc cuccauaaag | 1500 |
| uaggaaacac uacagugguc uuugaauaaa gucugagugg cggc | 1545 |

<210> SEQ ID NO 58
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

| | |
|---|---|
| gggaaauaag agagaaaaga agaguaagaa gaaauauaag agccaccaug uccacggccg | 60 |
| uccuggagaa uccgggccug gggaggaaac ugagcgacuu cgggcaggag acauccuaca | 120 |
| ucgaggacaa cugcaaccag aacggagcca ucagccugau cuucagccuc aaagaggagg | 180 |
| ugggcgcucu cgccaaggug cugagacugu cgaggagaa cgacgucaac cucacgcaca | 240 |
| ucgaaucccg acccagccgu cugaagaagg acgaguacga guucuuaccc caucucgaca | 300 |
| agcgguccu gcccgcccuc acaaacauca ucaagauccu gcggcacgac aucggcgcca | 360 |
| ccgugcacga gcuguccagg acaagaaga agauaccgu gccguggauc cccaggacga | 420 |
| uccaggagcu cgaccgguuc gccaaccaga uccugagcua cggcgccgaa cucgacgccg | 480 |
| accaccccgg cuuuaaggau cccguguaca gagccaggag gaagcaguuu gccgacaucg | 540 |
| cguacaacua cagacacggg cagcccaucc ccagggugga guacauggag gaggagaaga | 600 |
| agaccugggg caccgucuuc aagacacuga aguccccugua caagacccac gccugcuacg | 660 |
| aguacaacca cauuucccu cugcuggaga aguacugcgg cuuccacgaa gacaacauac | 720 |
| cgcagcucga ggacgugagc caauuucugc agaccgcac cgguuuaga cugaggcccg | 780 |
| uggccggccu gcugagcagc agggauuuuc ucgguggacu ggccuucaga guguccacu | 840 |
| gcacccagua uaagacac ggcuccaagc ccauguacac cccagagccu gacaucugcc | 900 |

| | |
|---|---|
| acgaacugcu gggucacgug ccccucuuca gcgacagguc cuucgcccag uucagccagg | 960 |
| aaaucggccu ggccuccccuc ggcgcucccg acgaauacau cgagaagcug gccacaaucu | 1020 |
| acugguucac cgucgaguuc ggccugugca agcagggcga cuccaucaag gccuacggcg | 1080 |
| cggggcugcu auccuccuuc ggggagcucc aguacgccu guccgagaag cccaagcucc | 1140 |
| ugccccugga acuggagaag accgccaucc agaacuacac cgugaccgag uuccagccac | 1200 |
| uguacuacgu cgccgagagu uucaacgacg ccaaagagaa agugcggaac uucgccgcca | 1260 |
| ccaucccuag accuuucucc gucagauacg acccauacac gcagcggauc gagguccugg | 1320 |
| acaacacuca gcaacucaag auucuggcug acaguaucaa uagcgagauc gggauccugu | 1380 |
| guagcgcccu ucagaagauc aagugauaau aggcuggagc cucggguggcc uagcuucuug | 1440 |
| ccccuugggc cucccccag ccccuccucc ccuuccugca cccguacccc cuccauaaag | 1500 |
| uaggaaacac uacagugguc uuugaauaaa gucugagugg gcggc | 1545 |

<210> SEQ ID NO 59
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59

| | |
|---|---|
| gggaauaaag agagaaaaga agaguaagaa gaaauauaag agccaccaug agcaccgccg | 60 |
| ugcuggagaa ccccggccug ggccggaagc ugagcgacuu cggccaggag acgagcuaca | 120 |
| ucgaggacaa cugcaaccag aacggcgcca ucagccugau cuucucccug aaggaggagg | 180 |
| ugggcgcccu ggccaaggug cugcggcugu cgaggagaa cgacugaac cugacccaca | 240 |
| ucgagagccg gccagccgg cugaagaagg acgaguacga guucuucacc caccuggaca | 300 |
| agcggagccu gccgcccug accaacauca ucaagaugccu gcggcacgac aucgcgcca | 360 |
| ccgugcacga gcugagccgg acaagaaga agacaccgu gcccugguuc ccacggacca | 420 |
| uccaggagcu ggaccgguuc gccaaccaga uccugagcua cggcgccgag cuggacgccg | 480 |
| accaccccgg cuucaaggac cccguguacc gggcccggcg gaagcaguuc gccgacaucg | 540 |
| ccuacaacua ccggcacggc cagcccaucc cacggguga guacauggag gaggagaaga | 600 |
| agaccugggg caccguguuc aagacccuga gucccugua caagacccac gccugcuacg | 660 |
| aguacaacca caucuuuccc cuucggaga guacgcgg cuccacgag acaauauccc | 720 |
| cucagcugga ggacgugagc caguccugcc agaccugcac cggcuuccgc cugaggcccg | 780 |
| uggccggccu gcuagcucc agggacuucc ugggcggccu ggccuuccgg guguccacu | 840 |
| gcacccagua cauccgacac ggcagcaagc ccauguacac gccgagccc gacaucugcc | 900 |
| acgagcuccu gggccacgug ccccuguuca gcgaccggag cuucgcccag uucucccagg | 960 |
| agaucggacu ggccagccug ggagcacccg acgaauacau cgagaagcug gccaccaucu | 1020 |
| acugguucac cgucgaguuc ggccugugca agcagggcga cagcaucaag gccuacggcg | 1080 |
| ccggucugcu guccagcuuc ggcgagcugc aguacgccu gagcgagaag cccaagcugc | 1140 |
| ugccccugga acuggagaag accgccaucc agaacuacac cgugaccgag uuccagcccc | 1200 |
| uguacuacgu ggccgagagc uucaacgacg ccaaggagaa ggugcggaac uucgccgcca | 1260 |
| ccauccccg ccccuucagc gugcggguacg accccuacac ccagcggauc gaggugcugg | 1320 |
| acaacaccca acagcugaag auccuggccg auagcaucaa cagcgagauc ggcauccugu | 1380 |

```
gcagcgcccu gcagaagauc aagugauaau aggcuggagc cucgguggcc uagcuucuug   1440
ccccuugggc cuccccccag ccccuccucc ccuuccugca cccguacccc cuccauaaag   1500
uaggaaacac uacagugguc uuugaauaaa gucugagugg gcggc                  1545

<210> SEQ ID NO 60
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60 gggaauaag agagaaaaga agaguaagaa gaaauauaag agccaccaug agcaccgccg    60
ugcuggagaa ccccggccug ggccggaagc ugagcgacuu cggccaggaa accagcuaca   120
ucgaggacaa cugcaaccag aacggcgcca ucagccugau cuucagccuc aaggaggagg   180
ugggcgcccu ggccaaggug cugcggcugu ucgaggagaa cgacgugaac cugacccaca   240
ucgagagccg gccagccgg cugaagaagg acgaguacga guucuucacc caccuggaca   300
agcggagccu gccccgcccug accaacauca ucaagauccu gcggcacgac aucggcgcca   360
ccgugcacga gcugagccgg gacaagaaga aggauaccgu gcccugguuc ccgcggacca   420
uccaggagcu ggaccgguuc gccaaccaga uccugagcua cggcgccgag cuggacgccg   480
accaccccgg cuucaaggac cccguguacc gggcccggcg gaagcaguuc gccgacaucg   540
ccuacaacua ccggcacggc cagcccaucc cgcgggugga guacauggag gaggagaaga   600
agaccugggg caccguguuc aagacccuga agucucugua caagacccac gccugcuacg   660
aguacaacca caucuuuccc cugcucgaga guacgcgg cuuccacgag gauaacauac   720
cgcagcugga ggacgugagc caguccugc agaccugcac cggcuucaga ugaggcccg   780 ucgcuggucu gcugagcucc agggacuucc uggggccu ggccuuccgg guguccacu    840 gcacccagua caucaggcac ggcagcaagc ccaugaacac gcccgagccc gacaucugcc   900
acgagccucc ugggccacgug ccccuguuca gcgaccggag cuucgcccag uucagccaag   960
agaucggacu ggcuagccuc ggcgccccgg acgaguauau cgagaagcug gccaccaucu  1020
acugguucac cguggaguuc ggccugugca agcagggcga cagcaucaag gccuacggcg  1080
ccggccuccu cagcucuuuc ggcgagcugc aguacugccu gagcgagaag cccaagcugc  1140
ugccccucga acuggagaag accgccaucc agaacuacac cgugaccgag uuccagcccc  1200
uguacuacgu ggccgagagc uucaacgacg ccaaggagaa ggugcggaac uucgccgcga  1260
ccaucccuag gccuucagc gugcgguacg accccuacac ccagcggauc gaggugcugg  1320
acaauaccca gcagcugaag auucucgccg acucgaucaa cagcgagauc gggauccugu  1380
gcagcgcccu gcagaagauc aagugauaau aggcuggagc cucgguggcc uagcuucuug  1440
ccccuugggc cuccccccag ccccuccucc ccuuccugca cccguacccc cuccauaaag  1500
uaggaaacac uacagugguc uuugaauaaa gucugagugg gcggc                 1545

<210> SEQ ID NO 61
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 61

| | |
|---|---|
| gggaaauaag agagaaaaga agaguaagaa gaaauauaag agccaccaug agcaccgccg | 60 |
| ugcuggagaa ccccggccug ggccggaagc ugagcgacuu cggccaggag acguccuaca | 120 |
| ucgaggacaa cugcaaccag aacggcgcca ucuccucau cuucagccug aaggaggagg | 180 |
| ucggcgcccu cgccaagguc cuccgccucu cgaggagaa cgacgucaac cucacccaca | 240 |
| ucgagucccg ccccucccgc ucaagaagg acgaguacga guucuucacc caccucgaca | 300 |
| agcgcucccu ccccgcccuc accaacauca ucaagauccu gagacacgac aucggcgcca | 360 |
| ccguccacga gcucucccgc gacaagaaga aggauaccgu ccccugguuc ccacgcacca | 420 |
| uccaggagcu cgaccgcuuc gccaaccaga uccucuccua cggcgccgag cuggacgccg | 480 |
| accaccccgg cuucaaggac cccgucuacc gcgcccgccg caagcaguuc gccgacaucg | 540 |
| ccuacaacua ccgccacggc cagcccauuc cccgcgucga guacauggag gaggagaaga | 600 |
| agaccugggg caccgucuuu aagacccuca aguccucua caagacccac gccugcuacg | 660 |
| aguacaacca caucuuuccc cuccucgaga auacugcgg cuuccacgag gacaauuaucc | 720 |
| cucagcucga ggacgucucc caguccucc agaccugcac cggcuuucgg cugcgcccgg | 780 |
| ucgccggccu gcuguccagc agggacuucc ucggcggccu cgccuccgc gucuccacu | 840 |
| gcacccagua cauucggcac ggcuccaagc ccauguacac acccgagccc gacaucugcc | 900 |
| acgagcugcu cggccacgug cccucucucu ccgaccgcuc cuucgcccag uucucccagg | 960 |
| agauugggcu ggccucccug ggagcgcccg acgaguacau ugagaagcuc gccaccaucu | 1020 |
| acugguucac cgucgaguuc ggccucgca agcagggcga cuccaucaag gcuuacgggg | 1080 |
| cggggcuccu cuccagcuuc ggcgagcucc aguacugccu cuccgagaag cccaagcucc | 1140 |
| ucccgcugga acuggagaag accgccaucc agaacuacac cgucaccgag uuccagcccc | 1200 |
| ucuacuacgu cgccgagucc uucaacgacg ccaaggagaa ggccgcaac uucgcggcua | 1260 |
| ccauccgcg gccuucccc gucccgcuacg accccuacac ccagcgcauc gaggugcucg | 1320 |
| acaauaccca acagcugaag auccuggcgg acagcauuaa uccgagauc gggauccucu | 1380 |
| gcuccgcccu ccagaagauc aagugauaau aggcuggagc cucgguggcc uagcuucuug | 1440 |
| ccccuugggc cuccccccag ccccuccucc ccuuccugca cccguacccc cuccauaaag | 1500 |
| uaggaaacac uacagugguc uuugaauaaa gucugagugg gcggc | 1545 |

<210> SEQ ID NO 62
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

| | |
|---|---|
| gggaaauaag agagaaaaga agaguaagaa gaaauauaag agccaccaug agcaccgccg | 60 |
| uccucgagaa ccccggccug ggcagaaagc ugagcgacuu cggccaggaa accagcuaca | 120 |
| ucgaggacaa cugcaaccag aacggcgcca ucagccugau cuucagccug aaggaggagg | 180 |
| ugggcgcccu ggcaagggug cugagacugu cgaggagaa cgacgugaac cugacccaca | 240 |
| ucgagagcag accccuccaga cugaagaagg acgaguacga guucuucacc caccuggaca | 300 |
| agagaagccu gccccgcccug accaacauca ucaagauccu gagacacgac aucggagcca | 360 |
| ccgugcacga gcugagcaga gacaagaaga aggacaccgu gcccuuguuc cccagaacca | 420 |

| | |
|---|---|
| uccaggagcu ggacagauuc gccaaccaga uccugagcua cggugccgag cuagacgccg | 480 |
| accaccccgg cuucaaggac cccguguaca gagccagaag aaagcaguuc gccgacaucg | 540 |
| ccuacaacua cagacacggg cagccgaucc ccagagugga guacauggag gaggagaaga | 600 |
| agaccugggg caccguguuc aagacccuca gagccuguac caagacccac gccugcuacg | 660 |
| aguacaacca caucuucccu cugcuggaga aguacugcgg cuuccacgag gacaacaucc | 720 |
| cacagcugga ggacgugagc caguccugc agaccgcac cggcuucaga ucaggcccg | 780 |
| uugccggacu gcugagcagc agagacuucc ugggcggccu ggccuucaga guguccacu | 840 |
| gcacccagua caucagacac ggcagcaagc ccauguacac acccgagccc gacaucugcc | 900 |
| acgaacugcu gggccacgug ccccuguuca gcgacagaag cuucgcccag ucagccagg | 960 |
| agaucggucu ggcuagccuug ggagcccag acgaguacau cgagaagcug gccaccaucu | 1020 |
| acugguucac cguggaguuc ggccugugca agcagggaga cagcaucaag gccuacggag | 1080 |
| ccggccuacu gagcagcuuc ggcgagcugc aguacugccu gagcgagaag cccaagcugu | 1140 |
| ugccucugga gcuggagaag accgccaucc agaacuacac cgugaccgag uuccagcccc | 1200 |
| uguacuacgu ggccgagagc uucaacgacg ccaaggagaa ggugagaaac uucgccgcca | 1260 |
| cuaucccag acccuucagc gugagauacg accccuacac cagagaauc gaggugcugg | 1320 |
| acaacaccca gcagcugaag auucuggccg auagcaucaa cagcgagauc ggcauccugu | 1380 |
| gcagcgcccu gcagaagauc aagugauaau aggcuggagc cucggguggcc uagcuucuug | 1440 |
| cccccuuggg cuccccccag ccccuccucc ccuuccugca cccguacccc cuccauaaag | 1500 |
| uaggaaacac uacagugguc uuugaauaaa gucugagugg gcggc | 1545 |

<210> SEQ ID NO 63
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63

| | |
|---|---|
| gggaauaaag agagaaaaga agaguaagaa gaaauauaag agccaccaug agcaccgccg | 60 |
| uccucgagaa ccccggccug gcagaaaagc ugagcgacuu cggccaggaa accagcuaca | 120 |
| ucgaggacaa cugcaaccag aacggcgcca ucagccugau cuucucacuc aaagaagaag | 180 |
| uuggugcauu ggccaaagua uugcgcuuau ugaggagaa cgacgugaac cugacccaca | 240 |
| ucgagagcag acccuccaga cugaagaagg acgaguacga guucuucacc caccuggaca | 300 |
| agagaagccu gccccgcccug accaacauca ucaagauccu gagacacgac aucgagcca | 360 |
| ccgugcacga gcugagcaga gacaagaaga aggacaccgu gcccuugguuc cccagaacca | 420 |
| uccaggagcu ggacagauuc gccaaccaga uccugagcua cggugccgag cuagacgccg | 480 |
| accaccccgg cuucaaggac cccguguaca gagccagaag aaagcaguuc gccgacaucg | 540 |
| ccuacaacua cagacacggg cagccgaucc ccagaguga guacauggag gaggagaaga | 600 |
| agaccugggg caccguguuc aagacccuca gagccuguac caagacccac gccugcuacg | 660 |
| aguacaacca caucuucccu cugcuggaga aguacugcgg cuuccacgag gacaacaucc | 720 |
| cacagcugga ggacgugagc caguccugc agaccgcac cggcuucaga ucaggcccg | 780 |
| uugccggacu gcugagcagc agagacuucc ugggcggccu ggccuucaga guguccacu | 840 |
| gcacccagua caucagacac ggcagcaagc ccauguacac acccgagccc gacaucugcc | 900 |

| | |
|---|---:|
| acgaacugcu gggccacgug cccuguuca gcgacagaag cuucgcccag uucagccagg | 960 |
| agaucggucu ggcuagcuug ggagccccag acgaguacau cgagaagcug gccaccaucu | 1020 |
| acugguucac cguggaguuc ggccugugca agcagggaga cagcaucaag gccuacggag | 1080 |
| ccggccuacu gagcagcuuc ggcgagcugc aguacgccu gagcgagaag cccaagcugu | 1140 |
| ugccucugga gcuggagaag accgccaucc agaacuacac cgugaccgag uuccagcccc | 1200 |
| uguacuacgu ggccgagagc uucaacgacg ccaaggagaa ggugagaaac uucgccgcca | 1260 |
| cuaucccccag acccuucagc gugagauacg accccuacac ccagagaauc gaggugcugg | 1320 |
| acaacacccca gcagcugaag auucuggccg auagcaucaa cagcgagauc ggcauccugu | 1380 |
| gcagcgcccu gcagaagauc aagugauaau aggcuggagc ucggguggcc uagcuucuug | 1440 |
| cccccuuggggc cucccccag cccucccucc ccuuccugca cccguacccc cuccauaaag | 1500 |
| uaggaaacac acaguggguc uuugaauaaa gucugagugg gcggc | 1545 |

<210> SEQ ID NO 64
<211> LENGTH: 1545
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64

| | |
|---|---:|
| gggaaauaag agagaaaaga agaguaagaa gaaauauaag agccaccaug agcaccgccg | 60 |
| ugcuggagaa ccccggccug ggccggaagc ugagcgacuu cggccaggag accagcuaca | 120 |
| ucgaggacaa cugcaaccag aacggcgcca ucagccugau cuucagccug aaggaggagg | 180 |
| ugggcgcccu ggccaaggug cugcggcugu ucgaggagaa cgacgugaac cugacccaca | 240 |
| ucgagagccg gccagccgg cugaagaagg acgaguacga guucuucacc caccuggaca | 300 |
| agcggagccu gccccgcccug accaacauca ucaagauccu gcggcacgac aucgccgcca | 360 |
| ccgugcacga gcugagccgg acaagaaga aggacaccgu gcccugguuc ccgcggacca | 420 |
| uccaggagcu ggaccgguuc gccaaccaga uccugagcua cggcgccgag cuggacgccg | 480 |
| accaccccgg cuucaaggac cccguguacc gggcccggcg gaagcaguuc gccgacaucg | 540 |
| ccuacaacua ccggcacggc cagcccaucc gcggggugga guacauggag gaggagaaga | 600 |
| agaccugggg caccgguguuc aagaccccuga agagccugua caagacccac gccugcuacg | 660 |
| aguacaacca caucuucccca cugcuggaga guacgcgg cuccacgag acaacaucc | 720 |
| cacagcugga ggacgugagc caguccugc agaccugcac cggcuuccgg cugcggcccg | 780 |
| uggccggccu gcugagcagc cgggacuucu ggggcggccu ggccuuccgg guguccacu | 840 |
| gcacccagua caucggcac ggcagcaagc ccauguacac gcccgagccc gacaucugcc | 900 |
| acgagcugcu gggccacgug cccuguuca gcgaccggag cuucgcccag uucagccagg | 960 |
| agaucggccu ggccagccug ggcgcgcccg acgaguacau cgagaagcug gccaccaucu | 1020 |
| acugguucac cguggaguuc ggccugugca agcagggcga cagcaucaag gccuacggcg | 1080 |
| ccggccugcu gagcagcuuc ggcgagcugc aguacgccu gagcgagaag cccaagcugc | 1140 |
| ugccccugga gcuggagaag accgccaucc agaacuacac cgugaccgag uuccagcccc | 1200 |
| uguacuacgu ggccgagagc uucaacgacg ccaaggagaa ggugcgcgaac uucgccgcca | 1260 |
| ccaucccacg gcccuucagc gugcgguacg accccuacac ccagcggauc gaggugcugg | 1320 |
| acaacacccca gcagcugaag auccuggccg acagcaucaa cagcgagauc ggcauccugu | 1380 |

| | |
|---|---|
| gcagcgcccu gcagaagauc aagugauaau aggcuggagc cucgguggcc uagcuucuug | 1440 |
| cccccuuggc cucccccag ccccuccucc ccuuccugca cccguacccc cuccauaaag | 1500 |
| uaggaaacac uacagugguc uuugaauaaa gucugagugg gcggc | 1545 |

```
<210> SEQ ID NO 65
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
```

| | |
|---|---|
| gggaaauaag agagaaaaga agaguaagaa gaaauauaag agccaccaug gugcccuggu | 60 |
| uucccagaac cauccaggag cuggacaggu ucgcaaacca gauacucucc uacggcgcag | 120 |
| agcuggacgc cgaccaccca ggcuucaagg accccgucua cagggccagg cgcaagcagu | 180 |
| ucgcagauau ugccuacaau uaucgacacg gucagcccau cccuagagug gaguacaugg | 240 |
| aggaagagaa gaagaccugg ggcaccgugu ucaagacucu gaagagucug uacaagacac | 300 |
| acgcuuguua cgaguauaau cacaucuucc cucgcugga gaaguacgc gguuccacg | 360 |
| aagauaacau cccgcagcuc gaggacgugu cccaguuucu gcagacuugc acuggcuuua | 420 |
| gacugaggcc cgucgccgga cugcugcuccu ccagagacuu ccgggcgggg cuugcuuuca | 480 |
| gaguguuuca cuguacacag uauauucgcc acggagcaa acccauguac accccugagc | 540 |
| ccgacauuug ucacgaauug cugggacacg ugccucuguu uagcgauaga agcuucgccc | 600 |
| aguucagcca ggaaaucggg cuggccucac ugggcgcccc agacgaguac aucgagaagc | 660 |
| uggccaccau auacugguuc acaguggagu ucggccugug caagcaaggc gacucuauca | 720 |
| aggcuuacgg ugccgggcug uugagcucau ucggagagcu gcaauauugu uuaucagaga | 780 |
| aaccuaagcu gcugccccuu gagcucgaga agacagccau acagaacuac accgugaccg | 840 |
| aguuccagcc acuguauuac guggccgaau ccuucaacga cgcaaaggag aaggugagaa | 900 |
| acuuugccgc uaccaucccu cggcccuucu ccguuagaua cgaccccuac acccaacgga | 960 |
| uugaggugcu ggacaauacc cagcaauuga agauccuugc cgacucgauc aacagcgaga | 1020 |
| ucggcauucu gugcagcgcg uugcagaaga ucaagugaua auaggcugga gcccggugg | 1080 |
| ccuagcuucu ugcccccuugg gccucccccc agccccuccu cccuuccug cacccguacc | 1140 |
| cccuccauaa aguaggaaac acuacagugg ucuuugaaua aagucugagu gggcggc | 1197 |

```
<210> SEQ ID NO 66
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
```

| | |
|---|---|
| gggaaauaag agagaaaaga agaguaagaa gaaauauaag agccaccaug gugcccuggu | 60 |
| ucccacguac uauccaggag cuggauagau ucgcgaacca gauccugagc uacggcgccg | 120 |
| agcucgacgc cgaccauccc ggauuuaagg aucccgugua uagggcuagg aggaaacagu | 180 |
| ucgccgauau ugccuauaau uauagacacg ggcagccuau uccaagagug gaguauaugg | 240 |
| aggaggagaa gaagaccugg ggcacagugu ucaagaccuu gaagagucug uacaagacac | 300 |

| | | |
|---|---|---|
| acgccuguua cgaguacaac cacaucuuuc cccugcugga gaaguacugc ggcuuccacg | 360 | |
| aggauaauau cccacaacug gaggacguga gccaguuccu gcaaaccugc acuggcuucc | 420 | |
| gucucgacc cgucgccggc cuccucagca gccgggauuu ccuuggcggg cuggccuuuc | 480 | |
| ggguguuuca cugcacucag uacauccggc acgguucuaa gcccauguau acccagagc | 540 | |
| cugacaucug ucacgagcug cucggccacg ugcccuguu cagcgaccgg ccuucgccc | 600 | |
| aguucagcca ggagaucggc cuggccucuc ugggcgcucc cgacgaguau aucgagaagc | 660 | |
| uggcuacgau uuacugguuc accgucgaau ucggccugug caagcaaggg gacagcauua | 720 | |
| aagccuacgg ggcuggauua cugucaagcu cggggaacu gcaguauugc cugucccgaga | 780 | |
| aacccaaacu gcuuccgcug gagcucgaga agacugccau ccagaacuac acggugaccg | 840 | |
| aguuccagcc ccuguacuac gucgcugagu cauucaacga cgcuaaggag aaggugcgca | 900 | |
| auuucgcugc caccaucccc aggcccuuua gcgugagaua cgauccuuac acccagagga | 960 | |
| uugaagugcu ggauaacacu cagcaacuga agauccuggc agacagcauc aauagcgaga | 1020 | |
| uuggcauccu gugcagcgcc cugcagaaga uuaaaugaua auaggcugga gccucggugg | 1080 | |
| ccuagcuucu ugcccuugg gccucccccc agccccuccu ccccuuccug cacccguacc | 1140 | |
| cccuccauaa aguaggaaac acuacagugg ucuuugaaua aagucugagu gggcggc | 1197 | |

<210> SEQ ID NO 67
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 67

| | | |
|---|---|---|
| gggaaauaag agagaaaaga agaguaagaa gaaauauaag agccaccaug gugcccuggu | 60 | |
| ucccucggac cauccaggag cuggacagau cgccaacca gauucugagc uacggggccg | 120 | |
| aauuggacgc cgaccaccca ggcuuuaagg acccuguuua cagagcuagg aggaagcagu | 180 | |
| ucgccgauau ugccuauaac uacagacacg gccagccuau ccccagagug gaguacaugg | 240 | |
| aggaggagaa gaagacgugg ggcaccgugu ucaagacucu gaagucucuu acaagacac | 300 | |
| acgcuugcua cgaguacaau cacaucuuuc cacugcugga gaaguacugu ggcuuccacg | 360 | |
| aagacaacau uccccagcuu gaggacguga gucaguuccu gcagaccugc acaggcuucc | 420 | |
| gucuccggcc uguggcuggg cugcugagca gcagagacuu ccugggaggc cuggcuuucc | 480 | |
| ggguguuuca uugcacgcag uacauuagac acggcuccaa gccaauguac acaccagagc | 540 | |
| ccgacaucug ccacgagcug cugggacacg ugccacucuu cagcgacaga ucauucgccc | 600 | |
| aguucucuca ggagaucgga cuggcuuccc uggagcacc ugacgaguac aucgagaaac | 660 | |
| uggccacuau cuauugguuc acaguggaau uggccugug caagcagggc gacucuauca | 720 | |
| aggccuacgg cgccggacug cugucccucu ucggcgaacu gcaguauugu cugucagaga | 780 | |
| agcccaagcu gcugccccua gaacucgaga agacagccau acagaauuac accgugaccg | 840 | |
| aguuucagcc ccucuacuac guggccgaau cuuucaacga cgccaaggag aaggugagga | 900 | |
| auuucgccgc caccauccu cggccguuuu ccgugcgaua cgaccccuau acccagcgga | 960 | |
| ucgaggugcu ggacaacacg cagcaacuga agauucggc ggacucaauc aacagcgaga | 1020 | |
| ucggcauccu guguagcgca cugcagaaga uuaagugaua auaggcugga gccucggugg | 1080 | |

| | |
|---|---|
| ccuagcuucu ugccccuugg gccucccccc agccccuccu ccccuuccug cacccguacc | 1140 |
| cccuccauaa aguaggaaac acuacagugg ucuuugaaua aagucugagu gggcggc | 1197 |

<210> SEQ ID NO 68
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

| | |
|---|---|
| gggaaauaag agagaaaaga agaguaagaa gaaauauaag agccaccaug guaccuuggu | 60 |
| uucccagaac aauucaggaa cuggaccggu uugccaacca gauccuuagu uacggcgccg | 120 |
| agcucgacgc cgaccacccc ggcuuuaagg auccugugua uagagccagg aggaagcagu | 180 |
| ucgcugauau ugccuacaau uacaggcacg gucaacccau ccccaggguu gaguacaugg | 240 |
| aggaggagaa gaagaccugg ggcaccgucu ucaagacccu gaagucucua uauaagacuc | 300 |
| acgccugcua cgaguacaau cacaucuucc cacuccugga gaaguacugc ggcuuccacg | 360 |
| aggacaacau uccccagcug gaggacgugu cccaguccu gcagaccugc accggcuucc | 420 |
| ggcugcgucc ggucgccggg cugcugucuu cacgcgauuu ucugggcgga uuggccuuua | 480 |
| gggucuucca cugcacccag uacaucagac acggaucuaa gcccauguac acacccgagc | 540 |
| cugauauuug ccacgaacug uugggacacg ugccucuguu ucucgacaga agcuucgccc | 600 |
| aguuuuccca ggagaucggc cuggccucc ucggagcacc cgacgaguac auagagaagc | 660 |
| uggccacuau auacugguuc acuguugagu uugggcugug caagcagggc gauucuauaa | 720 |
| aggccuacgg ggccggacug cuguccuccu ugggggagcu gcaguacugu cuuucugaga | 780 |
| agcccaaacu ucugccccug gagcuugaga agacggccau ccagaauuac accgugacug | 840 |
| aguuccaacc acuuuauuac guggcugaau ccuucaacga cgccaaggag aaggugagga | 900 |
| acuuugccgc cacaauuccu cgcccuuucu ccgugagaua cgaccccuau acccaacgga | 960 |
| uugaaguucu ugacaacacc cagcagcuga agauacuggc cgacucaaua aacucugaga | 1020 |
| ucggaauccu gugcagugcc cugcagaaga ucaagugaua auaggcugga gccucgguga | 1080 |
| ccuagcuucu ugccccuugg gccucccccc agccccuccu ccccuuccug cacccguacc | 1140 |
| cccuccauaa aguaggaaac acuacagugg ucuuugaaua aagucugagu gggcggc | 1197 |

<210> SEQ ID NO 69
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

| | |
|---|---|
| gggaaauaag agagaaaaga agaguaagaa gaaauauaag agccaccaug gugcccuggu | 60 |
| uuccccggac cauccaggag cuggaccggu ucgccaacca gauccugagc uacggcgccg | 120 |
| agcuggacgc cgaccacccc ggcuucaagg acccgugua ccgggcccgg cggaagcagu | 180 |
| ucgccgacau cgccuacaac uaccggcacg gccagcccau cccgcggguu gaguacaugg | 240 |
| aggaggagaa gaagaccugg ggcaccgugu ucaagacccu aagagccug uacaagaccc | 300 |
| acgccugcua cgaguacaac cacaucuuuc cccugcugga gaaguacugc ggcuuccacg | 360 |

| | |
|---|---|
| aggacaacau uccacagcug gaggacguga gccaguuccu gcagaccugc accggcuucc | 420 |
| gccugcggcc uguggccgga cugcugagca gccgggacuu ccugggcggc cuggccuucc | 480 |
| ggguguucca cugcacccag uacauccggc acggcagcaa gcccauguac acccgagc | 540 |
| ccgacaucug ccacgagcug cugggccacg ugcccuguu cagcgaccgg agcuucgccc | 600 |
| aguucagcca ggagaucggg uuagccagcc ugggcgcucc cgacgaguac aucgagaagc | 660 |
| uggccaccau cuacugguuc accguggagu cggccugug caagcagggc gacagcauca | 720 |
| aggccuacgg ggccgggcug cucagcagcu cggcgagcu gcaguacgc cugagcgaga | 780 |
| agcccaagcu gcugcccug gaguuggaga agaccgccau ccagaacuac accgugaccg | 840 |
| aguuccagcc ccuguacuac guggccgaga gcuucaacga cgccaaggag aaggugcgga | 900 |
| acuucgccgc cacaauccc agacccuuca gcgugcggua cgaccccuac acccagcgga | 960 |
| ucgaggugcu ggacaacaca cagcagcuga agauccuggc cgacucaauc aacagcgaaa | 1020 |
| ucggcauccu gugcagcgcc cugcagaaga ucaagugaua auaggcugga gccucgguggg | 1080 |
| ccuagcuucu ugcccuuugg gccucccccc agccccuccu ccccuuccug cacccguacc | 1140 |
| cccuccauaa aguaggaaac acuacagugg ucuuugaaua aagucugagu gggcggc | 1197 |

<210> SEQ ID NO 70
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 70

| | |
|---|---|
| gggaaauaag agagaaaaga agaguaagaa gaaauauaag agccaccaug gugcccuggu | 60 |
| uuccccggac cauccaggag cuggaccggu cgccaaccga gauccugagc uacggcgccg | 120 |
| aacucgacgc cgaccacccc ggcuucaagg accccgugua ccgggcccgg cggaagcagu | 180 |
| ucgccgacau cgccuacaac uaccggcacg gccagcccau uccccggggug gaguacaugg | 240 |
| aggaggagaa gaagaccugg ggcaccgugu caagacccu caagucccug uacaagaccc | 300 |
| acgccugcua cgaguacaac cacaucuucc cgcugcugga agagaucugc ggcuuccacg | 360 |
| aggacaacau uccucagcug gaggacguga gccaguccu gcagaccugc accggcuuca | 420 |
| ggcugcgacc cgucgccggc cugcugagca gccgggacuu ccugggcggc cuggccuucc | 480 |
| ggguguucca cugcacccag uacauccgac acggcagcaa gcccauguac acgcccgagc | 540 |
| ccgacaucug ccacgagcug cugggccacg ugcccuguu cagcgaccgg agcuucgccc | 600 |
| aguucagcca ggagaucgga cuggcuagcc ugggcgcucc agacgaauac aucgagaagc | 660 |
| uggccaccau cuacugguuc accguggagu cggccugug caagcagggc gacagcauca | 720 |
| aggccuacgg agcaggccuu cugucaagcu cggcgagcu gcaguacgc cugagcgaga | 780 |
| agcccaagcu gcugcccug gaguuggaga agaccgccau ccagaacuac accgugaccg | 840 |
| aguuccagcc ccuguacuac guggccgaga gcuucaacga cgccaaggag aaggugcgga | 900 |
| acuucgccgc uaccauuccc ggccccuuca gcgugcggua cgaccccuac acccagcgga | 960 |
| ucgaggugcu ggacaacaca cagcagcuga agauccuggc ugauccauc aacagcgaga | 1020 |
| uugggauccu gugcagcgcc cugcagaaga ucaagugaua auaggcugga gccucgguggg | 1080 |
| ccuagcuucu ugcccuuugg gccucccccc agccccuccu ccccuuccug cacccguacc | 1140 |
| cccuccauaa aguaggaaac acuacagugg ucuuugaaua aagucugagu gggcggc | 1197 |

```
<210> SEQ ID NO 71
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
gggaaauaag agagaaaaga agaguaagaa gaaauauaag agccaccaug gugcccuggu      60
ucccgcggac cauccaggag cuggaccggu ucgccaacca gauccugagc uacggcgccg     120
agcucgacgc cgaccacccc ggcuucaagg accccgucua ccgcgcccgc cgcaagcagu     180
ucgccgacau cgccuacaac uaccgccacg gccagcccau uccccgcguc gaguacaugg     240
aggaggagaa gaagaccugg ggcaccgucu ucaagacccu caagucccuc uacaagaccc     300
acgccugcua cgaguacaac cacaucuuuc cccuccucga gaaguacugc ggcuuccacg     360 aggacaaacau cccucagcuc gaggacgucu cccaguuccu ccagaccugc accggcuucc     420
ggcugaggcc cguggcugga cuccucuccu cccgcgacuu ccuccggcggc cucgccuucc     480 gcgucuucca cugcacccag uacauaagac acggguccaa gcccauguac acgcccgagc     540
ccgacaucug ccacgagcuc cucggccacg ugccccucuu cuccgaccgc uccuucgccc     600
aguucuccca ggagaucggc cuggccuccc ugggagcgcc cgacgaguac aucgagaagc     660
ucgccaccau cuacugguuc accgucgagu ucggccucug caagcagggc gacuccauca     720
aggccuacgg agcuggccug cuguccuccu ucggcgagcu ccaguacugc cucuccgaga     780
agcccaagcu ccucccacug gaguuggaga agaccgccau ccagaacuac accgucaccg     840
aguuccagcc ccucuacuac gucgccgagu ccuucaacga cgccaaggag aaggucccgca     900 acuucgcugc aaccauccca cggcccuucu ccguccgcua cgaccccuac acccagcgca     960
ucgagguccu cgacaauacg cagcagcuca gagaucucgc cgacucgauu aacuccgaaa    1020
ucggcauccu cugcuccgcc cuccagaaga ucaagugaua auaggcugga gccucggugg    1080
ccuagcuucu ugccccuugg gccucccccc agccccuccu ccccuuccug cacccguacc    1140
cccuccauaa aguaggaaac acuacaguggu ucuuugaaua aagucugagu gggcggc      1197

<210> SEQ ID NO 72
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
gggaaauaag agagaaaaga agaguaagaa gaaauauaag agccaccaug gugcccuggu      60 ucccagaac cauccaggag cuggacagau ucgccaacca gauccugagc uacggcgccg     120
agcucgacgc cgaccacccc ggcuucaagg accccgugua cagagccaga agaaagcagu     180
ucgccgacau cgccuacaac uacagacacg gccagcccau cccaagagug gaguacaugg     240
aggaggagaa gaagaccugg ggcaccgugu ucaagacccu caagagccug uacaagaccc     300
acgccugcua cgaguacaac cacaucuuuc cccugcugga gaaguacugc ggcuuccacg     360 aggacaaacau ccccagcug gaggacguga gccaguccu gcagaccugc accggcuuca     420
gacugaggcc cguggccggc cugcugucca guagagacuu ccugggcggc cuggccuuca     480
```

| | |
|---|---|
| gaguguucca cugcacccag uacaucagac acggcagcaa gcccauguac accccagagc | 540 |
| ccgacaucug ccacgagcug cugggacacg ugcccuguu cagcgacaga agcuucgccc | 600 |
| aguucuccca ggaaaucggc cucgccaguc ugggcgcccc ggacgaguac aucgagaagc | 660 |
| uggccaccau cuacugguuc accguggagu cggccugug caagcaaggg gacuccauca | 720 |
| aggccuacgg agccggacug cugagcagcu ucggcgagcu gcaguacugc cugagcgaga | 780 |
| agcccaagcu gcugcccuug gagcuggaga agaccgccau ccagaacuac accgugaccg | 840 |
| aguuccagcc ccuguacuac guggccgaga gcuucaacga cgccaaggag aaggugagaa | 900 |
| acuucgccgc caccaucccc agacccuuca gcgugagaua cgaccccuac acccagagaa | 960 |
| ucgaggugcu ggacaacacc cagcagcuga agauccuggc cgacagcauc aacagcgaga | 1020 |
| ucggcauccu gugcagcgcc cugcagaaga ucaagugaua auaggcugga gccucggugg | 1080 |
| ccuagcuucu ugcccuuugg gccuccccc agccccuccu ccccuuccug cacccguacc | 1140 |
| cccuccauaa aguaggaaac acuacagugg ucuuugaaua aagucugagu gggcggc | 1197 |

<210> SEQ ID NO 73
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 73

| | |
|---|---|
| gggaaauaag agagaaaaga agaguaagaa gaaauauaag agccaccaug gugcccuggu | 60 |
| uccccagaac cauccaggag cuggacagau cgccaaccag auccugagc uacggcgccg | 120 |
| agcuggacgc cgaccacccc ggcuucaagg accccgugua cagagccaga agaaagcagu | 180 |
| ucgccgacau cgccuacaac uacagacacg gccagcccau ccccagagug gaguacaugg | 240 |
| aggaggagaa gaagaccugg ggcaccgugu caagacccu aagagccug uacaagaccc | 300 |
| acgccugcua cgaguacaac cacaucuucc cacugcugga aaguacugc ggcuuccacg | 360 |
| aggacaacau uccgcagcug gaggacguga gccaguuccu gcagaccugc accggcuuca | 420 |
| gacuucgccc cguggccggc cugcugagca gcagagacuu ccugggcggc cuggccuuca | 480 |
| gaguguucca cugcacccag uacaucagac acggcagcaa gcccauguac acaccugagc | 540 |
| ccgacaucug ccacgagcug cugggccacg ugcccuguu cagcgacaga agcuucgccc | 600 |
| aguucagcca ggagaucggc cuggcaaguc ugggcgcucc ugacgaguac aucgagaagc | 660 |
| uggccaccau cuacugguuc accguggagu cggccugug caagcagggc gacagcauca | 720 |
| aggccuacgg cgcuggccug cuguccaguu ucggcgagcu gcaguacugc cugagcgaga | 780 |
| agcccaagcu gcugcccug gagcuggaga agaccgccau ccagaacuac accgugaccg | 840 |
| aguuccagcc ccuguacuac guggccgaga gcuucaacga cgccaaggag aaggugagaa | 900 |
| acuucgccgc caccaucccc agacccuuca gcgugagaua cgaccccuac acccagagaa | 960 |
| ucgaggugcu ggacaacacc cagcagcuga agauccuggc cgauagcauc aacagcgaga | 1020 |
| ucggcauccu gugcagcgcc cugcagaaga ucaagugaua auaggcugga gccucggugg | 1080 |
| ccuagcuucu ugcccuuugg gccuccccc agccccuccu ccccuuccug cacccguacc | 1140 |
| cccuccauaa aguaggaaac acuacagugg ucuuugaaua aagucugagu gggcggc | 1197 |

-continued

```
<210> SEQ ID NO 74
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
gggaauuaag agagaaaaga agaguaagaa gaaauauaag agccaccaug gugcccuggu    60
ucccacggac cauccaggag cuggaccggu ucgccaacca gauccugagc uacggcgccg   120
agcuggacgc cgaccacccc ggcuucaagg accccgugua ccgggcccgg cggaagcagu   180
ucgccgacau cgccuacaac uaccggcacg gccagcccau cccgcggggug gaguacaugg   240 aggaggagaa gaagaccugg ggcaccgugu ucaagacccu gaagagccug uacaagaccc   300
acgccugcua cgaguacaac cacaucuucc cucugcugga aaguacugc ggcuuccacg   360 aggacaaacau cccgcagcug gaggacguga ccaguuccu gcagaccugc accggcuucc   420
ggcugcggcc cguggccggc cugcugagca gccgggacuu ccugggcggc cuggccuucc   480
ggguguucca cugcacccag uacauccggc acggcagcaa gcccauguac acgcccgagc   540
ccgacaucug ccacgagcug cugggccacg ugccccuguu cagcgaccgg agcuucgccc   600
aguucagcca ggagaucggc cuggccagcc ugggcgcgcc cgacgaguac aucgagaagc   660
uggccaccau cuacugguuc accggagagu ucggccugug caagcagggc gacagcauca   720
aggccuacgg cgccggccug cugagcagcu ucggcgagcu gcaguacugc cugagcgaga   780
agcccaagcu gcugccccug gagcuggaga agaccgccau ccagaacuac accgugaccg   840
aguuccagcc ccuguacuac guggccgaga gcuucaacga cgccaaggag aaggugcgga   900
acuucgccgc caccaucccu cggcccuuca gcgugcggua cgaccccuac acccagcgga   960
ucgaggugcu ggacaacacc cagcagcuga agauccuggc cgacagcauc aacagcgaga  1020
ucggcauccu gugcagcgcc cugcagaaga ucaagugaua auaggcugga gccucggugg  1080
ccuagcuucu ugcccuugg gccucccccc agcccuccu ccccuuccug cacccguacc    1140
cccuccauaa aguaggaaac acuacagugg ucuuugaaua aagucugagu gggcggc      1197

<210> SEQ ID NO 75
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gggaauuaag agagaaaaga agaguaagaa gaaauauaag agccaccaug gugcccuggu    60 ucccaggac cauucaggag cuggacaggu ucgccaacca aauccucucc uacgcgccg     120 agcucgacgc ugaccacccc ggcuucaagg accccgugua ccgggccagg aggaagcagu   180
ucgccgauau cgccuacaac uacaggcacg gccagcccau cccgagggug gaguacaugg   240
aggaggagaa gaagaccugg ggaaccgugu ucaagacccu caagucccug uacaagaccc   300
acgccugcua cgaguacaac cacaucuuuc cccugcucga aaguacugc gguuuccacg    360 aggacaaacau cccgcagcug gaggacgugu cgcaguccu gcagcuugu accggauucc    420 ggcugcggcc cguggcagga cugcugagca gccgggacuu ccugggcggu cuggccuuuc   480
```

| | |
|---|---|
| guguguucca cugcacccag uacauccggc acggcuccaa gcccauguac accccugagc | 540 |
| ccgacaucug ccacgagcug cugggccacg ugcccuguu uagcgacagg agcuucgccc | 600 |
| aguuuagcca ggagaucggc uuggccagcc ugggugcccc agacgaguau aucgagaagc | 660 |
| uggccaccau cuacuggUuu acgguggagu cggccugug caagcaggga gacagcauca | 720 |
| aggcguacgg agccggccug cucagcuccu ucggcgagcu gcaauacugc cugagcgaga | 780 |
| agccuaagcu ccugccucug gaacuggaga agacugccau ccagaacuac acagucaccg | 840 |
| aguuccagcc gcucuauuac guggccgaga gcuucaacga cgcgaaggag aaggugagaa | 900 |
| auuucgcggc aaccauccc agacccuuca gcgugcgcua cgaccccuau acccagcgga | 960 |
| ucgaggugcu agauaacacc cagcagcuga agauccuggc cgacucgauu aacucagaga | 1020 |
| ucggaauccu gugcagcgcc cugcagaaga ucaagugaua auaggcugga gcccucggugg | 1080 |
| ccuagcuucu ugcccuugg gccucccccc agccccuccu ccccuuccug caccccguacc | 1140 |
| cccuccauaa aguaggaaac acuacagugg ucuuugaaua aagucugagu gggcggc | 1197 |

<210> SEQ ID NO 76
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic polynucleotide"

<400> SEQUENCE: 76

| | |
|---|---|
| gggaaauaag agagaaaaga agaguaagaa gaaauauaag agccaccaug guucccuggu | 60 |
| uccccagaac cauucaggag cuggaucggu ucgccaacca aauccucucc uacggggccg | 120 |
| agcuggacgc agaccaccca ggcuucaaag auccugugua ccgggcccgc cgcaagcagu | 180 |
| ucgccgacau cgccuacaac uacagacacg gccagcccau cccgcgcgug gaguacaugg | 240 |
| aggaggagaa gaagaccugg ggcacggucu ucaagacccu gaagucucuc uacaagacgc | 300 |
| acgcgugcua cgaguacaau cacaucuuuc cgcugcugga gaaguacugc ggcuuccacg | 360 |
| aggacaacau accccagcug gaggacguga gccaguuccu ccagaccugu acgggcuuca | 420 |
| gacugcgccc aguggcuggu cugcugagca gcagggacuu ucugggcggg cucgccuucc | 480 |
| gggguguuuca uugcacccag uacauccggc acggcagcaa gccuauguac acucccgagc | 540 |
| ccgacaucug ccacgagcug cugggccacg ugccgcuguu ucccgacagg agcuucgccc | 600 |
| aguucagcca ggagaucggc cucgccagcc ucggagcacc cgacgaguau auugagaagc | 660 |
| uggccaccau cuacuggUuc accguggagu cggacugug caagcagggc gacagcauaa | 720 |
| aggcuacgg cgccggccuc cugccaguc ucggcgagcu ccaguacugc cucuccgaga | 780 |
| agcccaagcu gcugcccug gagcucgaga agaccgccau ccagaauuac accgugaccg | 840 |
| aguuccaacc ccuguacuac guggccgagu ccuucaacga cgccaaggag aaggugcgga | 900 |
| acuuugccgc cacaauuccu cgaccauucu cggugcgcua cgacccguac acccagcgaa | 960 |
| ucgagguacu ggacaacaca cagcagcuga agauccuggc cgauuccauc aacuccgaaa | 1020 |
| ucggcauccu gugcagcgcc cugcagaaga ucaagugaua auaggcugga gcccggugg | 1080 |
| ccuagcuucu ugcccuugg gccucccccc agccccuccu ccccuuccug caccccguacc | 1140 |
| cccuccauaa aguaggaaac acuacagugg ucuuugaaua aagucugagu gggcggc | 1197 |

```
<210> SEQ ID NO 77
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
gggaaauaag agagaaaaga agaguaagaa gaaauauaag agccaccaug gugcccuggu      60
ucccgcggac gauccaagag cuggacaggu ucgccaacca gauccugagc uacggggccg     120
agcucgacgc cgaccacccc ggcuucaagg acccugucua cagagccagg cggaaacagu     180
ucgccgauau cgccuauaac uacaggcacg gccagcccau ccccagaguc gaguacaugg     240
aggaagagaa gaagaccugg ggcaccgucu ucaagacccu caaaucgcug uacaagaccc     300
acgccugcua cgaguacaac cacaucuucc cacuccugga aaguacugu ggcuuccacg      360 aggauaacau uccccagcug gaagacguga gccaauuccu gcagaccugc accggauuca     420
gacugcgccc cguggccgga cugcugucau ccagagauuu ccuggcggg cuggccuuuc      480 gaguuuucca cugcacccag uacauccguc acgggagcaa gcccauguau acaccggagc     540
ccgauaucug ccacgagcug cucggacacg ugccccuguu cagugacaga aguuuugccc     600
aauuuagcca agagaucggc cuggccucc ugggagcccc ugacgaguac aucgagaagc      660
uggccaccau cuacugguuc accggagagu cgggüugug caagcagggc gacuccauca     720
aagccuacgg cgccggccug cuguccuccu ucggcgagcu gcaauacugc cuguccgaga     780
agcccaagcu gcugccccuu gaacuggaga agaccgccau ccagaacuau accgugaccg     840
aguuccaacc ccuguacuac guggccgaga gcuucaacga cgccaaggag aaguccgca     900 auuuugccgc cacuauccca cggcccuucu ccgugcggua cgauccuac acccagcgua     960 ucgaggugcu cgacaauacc cagcaacuga gauccucgc cgacagcauc aacagcgaga    1020
uaggaauccu guguagcgcc cugcagaaga uuaaaugaua auaggcugga gccucggugg    1080
ccuagcuucu ugcccuuug gccucccccc agccccuccu ccccuuccug cacccguacc    1140
cccuccauaa aguaggaaac acuacagugg ucuuugaauaa aagucugagu gggcggc     1197

<210> SEQ ID NO 78
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
gggaaauaag agagaaaaga agaguaagaa gaaauauaag agccaccaug gugcccuggu      60 uccacggac cauccaggag cuggacagau ucgccaacca gauucugagc uacggggccg      120
agcucgacgc cgaccacccc ggcuucaagg acccgugua cagggccagg aggaagcagu      180
ucgccgacau cgccuauaac uaccggcacg gacagcccau cccacggug gaguauaugg      240 aggaggagaa gaagaccugg ggcaccgugu uuaagacccu caagagccuu uacaagacac      300
acgccugcua cgaguacaac cauaucuuuc cccugcuaga aaguacugc ggguuccacg      360 aagauaauau accccagcug gaagacgucu cccaguccu gcagaccugc accggcuucc     420
gccucagacc cguggcgggu cugcugagca gccgggacuu ccucggcgga cuggccuuua    480
```

| | |
|---|---|
| gaguguucca uugcacccag uacauccgcc acggcuccaa gcccauguac accccggagc | 540 |
| ccgauaucug ccacgagcuc cucggacacg ugcccuguu uuccgaccgg uccuucgccc | 600 |
| aguucagcca ggaaaucggg cuugcaagcc ugggagcucc cgacgaguau aucgagaagc | 660 |
| uggccacaau cuacugguuc acgguggagu ucggccugug caaacaggga gauagcauca | 720 |
| aggccuacgg cgccggccug cucagcagcu uggggagcu gcaguacugc ucagcgaga | 780 |
| agcccaagcu gcugccccuc gagcuggaga agaccgccau ccagaacuac accgugaccg | 840 |
| aguuccagcc ccuguauuac guugccgaga gcuucaacga cgccaaggag aagguccgaa | 900 |
| auuucgccgc gaccauccc aggcccuucu ccgugaggua cgaccuuac acccagcgga | 960 |
| ucgaggugcu ggacaauacc cagcagcuga agauccuggc ggauagcaua aacagcgaaa | 1020 |
| ucggaauccu cugcagcgcc cugcagaaga ucaaaugaua auaggcugga gccucggugg | 1080 |
| ccuagcuucu ugcccuugg gccucccccc agccccuccu ccccuuccug cacccguacc | 1140 |
| cccuccauaa aguaggaaac acuacagugg ucuuugaaua aagucugagu gggcggc | 1197 |

<210> SEQ ID NO 79
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 79

| | |
|---|---|
| gggaaauaag agagaaaaga agaguaagaa gaaauauaag agccaccaug gugcccuggu | 60 |
| uuccccggac cauccaggag cuggaccggu ucgccaacca gauccugagc uacggcgccg | 120 |
| agcuggacgc cgaccacccc ggcuucaagg accccgugua ccgggcccgg cggaagcagu | 180 |
| ucgccgacau cgccuacaac uaccggcacg gccagcccau cccucggug gaguacaugg | 240 |
| aggaggagaa gaagaccugg ggcaccgugu caagacccu gaaguccug uacaagaccc | 300 |
| acgccugcua cgaguacaac cacaucuuuc cccgcugga gaaguacugc ggcuuccacg | 360 |
| aggacaacau cccgcagcug gaggacguga gccaguuccu gcagaccugc accggcuucc | 420 |
| ggcugcggcc cguggccggc cugcugagca gccgggacuu ccggcggc cuggccuucc | 480 |
| ggguguucca cugcacccag uacauccgcc acggcagcaa gcccauguac accccagagc | 540 |
| ccgacaucug ccacgagcug cugggccacg ugcccuguu cagcgaccgg agcuucgccc | 600 |
| aguucagcca ggagaucggc cuggccucuc ugggcgcccc ugacgaguau aucgagaagc | 660 |
| uggccaccau cuacugguuc accguggagu ucggccugug caagcagggc gacagcauca | 720 |
| aggccuacgg cgccgggcug cuguccuccu ucggcgagcu gcaguacugc cugagcgaga | 780 |
| agcccaagcu gcugccccug gaacucgaga agaccgccau ccagaacuac accgugaccg | 840 |
| aguuccagcc ccuguacuac guggccgaga gcuucaacga cgccaaggag aaggugcgga | 900 |
| acuucgccgc caccaucccc aggcccuuca gcgugcggua cgaccccuac acccagcgga | 960 |
| ucgaggugcu ggacaauacc cagcagcuga agauccuggc cgacccauc aacagcgaga | 1020 |
| ucggaauccu gugcagcgcc cugcagaaga ucaagugaua auaggcugga gccucggugg | 1080 |
| ccuagcuucu ugcccuugg gccucccccc agccccuccu ccccuuccug cacccguacc | 1140 |
| cccuccauaa aguaggaaac acuacagugg ucuuugaaua aagucugagu gggcggc | 1197 |

```
<210> SEQ ID NO 80
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
gggaauuaag agagaaaaga agaguaagaa gaaauauaag agccaccaug gugcccuggu      60 uucccggac cauccaggag cuggaccggu ucgccaacca gauccugagc uacggcgccg      120
agcuggacgc cgaccacccc ggcuucaagg accccguguia ccgggcccgg cggaagcagu    180
ucgccgacau cgccuacaac uaccggcacg gccagcccau cccacggguig gaguacaugg    240 aggaggagaa gaagaccugg ggcaccgugu ucaagacccu gaagucucug uacaagaccc     300
acgccugcua cgaguacaac cacaucuucc cgcugcugga aaguacugc ggcuuccacg      360 aggacaaacau cccgcagcug gaggacguga ccaguuccu gcagaccugc accggcuucc    420
gccugcgacc cguggcgggc cugcugagca gccgggacuu ccugggcggc cuggccuucc   480
ggguguucca cugcacccag uacauccgcc acgggagcaa gcccauguac accccugagc    540
ccgacaucug ccacgagcug cugggccacg ugcccccuguu cagcgaccgg agcuucgccc   600
aguucagcca ggagaucggc cuggccagcc ugggagcccc ggacgaguau aucgagaagc   660
uggccaccau cuacugguuc accgggagu ucggccugug caagcagggc gacagcauca    720
aggccuacgg ggccgggcug cuguccagcu ucggcgagcu gcaguacugc cugagcgaga   780
agcccaagcu gcugccccuc gagcucgaga agaccgccau ccagaacuac accgugaccg    840
aguuccagcc ccuguacuac guggccgaga gcuucaacga cgccaaggag aaggugcgga    900
acuucgccgc cacaaucccc aggcccuuca gcgugcggua cgaccccuac acccagcgga    960
ucgaggugcu ggacaauacc cagcagcuga agauccuggc ggacuccauc aacagcgaga    1020
ucggaauccu gugcagcgcc cugcagaaga ucaagugaua auaggcugga gccucgguigg    1080 ccuagcuucu ugcccucugg gccucccccc agcccccuccuu ccccuuccug cacccguacc    1140
cccuccauaa aguaggaaac acuacagugg ucuuugaaua aagucugagu gggcggc      1197

<210> SEQ ID NO 81
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 81
gggaauuaag agagaaaaga agaguaagaa gaaauauaag agccaccaug gugcccuggu      60
ucccgcggac cauccaggag cuggaccggu ucgccaacca gauccugagc uacggcgccg     120
agcucgacgc cgaccacccc ggcuucaagg accccgucua ccgcgcccgc cgcaagcagu    180
ucgccgacau cgccuacaac uaccgccacg gccagcccau cccgcgcguc gaguacaugg   240
aggaggagaa gaagaccugg ggcaccgucu ucaagacccu caagucccuc uacaagaccc    300
acgccugcua cgaguacaac cacaucuucc cgcuccucga aaguacugc ggcuuccacg      360 aggacaaacau cccgcagcuc gaggacgucu ccaguuccu ccagaccugc accggcuuua    420
gacugcggcc cguggccgga cuucucuccu cccgcgacuu ccucggcggc cucgccuucc    480
```

| | |
|---|---|
| gcgucuucca cugcacccag uacauuagac acggguccaa gcccauguac acgcccgagc | 540 |
| ccgacaucug ccacgagcuc cucggccacg ugcccucuu cuccgaccgc uccuucgccc | 600 |
| aguucuccca ggagaucggc cuggcccac ugggcgcccc ugacgaauac aucgagaagc | 660 |
| ucgccaccau cuacugguuc accgucgagu cggccucug caagcagggc gacuccauca | 720 |
| aggcauacgg cgcuggccug cugagcagcu cggcgagcu ccaguacugc cucuccgaga | 780 |
| agcccaagcu ccugccccua gaacuggaga agaccgccau ccagaacuac accgucaccg | 840 |
| aguuccagcc ccucuacuac gucgccgagu ccuucaacga cgccaaggag aaggucgca | 900 |
| acuucgccgc cacgaucccg cggcccuucu ccguccgcua cgaccccuac acccagcgca | 960 |
| ucgaggaccu cgacaauacg cagcagcuca agauccucgc cgacucgauc aacuccgaga | 1020 |
| uugggauccu cugcuccgcc cuccagaaga ucaagugaua auaggcugga gcccggugg | 1080 |
| ccuagcuucu ugcccuugg gccucccccc agccccuccu ccccuuccug cacccguacc | 1140 |
| cccuccauaa aguaggaaac acuacagugg ucuuugaaua aagucugagu gggcggc | 1197 |

<210> SEQ ID NO 82
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 82

| | |
|---|---|
| gggaaauaag agagaaaaga agaguaagaa gaaauauaag agccaccaug gugcccuggu | 60 |
| uccccagaac cauccaggag cuggacagau cgccaaccga gauccugagc uacggcgccg | 120 |
| agcucgacgc cgaccacccc ggcuucaagg accccgugua cagagccaga agaaagcagu | 180 |
| ucgccgacau cgccuacaac uacagacacg gccagcccau cccaagagug gaguacaugg | 240 |
| aggaggagaa gaagaccugg ggcaccgugu ucaagacccu caagagccug uacaagaccc | 300 |
| acgccugcua cgaguacaac cacaucuuuc cccgcuggga gaaguacugc ggcuuccacg | 360 |
| aggacaacau accccagcug gaggacguga gccaguuccu gcagaccugc accggcuuca | 420 |
| gacugaggcc cguggccggc cugcugucca guagagacuu ccgggcgcc cuggccuuca | 480 |
| gaguguucca cugcacccag uacaucagac acggcagcaa gcccauguac acccccagagc | 540 |
| ccgacaucug ccacgagcug cugggacacg ugcccucuu cagcgacaga gcuucgccc | 600 |
| aguucuccca ggaaaucggc cucgccaguc ugggcgcccc ggacgaguac aucgagaagc | 660 |
| uggccaccau cuacugguuc accguggagu cggccugug caagcaaggg gacuccauca | 720 |
| aggcuacgg agccggacug cugagcagcu cggcgagcu gcaguacugc cugagcgaga | 780 |
| agcccaagcu gcugccccug gagcuggaga agaccgccau ccagaacuac accgugaccg | 840 |
| aguuccagcc ccuguacuac guggccgaga gcuucaacga cgccaaggag aaggugagaa | 900 |
| acuucgccgc caccauccc agacccuuca gcgugagaua cgaccccuac acccagagaa | 960 |
| ucgaggugcu ggacaacacc cagcagcuga agauccugcc cgacagcauc aacagcgaga | 1020 |
| ucggcauccu gugcagcgcc cugcagaaga ucaagugaua auaggcugga gcccggugg | 1080 |
| ccuagcuucu ugcccuugg gccucccccc agccccuccu ccccuuccug cacccguacc | 1140 |
| cccuccauaa aguaggaaac acuacagugg ucuuugaaua aagucugagu gggcggc | 1197 |

```
<210> SEQ ID NO 83
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
gggaaauaag agagaaaaga agaguaagaa gaaauauaag agccaccaug gugcccuggu     60
uccccagaac cauccaggag cuggacagau cgccaacca gauccugagc uacggcgccg    120
agcuggacgc cgaccacccc ggcuucaagg accccgugua cagagccaga agaaagcagu    180
ucgccgacau cgccuacaac uacagacacg gccagcccau cccagagug gaguacaugg    240 aggaggagaa gaagaccugg ggcaccgugu ucaagacccu aagagccug uacaagaccc    300 acgccugcua cgaguacaac cacaucuucc cacugcugga aaguacugc ggcuuccacg    360 aggacaaacau uccgcagcug gaggacguga gccaguccu gcagaccugc accggcuuca    420
gacuucgccc cguggccggc cugcugagca gcagagacuu ccugggcggc cuggccuuca    480
gaguguucca cugcacccag uacaucgagc acggcagcaa gcccauguac acaccugagc    540
ccgacaucug ccacgagcug cugggccacg ugccccuguu cagcgacaga agcuucgccc    600
aguucagcca ggagaucggc cuggcaaguc ugggcgcucc ugacgaguac aucgagaagc    660
uggccaccau cuacugguuc accgggagu ucggccugu caagcagggc gacagcauca    720
aggccuacgg cgcuggccug cuguccaguu ucggcgagcu gcaguacugc cugagcgaga    780
agcccaagcu gcugccccug gagcuggaga agaccgccau ccagaacuac accgugaccg    840
aguuccagcc ccuguacuac guggccgaga gcuucaacga cgccaaggag aaggugagaa    900
acuucgccgc caccauccccc agacccuuca gcgugagaua cgaccccuac acccagagaa    960
ucgaggugcu ggacaacacc cagcagcuga agauccuggc cgauagcauc aacagcgaga   1020
ucggcauccu gugcagcgcc cugcagaaga ucaagugaua auaggcugga gccucggugg   1080
ccuagcuucu ugcccccuug gccucccccc agcccucccu ccccuuccug cacccguacc   1140
cccuccauaa aguaggaaac acuacagugg ucuuugaaua aagucugagu gggcggc      1197

<210> SEQ ID NO 84
<211> LENGTH: 1197
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
gggaaauaag agagaaaaga agaguaagaa gaaauauaag agccaccaug gugcccuggu     60 uccccacggac cauccaggag cuggaccggu cgccaacca gauccugagc uacggcgccg    120
agcuggacgc cgaccacccc ggcuucaagg accccgugua ccgggcccgg cggaagcagu    180
ucgccgacau cgccuacaac uaccggcacg gccagcccau cccgcggug gaguacaugg    240 aggaggagaa gaagaccugg ggcaccgugu ucaagacccu gaagagccug uacaagaccc    300
acgccugcua cgaguacaac cacaucuucc cucugcugga aaguacugc ggcuuccacg    360 aggacaaacau cccgcagcug gaggacguga gccaguccu gcagaccugc accggcuuca    420
ggcugcggcc cguggccggc cugcugagca gccgggacuu ccugggcggc cuggccuucc    480
```

```
ggguguucca cugcacccag uacauccggc acggcagcaa gcccauguac acgcccgagc    540
ccgacaucug ccacgagcug cugggccacg ugcccuguu cagcgaccgg agcuucgccc    600
aguucagcca ggagaucggc cuggccagcc ugggcgcgcc cgacgaguac aucgagaagc    660
uggccaccau cuacugguuc accguggagu cggccugug caagcagggc gacagcauca    720
aggccuacgg cgccggccug cugagcagcu cggcgagcu gcaguacugc cugagcgaga    780
agcccaagcu gcugcccug gagcuggaga agaccgccau ccagaacuac accgugaccg    840
aguuccagcc ccuguacuac guggccgaga gcuucaacga cgccaaggag aaggugcgga    900
acuucgccgc caccauccu cggcccuuca gcgugcggua cgaccccuac acccagcgga    960
ucgaggugcu ggacaacacc cagcagcuga agauccuggc cgacagcauc aacagcgaga   1020
ucggcauccu gugcagcgcc cugcagaaga ucaagugaua auaggcugga gccucggugg   1080
ccuagcuucu ugcccuugg gccucccccc agcccuccu ccccuuccug cacccguacc    1140
cccuccauaa aguaggaaac acuacagugg ucuuugaaua aagucgagu gggcggc      1197
```

<210> SEQ ID NO 85
<211> LENGTH: 41
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
gggaaauaag agagaaaaga agaguaagaa gaaauauaag a                       41

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Gly Gly Gly Ser
1               5

<210> SEQ ID NO 87
<211> LENGTH: 9
<212> TYPE: RNA
<213> ORGANISM: Unknown
<220> FEATURE:
<221> NAME/KEY: source
<223> OTHER INFORMATION: /note="Description of Unknown:
      Kozak sequence"

<400> SEQUENCE: 87 ccrccaugg                                                            9

<210> SEQ ID NO 88
<211> LENGTH: 92
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 88
ucaagcuuuu ggacccucgu acagaagcua auacgacuca cuauagggaa auaagagaga    60
aaagaagagu aagaagaaau auaagagcca cc                                 92

<210> SEQ ID NO 89
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
gggagaucag agagaaaaga agaguaagaa gaaauauaag agccacc                 47

<210> SEQ ID NO 90
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gggagacaag cuuggcauuc cgguacuguu gguaaagcca cc                      42

<210> SEQ ID NO 91

<400> SEQUENCE: 91

000

<210> SEQ ID NO 92

<400> SEQUENCE: 92

000

<210> SEQ ID NO 93
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gggaauuaac agagaaaaga agaguaagaa gaaauauaag agccacc                 47

<210> SEQ ID NO 94
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
gggaaauuag acagaaaaga agaguaagaa gaaauauaag agccacc                 47
```

-continued

```
<210> SEQ ID NO 95
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gggaaauaag agaguaaaga acaguaagaa gaaauauaag agccacc            47

<210> SEQ ID NO 96
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gggaaaaaag agagaaaaga agacuaagaa gaaauauaag agccacc            47

<210> SEQ ID NO 97
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
gggaaauaag agagaaaaga agaguaagaa gauauauaag agccacc            47

<210> SEQ ID NO 98
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
gggaaauaag agacaaaaca agaguaagaa gaaauauaag agccacc            47

<210> SEQ ID NO 99
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
gggaaauuag agaguaaaga acaguaagua gaauuaaaag agccacc            47

<210> SEQ ID NO 100
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 100
gggaaauaag agagaauaga agaguaagaa gaaauauaag agccacc          47

<210> SEQ ID NO 101
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gggaaauaag agagaaaaga agaguaagaa gaaaauuaag agccacc          47

<210> SEQ ID NO 102
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
gggaaauaag agagaaaaga agaguaagaa gaaauuuaag agccacc          47

<210> SEQ ID NO 103

<400> SEQUENCE: 103

000

<210> SEQ ID NO 104
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
ugauaauagu ccauaaagua ggaaacacua cagcuggagc cucgguggcc augcuucuug     60
ccccuugggc cucccccag ccccuccucc ccuuccugca cccguacccc cguggucuuu    120
gaauaaaguc ugagugggcg gc                                           142

<210> SEQ ID NO 105
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
ugauaauagg cuggagccuc gguggcucca uaaaguagga aacacuacac augcuucuug     60
ccccuugggc cucccccag ccccuccucc ccuuccugca cccguacccc cguggucuuu    120
gaauaaaguc ugagugggcg gc                                           142
```

```
<210> SEQ ID NO 106
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
ugauaauagg cuggagccuc gguggccaug cuucuugccc cuuccauaaa guaggaaaca    60
cuacaugggc ucccccccag ccccuccucc ccuuccugca cccguacccc cguggucuuu   120
gaauaaaguc ugagugggcg gc                                            142

<210> SEQ ID NO 107
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
ugauaauagg cuggagccuc gguggccaug cuucuugccc cuugggccuc ccccccaguucc   60 auaaaguagg aaacacuaca ccccuccucc ccuuccugca cccguacccc cguggucuuu   120
gaauaaaguc ugagugggcg gc                                            142

<210> SEQ ID NO 108
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
ugauaauagg cuggagccuc gguggccaug cuucuugccc cuugggccuc ccccagccc     60 cuccuccccu ucuccauaaa guaggaaaca cuacacugca cccguacccc cguggucuuu   120
gaauaaaguc ugagugggcg gc                                            142

<210> SEQ ID NO 109
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
ugauaauagg cuggagccuc gguggccaug cuucuugccc cuugggccuc ccccagccc     60 cuccuccccu uccugcaccc guaccccuc cauaaaguag gaaacacuac aguggucuuu    120
gaauaaaguc ugagugggcg gc                                            142

<210> SEQ ID NO 110
<211> LENGTH: 142
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 110
ugauaauagg cuggagccuc gguggccaug cuucuugccc cuugggccuc cccccagccc    60
cucccccccu uccugcaccc guaccccgu ggucuugaa uaaaguucca uaaaguagga     120
aacacuacac ugagugggcg gc                                            142

<210> SEQ ID NO 111
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 111
ugauaauagu ccauaaagua ggaaacacua cagcuggagc cucgguggcc augcuucuug    60
ccccuugggc cucccccccag ccccuccucc ccuuccugca cccguacccc cgcauuauu   120 acucacggua cgagggucu uugaauaaag ucgaguggg cggc                      164

<210> SEQ ID NO 112
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112
ugauaauagu ccauaaagua ggaaacacua cagcuggagc cucgguggcc uagcuucuug    60
ccccuugggc cucccccccag ccccuccucc ccuuccugca cccguacccc cgcauuauu   120 acucacggua cgaguggucu uugaauaaag ucgagugggg cggc                    164

<210> SEQ ID NO 113

<400> SEQUENCE: 113

000

<210> SEQ ID NO 114
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
gacagugcag ucacccauaa aguagaaagc acuacuaaca gcacuggagg guguagugu     60 uccuacuuua uggaugagug uacugug                                       87

<210> SEQ ID NO 115
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 115
uguaguguuu ccuacuuuau gga                                            23

<210> SEQ ID NO 116
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
uccauaaagu aggaaacacu aca                                            23

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
cauaaaguag aaagcacuac u                                              21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
aguagugcuu ucuacuuuau g                                              21

<210> SEQ ID NO 119
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
cgcuggcgac gggacauuau uacuuuuggu acgcgcugug acacuucaaa cucguaccgu     60
gaguaauaau gcgccgucca cggca                                          85

<210> SEQ ID NO 120
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 120
ucguaccgug aguaauaaug cg                                           22

<210> SEQ ID NO 121
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
cgcauuauua cucacgguac ga                                           22

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
cauuauuacu uuugguacgc g                                            21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
cgcguaccaa aaguaauaau g                                            21

<210> SEQ ID NO 124
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124 ugauaauag                                                           9

<210> SEQ ID NO 125
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125 ugauaguaa                                                           9

<210> SEQ ID NO 126
<211> LENGTH: 9
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 126 uaaugauag                                                                 9

<210> SEQ ID NO 127
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127 ugauaauaa                                                                 9

<210> SEQ ID NO 128
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128 ugauaguag                                                                 9

<210> SEQ ID NO 129
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129 uaaugauga                                                                 9

<210> SEQ ID NO 130
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130 uaauaguag                                                                 9

<210> SEQ ID NO 131
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 131 ugaugauga                                                              9

<210> SEQ ID NO 132
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132 uaauaauaa                                                              9

<210> SEQ ID NO 133
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133 uaguaguag                                                              9

<210> SEQ ID NO 134
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
gcuggagccu cgguggccau gcuucuugcc ccuugggccu cccccagcc ccuccuccc       60 uuccugcacc cguaccccu ccauaaagua ggaaacacua cagggucuu ugaauaaagu      120 cugagugggc ggc                                                       133

<210> SEQ ID NO 135
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
ccucugaaau ucaguucuuc ag                                              22

<210> SEQ ID NO 136
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
ugagaacuga auuccauggg uu                                              22
```

```
<210> SEQ ID NO 137
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cuccuacaua uuagcauuaa ca                                              22

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
uuaaugcuaa ucgugauagg ggu                                             23

<210> SEQ ID NO 139
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
ccaguauuaa cugugcugcu ga                                              22

<210> SEQ ID NO 140
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
uagcagcacg uaaauauugg cg                                              22

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
caacaccagu cgaugggcug u                                               21

<210> SEQ ID NO 142
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 142
uagcuuauca gacugauguu ga                                              22

<210> SEQ ID NO 143
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
ugucaguuug ucaaauaccc ca                                              22

<210> SEQ ID NO 144
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
cguguauuug acaagcugag uu                                              22

<210> SEQ ID NO 145
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
uggcucaguu cagcaggaac ag                                              22

<210> SEQ ID NO 146
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ugccuacuga gcugauauca gu                                              22

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
uucacagugg cuaaguuccg c                                               21

<210> SEQ ID NO 148
<211> LENGTH: 22
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 148
agggcuuagc ugcuugugag ca                                             22

<210> SEQ ID NO 149
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 149
ugauaauagg cuggagccuc gguggccaug cuucuugccc cuugggccuc ccccagccc     60 cuccuccccu uccugcaccc guaccccccg cauuauuacu cacgguacga guggucuuug   120
aauaaagucu gagugggcgg c                                            141

<210> SEQ ID NO 150
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 150
ugauaauagg cuggagccuc gguggccaug cuucuugccc cuugggccuc ccccagccc     60 cuccuccccu uccugcaccc guaccccgu ggucuuugaa uaaagucuga gugggcggc    119

<210> SEQ ID NO 151

<400> SEQUENCE: 151

000

<210> SEQ ID NO 152

<400> SEQUENCE: 152

000

<210> SEQ ID NO 153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
uuaaugcuaa uugugauagg ggu                                            23

<210> SEQ ID NO 154
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 154
accccuauca caauuagcau uaa                                           23

<210> SEQ ID NO 155
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
ugauaauagu ccauaaagua ggaaacacua cagcuggagc cucgguggcc augcuucuug    60
ccccuugggc cuccauaaag uaggaaacac uacaucccccc cagcccccucc ucccccuuccu   120 gcacccguac ccccuccaua aaguaggaaa cacuacagug gucuuugaau aaagucugag   180
ugggcggc                                                            188

<210> SEQ ID NO 156
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
ugauaauagg cuggagccuc gguggccaug cuucuugccc cuugggccuc ccccagccc     60 cuccucccccu uccugcaccc guaccccag uagugcuuuc uacuuuaugg ggucuuuga    120 auaaagucug agugggcggc                                               140

<210> SEQ ID NO 157
<211> LENGTH: 182
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
ugauaauaga guagugcuuu cuacuuuaug gcuggagccu cgguggccau gcuucuugcc    60
ccuugggcca guagugcuuu cuacuuuaug ucccccagc cccuccuccc cuuccugcac   120
ccguaccccc aguagugcuu ucuacuuuau ggugggucuuu gaauaaaguc ugaguggggcg   180 gc                                                                 182

<210> SEQ ID NO 158
<211> LENGTH: 184
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 158
ugauaauaga guagugcuuu cuacuuuaug gcuggagccu cgguggccau gcuucuugcc    60
ccuugggccu ccauaaagua ggaaacacua cauccccca gccccuccuc cccuuccugc    120
acccguaccc ccaguagugc uuucuacuuu augguggucu ugaauaaag ucgaguggg    180 cggc                                                                184

<210> SEQ ID NO 159
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 159
ugauaauagg cuggagccuc gguggccaug cuucuugccc cuugggccuc ccccagccc    60 cuccucccu uccugcaccc guaccccac cccaucaca auuagcauua agugucuuu    120 gaauaaaguc ugagugggcg gc                                            142

<210> SEQ ID NO 160
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160
ugauaauaga ccccuaucac aauuagcauu aagcuggagc cucgguggcc augcuucuug    60
ccccuugggc caccccuauc acaauuagca uuaauccccc cagccccucc ucccuuccu    120 gcacccguac ccccacccu aucacaauua gcauuaagug ucuuugaau aaagucugag    180 ugggcggc                                                            188

<210> SEQ ID NO 161
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161
ugauaauaga ccccuaucac aauuagcauu aagcuggagc cucgguggcc augcuucuug    60
ccccuugggc cuccauaaag uaggaaacac uacauccccc cagccccucc ucccuuccu    120 gcacccguac ccccacccu aucacaauua gcauuaagug ucuuugaau aaagucugag    180 ugggcggc                                                            188

<210> SEQ ID NO 162

<400> SEQUENCE: 162

000
```

<210> SEQ ID NO 163

<400> SEQUENCE: 163

000

<210> SEQ ID NO 164
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164
ugauaauagg cuggagccuc gguggccaug cuucuugccc cuugggccuc cauaaaguag      60
gaaacacuac auccccccag ccccuccucc ccuuccugca cccguacccc cguggucuuu    120
gaauaaaguc ugagugggcg gc                                              142

<210> SEQ ID NO 165
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
gggaaauaag aguccauaaa guaggaaaca cuacaagaaa agaagaguaa gaagaaauau      60
aagagccacc                                                            70

<210> SEQ ID NO 166
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gggaaauaag agagaaaaga agaguaaucc auaaaguagg aaacacuaca gaagaaauau      60
aagagccacc                                                            70

<210> SEQ ID NO 167
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gggaaauaag agagaaaaga agaguaagaa gaaauauaau ccauaaagua ggaaacacua      60
cagagccacc                                                            70

<210> SEQ ID NO 168

<400> SEQUENCE: 168

000

```
<210> SEQ ID NO 169
<211> LENGTH: 181
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169
ugauaauaga guagugcuuu cuacuuuaug gcuggagccu cgguggccau gcuucuugcc      60
ccuugggcca guagugcuuu cuacuuuaug uccccccagc cccucucccc uuccugcacc     120
cguaccccca guagugcuuu cuacuuuaug guggucuuug aauaaagucu gagugggcgg     180
c                                                                    181

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 175
ugauaauagg cuggagccuc gguggccuag cuucuugccc cuugggccuc ccccagccc       60 cuccucccu uccugcaccc guaccccgu ggucuuugaa uaaagucuga gugggcggc        119

<210> SEQ ID NO 176

<400> SEQUENCE: 176

000
```

<210> SEQ ID NO 177
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 177
ugauaauagg cuggagccuc gguggccuag cuucuugccc cuugggccuc ccccagccc      60 cuccuccccu uccugcaccc guacccccg cauuauuacu cacgguacga guggucuuug    120
aauaaagucu gagugggcgg c                                             141

<210> SEQ ID NO 178
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 178
ugauaauagu ccauaaagua ggaaacacua cagcuggagc cucgguggcc uagcuucuug     60
ccccuugggc cuccauaaag uaggaaacac uacaucccc cagccccucc ucccuuccu     120 gcacccguac ccccuccaua aaguaggaaa cacuacagug gucuuugaau aaagucugag   180
ugggcggc                                                            188

<210> SEQ ID NO 179
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 179
ugauaauagu ccauaaagua ggaaacacua cagcuggagc cucgguggcc uagcuucuug     60
ccccuugggc cuccccccag ccccuccucc ccuuccugca cccguacccc cguggucuuu   120
gaauaaaguc ugagugggcg gc                                            142

<210> SEQ ID NO 180
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 180
ugauaauagg cuggagccuc gguggcucca uaaaguagga aacacuacac uagcuucuug     60
ccccuugggc cuccccccag ccccuccucc ccuuccugca cccguacccc cguggucuuu   120
gaauaaaguc ugagugggcg gc                                            142

<210> SEQ ID NO 181
<211> LENGTH: 142
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 181
ugauaauagg cuggagccuc gguggccuag cuucuugccc cuugggccuc cauaaaguag        60
gaaacacuac auccccccag ccccuccucc ccuuccugca cccguacccc cguggucuuu       120
gaauaaaguc ugagugggcg gc                                                142

<210> SEQ ID NO 182
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
ugauaauagg cuggagccuc gguggccuag cuucuugccc cuugggccuc ccccagccc         60 cuccccccu uccugcaccc guaccccac cccaucaca auuagcauua agugucuuu           120 gaauaaaguc ugagugggcg gc                                                142

<210> SEQ ID NO 183
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
ugauaauaga ccccuaucac aauuagcauu aagcuggagc cucggguggcc uagcuucuug        60 ccccuuggc caccccuauc acaauuagca uuaauccccc cagccccucc ucccuuccu         120 gcacccguac ccccacccu aucacaauua gcauuaagug gucuuugaau aaagucugag        180
ugggcggc                                                                188

<210> SEQ ID NO 184
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
ugauaauaga ccccuaucac aauuagcauu aagcuggagc cucggguggcc uagcuucuug        60 ccccuuggc cuccauaaag uaggaaacac uacaucccc cagccccucc ucccuuccu          120 gcacccguac ccccacccu aucacaauua gcauuaagug gucuuugaau aaagucugag        180
ugggcggc                                                                188

<210> SEQ ID NO 185
<211> LENGTH: 18
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 185
attgggcacc cgtaaggg                                                    18

<210> SEQ ID NO 186
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 187
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 188
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 189
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 189

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 190
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 2-5 'Gly Gly
      Gly Ser' repeating units"

<400> SEQUENCE: 190

Gly Gly Gly Ser Gly Gly Gly Ser Gly Gly Gly Ser Gly Gly Gly Ser
1               5                   10                  15

Gly Gly Gly Ser
            20

<210> SEQ ID NO 191
<211> LENGTH: 66
<212> TYPE: RNA
<213> ORGANISM: Unknown
<220> FEATURE:
<221> NAME/KEY: source
<223> OTHER INFORMATION: /note="Description of Unknown:
      2A sequence"

<400> SEQUENCE: 191
ggaagcggag cuacuaacuu cagccugcug aagcaggcug gagacgugga ggagaacccu      60
ggaccu                                                                66

<210> SEQ ID NO 192
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="Description of Combined DNA/RNA
      Molecule: Synthetic polynucleotide"

<400> SEQUENCE: 192
uccggacuca gauccgggga ucucaaaauu gucgcuccug ucaaacaaac ucuuaacuuu      60
gauuuacuca aacuggctgg ggauguagaa agcaauccag gtccacuc                 108

<210> SEQ ID NO 193

<400> SEQUENCE: 193

000
```

```
<210> SEQ ID NO 194
<400> SEQUENCE: 194

000

<210> SEQ ID NO 195
<211> LENGTH: 460
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195
```

Met Asp Tyr Lys Asp Asp Asp Lys Ser Thr Ala Val Leu Glu Asn
1               5                   10                  15

Pro Gly Leu Gly Arg Lys Leu Ser Asp Phe Gly Gln Glu Thr Ser Tyr
                20                  25                  30

Ile Glu Asp Asn Cys Asn Gln Asn Gly Ala Ile Ser Leu Ile Phe Ser
            35                  40                  45

Leu Lys Glu Glu Val Gly Ala Leu Ala Lys Val Leu Arg Leu Phe Glu
    50                  55                  60

Glu Asn Asp Val Asn Leu Thr His Ile Glu Ser Arg Pro Ser Arg Leu
65                  70                  75                  80

Lys Lys Asp Glu Tyr Glu Phe Phe Thr His Leu Asp Lys Arg Ser Leu
                85                  90                  95

Pro Ala Leu Thr Asn Ile Ile Lys Ile Leu Arg His Asp Ile Gly Ala
            100                 105                 110

Thr Val His Glu Leu Ser Arg Asp Lys Lys Lys Asp Thr Val Pro Trp
        115                 120                 125

Phe Pro Arg Thr Ile Gln Glu Leu Asp Arg Phe Ala Asn Gln Ile Leu
    130                 135                 140

Ser Tyr Gly Ala Glu Leu Asp Ala Asp His Pro Gly Phe Lys Asp Pro
145                 150                 155                 160

Val Tyr Arg Ala Arg Arg Lys Gln Phe Ala Asp Ile Ala Tyr Asn Tyr
                165                 170                 175

Arg His Gly Gln Pro Ile Pro Arg Val Glu Tyr Met Glu Glu Glu Lys
            180                 185                 190

Lys Thr Trp Gly Thr Val Phe Lys Thr Leu Lys Ser Leu Tyr Lys Thr
        195                 200                 205

His Ala Cys Tyr Glu Tyr Asn His Ile Phe Pro Leu Leu Glu Lys Tyr
    210                 215                 220

Cys Gly Phe His Glu Asp Asn Ile Pro Gln Leu Glu Asp Val Ser Gln
225                 230                 235                 240

Phe Leu Gln Thr Cys Thr Gly Phe Arg Leu Arg Pro Val Ala Gly Leu
                245                 250                 255

Leu Ser Ser Arg Asp Phe Leu Gly Gly Leu Ala Phe Arg Val Phe His
            260                 265                 270

Cys Thr Gln Tyr Ile Arg His Gly Ser Lys Pro Met Tyr Thr Pro Glu
        275                 280                 285

Pro Asp Ile Cys His Glu Leu Leu Gly His Val Pro Leu Phe Ser Asp
    290                 295                 300

Arg Ser Phe Ala Gln Phe Ser Gln Glu Ile Gly Leu Ala Ser Leu Gly
305                 310                 315                 320

```
Ala Pro Asp Glu Tyr Ile Glu Lys Leu Ala Thr Ile Tyr Trp Phe Thr
            325                 330                 335

Val Glu Phe Gly Leu Cys Lys Gln Gly Asp Ser Ile Lys Ala Tyr Gly
        340                 345                 350

Ala Gly Leu Leu Ser Ser Phe Gly Glu Leu Gln Tyr Cys Leu Ser Glu
            355                 360                 365

Lys Pro Lys Leu Leu Pro Leu Glu Leu Glu Lys Thr Ala Ile Gln Asn
        370                 375                 380

Tyr Thr Val Thr Glu Phe Gln Pro Leu Tyr Tyr Val Ala Glu Ser Phe
385                 390                 395                 400

Asn Asp Ala Lys Glu Lys Val Arg Asn Phe Ala Ala Thr Ile Pro Arg
                405                 410                 415

Pro Phe Ser Val Arg Tyr Asp Pro Tyr Thr Gln Arg Ile Glu Val Leu
            420                 425                 430

Asp Asn Thr Gln Gln Leu Lys Ile Leu Ala Asp Ser Ile Asn Ser Glu
        435                 440                 445

Ile Gly Ile Leu Cys Ser Ala Leu Gln Lys Ile Lys
    450                 455                 460
```

<210> SEQ ID NO 196
<211> LENGTH: 1380
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 196

```
auggacuaca aggacgacga cgacaagagc accgccgugc uggagaaccc cggccugggc    60
cggaagcuga gcgacuucgg ccaggagaca agcuacaucg aggacaacug caaccagaac   120
ggcgccauca gccugaucuu uucucugaag gaggagguqg gcgcccuggc caaggugcug   180
cggcuguucg aggagaacga cgugaaccug acccacaucg agagccggcc cagccggcug   240
aagaaggacg aguacgaguu cuucaccccac cuggacaagc ggagccugcc cgcccugacc   300
aacaucauca gauccugcg gcacgacauc ggcgccaccg ugcacgagcu gagccgggac   360
aagaagaagg acaccgugcc cugguucccu cggaccaucc aggagcugga ccgguucgcc   420
aaccagaucc ugagcuacgg cgccgagcug acgccgacc accccggcuu caaggacccc   480
guguaccggg cccggcggaa gcaguucgcc gacaucgccu acaacuaccg gcacggccag   540
cccaucccuc ggguggagua cauggaggag gagaagaaga ccuggggcac cguguucaag   600
acccugaagu cucuguacaa gacccacgcc ugcuacgagu acaaccacau cuuuccucuc   660
cuggagaagu acugcggcuu ccacgaggac aauaucccuc agcuggagga cgugagccag   720
uuccugcaga ccugcaccgg cuuccggcug aggccugugg ccgggcugcu gagcagcaga   780
gacuuccugg gcgccugggc cuuccggguy uccacugca cccaguacau cagacacggg   840
agcaagccca uguacacucc cgagcccgac aucugccacg aguuacuggg ccacgugccc   900
cuguucagcg accggagcuu cgcccaguuc ucacaggaga ucgggcuggc aagccugggc   960
gcucccgacg aguauauaga gaagcuggcc accaucuacu gguucaccgu ggaguucggc  1020
cugugcaagc agggcgacag caucaaggcu uacggagcug gcugcuuag cuccuucggc  1080
gagcugcagu acugccugag cgagaagccc aagcugcugc ccuugagcu cgagaagacc  1140
gccauccaga acuacaccgu gaccgaguuc cagcccugu acuacguggc cgagagcuuc  1200
```

```
aacgacgcca aggagaaggu gcggaacuuc gccgcaaacca ucccuaggcc cuucagcgug   1260
cgguacgacc ccuacaccca gcggaucgag gugcuggaca auacccagca gcugaagauc   1320
uuagcugacu caaucaacag cgagauuggc auccugugca gcgcccugca aagaucaag    1380
```

<210> SEQ ID NO 197
<211> LENGTH: 344
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 197

```
Met Asp Tyr Lys Asp Asp Asp Lys Val Pro Trp Phe Pro Arg Thr
1               5                  10                  15

Ile Gln Glu Leu Asp Arg Phe Ala Asn Gln Ile Leu Ser Tyr Gly Ala
                20                  25                  30

Glu Leu Asp Ala Asp His Pro Gly Phe Lys Asp Pro Val Tyr Arg Ala
            35                  40                  45

Arg Arg Lys Gln Phe Ala Asp Ile Ala Tyr Asn Tyr Arg His Gly Gln
        50                  55                  60

Pro Ile Pro Arg Val Glu Tyr Met Glu Glu Glu Lys Lys Thr Trp Gly
65                  70                  75                  80

Thr Val Phe Lys Thr Leu Lys Ser Leu Tyr Lys Thr His Ala Cys Tyr
                85                  90                  95

Glu Tyr Asn His Ile Phe Pro Leu Leu Glu Lys Tyr Cys Gly Phe His
            100                 105                 110

Glu Asp Asn Ile Pro Gln Leu Glu Asp Val Ser Gln Phe Leu Gln Thr
        115                 120                 125

Cys Thr Gly Phe Arg Leu Arg Pro Val Ala Gly Leu Leu Ser Ser Arg
130                 135                 140

Asp Phe Leu Gly Gly Leu Ala Phe Arg Val Phe His Cys Thr Gln Tyr
145                 150                 155                 160

Ile Arg His Gly Ser Lys Pro Met Tyr Thr Pro Glu Pro Asp Ile Cys
                165                 170                 175

His Glu Leu Leu Gly His Val Pro Leu Phe Ser Asp Arg Ser Phe Ala
            180                 185                 190

Gln Phe Ser Gln Glu Ile Gly Leu Ala Ser Leu Gly Ala Pro Asp Glu
        195                 200                 205

Tyr Ile Glu Lys Leu Ala Thr Ile Tyr Trp Phe Thr Val Glu Phe Gly
    210                 215                 220

Leu Cys Lys Gln Gly Asp Ser Ile Lys Ala Tyr Gly Ala Gly Leu Leu
225                 230                 235                 240

Ser Ser Phe Gly Glu Leu Gln Tyr Cys Leu Ser Glu Lys Pro Lys Leu
                245                 250                 255

Leu Pro Leu Glu Leu Glu Lys Thr Ala Ile Gln Asn Tyr Thr Val Thr
            260                 265                 270

Glu Phe Gln Pro Leu Tyr Tyr Val Ala Glu Ser Phe Asn Asp Ala Lys
        275                 280                 285

Glu Lys Val Arg Asn Phe Ala Ala Thr Ile Pro Arg Pro Phe Ser Val
    290                 295                 300

Arg Tyr Asp Pro Tyr Thr Gln Arg Ile Glu Val Leu Asp Asn Thr Gln
305                 310                 315                 320
```

Gln Leu Lys Ile Leu Ala Asp Ser Ile Asn Ser Glu Ile Gly Ile Leu
            325                 330                 335

Cys Ser Ala Leu Gln Lys Ile Lys
            340

<210> SEQ ID NO 198
<211> LENGTH: 1032
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 198

| | | |
|---|---|---|
| auggacuaca aggacgacga cgacaaggug cccugguucc cacggaccau ccaggagcug | 60 |
| gaccgguucg ccaaccagau ccugagcuac ggcgccgagc uggacgccga ccaccccggc | 120 |
| uucaaggacc ccguguaccg ggccggcgg aagcaguucg ccgacaucgc cuacaacuac | 180 |
| cggcacggcc agcccauccc gcgggugag uacauggagg aggagaagaa gaccggggc | 240 |
| accguguuca agacccugaa gagccuguac aagacccacg ccugcuacga guacaaccac | 300 |
| aucuucccuc ugcuggagaa guacugcggc uuccacgagg acaacauccc gcagcuggag | 360 |
| gacgugagcc aguccugca gaccugcacc ggcuuccggc ugcggcccgu ggccggccug | 420 |
| cugagcagcg ggacuuccu gggcggccug gccuuccggg uguuccacug cacccaguac | 480 |
| auccggcacg gcagcaagcc caguacacg cccgagcccg acaucugcca cgagcugcug | 540 |
| ggccacgugc cccuguucag cgaccggagc uucgcccagu ucagcagga gaucggccug | 600 |
| gccagccugg gcgcgcccga cgaguacauc gagaagcugg ccaccaucua cugguucacc | 660 |
| guggaguucg gccugugcaa gcagggcgac agcaucaagg ccuacggcgc cggccugcug | 720 |
| agcagcuucg gcgagcugca guacugccug agcgagaagc ccaagcugcu gccccuggag | 780 |
| cuggagaaga ccgccaucca gaacuacacc gugaccgagu ccagcccccu guacuacgug | 840 |
| gccgagagcu caacgacgc caaggagaag gugcggaacu cgccgccac caucccucgg | 900 |
| ccccuucagcg ugcgguacga cccccuacacc cagcggaucg aggugcugga caacacccag | 960 |
| cagcugaaga uccuggccga cagcaucaac agcgagaucg gcauccugug cagcgcccug | 1020 |
| cagaagauca ag | 1032 |

<210> SEQ ID NO 199
<211> LENGTH: 1569
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199

| | | |
|---|---|---|
| gggaauaaag agagaaaaga agaguaagaa gaaauauaag agccaccaug gacuacaagg | 60 |
| acgacgacga caagagcacc gccgugcugg agaaccccgg ccugggccgg aagcugagcg | 120 |
| acuucggcca ggagacaagc uacaucgagg acaacugcaa ccagaacggc gccaucagcc | 180 |
| ugaucuuuuc ucugaaggag gaggugggcg cccuggccaa ggugcugcgg cuguucgagg | 240 |
| agaacgacgu gaaccugacc cacaucgaga gccggcccag ccggcugaag aaggacgagu | 300 |
| acgaguucuu cacccaccug gacaagcgga gccgccccgc ccugaccaac aucaucaaga | 360 |
| uccugcggca cgacaucggc gccaccgugc acgagcugag ccgggacaag aagaaggaca | 420 |

| | |
|---|---|
| ccgugcccug guucccucgg accauccagg agcuggaccg guucgccaac cagauccuga | 480 |
| gcuacggcgc cgagcuggac gccgaccacc ccggcuucaa ggaccccgug uaccgggccc | 540 |
| ggcggaagca guucgccgac aucgccuaca acuaccggca cggccagccc aucccucggg | 600 |
| uggaguacau ggaggaggag aagaagaccu ggggcaccgu guucaagacc cugaagucuc | 660 |
| uguacaagac ccacgccugc uacgaguaca accacaucuu uccucuccug gagaaguacu | 720 |
| gcggcuucca cgaggacaau aucccucagc uggaggacgu gagccaguuc cugcagaccu | 780 |
| gcaccggcuu ccggcugagg ccuguggccg ggcugcugag cagcagagac uuccugggcg | 840 |
| gccuggccuu ccggguguuc cacugcaccc aguacaucag acacgggagc aagcccaugu | 900 |
| acacucccga gcccgacauc ugccacgagu acugggccca cgugcccoug uucagcgacc | 960 |
| ggagcuucgc ccaguucuca caggagaucg gcuggcaag ccugggcgcu cccgacgagu | 1020 |
| auauagagaa gcuggccacc aucuacuggu ucaccgugga guucggccug gcaagcagg | 1080 |
| gcgacagcau caaggcuuac ggagcugggc ugcuuagcuc cuucggcgag cugcaguacu | 1140 |
| gccugagcga gaagcccaag cugcugcccc uugagcucga aagaccgcc auccagaacu | 1200 |
| acaccgugac cgaguccag ccccuguacu acggggccga gagcuucaac gacgccaagg | 1260 |
| agaaggugcg gaacuucgcc gcaaccaucc cuaggcccuu cagcgugcgg uacgaccccu | 1320 |
| acacccagcg gaucgaggug cuggacaaua cccagcagcu gaagaucuua gcugacucaa | 1380 |
| ucaacagcga gauuggcauc cugugcagcg cccugcagaa gaucaaguga uaauaggcug | 1440 |
| gagcccucggu ggccuagcuu cuugcccuu gggccucccc ccagcccouc cuccccuucc | 1500 |
| ugcacccgua ccccccuccau aaaguaggaa acacuacagu ggucuuugaa uaaagucuga | 1560 |
| gugggcggc | 1569 |

<210> SEQ ID NO 200
<211> LENGTH: 1221
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 200

| | |
|---|---|
| gggaaauaag agagaaaaga agaguaagaa gaaauauaag agccaccaug gacuacaagg | 60 |
| acgacgacga caaggugccc ugguucccac ggaccauccca ggagcuggac cgguucgcca | 120 |
| accagauccu gagcuacggc gccgagcugg acgccgacca ccccggcuuc aaggaccccg | 180 |
| uguaccgggc ccggcggaag caguucgccg acaucgccua caacuaccgg cacggccagc | 240 |
| ccaucccgcg gguggaguac augggaggag agaagaagac cuggggcacc guguucaaga | 300 |
| cccugaagag ccuguacaag acccacgccu gcuacgagua caaccacauc uucccucugc | 360 |
| uggagaagua cugcggcuuc cacgaggaca caucccgca gcuggaggac gugagccagu | 420 |
| uccugcagac cugcaccggc uuccggcugc ggcccgugc cggccugcug agcagccggg | 480 |
| acuuccuggg cggccuggcc uuccggggugu uccacugcac ccaguacauc ggcacggca | 540 |
| gcaagcccau guacacgccc gagcccgaca ucugccacga gcugcugggc cacgugcccc | 600 |
| uguucagcga ccggagcuuc gcccaguuca gccaggagau cggccuggcc agccugggcg | 660 |
| cgcccgacga guacaucgag aagcuggcca ccaucuacug guucaccgug gaguucggcc | 720 |
| ugucaagca gggcgacagc aucaaggccu acggcgccgg ccugcugagc agcuucggcg | 780 |
| agcugcagua cugccugagc gagaagccca agcugcugcc ccuggagcug gagaagaccg | 840 |

```
ccauccagaa cuacaccgug accgaguucc agccccugua cuacguggcc gagagcuuca    900
acgacgccaa ggagaaggug cggaacuucg ccgccaccau cccucggccc uucagcgugc    960
gguacgaccc cuacacccag cggaucgagg ugcuggacaa cacccagcag cugaagaucc   1020
uggccgacag caucaacagc gagaucggca uccugugcag cgcccugcag aagaucaagu   1080
gauaauaggc uggagccucg guggccuagc uucuugcccc uugggccucc cccagcccc    1140 uccucccuu ccugcacccg uacccccucc auaaaguagg aaacacuaca ggugucuuug    1200
aauaaagucu gagugggcgg c                                            1221
```

<210> SEQ ID NO 201
<211> LENGTH: 1243
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 201

```
gggaaauaag agagaaaaga agaguaagaa gaaauauaag agccaccaug gugcccuggu     60
ucccacggac cauccaggag cuggaccggu ucgccaacca gauccugagc uacggcgccg    120
agcuggacgc cgaccacccc ggcuucaagg accccgugua ccgggcccgg cggaagcagu    180
ucgccgacau cgccuacaac uaccggcacg gccagcccau cccgcggug gaguacaugg     240 aggaggagaa gaagaccugg ggcaccgugu ucaagacccu gaagagccug uacaagaccc    300
acgccugcua cgaguacaac cacaucuucc cucugcugga aguacugc ggcuuccacg      360 aggacaacau cccgcagcug gaggacguga gccaguccu gcagaccugc accggcuucc    420
ggcugcggcc cguggccggc cugcugagca gcgggacuu ccugggcggc cuggccuucc    480
gggguuccca cugcacccag uacauccggc acggcagcaa gcccauguac acgcccgagc    540
ccgacaucug ccacgagcug cugggccacg ugccccuguu cagcgaccgg agcuucgccc    600
aguucagcca ggagaucggc cuggccagcc ugggcgcgcc cgacgaguac aucgagaagc    660
uggccaccau cuacugguuc accguggagu ucggccugug caagcagggc gacagcauca    720
aggccuacgg cgccggccug cugagcagcu acggcgagcu gcaguacugc cugagcgaga    780
agcccaagcu gcugcccug gagcuggaga agaccgccau ccagaacuac accgugaccg    840
aguuccagcc ccuguacuac guggccgaga gcuucaacga cgccaaggag aaggugcgga    900
acuucgccgc caccauccc cggccuuca gcgugcggua cgaccccuac acccagcgga    960
ucgaggugcu ggacaacacc cagcagcuga agaccuggc cgacagcauc aacagcgaga   1020
ucggcauccu gugcagcgcc cugcagaaga ucaagugaua auaguccaua aaguaggaaa   1080
cacuacagcu ggagccucgg uggccuagcu ucuugcccu ugggccucca uaaaguagga    1140
aacacuacau cccccccagcc ccuccucccc uuccugcacc cguaccccu ccauaaagua    1200 ggaaacacua cagguguucuu ugaauaaagu cugagugggc ggc                      1243
```

<210> SEQ ID NO 202
<211> LENGTH: 1196
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 202

```
gggaaauaag agagaaaaga agaguaagaa gaaauauaag agccaccaug gugcccuggu      60
ucccacggac cauccaggag cuggaccggu ucgccaacca gauccugagc uacggcgccg     120
agcuggacgc cgaccacccc ggcuucaagg accccgugua ccggggccggg cggaagcagu    180
ucgccgacau cgccuacaac uaccggcacg gccagcccau cccgcggguug gaguacaugg    240
aggaggagaa gaagaccugg ggcaccgugu ucaagacccu gaagagccug uacaagaccc     300
acgccugcua cgaguacaac cacaucuucc cucugcugga aguacugc ggcuccacg        360
aggacaacau cccgcagcug gaggacguga gccaguccu gcagaccugc accggcuucc     420
ggcugcggcc cguggccggc cugcugagca gccgggacuu ccugggcggc cuggccuucc    480
ggguguucca cugcacccag uacauccggc acggcagcaa gcccauguac acgcccgagc    540
ccgacaucug ccacgagcug cugggccacg ugccccuguu cagcgaccgg agcuucgccc    600
aguucagcca ggagaucggc cuggccagcc ugggcgcgcc cgacgaguac aucgagaagc    660
uggccaccau cuacugguuc accgugagu ucggccugu caagcagggc gacagcauca     720
aggccuacgg cgccggccug cugagcagcu ucggcgagcu gcaguacugc cugagcgaga    780
agcccaagcu gcugccccug gagcuggaga agaccgccau ccagaacuac accgugaccg    840
aguuccagcc ccuguacuac guggccgaga gcuucaacga cgccaaggag aaggugcgga    900
acuucgccgc caccacccu cggcccuuca gcgugcggua cgaccccuac acccagcgga    960
ucgaggugcu ggacaacacc cagcagcuga agauccuggc cgacagcauc aacagcgaga   1020
ucggcauccu gugcagcgcc cugcagaaga ucaagugaua auaggcugga gccucggugg   1080
ccuagcuucu ugcccuuggg ccuccccccc agccccuccu cccuuccug cacccguacc    1140
ccccgcauua uuacucacgg uacgaguggu cuuugaauaa agcugagug ggcggc         1196
```

<210> SEQ ID NO 203
<211> LENGTH: 1174
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 203

```
gggaaauaag agagaaaaga agaguaagaa gaaauauaag agccaccaug gugcccuggu      60
ucccacggac cauccaggag cuggaccggu ucgccaacca gauccugagc uacggcgccg     120
agcuggacgc cgaccacccc ggcuucaagg accccgugua ccggggccggg cggaagcagu    180
ucgccgacau cgccuacaac uaccggcacg gccagcccau cccgcggguug gaguacaugg    240
aggaggagaa gaagaccugg ggcaccgugu ucaagacccu gaagagccug uacaagaccc     300
acgccugcua cgaguacaac cacaucuucc cucugcugga aguacugc ggcuccacg        360
aggacaacau cccgcagcug gaggacguga gccaguccu gcagaccugc accggcuucc     420
ggcugcggcc cguggccggc cugcugagca gccgggacuu ccugggcggc cuggccuucc    480
ggguguucca cugcacccag uacauccggc acggcagcaa gcccauguac acgcccgagc    540
ccgacaucug ccacgagcug cugggccacg ugccccuguu cagcgaccgg agcuucgccc    600
aguucagcca ggagaucggc cuggccagcc ugggcgcgcc cgacgaguac aucgagaagc    660
uggccaccau cuacugguuc accgugagu ucggccugu caagcagggc gacagcauca     720
aggccuacgg cgccggccug cugagcagcu ucggcgagcu gcaguacugc cugagcgaga    780
```

```
agcccaagcu gcugccccug gagcuggaga agaccgccau ccagaacuac accgugaccg      840
aguuccagcc ccuguacuac guggccgaga gcuucaacga cgccaaggag aaggugcgga      900
acuucgccgc caccaucccu cggcccuuca gcgugcggua cgaccccuac acccagcgga      960
ucgaggugcu ggacaacacc cagcagcuga agauccuggc cgacagcauc aacagcgaga     1020
ucggcauccu gugcagcgcc cugcagaaga ucaagugaua auaggcugga gccucgguggg    1080 ccuagcuucu ugcccuugg gccuccccc agcccuccu ccccuuccug cacccguacc       1140 cccgugguucu uugaauaaag ucugagugggg cggc                              1174
```

<210> SEQ ID NO 204
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204

```
aggaaauaag agagaaaaga agaguaagaa gaaauauaag agccacc                    47
```

<210> SEQ ID NO 205
<211> LENGTH: 57
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205

```
aggaaauaag agagaaaaga agaguaagaa gaaauauaag accccggcgc cgccacc          57
```

<210> SEQ ID NO 206
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 206

```
ugauaauagg cuggagccuc gguggccaug cuucuugccc cuugggccuc ccccagccc       60 cuccucccu uccugcaccc guaccccca aacaccauug ucacaaucca guggucuuug       120
aauaaagucu gagugggcgg c                                                141
```

<210> SEQ ID NO 207
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 207

```
ugauaauagg cuggagccuc gguggccuag cuucuugccc cuugggccuc ccccagccc       60 cuccucccu uccugcaccc guaccccca aacaccauug ucacaaucca guggucuuug       120
aauaaagucu gagugggcgg c                                                141
```

```
<210> SEQ ID NO 208
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                         100

<210> SEQ ID NO 209
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      2A sequence"

<400> SEQUENCE: 209

Asn Pro Gly Pro
1

<210> SEQ ID NO 210
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="This sequence may encompass 1-10 'ccg'
      repeating units"

<400> SEQUENCE: 210
ccgccgccgc cgccgccgcc gccgccgccg                                     30

<210> SEQ ID NO 211
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(24)
<223> OTHER INFORMATION: /note="This sequence may encompass 2-8 'ccg'
      repeating units"

<400> SEQUENCE: 211
ccgccgccgc cgccgccgcc gccg                                           24

<210> SEQ ID NO 212
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: misc_feature
<222> LOCATION: (1)..(18)
<223> OTHER INFORMATION: /note="This sequence may encompass 3-6 'ccg'
      repeating units"

<400> SEQUENCE: 212
ccgccgccgc cgccgccg                                                          18

<210> SEQ ID NO 213
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(15)
<223> OTHER INFORMATION: /note="This sequence may encompass 4-5 'ccg'
      repeating units"

<400> SEQUENCE: 213
ccgccgccgc cgccg                                                             15

<210> SEQ ID NO 214
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(15)
<223> OTHER INFORMATION: /note="This sequence may encompass 1-5 'ccg'
      repeating units"

<400> SEQUENCE: 214
ccgccgccgc cgccg                                                             15

<210> SEQ ID NO 215
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
ccgccgccgc cg                                                                12

<210> SEQ ID NO 216
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
ccgccgccgc cgccg                                                             15
```

-continued

```
<210> SEQ ID NO 217
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="This sequence may encompass 1-10 'gcc'
      repeating units"

<400> SEQUENCE: 217
gccgccgccg ccgccgccgc cgccgccgcc                                      30

<210> SEQ ID NO 218
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120

<210> SEQ ID NO 219
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 219
tttttttttt tttttttttt tttttttttt tttttttttt tttttttttt tttttttttt     60
tttttttttt tttttttttt tttttttttt tttttttttt tttttttttt tttttttttt    120

<210> SEQ ID NO 220
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Gly Gly Gly Ser
1

<210> SEQ ID NO 221
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 50-150
      nucleotides"
```

```
<400> SEQUENCE: 221
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150

<210> SEQ ID NO 222
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 75-150
      nucleotides"

<400> SEQUENCE: 222
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150

<210> SEQ ID NO 223
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 85-150
      nucleotides"

<400> SEQUENCE: 223
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150

<210> SEQ ID NO 224
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 90-150
      nucleotides"

<400> SEQUENCE: 224
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                      150
```

```
<210> SEQ ID NO 225
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(120)
<223> OTHER INFORMATION: /note="This sequence may encompass 90-120
      nucleotides"

<400> SEQUENCE: 225
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120

<210> SEQ ID NO 226
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(130)
<223> OTHER INFORMATION: /note="This sequence may encompass 90-130
      nucleotides"

<400> SEQUENCE: 226
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa                                                            130
```

POLYNUCLEOTIDES ENCODING PHENYLALANINE HYDROXYLASE FOR THE TREATMENT OF PHENYLKETONURIA

CROSS-REFERENCE TO RELATED APPLICATIONS

This application claims priority to U.S. Provisional Appl. No. 62/590,128, filed Nov. 22, 2017, and U.S. Provisional Appl. No. 62/679,081, filed Jun. 1, 2018. The content of the prior applications are incorporated by reference herein in their entirety.

BACKGROUND

Phenylketonuria (PKU) is an autosomal recessive inborn error of metabolism that results from a deficiency in the hepatic enzyme phenylalanine hydroxylase (PAH). This disease is found in all ethnic groups and its incidence varies widely around the world with the highest incidence being in Northern Europe. PKU is mainly caused by mutations in the PAH gene that results in decreased catalytic activity affecting the catabolic pathway of phenylalanine (Phe). The PAH enzyme requires the activity of the cofactor tetrahydrobiopterin ($BH_4$) in order to convert Phe to tyrosine (Tyr). A deficiency in either PAH or its cofactor, results in the accumulation of excess phenylalanine. This can result in severe and irreversible intellectual disability if left untreated. Other clinical features associated with untreated PKU include autistic behaviors, motor deficits, eczematous rash, and seizures. Behavioral impairment as well as psychiatric disturbances generally become apparent with age.

Currently, there is no cure for PKU. The prevailing treatment is mainly through dietary restriction of Phe to the minimum required for normal growth, supplemented with specifically designed medical foods. However, there are at least four major issues with current dietary treatment: (i) dietary compliance due to unpalatability of the diet; (ii) persisting neurological or psychosocial issues and poor quality of life despite early intervention; (iii) potential nutritional deficiencies resulting from restrictive diet; and (iv) financial burden due to the cost of special medical food and dietary supplements.

For a subset of patients with hyperphenylalaninemia that have mutations in the cofactor $BH_4$, a synthetic analogue of $BH_4$ called sapropterin is typically used for treatment. One can distinguish between PKU caused by a defect in PAH versus a defect in $BH_4$ by a $BH_4$ loading test. While treatment with synthetic biopterin compounds or sapropterin are generally successful in $BH_4$-responsive PKU patients, for about 90% of patients with classical PKU, who comprise about 50-80% of patients detected by newborn screening (PAHdb; pandb.mcgill.ca), $BH_4$ therapy has no beneficial effects.

Gene therapy by targeting a functional recombinant PAH gene to the liver using viral vectors including adenoviral and adeno-associated viral vectors have been tested for the ability to correct PKU in mouse models or to correct cultured hepatocytes derived from these mouse models. Within one week, complete normalization of the serum phenylalanine levels was achieved in PKU mice; however, the therapeutic effect of the adenoviral vector ceased after a few weeks and repeated administration did not recapitulate the original results due to development of an immune response. Another study showed that a recombinant adeno-associated virus (rAAV) vector carrying the mouse PAH cDNA delivered to the liver by portal vein injection reduced blood Phe levels in PKU mice; however, this reduction was only noted in male PKU mice. Three times more vector was needed for female PKU mice to achieve an equivalent reduction in serum Phe levels as that seen in male mice. Furthermore, correction did not persist beyond 40 weeks with blood Phe returning to pretreatment levels.

Another approach to treating PKU has been to use enzyme therapy by employing PAH-based fusion proteins to specifically target PAH to the liver. A decrease in plasma Phe levels for several hours after intravenous administration in mice treated with PAH-based fusion proteins was observed. However, it is likely that multiple frequent injections would be required, making this approach less practical from a clinical perspective.

Yet another approach for treating PKU has been by enzyme substitution therapy by using PAL (E.C.4.3.1.5). PAL is an enzyme found in higher plants and yeast that catalyzes the conversion of Phe to transcinnamic acid and insignificant amounts of ammonia. Unlike the mammalian enzyme (PAH), PAL is a monomer and requires no cofactors. Despite the advancement of a PAL formulation into phase III clinical trials, pre-clinical studies indicate that weekly injections are required to sustain a significant decrease in the Phe levels in the PKU mice for up to one year. Also, response to PAL dosing regimens was gender-dependent in mouse models, similar to what was observed in mice undergoing genome-targeted PAH gene therapy. Although PAL therapy reduced Phe levels and reversed PKU induced hypopigmentation in mice, repeated injections of this agent would be invasive and burdensome to the patients and their families. In fact, there have been reports of adverse immune reactions. Moreover, physiological stress, pain, inconvenience, cost, and risks of infection are associated with repeated injections.

In view of the significant problems associated with existing PKU treatments there is an unmet need in the art for an improved treatment for PKU.

SUMMARY

The present disclosure provides messenger RNA (mRNA) therapeutics for the treatment of phenylketonuria (PKU). The mRNA therapeutics of the invention are particularly well-suited for the treatment of PKU as the technology provides for the intracellular delivery of mRNA encoding PAH (or a truncated version thereof comprising the catalytic and tetramerization domains of PAH) followed by de novo synthesis of functional PAH protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the disclosure feature a combination of nucleotide modification to reduce the innate immune response and sequence optimization, in particular, within the open reading frame (ORF) of therapeutic mRNAs encoding PAH (or a truncated version thereof comprising the catalytic domain of PAH) to enhance protein expression.

In further embodiments, the mRNA therapeutic technology of the instant disclosure also features delivery of mRNA encoding PAH (or a truncated version thereof comprising the catalytic domain of PAH) via a lipid nanoparticle (LNP) delivery system. The instant disclosure features ionizable lipid-based LNPs, which have improved properties when combined with mRNA encoding PAH and administered in vivo, for example, cellular uptake, intracellular transport and/or endosomal release or endosomal escape. The LNP formulations of the disclosure also demonstrate reduced immunogenicity associated with the in vivo administration of LNPs.

In certain aspects, the disclosure relates to compositions and delivery formulations comprising a polynucleotide, e.g., a ribonucleic acid (RNA), e.g., a mRNA, encoding PAH and methods for treating PKU in a human subject in need thereof by administering the same.

The present disclosure provides a pharmaceutical composition comprising a lipid nanoparticle encapsulated mRNA that comprises an open reading frame (ORF) encoding a PAH polypeptide, wherein the composition is suitable for administration to a human subject in need of treatment for PKU.

The present disclosure further provides a pharmaceutical composition comprising: (a) a mRNA that comprises (i) an open reading frame (ORF) encoding a PAH polypeptide, wherein the ORF comprises at least one chemically modified nucleobase, sugar, backbone, or any combination thereof and (ii) an untranslated region (UTR) comprising a microRNA (miRNA) binding site; and (b) a delivery agent, wherein the pharmaceutical composition is suitable for administration to a human subject in need of treatment for PKU.

In one aspect, the disclosure features a pharmaceutical composition comprising an mRNA comprising an open reading frame (ORF) encoding a phenylalanine hydroxylase (PAH) polypeptide. The composition when administered as a single intravenous dose to a human subject in need thereof is sufficient to:
(i) increase the level of PAH activity in liver tissue to within at least 10%, at least 20%, at least 30%, at least 40%, at least 50%, at least 60%, at least 70%, at least 80%, at least 90%, or at least 100% of normal PAH activity level for at least 12 hours, at least 24 hours, at least 48 hours, at least 72 hours, at least 96 hours, or at least 120 hours post-administration;
(ii) increase the level of PAH activity in liver tissue at least 1.5-fold, at least 2-fold, at least 3-fold, at least 4-fold, at least 5-fold, at least 10-fold, at least 20-fold, or at least 50-fold compared to the human subject's baseline PAH activity level or a reference PAH activity level in a human subject having phenylketonuria (PKU) for at least 12 hours, at least 24 hours, at least 48 hours, at least 72 hours, at least 96 hours, or at least 120 hours post-administration;
(iii) reduce liver levels of phenylalanine (Phe) at least 30%, at least 40%, at least 50%, at least 60%, at least 70%, at least 80%, at least 90%, or at least 100% compared to the human subject's baseline liver Phe level or a reference liver Phe level in a human subject having PKU for at least 12 hours, at least 24 hours, at least 48 hours, at least 72 hours, at least 96 hours, or at least 120 hours post-administration;
(iv) reduce plasma, serum, and/or urine levels of Phe at least 30%, at least 40%, at least 50%, at least 60%, at least 70%, at least 80%, at least 90%, or at least 100% compared to the human subject's baseline plasma, serum, or urine Phe level or a reference plasma, serum, or urine Phe level in a human subject having PKU for at least 12 hours, at least 24 hours, at least 48 hours, at least 72 hours, at least 96 hours, or at least 120 hours post-administration;
(v) reduce liver levels of Phe at least 1.5-fold, at least 2-fold, at least 5-fold, at least 10-fold, at least 20-fold, or at least 50-fold as compared to the human subject's baseline liver Phe level or a reference liver Phe level in a patient with PKU for at least 12 hours, at least 24 hours, at least 48 hours, at least 72 hours, at least 96 hours, or at least 120 hours post-administration;
(vi) reduce plasma, serum, and/or urine level of Phe at least 1.5-fold, at least 2-fold at least 5-fold, at least 10-fold, at least 20-fold or at least 50-fold as compared to the human subject's baseline plasma, serum, and/or urine Phe level or a reference plasma, serum, and/or urine Phe level in a patient with PKU for at least 12 hours, at least 24 hours, at least 48 hours, at least 72 hours, at least 96 hours, or at least 120 hours post-administration; and/or
(vii) reduce plasma levels of Phe to less than 1,110, less than 1,100, less than 1,000, less than 950, less than 900, less than 850, less than 800, less than 750, less than 700, less than 650, less than 600, less than 550, less than 500, less than 450, less than 400, less than 350, less than 300, less than 250, less than 200, less than 150, less than 100, or less than 95 µM for at least 6 hours, at least 12 hours, at least 24 hours, at least 48 hours, at least 72 hours, at least 96 hours, or at least 120 hours post-administration.

In some embodiments of this aspect, the pharmaceutical composition comprises a delivery agent. In some instances, the delivery agent comprises a lipid nanoparticle comprising: (i) Compound II, (ii) Cholesterol, and (iii) PEG-DMG or Compound I;
(i) Compound VI, (ii) Cholesterol, and (iii) PEG-DMG or Compound I; (i) Compound II, (ii) DSPC or DOPE, (iii) Cholesterol, and (iv) PEG-DMG or Compound I; (i) Compound VI, (ii) DSPC or DOPE, (iii) Cholesterol, and (iv) PEG-DMG or Compound I; (i) Compound II, (ii) Cholesterol, and (iii) Compound I; or (i) Compound II, (ii) DSPC or DOPE, (iii) Cholesterol, and (iv) Compound I.

In some embodiments of this aspect, the PAH polypeptide comprises the amino acid sequence set forth in SEQ ID NO:1 or SEQ ID NO:21.

In some embodiments of this aspect, the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 2, 5-20, and 22-38.

In some embodiments of this aspect, the mRNA comprises a microRNA (miR) binding site. In certain instances, the microRNA is expressed in an immune cell of hematopoietic lineage or a cell that expresses TLR7 and/or TLR8 and secretes pro-inflammatory cytokines and/or chemokines. In some instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In certain instances, the microRNA binding site is for a microRNA selected from the group consisting of miR126-3p, miR-142-3p, miR-142-5p, miR-155, or any combination thereof. In one instance, the microRNA binding site is a miR-142-3p binding site. In some instances, the microRNA binding site is located in the 3' UTR of the mRNA.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4 or 150.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:175, 177, or 178.

In some embodiments of this aspect, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4, SEQ ID NO:111, SEQ ID NO:150, SEQ ID NO:175, SEQ ID NO:177, SEQ ID NO:178, SEQ ID NO:206, or SEQ ID NO:207.

In some embodiments of this aspect, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3 or 88.

In some embodiments of this aspect, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3, SEQ ID NO:39, SEQ ID NO:204, or SEQ ID NO:205.

In some embodiments of this aspect, the mRNA comprises a 5' terminal cap. In certain instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azido-guanosine, Cap2, Cap4, 5' methylG cap, or an analog thereof.

In some embodiments, the mRNA comprises a poly-A region. In certain instances, the poly-A region is at least about 10, at least about 20, at least about 30, at least about 40, at least about 50, at least about 60, at least about 70, at least about 80, at least about 90 nucleotides in length, or at least about 100 nucleotides in length. In some instances, the poly-A region has about 10 to about 200, about 20 to about 180, about 50 to about 160, about 70 to about 140, or about 80 to about 120 nucleotides in length.

In some embodiments, the mRNA comprises at least one chemically modified nucleobase, sugar, backbone, or any combination thereof. In certain instances, the at least one chemically modified nucleobase is selected from the group consisting of pseudouracil (ψ), N1 methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils.

In some embodiments, the human subject has PKU. In certain instances, the human subject is on a Phe restricted diet. In other instances, the human subject is not on a Phe restricted diet.

In another aspect, the disclosure features a polynucleotide comprising an mRNA comprising: (i) a 5' UTR; (ii) an open reading frame (ORF) encoding a human PAH polypeptide, wherein the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs:2, 5-20, and 22-38; (iii) a stop codon; and (iv) a 3' UTR.

In some embodiments, the PAH polypeptide comprises or consists of the amino acid sequence of SEQ ID NO:1. In some embodiments, the PAH polypeptide comprises or consists of the amino acid sequence of SEQ ID NO:21.

In another aspect, the disclosure features a polynucleotide comprising an mRNA comprising: (i) a 5' UTR; (ii) an open reading frame (ORF) encoding a human PAH polypeptide, wherein the ORF comprises a nucleic acid sequence selected from the group consisting of SEQ ID NOs:2, 5-20, and 22-38; (iii) a stop codon; and (iv) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 80% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 85% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 90% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 95% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 97% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 98% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF has at least 99% sequence identity to SEQ ID NO:31; and (iii) a 3' UTR.

In one aspect, the disclosure features a polynucleotide comprising an mRNA comprising: (i) a 5' UTR; (ii) an open reading frame (ORF) encoding a human PAH polypeptide (e.g., SEQ ID NO:21), wherein the ORF comprises SEQ ID NO:31; and (iii) a 3' UTR.

In some embodiments, the polynucleotide comprises a microRNA (miR) binding site. In some embodiments, the microRNA is expressed in an immune cell of hematopoietic lineage or a cell that expresses TLR7 and/or TLR8 and secretes pro-inflammatory cytokines and/or chemokines. In certain instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In some instances, the microRNA binding site is for a microRNA selected from the group consisting of miR126-3p, miR-142-3p, miR-142-5p, miR-155, or any combination thereof. In one instance, the microRNA binding site is a miR-142-3p binding site. In certain instances, the microRNA binding site is located in the 3' UTR of the mRNA.

In some embodiments, the 3' UTR comprises a nucleic acid sequence at least about 90%, at least about 95%, at least about 96%, at least about 97%, at least about 98%, at least about 99%, or 100% identical to a 3' UTR of SEQ ID NO: 4 or 150.

In some embodiments, the 3' UTR comprises a nucleic acid sequence at least about 90%, at least about 95%, at least about 96%, at least about 97%, at least about 98%, at least about 99%, or 100% identical to a 3' UTR of SEQ ID NO:175, 177, or 178.

In some embodiments, the 3' UTR comprises a nucleic acid sequence at least about 90%, at least about 95%, at least about 96%, at least about 97%, at least about 98%, at least about 99%, or 100% identical to a 3' UTR of SEQ ID NO:4, SEQ ID NO:111, SEQ ID NO:150, SEQ ID NO:175, SEQ ID NO:177, SEQ ID NO:178, SEQ ID NO:206, or SEQ ID NO:207.

In some embodiments, the 5' UTR comprises a nucleic acid sequence at least about 90%, at least about 95%, at least about 96%, at least about 97%, at least about 98%, at least about 99%, or 100% identical to a 5' UTR of SEQ ID NO: 3 or 88.

In some embodiments, the 5' UTR comprises a nucleic acid sequence at least about 90%, at least about 95%, at least about 96%, at least about 97%, at least about 98%, at least about 99%, or 100% identical to a 5' UTR of SEQ ID NO:3, SEQ ID NO:39, SEQ ID NO:204, or SEQ ID NO:205.

In some embodiments, the polynucleotide comprises a 5' terminal cap. In certain instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the polynucleotide comprises a poly-A region. In certain instances, the poly-A region is at least about 10, at least about 20, at least about 30, at least about 40, at least about 50, at least about 60, at least about 70, at least about 80, at least about 90 nucleotides in length, or at least about 100 nucleotides in length. In other instances, the poly-A region has about 10 to about 200, about 20 to about 180, about 50 to about 160, about 70 to about 140, or about 80 to about 120 nucleotides in length.

In certain embodiments, the polynucleotide comprises at least one chemically modified nucleobase, sugar, backbone, or any combination thereof. In some instances, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils.

In certain embodiments, the polynucleotide comprises a nucleic acid sequence selected from the group consisting of SEQ ID NO:45-84 or 201-203.

In another aspect the disclosure features a polynucleotide comprising an mRNA that includes: (i) a 5'-terminal cap; (ii) a 5' UTR comprising the nucleic acid sequence of SEQ ID NO:3; (iii) an open reading frame (ORF) encoding a PAH polypeptide, wherein the ORF comprises a sequence selected from the group consisting of SEQ ID NOs:2, 5-20, and 22-38; (iv) a 3' UTR comprising the nucleic acid sequence of SEQ ID NO:4, 175, 177, or 178; and (vi) a poly-A-region.

In another aspect the disclosure features a polynucleotide comprising an mRNA that includes: (i) a 5'-terminal cap; (ii) a 5' UTR comprising the nucleic acid sequence of SEQ ID NO:3, SEQ ID NO:39, SEQ ID NO:204, or SEQ ID NO:205; (iii) an open reading frame (ORF) encoding a PAH polypeptide, wherein the ORF comprises a sequence selected from the group consisting of SEQ ID NOs:2, 5-20, and 22-38; (iv) a 3' UTR comprising the nucleic acid sequence of SEQ ID NO:4, SEQ ID NO:111, SEQ ID NO:150, SEQ ID NO:175, SEQ ID NO:177, SEQ ID NO:178, SEQ ID NO:206, or SEQ ID NO:207; and (vi) a poly-A-region.

In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the poly-A region is at least about 10, at least about 20, at least about 30, at least about 40, at least about 50, at least about 60, at least about 70, at least about 80, at least about 90 nucleotides in length, or at least about 100 nucleotides in length. In certain instances, the poly-A region has about 10 to about 200, about 20 to about 180, about 50 to about 160, about 70 to about 140, or about 80 to about 120 nucleotides in length.

In certain embodiments, the mRNA comprises at least one chemically modified nucleobase, sugar, backbone, or any combination thereof. In some instances, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

In certain embodiments, the polynucleotide comprises a nucleic acid sequence selected from the group consisting of SEQ ID NO:45-84 or 201-203. In certain instances, the 5' terminal cap comprises Cap1 and all of the uracils of the polynucleotide are N1-methylpseudouracils. In certain instances, the poly-A-region is 100 nucleotides in length.

In another aspect the disclosure provides a pharmaceutical composition comprising a polynucleotide described herein and a delivery agent.

In certain embodiments, the delivery agent comprises a lipid nanoparticle comprising: (i) Compound II, (ii) Cholesterol, and (iii) PEG-DMG or Compound I; (i) Compound VI, (ii) Cholesterol, and (iii) PEG-DMG or Compound I; (i) Compound II, (ii) DSPC or DOPE, (iii) Cholesterol, and (iv) PEG-DMG or Compound I; (i) Compound VI, (ii) DSPC or DOPE, (iii) Cholesterol, and (iv) PEG-DMG or Compound I; (i) Compound II, (ii) Cholesterol, and (iii) Compound I; or (i) Compound II, (ii) DSPC or DOPE, (iii) Cholesterol, and (iv) Compound I.

In another aspect, the disclosure features a method of expressing a phenylalanine hydroxylase (PAH) polypeptide in a human subject in need thereof. The method involves administering to the subject an effective amount of a pharmaceutical composition or a polynucleotide described herein.

In another aspect, the disclosure features a method of treating, preventing, or delaying the onset and/or progression of PKU in a human subject in need thereof. The method involves administering to the subject an effective amount of a pharmaceutical composition or a polynucleotide described herein.

In another aspect, the disclosure features a method of reducing phenylalanine blood level in a human subject in need thereof. The method involves administering to the subject an effective amount of a pharmaceutical composition or a polynucleotide described herein. In certain embodiments, the method results in reducing the levels of blood or plasma Phe levels to less than 1,150 µM (e.g., less than 1,110, less than 1,100, less than 1,000, less than 950, less than 900, less than 850, less than 800, less than 750, less than 700, less than 650, less than 600, less than 550, less than 500, less than 450, less than 400, less than 350, less than 300, less than 250, less than 200, less than 150, less than 100, or less than 95 µM) for at least 6 hours, at least 12 hours, at least 24 hours, at least 48 hours, at least 72 hours, at least 96 hours, or at least 120 hours post-administration of a single intravenous dose of the pharmaceutical composition or a polynucleotide described herein.

In certain embodiments of the above methods:

(i) the Phe blood and/or liver level is reduced at least 20%, at least 30%, at least 40%, at least 50%, at least 60%, at least 70%, at least 80%, at least 90%, or at least 100% as compared to the subject's baseline Phe blood and/or liver level or a reference Phe blood and/or liver level in a patient with PKU, for at least 24 hours, at least 48 hours, at least 72 hours, at least 96 hours, at least 120 hours, 6 days, 1 week, 8 days, 9 days, 10 days, 11 days, or 12 days after a single administration;

(ii) the Phe plasma, serum, and/or urine level is reduced at least 20%, at least 30%, at least 40%, at least 30%, at least 40%, at least 50%, at least 60%, at least 70%, at least 80%, at least 90%, or at least 100% as compared to the subject's baseline Phe plasma, serum, and/or urine level or a reference Phe plasma, serum, and/or urine level in a patient with PKU, for at least 24 hours, at least 48 hours, at least 72 hours, at least 96 hours, at least 120 hours, 6 days, 1 week, 8 days, 9 days, 10 days, 11 days, or 12 days after a single administration;

(iii) the Phe blood and/or liver level is reduced to at least within 10-fold, at least within 5-fold, at least within 2-fold, or at least within 1.5-fold as compared to a normal Phe blood and/or liver level within at least 24 hours, at least 48 hours, at least 72 hours, at least 96 hours, or at least 120 hours after a single administration; and/or (iv) the Phe plasma, serum, and/or urine level is reduced to at least within 10-fold, at least within 5-fold, at least within 2-fold, or at least within 1.5-fold, as compared to a normal Phe plasma, serum, and/or urine level, for at least 24 hours, at least 48 hours, at least 72 hours, at least 96 hours, or at least 120 hours after a single administration.

In another aspect, the disclosure provides a method of increasing PAH activity in a human subject in need thereof. The method involves administering to the subject an effective amount of a pharmaceutical composition or a polynucleotide described herein.

In certain embodiments of this method:

(i) the level of PAH activity in the subject is increased at least 1.5-fold, at least 2-fold, at least 5-fold, at least 10-fold, at least 20-fold, or at least 50-fold as compared to a reference PAH activity level in a subject having PKU for at least 24 hours, at least 48 hours, at least 72 hours, at least 96 hours, or at least 120 hours after a single administration; and/or (ii) 12 hours after a single administration of the pharmaceutical composition or polynucleotide is administered to the subject, the PAH activity in the subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline PAH activity.

In certain embodiments, the PAH activity is increased in the liver or blood of the subject.

In some embodiments of any of the methods described herein, tetrahydrobiopterin ($BH_4$), an analogue thereof, a salt of tetrahydrobiopterin ($BH_4$), or a salt of the analogue thereof is co-administered (e.g., orally) to the human subject in combination with the pharmaceutical composition or polynucleotide. In some embodiments, the tetrahydrobiopterin ($BH_4$) analogue or salt thereof is sapropterin, 6-hydroxymethyl pterin (HMP), 6-acetyl-7,7-dimethyl-7,8-dihydropterin (ADDP), or a salt thereof. Tetrahydrobiopterin ($BH_4$), the analogue thereof, the salt of tetrahydrobiopterin ($BH_4$), or the salt of the analogue thereof can be administered concurrently with administration of the pharmaceutical composition or polynucleotide or before or after administration of the pharmaceutical composition or polynucleotide.

In some embodiments, the administration to the subject is about once a week, about once every two weeks, or about once a month.

In certain embodiments, the pharmaceutical composition or polynucleotide is administered intravenously. In some instances, the pharmaceutical composition or polynucleotide is administered at a dose of 0.1 mg/kg to 5.0 mg/kg. In some instances, the pharmaceutical composition or polynucleotide is administered at a dose of 0.1 mg/kg to 2.0 mg/kg. In some instances, the pharmaceutical composition or polynucleotide is administered at a dose of 0.1 mg/kg to 1.5 mg/kg. In some instances, the pharmaceutical composition or polynucleotide is administered at a dose of 0.1 mg/kg to 1.0 mg/kg. In some instances, the pharmaceutical composition or polynucleotide is administered at a dose of 0.1 mg/kg to 0.5 mg/kg.

In certain embodiments, the pharmaceutical composition or polynucleotide is administered subcutaneously. In some instances, the pharmaceutical composition or polynucleotide is administered at a dose of 0.1 mg/kg to 5.0 mg/kg. In some instances, the pharmaceutical composition or polynucleotide is administered at a dose of 0.1 mg/kg to 2.0 mg/kg. In some instances, the pharmaceutical composition or polynucleotide is administered at a dose of 0.1 mg/kg to 1.5 mg/kg. In some instances, the pharmaceutical composition or polynucleotide is administered at a dose of 0.1 mg/kg to 1.0 mg/kg. In some instances, the pharmaceutical composition or polynucleotide is administered at a dose of 0.1 mg/kg to 0.5 mg/kg.

In certain embodiments, the pharmaceutical composition or polynucleotide is administered intravenously and subcutaneously. In some instances, the method comprises one or more intravenous administrations of the pharmaceutical composition or polynucleotide followed by one or more subcutaneous administrations of the pharmaceutical composition or polynucleotide.

BRIEF DESCRIPTION OF THE DRAWINGS

FIG. 7A-B are graphs showing that systemic exposure of phenylalanine can be observed for 60-90 minutes in rats (FIG. 7A) and less than 40 minutes in mice (FIG. 7B) following administration of aspartame, irrespective of delivery route.

FIG. 20A shows the blood Phe levels before (pre-challenge) and 2, 10, 30, 45, 60, 120, 180, and 240 minutes after Phe was administered 8 hours following mRNA injection. FIG. 20B shows the blood Phe levels before (pre-challenge) and 2, 10, 30, 45, 60, 120, 180, and 240 minutes after Phe was administered 48 hours following mRNA injection.

DETAILED DESCRIPTION

Figure 1:
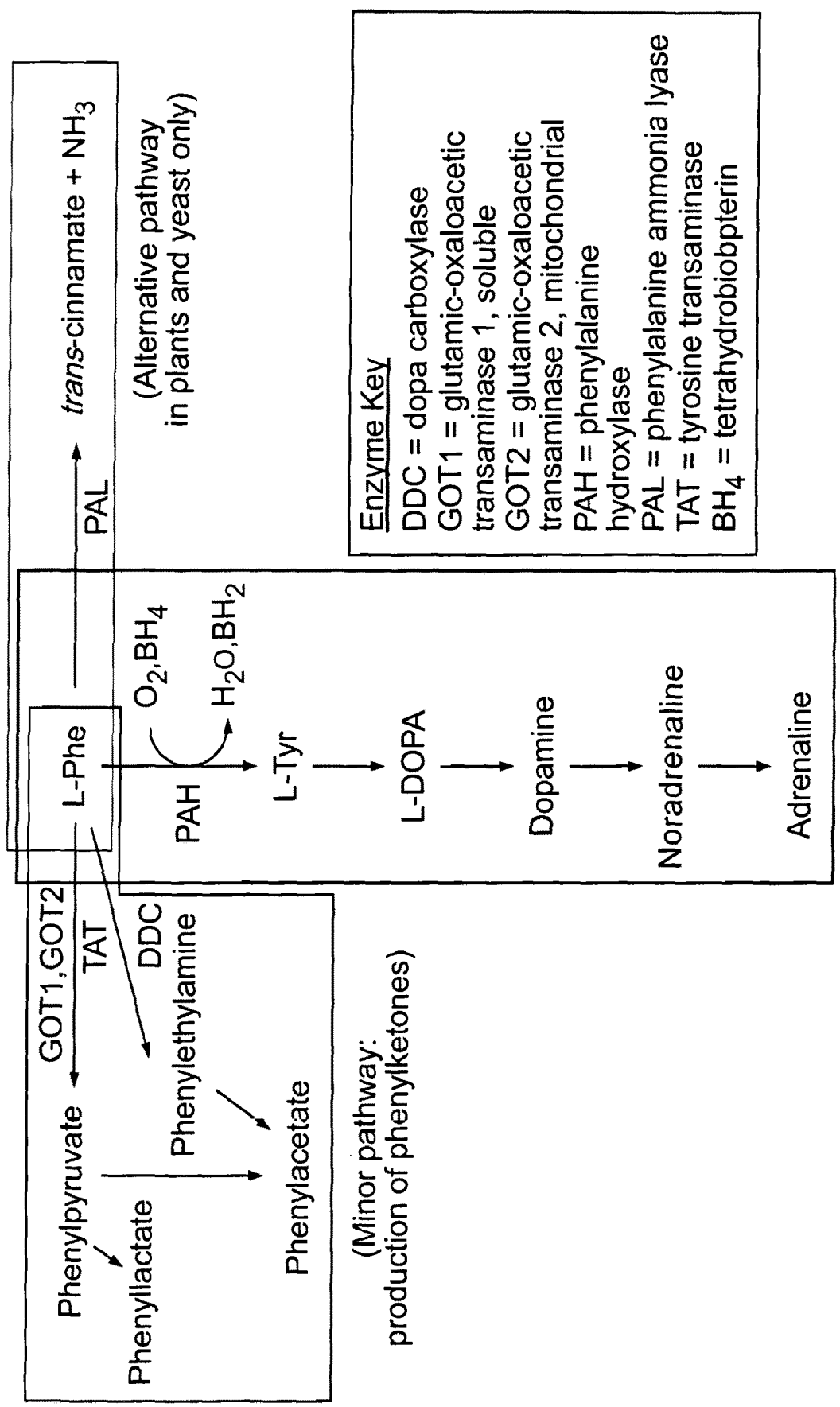
FIG. 1 shows the metabolic pathway of phenylalanine. The main pathway (central rectangle) leads to the catalytic conversion of phenylalanine to tyrosine by phenylalanine hydroxylase (PAH) in the presence of the cofactor, tetrahydrobiopterin ($BH_4$). In phenylketonuria (PKU), the PAH enzyme deficiency results in the production of phenylketones by an alternative pathway (left box). A third pathway (right box) is utilized in plants and yeast involving the enzyme phenylalanine ammonia lyase (PAL).

The present disclosure provides mRNA therapeutics for the treatment of phenylketonuria (PKU). PKU is an autosomal recessive inborn error of metabolism disorder affecting the ability to metabolize phenylalanine. PKU is caused by mutations in the PAH gene, which codes for the enzyme phenylalanine hydroxylase (PAH). Without PAH, phenylalanine catabolism is impaired, resulting in the abnormal accumulation of phenylalanine. mRNA therapeutics are particularly well-suited for the treatment of PKU as the technology provides for the intracellular delivery of mRNA encoding PAH followed by de novo synthesis of functional PAH protein within target cells. After delivery of mRNA to the target cells, the desired PAH protein is expressed by the cells' own translational machinery, and hence, fully functional PAH protein replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. This disclosure features the incorporation of different modified nucleotides within therapeutic mRNAs to minimize the immune activation and optimize the translation efficiency of mRNA to protein. Particular aspects feature a combination of nucleotide modification to reduce the innate immune response and sequence optimization, in particular, within the open reading frame (ORF) of therapeutic mRNAs encoding PAH to enhance protein expression.

Certain embodiments of the mRNA therapeutic technology of the instant disclosure also feature delivery of mRNA encoding PAH via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features ionizable lipid-based LNPs combined with mRNA encoding PAH which have improved properties when administered in vivo. Without being bound in theory, it is believed that the ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., PAH) in a therapeutic context. This is because repeat administration of mRNA therapeutics is in most instances essential to maintain necessary levels of enzyme in target tissues in subjects (e.g., subjects suffering from PKU.) Repeat dosing challenges can be addressed on multiple levels. mRNA engineering and/or efficient delivery by LNPs can result in increased levels and or enhanced duration of protein (e.g., PAH) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the disclosure in one aspect, combats the ABC phenomenon. Moreover, LNPs can be engineered to avoid immune sensing and/or recognition and can thus further avoid ABC upon subsequent or repeat dosing. An exemplary aspect of the disclosure features LNPs which have been engineered to have reduced ABC.

1. Phenylalanine Hydroxylase (PAH)

Phenylalanine hydroxylase (PAH, EC 1.14.16.1) catalyzes the conversion of L-phenylalanine (L-Phe) to L-tyrosine (L-Tyr) by para-hydroxylation of the aromatic sidechain (see, FIG. 1). In mammals, this tetrahydrobiopterin ($BH_4$)-dependent reaction is the initial and rate-limiting step in the degradation of excess L-Phe from dietary proteins, where L-Tyr is further degraded to products that feed into the citric acid cycle. PAH consumes about 75% of the phenylalanine input from the diet and protein catabolism under physiological conditions.

PAH is primarily present in the liver, where removal of excess L-Phe prevents the neurotoxic effect of hyperphenylalaninemia (HPA). However, L-Phe is also an essential proteinogenic amino acid so it is important that it is not fully catabolized. To accomplish this dual role of preserving, yet removing excess L-Phe effectively, mammalian PAH has developed several regulatory mechanisms.

Figure 2:
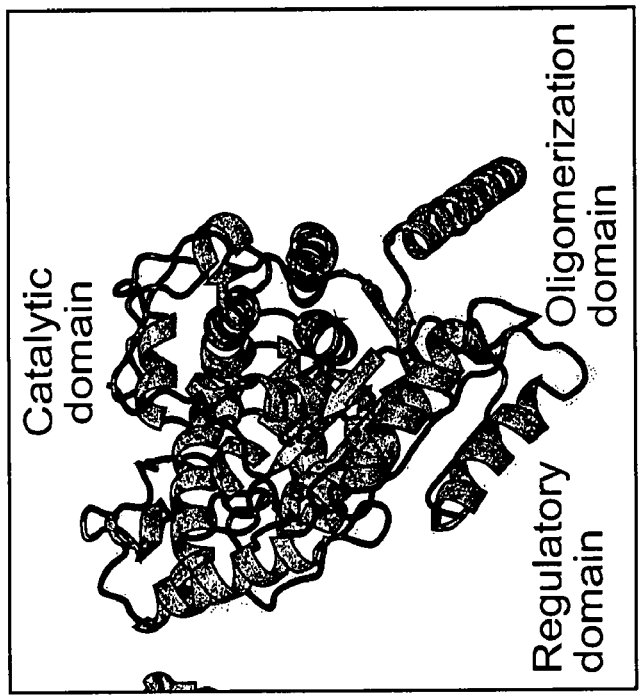
FIG. 2 provides a ribbon diagram and schematic diagram of the domain organization and structure of PAH.
Figure 2:
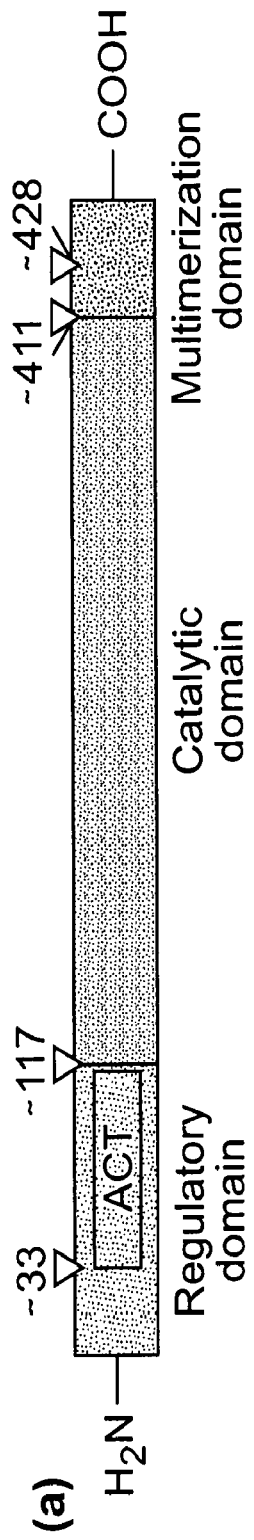

Mammalian PAH is a homo-tetrameric enzyme of 50 kDa subunits. Each PAH subunit is composed of an N-terminal regulatory domain (residues 1-110), a central catalytic domain (residues 111-410), and a C-terminal oligomerization domain (residues 411-452) (see, FIG. 2). The N-terminal regulatory domain is flexibly attached to the catalytic domain via a hinge region (Arg111-Thr117). The regulatory domain is necessary for manifestation of the regulatory properties, such as activation by L-Phe, and there is an ongoing debate as to whether or not it includes an allosteric binding-site for L-Phe. The catalytic domain contains the binding sites for iron, cofactor, and substrate. At the active site iron binds to two histidines (His285 and His290 in hPAH) and a glutamate (Glu330 in hPAH). The oligomerization domain starts by an antiparallel-sheet (residues 411-414, 421-424), responsible for dimerization, followed by a 40 Å long-helix (428-452) that mediates tetramerization through domain swapping and antiparallel coiled-coil formation with the other monomers.

In humans, mutations in the PAH gene lead to phenylketonuria (PKU), and most mutations are mainly associated with PAH misfolding and instability. There are more than 500 disease-causing mutations (pandb.mcgill.ca and biopku.org). Dysfunctional PAH leads to increased concentration of L-Phe in the blood and the appearance in urine of metabolites that arise from the transamination of L-Phe to phenylpyruvate. This is the hallmark of the hyperphenylalaninemias (HPAs), of which classic phenylketonuria (PKU) is the most severe form with plasma L-Phe levels greater than 1,200 µM. The accumulation of L-Phe and the subsequent disturbance in brain neurotransmitters leads to neurological symptoms including mental retardation, purposeless movements, and depression. The dietary intake of L-Phe must therefore be strictly controlled in PKU patients.

The amino acid sequence of human PAH is provided in SEQ ID NO:1. The amino acid sequence of a truncated version of human PAH (referred to as PAH-ΔRD protein, PAHARD protein, or ΔrdPAH protein) is provided in SEQ ID NO:21. This truncated version is 336 amino acids in length and comprises the catalytic domain of PAH. A significant number of the human PAH mutations are found in the catalytic domain.

In certain aspects, the disclosure provides a polynucleotide (e.g., a RNA, e.g., a mRNA) comprising a nucleotide sequence (e.g., an open reading frame (ORF)) encoding a PAH polypeptide. In some embodiments, the PAH polypeptide of the invention is a wild type full length human PAH protein. In some embodiments, the PAH polypeptide of the invention is a variant, a peptide or a polypeptide containing a substitution, and insertion and/or an addition, a deletion and/or a covalent modification with respect to a wild-type PAH sequence. In some embodiments, the PAH polypeptide of the invention is a truncated human PAH protein (e.g., the protein of SEQ ID NO:21). In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a human PAH sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

PAH protein fragments, functional protein domains, variants, and homologous proteins (orthologs) are also within the scope of the PAH polypeptides of the disclosure. Non-limiting examples of polypeptides encoded by the polynucleotides of the invention are shown in SEQ ID NO:1 and SEQ ID NO:21.

Certain compositions and methods presented in this disclosure refer to the protein or polynucleotide sequences of wild type human PAH. Such disclosures are equally applicable to other variants of PAH known in the art such as the truncated version (a PAH comprising the catalytic and tetramerization domains) set forth in SEQ ID NO:21.

2. Polynucleotides and Open Reading Frames (ORFs)

The instant invention features mRNAs for use in treating or preventing a hyperphenylalaninema such as PKU. The mRNAs featured for use in the invention are administered to subjects and encode human PAH protein in vivo. Accordingly, the invention relates to polynucleotides, e.g., mRNA, comprising an open reading frame of linked nucleosides encoding human PAH (SEQ ID NO:1), functional fragments thereof (e.g., SEQ ID NO:21), and fusion proteins comprising PAH. In some embodiments, the open reading frame is sequence-optimized. In particular embodiments, the invention provides sequence-optimized polynucleotides comprising nucleotides encoding the polypeptide sequence of human PAH, or sequence having high sequence identity with those sequence optimized polynucleotides.

In certain aspects, the invention provides polynucleotides (e.g., a RNA such as an mRNA) that comprise a nucleotide sequence (e.g., an ORF) encoding one or more PAH polypeptides. In some embodiments, the encoded PAH polypeptide of the invention can be selected from:

(i) a full length PAH polypeptide (e.g., having the same or essentially the same length as wild-type PAH; e.g., wild type human PAH);

(ii) a functional fragment of PAH described herein (e.g., a truncated (e.g., deletion of carboxy, amino terminal, or internal regions) sequence shorter than PAH; but still retaining PAH enzymatic activity) such as a PAH comprising the catalytic and tetramerization domains of human PAH;

(iii) a variant thereof (e.g., full length or truncated PAH proteins in which one or more amino acids have been replaced, e.g., variants that retain all or most of the PAH activity of the polypeptide with respect to a reference protein (such as any natural or artificial variants known in the art)); or (iv) a fusion protein comprising (i) a full length PAH protein (e.g., SEQ ID NO:1), a functional fragment (e.g., SEQ ID NO:21) or a variant thereof, and (ii) a heterologous protein.

In certain embodiments, the encoded PAH polypeptide is a mammalian PAH polypeptide, such as a human PAH polypeptide, a functional fragment or a variant thereof.

In some embodiments, the polynucleotide (e.g., a RNA, e.g., an mRNA) of the invention increases PAH protein expression levels and/or detectable PAH enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to PAH protein expression levels and/or detectable PAH enzymatic activity levels in the cells prior to the administration of the polynucleotide of the invention. PAH protein expression levels and/or PAH enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human PAH, e.g., (SEQ ID NO: 1) or a truncated version of human PAH (SEQ ID NO: 21).

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from a wild-type PAH sequence (e.g., wild-type human PAH). For example, for polynucleotides of invention comprising a sequence optimized ORF encoding PAH, the corresponding wild type sequence is the native human PAH. Similarly, for a sequence optimized mRNA encoding a functional fragment of human PAH, the corresponding wild type sequence is the corresponding fragment from human PAH.

In some embodiments, the polynucleotides (e.g., a RNA, e.g., an mRNA) of the invention comprise a nucleotide sequence encoding PAH having the full length sequence of human PAH (i.e., including the initiator methionine; amino acids 1-452).

In some embodiments, the polynucleotides (e.g., a RNA, e.g., an mRNA) of the invention comprise a nucleotide sequence (e.g., an ORF) encoding a mutant PAH polypeptide. In some embodiments, the polynucleotides of the invention comprise an ORF encoding a PAH polypeptide that comprises at least one point mutation in the PAH amino acid sequence and retains PAH enzymatic activity. In some embodiments, the mutant PAH polypeptide has a PAH activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PAH activity of the corresponding wild-type PAH (i.e., the same PAH polypeptide but without the mutation(s)). In some embodiments, the polynucleotide (e.g., a RNA, e.g., an mRNA) of the invention comprising an ORF encoding a mutant PAH polypeptide is sequence optimized.

In some embodiments, the polynucleotide (e.g., a RNA, e.g., an mRNA) of the invention comprises a nucleotide sequence (e.g., an ORF) that encodes a PAH polypeptide with mutations that do not alter PAH enzymatic activity. Such mutant PAH polypeptides can be referred to as function-neutral. In some embodiments, the polynucleotide comprises an ORF that encodes a mutant PAH polypeptide comprising one or more function-neutral point mutations.

In some embodiments, the mutant PAH polypeptide has higher PAH enzymatic activity than the corresponding wild-type PAH. In some embodiments, the mutant PAH polypeptide has a PAH activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type PAH (i.e., the same PAH protein but without the mutation(s)).

In some embodiments, the polynucleotides (e.g., a RNA, e.g., an mRNA) of the invention comprise a nucleotide sequence (e.g., an ORF) encoding a functional PAH fragment, e.g., where one or more fragments correspond to a polypeptide subsequence of a wild type PAH polypeptide and retain PAH enzymatic activity. In some embodiments, the PAH fragment has a PAH activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PAH activity of the corresponding full length PAH. In some embodiments, the polynucleotides (e.g., a RNA, e.g., an mRNA) of the invention comprising an ORF encoding a functional PAH fragment is sequence optimized.

In some embodiments, the polynucleotide (e.g., a RNA, e.g., an mRNA) of the invention comprises a nucleotide sequence (e.g., an ORF) encoding a PAH fragment that has higher PAH enzymatic activity than the corresponding full length PAH. Thus, in some embodiments the PAH fragment has a PAH activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the PAH activity of the corresponding full length PAH.

In some embodiments, the polynucleotide (e.g., a RNA, e.g., an mRNA) of the invention comprises a nucleotide sequence (e.g., an ORF) encoding a PAH fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type PAH.

In some embodiments, the polynucleotide (e.g., a RNA, e.g., an mRNA) of the invention comprises a nucleotide sequence (e.g., an ORF) encoding a PAH polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2, 5-20, or 22-38.

In some embodiments, the polynucleotide (e.g., a RNA, e.g., an mRNA) of the invention comprises a nucleotide sequence (e.g., an ORF) encoding a PAH polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 2, 5-20, or 22-38.

In some embodiments, the polynucleotide (e.g., a RNA, e.g., an mRNA) of the invention comprises a nucleotide sequence (e.g., an ORF) encoding a PAH polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 2, 5-20, or 22-38.

In some embodiments, the polynucleotide (e.g., a RNA, e.g., an mRNA) of the invention comprises an ORF encoding a PAH polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 8, 9, 10, 28, 30, or 31.

In some embodiments the polynucleotide (e.g., a RNA, e.g., an mRNA) of the invention comprises a nucleotide sequence (e.g., an ORF) encoding a PAH polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to the sequence of SEQ ID NO: 2, 5-20, or 22-38.

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to 25,000, from 1,187 to 50,000, from 1,187 to 70,000, or from 1,187 to 100,000).

In some embodiments, the polynucleotide of the invention (e.g., a RNA, e.g., an mRNA) comprises a nucleotide sequence (e.g., an ORF) encoding a PAH polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,100, 1,187, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a PAH polypeptide (e.g., the wild-type sequence, functional fragment, or variant thereof) further comprises at least one nucleic acid sequence that is noncoding, e.g., a microRNA binding site. In some embodiments, the polynucleotide (e.g., a RNA, e.g., an mRNA) of the invention further comprises a 5'-UTR (e.g., selected from the sequences of SEQ ID NOs: 3, 88-102, or 165-167 or selected from the sequences of SEQ ID NO:3, SEQ ID NO:39, SEQ ID NO:204, or SEQ ID NO:205) and a 3'UTR (e.g., selected from the sequences of SEQ ID NOs: 4, 104-112, or 150 or selected from the sequences of SEQ ID NO:4, SEQ ID NO:111, SEQ ID NO:150, SEQ ID NO:175, SEQ ID NO:177, SEQ ID NO:178, SEQ ID NO:206, or SEQ ID NO:207). In some embodiments, the polynucleotide (e.g., a RNA, e.g., an mRNA) of the invention comprises a sequence selected from the group consisting of SEQ ID NOs: 2, 5 to 20, and 22 to 38. In a further embodiment, the polynucleotide (e.g., a RNA, e.g., an mRNA) comprises a 5' terminal cap (e.g., Cap0, Cap1, ARCA, inosine, N1-methylguanosine, 2'-fluoro-guanosine, 7-deaza-guanosine, 8-oxoguanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 4, 111, or 112 or any combination thereof. In some embodiments, the polynucleotide (e.g., a RNA, e.g., an mRNA) a comprises a 3' UTR comprising a nucleic acid sequence selected from the group consisting of SEQ ID NO:4, SEQ ID NO:111, SEQ ID NO:150, SEQ ID NO:175, SEQ ID NO:177, SEQ ID NO:178, SEQ ID NO:206, or SEQ ID NO:207 or any combination thereof. In some embodiments, the mRNA comprises a 3' UTR comprising a nucleic acid sequence of SEQ ID NO: 111. In some embodiments, the mRNA comprises a 3' UTR comprising a nucleic acid sequence of SEQ ID NO: 150. In some embodiments, the mRNA comprises a 3' UTR comprising a nucleic acid sequence of SEQ ID NO: 175. In some embodiments, the mRNA comprises a 3' UTR comprising a nucleic acid sequence of SEQ ID NO: 177. In some embodiments, the mRNA comprises a 3' UTR comprising a nucleic acid sequence of SEQ ID NO: 178. In some embodiments, the mRNA comprises a 3' UTR comprising a nucleic acid sequence of SEQ ID NO: 206. In some embodiments, the mRNA comprises a 3' UTR comprising a nucleic acid sequence of SEQ ID NO: 207. In some embodiments, the mRNA comprises a 3' UTR comprising a nucleic acid sequence of SEQ ID NO: 4. In some embodiments, the mRNA comprises a polyA tail. In some instances, the poly A tail is 50-150, 75-150, 85-150, 90-150, 90-120, 90-130, or 90-150 nucleotides in length. In some instances, the poly A tail is 100 nucleotides in length.

In some embodiments, the polynucleotide of the invention (e.g., a RNA, e.g., an mRNA) comprises a nucleotide sequence (e.g., an ORF) encoding a PAH polypeptide is single stranded or double stranded.

In some embodiments, the polynucleotide of the invention comprising a nucleotide sequence (e.g., an ORF) encoding a PAH polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a mRNA. In some embodiments, the mRNA comprises a nucleotide sequence (e.g., an ORF) that encodes at least one PAH polypeptide, and is capable of being translated to produce the encoded PAH polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a PAH polypeptide (e.g., the wild-type sequence, functional fragment, or variant thereof, see e.g., SEQ ID NOs.; 2, 5-20, and 22-38), wherein the polynucleotide comprises at least one chemically modified nucleobase, e.g., N1-methylpseudouracil or 5-methoxyuracil. In certain embodiments, all uracils in the polynucleotide are N1-methylpseudouracils. In other embodiments, all uracils in the polynucleotide are 5-methoxyuracils. In some embodiments, the polynucleotide further comprises a miRNA binding site, e.g., a miRNA binding site that binds to miR-142 and/or a miRNA binding site that binds to miR-126.

In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3;

47.5:11:39.5:2; 47.5:10.5:39.5:2.5; 47.5:11:39:2.5; 48.5:10: 38.5:3; 48.5:10.5:39:2; 48.5:10.5:38.5:2.5; 48.5:10.5:39.5: 1.5; 48.5:10.5:38.0:3; 47:10.5:39.5:3; 47:10:40.5:2.5; 47:11: 40:2; 47:10.5:39.5:3; 48:10.5:38.5:3; 48:10:39.5:2.5; 48:11: 39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 50:10:38.5:1.5.

In some embodiments, the polynucleotide of the disclosure is an mRNA that comprises a 5'-terminal cap (e.g., Cap 1), a 5'UTR (e.g., SEQ ID NO:3), a ORF sequence selected from the group consisting of SEQ ID NOs.: 2, 5-20, and 22-38, a 3'UTR (e.g., SEQ ID NO:4, 175, 177, or 178), and a poly A tail (e.g., about 100 nt in length), wherein all uracils in the polynucleotide are N1-methylpseudouracils. In some embodiments, the delivery agent comprises Compound II or Compound VI as the ionizable lipid and PEG-DMG or Compound I as the PEG lipid.

In some embodiments, the polynucleotide of the disclosure is an mRNA that comprises a 5'-terminal cap (e.g., Cap 1), a 5'UTR (e.g., SEQ ID NO:3, SEQ ID NO:39, SEQ ID NO:204, or SEQ ID NO:205), a ORF sequence selected from the group consisting of SEQ ID NOs.: 2, 5-20, and 22-38, a 3'UTR (e.g., SEQ ID NO:4, SEQ ID NO:111, SEQ ID NO:150, SEQ ID NO:175, SEQ ID NO:177, SEQ ID NO:178, SEQ ID NO:206, or SEQ ID NO:207), and a poly A tail (e.g., about 100 nt in length), wherein all uracils in the polynucleotide are N1 methylpseudouracils. In some embodiments, the delivery agent comprises Compound II or Compound VI as the ionizable lipid and PEG-DMG or Compound I as the PEG lipid.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a PAH polypeptide described herein.

In some embodiments, the "signal sequence" or "signal peptide" is a polynucleotide or polypeptide, respectively, which is from about 30-210, e.g., about 45-80 or 15-60 nucleotides (e.g., about 20, 30, 40, 50, 60, or 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a PAH polypeptide, wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a PAH polypeptide, a functional fragment, or a variant thereof. However, in some embodiments, the polynucleotide of the invention can comprise more than one ORF, for example, a first ORF encoding a PAH polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a $G_4S$ (SEQ ID NO: 86) peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a PAH polypeptide and a second nucleic acid sequence (e.g., a second ORF) encoding a second polypeptide of interest.

Linkers and Cleavable Peptides

In certain embodiments, the mRNAs of the disclosure encode more than one PAH domain (e.g., PAH catalytic domain, PAH tetramerization domain) or a heterologous domain, referred to herein as multimer constructs. In certain embodiments of the multimer constructs, the mRNA further encodes a linker located between each domain. The linker can be, for example, a cleavable linker or protease-sensitive linker. In certain embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In certain embodiments, the linker is an F2A linker. In certain embodiments, the linker is a GGGS (SEQ ID NO: 86) linker. In certain embodiments, the linker is a (GGGS)n (SEQ ID NO: 190) linker, wherein n=2, 3,4, or 5. In certain embodiments, the multimer construct contains three domains with intervening linkers, having the structure: domain-linker-domain-linker-domain e.g., PAH domain-linker-PAH domain.

In one embodiment, the cleavable linker is an F2A linker (e.g., having the amino acid sequence GSGVKQTLNFDLLKLAGDVESNPGP (SEQ ID NO:186)). In other embodiments, the cleavable linker is a T2A linker (e.g., having the amino acid sequence GSGEGRGSLLTCGDVEENPGP (SEQ ID NO:187)), a P2A linker (e.g., having the amino acid sequence GSGATNFSLLKQAGDVEENPGP (SEQ ID NO:188)) or an E2A linker (e.g., having the amino acid sequence GSGQCTNYALLKLAGDVESNPGP (SEQ ID NO:189)). The skilled artisan will appreciate that other art-recognized linkers may be suitable for use in the constructs of the invention (e.g., encoded by the polynucleotides of the invention). The skilled artisan will likewise appreciate that other multicistronic constructs may be suitable for use in the invention. In exemplary embodiments, the construct design yields approximately equimolar amounts of intrabody and/or domain thereof encoded by the constructs of the invention.

In one embodiment, the self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the Thosea asigna virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence of SEQ ID NO: 188, fragments or variants thereof. In one embodiment, the 2A peptide cleaves between the last glycine and last proline. As another non-limiting example, the polynucleotides of the present invention may include a polynucleotide sequence encoding the 2A peptide having the protein sequence of fragments or variants of SEQ ID NO: 188. One example of a polynucleotide sequence encoding the 2A peptide is: GGAAGCGGAGCUACUAAC-UUCAGCCUGCUGAAGCAGGCUGGAGACGU GGAG-GAGAACCCUGGACCU (SEQ ID NO:191). In one illustrative embodiment, a 2A peptide is encoded by the following sequence: 5'-UCCGGACUCAGAUCCGGG-GAUCUCAAAAUUGUCGCUCCUGUCAAACAA ACU-CUUAACUUUGAUUUACUCAAACUGGCUGGGGAU-GUAGAAAGCAAU CCAGGUCCACUC-3'(SEQ ID NO: 192). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the F2A peptide may be between a first coding region A and a second coding region B (A-F2Apep-B). The presence of the F2A peptide results in the cleavage of the one long protein between the glycine and the proline at the end of the F2A peptide sequence (NPGP is cleaved to result in NPG and P) thus creating separate protein A (with 21 amino acids of the F2A peptide attached, ending with NPG) and separate protein B (with 1 amino acid, P, of the F2A peptide attached). Likewise, for other 2A peptides (P2A, T2A and E2A), the presence of the peptide in a long protein results in cleavage between the glycine and proline at the end of the 2A peptide sequence (NPGP is cleaved to result in NPG and P). Protein A and protein B may be the same or different peptides or polypeptides of interest (e.g., a PAH polypeptide such as full length human PAH or a truncated version thereof comprising the catalytic and tetramerization domain of PAH). In particular embodiments, protein A and protein B are a PAH catalytic domain, and a PAH tetramerization domain, in either order. In certain embodiments, the first coding region and the second coding region encode a PAH catalytic domain and a B PAH tetramerization domain, in either order.

5. Sequence Optimization of Nucleotide Sequence Encoding a PAH Polypeptide

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a PAH polypeptide, optionally, a nucleotide sequence (e.g., an ORF) encoding another polypeptide of interest, a 5'-UTR, a 3'-UTR, the 5' UTR or 3' UTR optionally comprising at least one microRNA binding site, optionally a nucleotide sequence encoding a linker, a polyA tail, or any combination thereof), in which the ORF(s) are sequence optimized.

A sequence-optimized nucleotide sequence, e.g., a codon-optimized mRNA sequence encoding a PAH polypeptide, is a sequence comprising at least one synonymous nucleobase substitution with respect to a reference sequence (e.g., a wild type nucleotide sequence encoding a PAH polypeptide).

A sequence-optimized nucleotide sequence can be partially or completely different in sequence from the reference sequence. For example, a reference sequence encoding polyserine uniformly encoded by UCU codons can be sequence-optimized by having 100% of its nucleobases substituted (for each codon, U in position 1 replaced by A, C in position 2 replaced by G, and U in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

Codon Options

| Amino Acid | Single Letter Code | Codon Options |
|---|---|---|
| Isoleucine | I | AUU, AUC, AUA |
| Leucine | L | CUU, CUC, CUA, CUG, UUA, UUG |
| Valine | V | GUU, GUC, GUA, GUG |
| Phenylalanine | F | UUU, UUC |
| Methionine | M | AUG |

TABLE 1-continued

Codon Options

| Amino Acid | Single Letter Code | Codon Options |
|---|---|---|
| Cysteine | C | UGU, UGC |
| Alanine | A | GCU, GCC, GCA, GCG |
| Glycine | G | GGU, GGC, GGA, GGG |
| Proline | P | CCU, CCC, CCA, CCG |
| Threonine | T | ACU, ACC, ACA, ACG |
| Serine | S | UCU, UCC, UCA, UCG, AGU, AGC |
| Tyrosine | Y | UAU, UAC |
| Tryptophan | W | UGG |
| Glutamine | Q | CAA, CAG |
| Asparagine | N | AAU, AAC |
| Histidine | H | CAU, CAC |
| Glutamic acid | E | GAA, GAG |
| Aspartic acid | D | GAU, GAC |
| Lysine | K | AAA, AAG |
| Arginine | R | CGU, CGC, CGA, CGG, AGA, AGG |
| Selenocysteine | Sec | UGA in mRNA in presence of Selenocysteine insertion element (SECTS) |
| Stop codons | Stop | UAA, UAG, UGA |

In some embodiments, a polynucleotide (e.g., a RNA, e.g., an mRNA) of the invention comprises a sequence-optimized nucleotide sequence (e.g., an ORF) encoding a PAH polypeptide, a functional fragment, or a variant thereof, wherein the PAH polypeptide, functional fragment, or a variant thereof encoded by the sequence-optimized nucleotide sequence has improved properties (e.g., compared to a PAH polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence (e.g., an ORF) is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g., an ORF) encoding a PAH polypeptide, a nucleotide sequence (e.g., an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding a PAH polypeptide) with an alternative codon to increase or decrease uridine content to generate a uridine-modified sequence;

(ii) substituting at least one codon in a reference nucleotide sequence (e.g., an ORF encoding a PAH polypeptide) with an alternative codon having a higher codon frequency in the synonymous codon set;

(iii) substituting at least one codon in a reference nucleotide sequence (e.g., an ORF encoding a PAH polypeptide) with an alternative codon to increase G/C content; or (iv) a combination thereof.

In some embodiments, the sequence-optimized nucleotide sequence (e.g., an ORF encoding a PAH polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the PAH polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a microRNA binding site. In some embodiments, the polynucleotide comprises two or more 5' UTRs and/or 3' UTRs, which can be the same or different sequences. In some embodiments, the polynucleotide comprises two or more microRNA binding sites, which can be the same or different sequences. Any portion of the 5' UTR, 3' UTR, and/or microRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

6. Sequence-Optimized Nucleotide Sequences Encoding PAH Polypeptides

In some embodiments, the polynucleotide of the invention comprises a sequence-optimized nucleotide sequence encoding a PAH polypeptide disclosed herein. In some embodiments, the polynucleotide of the invention comprises an open reading frame (ORF) encoding a PAH polypeptide, wherein the ORF has been sequence optimized.

Exemplary sequence-optimized nucleotide sequences encoding human full length PAH are set forth as SEQ ID NOs: 2 and 5-20 (PAH_001 (G5), PAH_002 (G5), PAH_003 (G5), PAH_004 (G5), PAH_005 (G5), PAH_006 (G5), PAH_007 (G5), PAH_008 (G5), PAH_009 (G5), PAH_010 (G5), PAH_011 (G6), PAH_012 (G6), PAH_013 (G6), PAH_014 (G6), PAH_015 (G6), PAH_016 (G6), PAH_017 (G6), PAH_008 (G6), PAH_009 (G6), and PAH_010 (G6), respectively). In some embodiments, the sequence optimized PAH sequences, fragments, and variants thereof are used to practice the methods disclosed herein.

Exemplary sequence optimized nucleotide sequences encoding human truncated PAH (that comprises the catalytic and tetramerization domains of PAH) are set forth as SEQ ID NOs: 22-38 (PAH_018 (G5), PAH_019 (G5), PAH_020 (G5), PAH_021 (G5), PAH_022 (G5), PAH_023 (G5), PAH_024 (G5), PAH_025 (G5), PAH_026 (G5), PAH_027 (G5), PAH_028 (G6), PAH_029 (G6), PAH_030 (G6), PAH_031 (G6), PAH_032 (G6), PAH_033 (G6), PAH_034 (G6), PAH_025 (G6), PAH_026 (G6), and PAH_027 (G6) respectively). In some embodiments, the sequence optimized PAH truncated sequences, fragments, and variants thereof are used to practice the methods disclosed herein.

In some embodiments, a polynucleotide of the present disclosure, for example a polynucleotide comprising an mRNA nucleotide sequence encoding a PAH polypeptide, comprises from 5' to 3' end:
  (i) a 5' cap provided herein, for example, Cap1;
  (ii) a 5' UTR, such as the sequences provided herein, for example, SEQ ID NO: 3;
  (iii) an open reading frame encoding a PAH polypeptide, e.g., a sequence optimized nucleic acid sequence encoding PAH set forth as SEQ ID NOs: 2, 5-20 and 22-38;
  (iv) at least one stop codon (if not present at 5' terminus of 3'UTR);
  (v) a 3' UTR, such as the sequences provided herein, for example, SEQ ID NO: 4, 175, 177, or 178; and
  (vi) a poly-A tail provided above.

In some embodiments, a polynucleotide of the present disclosure, for example a polynucleotide comprising an mRNA nucleotide sequence encoding a PAH polypeptide, comprises from 5' to 3' end:
  (i) a 5' cap provided herein, for example, Cap1;
  (ii) a 5' UTR, such as the sequences provided herein, for example, SEQ ID NO:3, SEQ ID NO:39, SEQ ID NO:204, or SEQ ID NO:205;
  (iii) an open reading frame encoding a PAH polypeptide, e.g., a sequence optimized nucleic acid sequence encoding PAH set forth as SEQ ID NOs: 2, 5-20 and 22-38;
  (iv) at least one stop codon (if not present at 5' terminus of 3'UTR);
  (v) a 3' UTR, such as the sequences provided herein, for example, SEQ ID NO:4, SEQ ID NO:111, SEQ ID NO:150, SEQ ID NO:175, SEQ ID NO:177, SEQ ID NO:178, SEQ ID NO:206, or SEQ ID NO:207; and
  (vi) a poly-A tail provided above.

In certain embodiments, all uracils in the polynucleotide are N1-methylpseudouracil (G5). In certain embodiments, all uracils in the polynucleotide are 5-methoxyuracil (G6).

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a PAH polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

Methods for optimizing codon usage are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

7. Characterization of Sequence Optimized Nucleic Acids

In some embodiments of the invention, the polynucleotide (e.g., a RNA, e.g., an mRNA) comprising a sequence optimized nucleic acid disclosed herein encoding a PAH polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a PAH polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a PAH polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an
in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half-life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a PAH polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a PAH polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding PAH polypeptide or a functional fragment thereof can trigger an immune response, which could be caused by (i) the therapeutic agent (e.g., an mRNA encoding a PAH polypeptide), or (ii) the expression product of such therapeutic agent (e.g., the PAH polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a PAH polypeptide or by the expression product of PAH encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

8. Modified Nucleotide Sequences Encoding PAH Polypeptides

In some embodiments, the polynucleotide (e.g., a RNA, e.g., an mRNA) of the invention comprises a chemically modified nucleobase, for example, a chemically modified uracil, e.g., pseudouracil, N1-methylpseudouracil, 5-methoxyuracil, or the like. In some embodiments, the mRNA is a uracil-modified sequence comprising an ORF encoding a PAH polypeptide, wherein the mRNA comprises a chemically modified nucleobase, for example, a chemically modified uracil, e.g., pseudouracil, N1-methylpseudouracil, or 5-methoxyuracil.

In certain aspects of the invention, when the modified uracil base is connected to a ribose sugar, as it is in polynucleotides, the resulting modified nucleoside or nucleotide is referred to as modified uridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% modified uracil. In one embodiment, uracil in the polynucleotide is at least 95% modified uracil. In another embodiment, uracil in the polynucleotide is 100% modified uracil.

In embodiments where uracil in the polynucleotide is at least 95% modified uracil overall uracil content can be adjusted such that an mRNA provides suitable protein expression levels while inducing little to no immune response. In some embodiments, the uracil content of the ORF is between about 100% and about 150%, between about 100% and about 110%, between about 105% and about 115%, between about 110% and about 120%, between about 115% and about 125%, between about 120% and about 130%, between about 125% and about 135%, between about 130% and about 140%, between about 135% and about 145%, between about 140% and about 150% of the theoretical minimum uracil content in the corresponding wild-type ORF (% $U_{TM}$). In other embodiments, the uracil content of the ORF is between about 121% and about 136% or between 123% and 134% of the % $U_{TM}$. In some embodiments, the uracil content of the ORF encoding a PAH polypeptide is about 115%, about 120%, about 125%, about 130%, about 135%, about 140%, about 145%, or about 150% of the % $U_{TM}$. In this context, the term "uracil" can refer to modified uracil and/or naturally occurring uracil.

In some embodiments, the uracil content in the ORF of the mRNA encoding a PAH polypeptide of the invention is less than about 30%, about 25%, about 20%, about 15%, or about 10% of the total nucleobase content in the ORF. In some embodiments, the uracil content in the ORF is between about 10% and about 20% of the total nucleobase content in the ORF. In other embodiments, the uracil content in the ORF is between about 10% and about 25% of the total nucleobase content in the ORF. In one embodiment, the uracil content in the ORF of the mRNA encoding a PAH polypeptide is less than about 20% of the total nucleobase content in the open reading frame. In this context, the term "uracil" can refer to modified uracil and/or naturally occurring uracil.

In further embodiments, the ORF of the mRNA encoding a PAH polypeptide having modified uracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the PAH polypeptide (% $G_{TMX}$; % $G_{TMX}$, or % $G/C_{TMX}$). In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a PAH polypeptide of the invention comprises modified uracil and has an adjusted uracil content containing less uracil pairs (UU) and/or uracil triplets (UUU) and/or uracil quadruplets (UUUU) than the corresponding wild-type nucleotide sequence encoding the PAH polypeptide. In some embodiments, the ORF of the mRNA encoding a PAH polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the PAH polypeptide. In a particular embodiment, the ORF of the mRNA encoding the PAH polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the PAH polypeptide contains no non-phenylalanine uracil pairs and/or triplets.

In further embodiments, the ORF of the mRNA encoding a PAH polypeptide of the invention comprises modified uracil and has an adjusted uracil content containing less uracil-rich clusters than the corresponding wild-type nucleotide sequence encoding the PAH polypeptide. In some embodiments, the ORF of the mRNA encoding the PAH polypeptide of the invention contains uracil-rich clusters that are shorter in length than corresponding uracil-rich clusters in the corresponding wild-type nucleotide sequence encoding the PAH polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the PAH polypeptide-encoding ORF of the modified uracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the PAH polypeptide is substituted with an alternative codon having a codon frequency lower than the codon frequency of the substituted codon in the synonymous codon set.

In some embodiments, the adjusted uracil content, PAH polypeptide-encoding ORF of the modified uracil-comprising mRNA exhibits expression levels of PAH when administered to a mammalian cell that are higher than expression levels of PAH from the corresponding wild-type mRNA. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, PAH is expressed a level higher than expression levels of PAH from the corresponding wild-type mRNA when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or 0.2 mg/kg or about 0.5 mg/kg. In some embodiments, the mRNA is administered intravenously or intramuscularly. In other embodiments, the PAH polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, PAH polypeptide-encoding ORF of the modified uracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a PAH polypeptide but does not comprise modified uracil under the same conditions, or relative to the immune response induced by an mRNA that encodes for a PAH polypeptide and that comprises modified uracil but that does not have adjusted uracil content under the same conditions. The innate immune response can be manifested by increased expression of pro-inflammatory cytokines, activation of intracellular PRRs (RIG-I, MDAS, etc.), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a PAH polypeptide but does not comprise modified uracil, or to an mRNA that encodes a PAH polypeptide and that comprises modified uracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a PAH polypeptide but does not comprise modified uracil, or an mRNA that encodes for a PAH polypeptide and that comprises modified uracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

9. Methods for Modifying Polynucleotides

The disclosure includes modified polynucleotides comprising a polynucleotide described herein (e.g., a polynucleotide, e.g. mRNA, comprising a nucleotide sequence encoding a PAH polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a PAH polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

In some embodiments, a polynucleotide of the present invention (e.g., a polynucleotide comprising a nucleotide sequence encoding a PAH polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-SmeC-G". The same polynucleotide can be structurally modified from "ATCG" to "ATCCCG". Here, the dinucleotide "CC" has been inserted, resulting in a structural modification to the polynucleotide.

Therapeutic compositions of the present disclosure comprise, in some embodiments, at least one nucleic acid (e.g., RNA) having an open reading frame encoding PAH (e.g., SEQ ID NOs: 2, 5-20, and 22-38), wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

In some embodiments, at least one RNA (e.g., mRNA) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise N1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises N1-methyl-pseudouridine (m1ψ) substitutions at one or more or all uridine positions of the nucleic acid.

In some embodiments, a RNA nucleic acid of the disclosure comprises N1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with N1-methyl-pseudouridine, meaning that all uridine residues in the mRNA sequence are replaced with N1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

10. Untranslated Regions (UTRs)

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854).

Untranslated regions (UTRs) are nucleic acid sections of a polynucleotide before a start codon (5' UTR) and after a stop codon (3' UTR) that are not translated. In some embodiments, a polynucleotide (e.g., a ribonucleic acid (RNA), e.g., a messenger RNA (mRNA)) of the invention comprising an open reading frame (ORF) encoding a PAH polypeptide further comprises UTR (e.g., a 5' UTR or functional fragment thereof, a 3' UTR or functional fragment thereof, or a combination thereof).

Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4. In some embodiments, the sequence comprises a repeating GC-motif [CCG]n, wherein n=5.

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 2. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC (SEQ ID NO: 43)] as set forth in Table 2, or derivatives or analogs thereof, preceding a Kozak consensus sequence in the 5' UTR of the mRNA. In some embodiments, the GC-rich element comprises the sequence V1 as set forth in Table 2 located immediately adjacent to and upstream of the Kozak consensus sequence in the 5' UTR of the mRNA. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence V2 [CCCCGGC (SEQ ID NO: 44)] as set forth in Table 2, or derivatives or analogs thereof, preceding a Kozak consensus sequence in the 5' UTR of the mRNA. In some embodiments, the GC-rich element comprises the sequence V2 as set forth in Table 2 located immediately adjacent to and upstream of the Kozak consensus sequence in the 5' UTR of the mRNA. In some embodiments, the GC-rich element comprises the sequence V2 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC (SEQ ID NO:42)] as set forth in Table 2, or derivatives or analogs thereof, preceding a Kozak consensus sequence in the 5' UTR of the mRNA. In some embodiments, the GC-rich element comprises the sequence EK as set forth in Table 2 located immediately adjacent to and upstream of the Kozak consensus sequence in the 5' UTR of the mRNA. In some embodiments, the GC-rich element comprises the sequence EK as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 2 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC (SEQ ID NO: 43)] as set forth in Table 2, or derivatives or analogs thereof, preceding a Kozak consensus sequence in the 5' UTR of the mRNA, wherein the 5' UTR comprises the following sequence shown in Table 2:

GGGAAAUAAGAGAGAAAAGAAGAGUAAGAA-GAAAUAUAAGA (SEQ ID NO:85). The skilled artisan will of course recognize that all Us in the RNA sequences described herein will be Ts in a corresponding template DNA sequence, for example, in DNA templates or constructs from which mRNAs of the disclosure are transcribed, e.g., via IVT.

In some embodiments, the GC-rich element comprises the sequence V1 as set forth in Table 2 located immediately adjacent to and upstream of the Kozak consensus sequence in the 5' UTR sequence shown in Table 2. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA, wherein the 5' UTR comprises the following sequence shown in Table 2:

(SEQ ID NO: 85)
GGGAAAUAAGAGAGAAAAGAAGAGUAAGAAGAAAUAUAAGA.

In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA, wherein the 5' UTR comprises the following sequence shown in Table 2:

(SEQ ID NO: 85)
GGGAAAUAAGAGAGAAAAGAAGAGUAAGAAGAAAUAUAAGA.

In some embodiments, the 5' UTR comprises the following sequence set forth in Table 2:

(SEQ ID NO: 39)
GGGAAAUAAGAGAGAAAAGAAGAGUAAGAAGAAAUAUAAGACCCCGGCGCCGCCACC

TABLE 2

| 5' UTRs | 5' UTR Sequence |
|---|---|
| Standard | GGGAAAUAAGAGAGAAAAGAAGAGUAAGAAGAAAUAUAAGAGCCACC (SEQ ID NO: 3) |
| V1-UTR | GGGAAAUAAGAGAGAAAAGAAGAGUAAGAAGAAAUAUAAGACCCCGGCGCCGCCACC (SEQ ID NO: 39) |
| V2-UTR | GGGAAAUAAGAGAGAAAAGAAGAGUAAGAAGAAAUAUAAGACCCCGGCGCCACC (SEQ ID NO: 40) |
| GC-Rich RNA Elements | Sequence |
| K0 (Traditional Kozak consensus) | [GCCA/GCC] (SEQ ID NO: 41) |
| EK | [GCCGCC] (SEQ ID NO: 42) |
| V1 | [CCCCGGCGCC] (SEQ ID NO: 43) |
| V2 | [CCCCGGC] (SEQ ID NO: 44) |
| $(CCG)_n$, where n = 1-10 | $[CCG]_n$ |
| $(GCC)_n$, where n = 1-10 | $[GCC]_n$ |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of the PIC or ribosome at a discrete position or location along an polynucleotide comprising any one or more of the RNA elements described herein is determined by ribosome profiling.

A UTR can be homologous or heterologous to the coding region in a polynucleotide. In some embodiments, the UTR is homologous to the ORF encoding the PAH polypeptide. In some embodiments, the UTR is heterologous to the ORF encoding the PAH polypeptide. In some embodiments, the polynucleotide comprises two or more 5' UTRs or functional fragments thereof, each of which has the same or different nucleotide sequences. In some embodiments, the polynucleotide comprises two or more 3' UTRs or functional fragments thereof, each of which has the same or different nucleotide sequences.

In some embodiments, the 5' UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., N1-methylpseudouracil or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5' UTR or 3' UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO:87), where R is a purine (adenine or guanine) three bases upstream of the start codon (AUG), which is followed by another 'G'. 5' UTRs also have been known to form secondary structures that are involved in elongation factor binding.

By engineering the features typically found in abundantly expressed genes of specific target organs, one can enhance the stability and protein production of a polynucleotide. For example, introduction of 5' UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5' UTR and the 3' UTR can be heterologous. In some embodiments, the 5' UTR can be derived from a different species than the 3' UTR. In some embodiments, the 3' UTR can be derived from a different species than the 5' UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H$^+$-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5' UTR is selected from the group consisting of a β-globin 5' UTR; a 5'UTR containing a strong Kozak translational initiation signal; a cytochrome b-245 α polypeptide (CYBA) 5' UTR; a hydroxysteroid (17-β) dehydrogenase (HSD17B4) 5' UTR; a Tobacco etch virus (TEV) 5' UTR; a Venezuelen equine encephalitis virus (TEEV) 5' UTR; a 5' proximal open reading frame of rubella virus (RV) RNA encoding nonstructural proteins; a Dengue virus (DEN) 5' UTR; a heat shock protein 70 (Hsp70) 5' UTR; a eIF4G 5' UTR; a GLUT1 5' UTR; functional fragments thereof and any combination thereof.

In some embodiments, the 3' UTR is selected from the group consisting of a β-globin 3' UTR; a CYBA 3' UTR; an albumin 3' UTR; a growth hormone (GH) 3' UTR; a VEEV 3' UTR; a hepatitis B virus (HBV) 3' UTR; α-globin 3'UTR; a DEN 3' UTR; a PAV barley yellow dwarf virus (BYDV-PAV) 3' UTR; an elongation factor 1 al (EEF1A1) 3' UTR; a manganese superoxide dismutase (MnSOD) 3' UTR; a (3 subunit of mitochondrial H(+)-ATP synthase (β-mRNA) 3' UTR; a GLUT1 3' UTR; a MEF2A 3' UTR; a β-F1-ATPase 3' UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5' UTR or 3' UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5' UTR and/or a 3' UTR selected from any of the UTRs disclosed herein. In some embodiments, the 5' UTR comprises:

```
5' UTR-001 (Upstream UTR)
                                    (SEQ ID NO: 3)
(GGGAAAUAAGAGAGAAAAGAAGAGUAAGAAGAAAUAUAAGAGCCACC);

5' UTR-002 (Upstream UTR)
                                   (SEQ ID NO: 89)
(GGGAGAUCAGAGAGAAAAGAAGAGUAAGAAGAAAUAUAAGAGCCACC);

5' UTR-003 (Upstream UTR)
(See WO2016/100812);

5' UTR-004 (Upstream UTR)
                                   (SEQ ID NO: 90)
(GGGAGACAAGCUUGGCAUUCCGGUACUGUUGGUAAAGCCACC);

5' UTR-005 (Upstream UTR)
                                   (SEQ ID NO: 89)
(GGGAGAUCAGAGAGAAAAGAAGAGUAAGAAGAAAUAUAAGAGCCACC);

5' UTR-006 (Upstream UTR)
(See WO2016/100812);

5' UTR-007 (Upstream UTR)
                                   (SEQ ID NO: 90)
(GGGAGACAAGCUUGGCAUUCCGGUACUGUUGGUAAAGCCACC);

5' UTR-008 (Upstream UTR)
                                   (SEQ ID NO: 93)
(GGGAAUUAACAGAGAAAAGAAGAGUAAGAAGAAAUAUAAGAGCCACC);

5' UTR-009 (Upstream UTR)
                                   (SEQ ID NO: 94)
(GGGAAAUUAGACAGAAAAGAAGAGUAAGAAGAAAUAUAAGAGCCACC);

5' UTR-010, Upstream
                                   (SEQ ID NO: 95)
(GGGAAAUAAGAGAGUAAAGAACAGUAAGAAGAAAUAUAAGAGCCACC);

5' UTR-011 (Upstream UTR)
                                   (SEQ ID NO: 96)
(GGGAAAAAGAGAGAAAAGAAGACUAAGAAGAAAUAUAAGAGCCACC);

5' UTR-012 (Upstream UTR)
                                   (SEQ ID NO: 97)
(GGGAAAUAAGAGAGAAAAGAAGAGUAAGAAGAUAUAUAAGAGCCACC);

5' UTR-013 (Upstream UTR)
                                   (SEQ ID NO: 98)
(GGGAAAUAAGAGACAAAACAAGAGUAAGAAGAAAUAUAAGAGCCACC);

5' UTR-014 (Upstream UTR)
                                   (SEQ ID NO: 99)
(GGGAAAUUAGAGAGUAAAGAACAGUAAGUAGAAUUAAAAGAGCCACC);

5' UTR-015 (Upstream UTR)
                                  (SEQ ID NO: 100)
(GGGAAAUAAGAGAGAAUAGAAGAGUAAGAAGAAAUAUAAGAGCCACC);

5' UTR-016 (Upstream UTR)
                                  (SEQ ID NO: 101)
(GGGAAAUAAGAGAGAAAAGAAGAGUAAGAAGAAAAUUUAAGAGCCACC);

5' UTR-017 (Upstream UTR);
                                  (SEQ ID NO: 102)
(GGGAAAUAAGAGAGAAAAGAAGAGUAAGAAGAAAUUUAAGAGCCACC);
or 5' UTR-018 (Upstream UTR) 5' UTR
                                   (SEQ ID NO: 88)
(UCAAGCUUUUGGACCCUCGUACAGAAGCUAAUACGACUCACUAUAGGGAA
AUAAGAGAGAAAAGAAGAGUAAGAAGAAAUAUAAGAGCCACC).
```

In some embodiments, the 3' UTR comprises:

```
142-3p 3' UTR (UTR including miR142-3p binding
site)
                                  (SEQ ID NO: 104)
(UGAUAAUAGUCCAUAAAGUAGGAAACACUACAGCUGGAGCCUCGGUGGC
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding
site)
                                  (SEQ ID NO: 105)
(UGAUAAUAGGCUGGAGCCUCGGUGGCUCCAUAAAGUAGGAAACACUACA
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);
or 142-3p 3' UTR (UTR including miR142-3p binding
site)
                                  (SEQ ID NO: 106)
(UGAUAAUAGGCUGGAGCCUCGGUGGCCAUGCUUCUUGCCCCUUCCAUAA
AGUAGGAAACACUACAUGGGCCUCCCCCCAGCCCCUCCUCCCCUUCCUGC
ACCCGUACCCCCGUGGUCUUUGAAUAAAGUCUGAGUGGGCGGC);

142-3p 3' UTR (UTR including miR142-3p binding
site)
                                  (SEQ ID NO: 107)
(UGAUAAUAGGCUGGAGCCUCGGUGGCCAUGCUUCUUGCCCCUUGGGCCU
CCCCCCAGUCCAUAAAGUAGGAAACACUACACCCCUCCUCCCCUUCCUGC
ACCCGUACCCCCGUGGUCUUUGAAUAAAGUCUGAGUGGGCGGC);

142-3p 3' UTR (UTR including miR142-3p binding
site)
                                  (SEQ ID NO: 108)
(UGAUAAUAGGCUGGAGCCUCGGUGGCCAUGCUUCUUGCCCCUUGGGCCU
CCCCCCAGCCCCUCCUCCCCUUCUCCAUAAAGUAGGAAACACUACACUGC
ACCCGUACCCCCGUGGUCUUUGAAUAAAGUCUGAGUGGGCGGC);

142-3p 3' UTR (UTR including miR142-3p binding
site)
                                  (SEQ ID NO: 109)
(UGAUAAUAGGCUGGAGCCUCGGUGGCCAUGCUUCUUGCCCCUUGGGCCU
CCCCCCAGCCCCUCCUCCCCUUCCUGCACCCGUACCCCCUCCAUAAAGUA
GGAAACACUACAGUGGUCUUUGAAUAAAGUCUGAGUGGGCGGC).

142-3p 3' UTR (UTR including miR142-3p binding
site)
                                  (SEQ ID NO: 110)
(UGAUAAUAGGCUGGAGCCUCGGUGGCCAUGCUUCUUGCCCCUUGGGCCU
CCCCCCAGCCCCUCCUCCCCUUCCUGCACCCGUACCCCCGUGGUCUUUGA
AUAAAGUUCCAUAAAGUAGGAAACACUACACUGAGUGGGCGGC);

3' UTR-018;
                                (See SEQ ID NO: 150)

3' UTR (miR142 and miR126 binding sites variant 1)
                                  (SEQ ID NO: 111)
(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCGCAUUAUUACUCACGGUACGAGUGGUCUUUGAAUAAA

GUCUGAGUGGGCGGC)

3' UTR (miR142 and miR126 binding sites variant 2)
                                  (SEQ ID NO: 112)
(UGAUAAUAGUCCAUAAAGUAGGAAACACUACAGCUGGAGCCUCGGUGGC
```

-continued
CUAGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC);
or

3'UTR (miR142-3p binding site variant 3)
(SEQ ID NO: 4)
UGAUAAUAGGCUGGAGCCUCGGUGGCCUAGCUUCUUGCCCCUUGGGCCUC
CCCCCAGCCCCUCCUCCCCUUCCUGCACCCGUACCCCUCCAUAAAGUAG
GAAACACUACAGUGGUCUUUGAAUAAAGUCUGAGUGGGCGGC.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NOs: 3, 88-102, or 165-167 and/or 3' UTR sequences comprises any of SEQ ID NOs:4, 104-112, or 150, and any combination thereof.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NO:3, SEQ ID NO:39, SEQ ID NO:204, or SEQ ID NO:205 and/or 3' UTR sequences comprises any of SEQ ID NO:4, SEQ ID NO:111, SEQ ID NO:150, SEQ ID NO:175, SEQ ID NO:177, SEQ ID NO:178, SEQ ID NO:206, or SEQ ID NO:207, and any combination thereof.

In some embodiments, the 5' UTR comprises an amino acid sequence set forth in Table 4B (SEQ ID NO:3, SEQ ID NO:39, SEQ ID NO:204, or SEQ ID NO:205). In some embodiments, the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO:178, SEQ ID NO:206, or SEQ ID NO:207). In some embodiments, the 5' UTR comprises an amino acid sequence set forth in Table 4B (SEQ ID NO:3, SEQ ID NO:39, SEQ ID NO:204, or SEQ ID NO:205) and the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO:178, SEQ ID NO:206, or SEQ ID NO:207).

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5' UTR sequence. In some embodiments, the polynucleotide comprises an ORF and a viral capsid sequence. In some embodiments, the polynucleotide comprises a synthetic 5' UTR in combination with a non-synthetic 3' UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can be located between the transcription promoter and the start codon. In some embodiments, the 5' UTR comprises a TEE.

In one aspect, a TEE is a conserved element in a UTR that can promote translational activity of a nucleic acid such as, but not limited to, cap-dependent or cap-independent translation.

11. MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences".

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5' UTR and/or 3' UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 nucleotide long miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5' UTR and/or 3' UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-id, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5' UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5' UTR and/or 3' UTR of a polynucleotide of the invention.

To further drive the selective degradation and suppression in APCs and macrophage, a polynucleotide of the invention can include a further negative regulatory element in the 5' UTR and/or 3' UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR- 199b-3p, miR-199b-5p, miR-296-5p, miR-557, miR-581, miR-939-3p, and miR-939-5p. miRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. miRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. miRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR- 1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). miRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) *PLoS One* 9:e102259; Landgraf, P. et al. (2007) Cell 129:1401-1414; Bissels, U. et al. (2009) RNA 15:2375-2384. Any one miR-site incorporation in the 3' UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plasmacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of a polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g., reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miRNA binding site. In certain embodiments, use of three copies of the same miR binding site can exhibit beneficial properties as compared to use of a single miRNA binding site. Non-limiting examples of sequences for 3' UTRs containing three miRNA bindings sites are shown in SEQ ID NO: 155 (three miR-142-3p binding sites) and SEQ ID NO: 157 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 111 (one miR-142-3p binding site and one miR-126-3p binding site), SEQ ID NO: 158 (two miR-142-5p binding sites and one miR-142-3p binding sites), and SEQ ID NO: 161 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from Table 3, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from Table 3, including any combination thereof.

In some embodiments, the miRNA binding site binds to miR-142 or is complementary to miR-142. In some embodiments, the miR-142 comprises SEQ ID NO:114. In some embodiments, the miRNA binding site binds to miR-142-3p or miR-142-5p. In some embodiments, the miR-142-3p binding site comprises SEQ ID NO:116. In some embodiments, the miR-142-5p binding site comprises SEQ ID NO:118. In some embodiments, the miRNA binding site comprises a nucleotide sequence at least 80%, at least 85%, at least 90%, at least 95%, or 100% identical to SEQ ID NO:116 or SEQ ID NO:118.

In some embodiments, the miRNA binding site binds to miR-126 or is complementary to miR-126. In some embodiments, the miR-126 comprises SEQ ID NO: 119. In some embodiments, the miRNA binding site binds to miR-126-3p or miR-126-5p. In some embodiments, the miR-126-3p binding site comprises SEQ ID NO: 121. In some embodiments, the miR-126-5p binding site comprises SEQ ID NO: 123. In some embodiments, the miRNA binding site comprises a nucleotide sequence at least 80%, at least 85%, at least 90%, at least 95%, or 100% identical to SEQ ID NO: 121 or SEQ ID NO: 123.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 98 or 105.

TABLE 3 miR-142, miR-126, and miR-142 and miR-126 binding sites

| SEQ ID NO. | Description | Sequence |
| --- | --- | --- |
| 114 | miR-142 | GACAGUGCAGUCACCCAUAAAGUAGAAAGCACUACUAACAGCACUGGAGGGUGUAGUGUUUCCUACUUUAUGGAUGAGUGUACUGUG |
| 115 | miR-142-3p | UGUAGUGUUUCCUACUUUAUGGA |
| 116 | miR-142-3p binding site | uCCAUAAAGUAGGAAACACUACA |
| 117 | miR-142-5p | CAUAAAGUAGAAAGCACUACU |
| 118 | miR-142-5p binding site | AGUAGUGCUUUCUACUUUAUG |
| 119 | miR-126 | CGCUGGCGACGGGACAUUAUUACUUUUGGUACGCGCUGUGACACUUCAAACUCGUACCGUGAGUAAUAAUGCGCCGUCCACGGCA |
| 120 | miR-126-3p | uCGUACCGUGAGUAAUAAUGCG |
| 121 | miR-126-3p binding site | CGCAUUAUUACUCACGGUACGA |
| 122 | miR-126-5p | CAUUAUUACUUUUGGUACGCG |
| 123 | miR-126-5p binding site | CGCGUACCAAAAGUAAUAAUG |

In some embodiments, a miRNA binding site is inserted in the polynucleotide of the invention in any position of the polynucleotide (e.g., the 5' UTR and/or 3' UTR). In some embodiments, the 5' UTR comprises a miRNA binding site. In some embodiments, the 3' UTR comprises a miRNA binding site. In some embodiments, the 5' UTR and the 3' UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 104, 105, and 164, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 165, 166, or 167, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3' UTR comprises more than one miRNA bindingsite (e.g., 2-4 miRNA binding sites), wherein there can be a spacer region (e.g., of 10-100, 20-70 or 30-50 nucleotides in length) between each miRNA bindingsite. In another embodiment, the 3' UTR comprises a spacer region between the end of the miRNA bindingsite(s) and the poly A tail nucleotides. For example, a spacer region of 10-100, 20-70 or 30-50 nucleotides in length can be situated between the end of the miRNA bindingsite(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5' UTR comprises more than one miRNA binding site (e.g., 2-4 miRNA binding sites), wherein there can be a spacer region (e.g., of 10-100, 20-70 or 30-50 nucleotides in length) between each miRNA binding site.

In one embodiment, the 3' UTR comprises more than one stop codon, wherein at least one miRNA binding site is positioned downstream of the stop codons. For example, a 3' UTR can comprise 1, 2 or 3 stop codons. Non-limiting examples of triple stop codons that can be used include: UGAUAAUAG (SEQ ID NO:124), UGAUAGUAA (SEQ ID NO:125), UAAUGAUAG (SEQ ID NO:126), UGAUAAUAA (SEQ ID NO:127), UGAUAGUAG (SEQ ID NO:128), UAAUGAUGA (SEQ ID NO:129), UAAUAGUAG (SEQ ID NO:130), UGAUGAUGA (SEQ ID NO:131), UAAUAAUAA (SEQ ID NO:132), and UAGUAGUAG (SEQ ID NO:133). Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 109, 104, 105, and 164.

TABLE 4A

5' UTRs, 3' UTRs, miR sequences, and miR binding sites

| SEQ ID NO: | Sequence |
|---|---|
| 134 | GCUGGAGCCUCGGUGGCCAUGCUUCUUGCCCCUUGGGCCUCCCCCCAGCCCC UCCUCCCCUUCCUGCACCCGUACCCCC<u>UCCAUAAAGUAGGAAACACUACAGU</u> GGUCUUUGAAUAAAGUCUGAGUGGGCGGC (3' UTR with miR 142-3p binding site) |
| 116 | UCCAUAAAGUAGGAAACACUACA (miR 142-3p binding site) |
| 115 | UGUAGUGUUUCCUACUUUAUGGA (miR 142-3p sequence) |
| 117 | CAUAAAGUAGAAAGCACUACU (miR 142-5p sequence) |
| 135 | CCUCUGAAAUUCAGUUCUUCAG (miR 146-3p sequence) |
| 136 | UGAGAACUGAAUUCCAUGGGUU (miR 146-5p sequence) |
| 137 | CUCCUACAUAUUAGCAUUAACA (miR 155-3p sequence) |
| 138 | UUAAUGCUAAUCGUGAUAGGGGU (miR 155-5p sequence) |
| 120 | UCGUACCGUGAGUAAUAAUGCG (miR 126-3p sequence) |
| 122 | CAUUAUUACUUUUGGUACGCG (miR 126-5p sequence) |
| 139 | CCAGUAUUAACUGUGCUGCUGA (miR 16-3p sequence) |
| 140 | UAGCAGCACGUAAAUAUUGGCG (miR 16-5p sequence) |
| 141 | CAACACCAGUCGAUGGGCUGU (miR 21-3p sequence) |
| 142 | UAGCUUAUCAGACUGAUGUUGA (miR 21-5p sequence) |
| 143 | UGUCAGUUUGUCAAAUACCCCA (miR 223-3p sequence) |
| 144 | CGUGUAUUUGACAAGCUGAGUU (miR 223-5p sequence) |
| 145 | UGGCUCAGUUCAGCAGGAACAG (miR 24-3p sequence) |
| 146 | UGCCUACUGAGCUGAUAUCAGU (miR 24-5p sequence) |
| 147 | UUCACAGUGGCUAAGUUCCGC (miR 27-3p sequence) |
| 148 | AGGGCUUAGCUGCUUGUGAGCA (miR 27-5p sequence) |
| 121 | CGCAUUAUUACUCACGGUACGA (miR 126-3p binding site) |

TABLE 4A-continued

5' UTRs, 3' UTRs, miR sequences, and miR binding sites

| SEQ ID NO: | Sequence |
|---|---|
| 149 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>GCAUUAUUACUCACG</u><br><u>GUACGA</u>GUGGUCUUUGAAUAAAGUCUGAGUGGGCGGC<br>(3' UTR with miR 126-3p binding site) |
| 150 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCGUGGUCUUUGAAUAAA<br>GUCUGAGUGGGCGGC<br>(3' UTR, no miR binding sites) |
| 109 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>UCCAUAAAGUAGGAAA</u><br><u>CACUACAG</u>UGGUCUUUGAAUAAAGUCUGAGUGGGCGGC<br>(3' UTR with miR 142-3p binding site) |
| 111 | UGAUAAUAGU<u>CCAUAAAGUAGGAAACACUACAG</u>CUGGAGCCUCGGUGGCCAU<br>GCUUCUUGCCCCUUGGGCCUCCCCCCAGCCCCUCCUCCCCUUCCUGCACCCG<br>UACCCCC<u>GCAUUAUUACUCACGGUACGA</u>GUGGUCUUUGAAUAAAGUCUGAG<br>UGGGCGGC<br>(3' UTR with miR 142-3p and miR 126-3p binding sites variant 1) |
| 153 | UUAAUGCUAAUUGUGAUAGGGGU<br>(miR 155-5p sequence) |
| 154 | ACCCCUAUCACAAUUAGCAUUAA<br>(miR 155-5p binding site) |
| 155 | UGAUAAUAGU<u>CCAUAAAGUAGGAAACACUACAG</u>CUGGAGCCUCGGUGGCCAU<br>GCUUCUUGCCCCUUGGGCCU<u>CCAUAAAGUAGGAAACACUACAU</u>CCCCCCAGC<br>CCCUCCUCCCCUUCCUGCACCCGUACCCCC<u>UCCAUAAAGUAGGAAACACUAC</u><br><u>AG</u>UGGUCUUUGAAUAAAGUCUGAGUGGGCGGC<br>(3' UTR with 3 miR 142-3p binding sites) |
| 156 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>AGUAGUGCUUUCUACU</u><br><u>UUAUG</u>GUGGUCUUUGAAUAAAGUCUGAGUGGGCGGC<br>(3' UTR with miR 142-5p binding site) |
| 157 | UGAUAAUAG<u>AGUAGUGCUUUCUACUUUAUG</u>GCUGGAGCCUCGGUGGCCAUGC<br>UUCUUGCCCCUUGGGCC<u>AGUAGUGCUUUCUACUUUAUG</u>UCCCCCCAGCCCCU<br>CCUCCCCUUCCUGCACCCGUACCCCC<u>AGUAGUGCUUUCUACUUUAUG</u>GUGGU<br>CUUUGAAUAAAGUCUGAGUGGGCGGC<br>(3' UTR with 3 miR 142-5p binding sites) |
| 158 | UGAUAAUAG<u>AGUAGUGCUUUCUACUUUAUG</u>GCUGGAGCCUCGGUGGCCAUGC<br>UUCUUGCCCCUUGGGCCU<u>CCAUAAAGUAGGAAACACUACAU</u>CCCCCCAGCCC<br>CUCCUCCCCUUCCUGCACCCGUACCCCC<u>AGUAGUGCUUUCUACUUUAUG</u>GUG<br>GUCUUUGAAUAAAGUCUGAGUGGGCGGC<br>(3' UTR with 2 miR 142-5p binding sites and 1 miR 142-3p binding site) |
| 159 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>ACCCCUAUCACAAUUA</u><br><u>GCAUUAA</u>GUGGUCUUUGAAUAAAGUCUGAGUGGGCGGC<br>(3' UTR with miR 155-5p binding site) |
| 160 | UGAUAAUAG<u>ACCCCUAUCACAAUUAGCAUUAA</u>GCUGGAGCCUCGGUGGCCAU<br>GCUUCUUGCCCCUUGGGCCA<u>CCCCUAUCACAAUUAGCAUUAA</u>UCCCCCCAGC<br>CCCUCCUCCCCUUCCUGCACCCGUACCCCC<u>ACCCCUAUCACAAUUAGCAUUA</u><br><u>A</u>GUGGUCUUUGAAUAAAGUCUGAGUGGGCGGC<br>(3' UTR with 3 miR 155-5p binding sites) |

TABLE 4A-continued

5' UTRs, 3' UTRs, miR sequences, and miR binding sites

| SEQ ID NO: | Sequence |
|---|---|
| 161 | UGAUAAUAGACCCCUAUCACAAUUAGCAUUAAGCUGGAGCCUCGGUGGCCAU GCUUCUUGCCCCUUGGGCCUCCAUAAAGUAGGAAACACUACAUCCCCCCAGC CCCUCCUCCCCUUCCUGCACCCGUACCCCCACCCCUAUCACAAUUAGCAUUA AGUGGUCUUUGAAUAAAGUCUGAGUGGGCGGC<br>(3' UTR with 2 miR 155-5p binding sites and 1 miR 142-3p binding site) |
| 104 | UGAUAAUAGUCCAUAAAGUAGGAAACACUACAGCUGGAGCCUCGGUGGCCAU GCUUCUUGCCCCUUGGGCCUCCCCCCAGCCCCUCCUCCCCUUCCUGCACCCG UACCCCCGUGGUCUUUGAAUAAAGUCUGAGUGGGCGGC<br>(3' UTR with miR 142-3p binding site, P1 insertion) |
| 105 | UGAUAAUAGGCUGGAGCCUCGGUGGCUCCAUAAAGUAGGAAACACUACACAU GCUUCUUGCCCCUUGGGCCUCCCCCCAGCCCCUCCUCCCCUUCCUGCACCCG UACCCCCGUGGUCUUUGAAUAAAGUCUGAGUGGGCGGC<br>(3' UTR with miR 142-3p binding site, P2 insertion) |
| 164 | UGAUAAUAGGCUGGAGCCUCGGUGGCCAUGCUUCUUGCCCCUUGGGCCUCCA UAAAGUAGGAAACACUACAUCCCCCCAGCCCCUCCUCCCCUUCCUGCACCCG UACCCCCGUGGUCUUUGAAUAAAGUCUGAGUGGGCGGC<br>(3' UTR with miR 142-3p binding site, P3 insertion) |
| 118 | AGUAGUGCUUUCUACUUUAUG<br>(miR-142-5p binding site) |
| 114 | GACAGUGCAGUCACCCAUAAAGUAGAAAGCACUACUAACAGCACUGGAGGGU GUAGUGUUUCCUACUUUAUGGAUGAGUGUACUGUG<br>(miR-142) |
| 3 | GGGAAAUAAGAGAGAAAAGAAGAGUAAGAAGAAAUAUAAGAGCCACC<br>(5' UTR) |
| 165 | GGGAAAUAAGAGUCCAUAAAGUAGGAAACACUACAAGAAAAGAAGAGUAAGA AGAAAUAUAAGAGCCACC<br>(5' UTR with miR142-3p binding site at position p1) |
| 166 | GGGAAAUAAGAGAGAAAAGAAGAGUAAUCCAUAAAGUAGGAAACACUACAGA AGAAAUAUAAGAGCCACC<br>(5' UTR with miR142-3p binding site at position p2) |
| 167 | GGGAAAUAAGAGAGAAAAGAAGAGUAAGAAGAAAUAUAAUCCAUAAAGUAGG AAACACUACAGAGCCACC<br>(5' UTR with miR142-3p binding site at position p3) |
| 169 | UGAUAAUAGAGUAGUGCUUUCUACUUUAUGGCUGGAGCCUCGGUGGCCAUGC UUCUUGCCCCUUGGGCCAGUAGUGCUUUCUACUUUAUGUCCCCCCAGCCCCU CUCCCCUUCCUGCACCCGUACCCCCAGUAGUGCUUUCUACUUUAUGGUGGUC UUUGAAUAAAGUCUGAGUGGGCGGC<br>(3' UTR with 3 miR 142-5p binding sites) |
| 106 | UGAUAAUAGGCUGGAGCCUCGGUGGCCAUGCUUCUUGCCCCUUCCAUAAAGU AGGAAACACUACAUGGGGCUCCCCCCAGCCCCUCCUCCCCUUCCUGCACCCG UACCCCCGUGGUCUUUGAAUAAAGUCUGAGUGGGCGGC<br>(3' UTR including miR142-3p binding site) |
| 107 | UGAUAAUAGGCUGGAGCCUCGGUGGCCAUGCUUCUUGCCCCUUGGGCCUCCC CCCAGUCCAUAAAGUAGGAAACACUACACCCCUCCUCCCCUUCCUGCACCCG UACCCCCGUGGUCUUUGAAUAAAGUCUGAGUGGGCGGC<br>(3' UTR including miR142-3p binding site) |
| 108 | UGAUAAUAGGCUGGAGCCUCGGUGGCCAUGCUUCUUGCCCCUUGGGCCUCCC CCCAGCCCCUCCUCCCCUUCUCCAUAAAGUAGGAAACACUACACUGCACCCG UACCCCCGUGGUCUUUGAAUAAAGUCUGAGUGGGCGGC<br>(3' UTR including including miR142-3p binding site) |
| 110 | UGAUAAUAGGCUGGAGCCUCGGUGGCCAUGCUUCUUGCCCCUUGGGCCUCCC CCCAGCCCCUCCUCCCCUUCCUGCACCCGUACCCCCGUGGUCUUUGAAUAAA GUUCCAUAAAGUAGGAAACACUACACUGAGUGGGCGGC<br>(3' UTR including including miR142-3p binding site) |

TABLE 4A-continued

5' UTRs, 3' UTRs, miR sequences, and miR binding sites

| SEQ ID NO: | Sequence |
|---|---|
| 112 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCC<u>CGCAUUAUUACUCACGGUACGA</u>GUGGUCUUUGAAUAAAGUCUGAG<br><br>UGGGCGGC<br>(3' UTR with miR 142-3p and miR 126-3p binding sites variant 2) |
| 175 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCGUGGUCUUUGAAUAAA<br>GUCUGAGUGGGCGGC<br>(3' UTR, no miR binding sites variant 2) |
| 4 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCC<u>UCCAUAAAGUAGGAAA</u><br><u>CACUACAG</u>UGGUCUUUGAAUAAAGUCUGAGUGGGCGGC<br>(3' UTR with miR 142-3p binding site variant 3) |
| 177 | UGAUAAUAGGCUGGAGCCUCGGUGGCCUAGCUUCUUGCCCCUUGGGCCUCCC<br>CCCAGCCCCUCCUCCCCUUCCUGCACCCGUACCCC<u>CGCAUUAUUACUCACG</u><br><br><u>GUACGA</u>GUGGUCUUUGAAUAAAGUCUGAGUGGGCGGC<br>(3' UTR with miR 126-3p binding site variant 3) |
| 178 | UGAUAAUAGUCCAUAAAGUAGGAAACACUACAGCUGGAGCCUCGGUGGCCUA<br>GCUUCUUGCCCCUUGGGCC<u>UCCAUAAAGUAGGAAACACUACAU</u>CCCCCAGC<br>CCCUCCUCCCCUUCCUGCACCCGUACCCCC<u>UCCAUAAAGUAGGAAACACUAC</u><br><u>AG</u>UGGUCUUUGAAUAAAGUCUGAGUGGGCGGC<br>(3' UTR with 3 miR 142-3p binding sites variant 2) |
| 179 | UGAUAAUAGUCCAUAAAGUAGGAAACACUACAGCUGGAGCCUCGGUGGCCUA<br>GCUUCUUGCCCCUUGGGCCUCCCCCCAGCCCCUCCUCCCCUUCCUGCACCCG<br>UACCCCCGUGGUCUUUGAAUAAAGUCUGAGUGGGCGGC<br>(3' UTR with miR 142-3p binding site, P1 insertion variant 2) |
| 180 | UGAUAAUAGGCUGGAGCCUCGGUGGCC<u>UCCAUAAAGUAGGAAACACUACACUA</u><br>GCUUCUUGCCCCUUGGGCCUCCCCC<u>AG</u>CCCCUCCUCCCCUUCCUGCACCCG<br>UACCCCCGUGGUCUUUGAAUAAAGUCUGAGUGGGCGGC<br>(3' UTR with miR 142-3p binding site, P2 insertion variant 2) |
| 181 | UGAUAAUAGGCUGGAGCCUCGGUGGCCUAGCUUCUUGCCCCUUGGGCCU<u>CCA</u><br><u>UAAAGUAGGAAACACUACAU</u>CCCCCAGCCCCUCCUCCCCUUCCUGCA<u>CCCG</u><br>UACCCCCGUGGUCUUUGAAUAAAGUCUGAGUGGGCGGC<br>(3' UTR with miR 142-3p binding site, P3 insertion variant 2) |
| 182 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCCACCCCUAUCACAAUUA<br><br>GCAUUAAGUGGUCUUUGAAUAAAGUCUGAGUGGGCGGC<br>(3' UTR with miR 155-5p binding site variant 2) |
| 183 | UGAUAAUAGACCCCUAUCACAAUUAGCAUUAAGCUGGAGCCUCGGUGGCCUA<br><br>GCUUCUUGCCCCUUGGGCCACCCCUAUCACAAUUAGCAUUAAUCCCCCAGC<br><br>CCCUCCUCCCCUUCCUGCACCCGUACCCCCACCCCUAUCACAAUUAGCAUUA<br><br>AGUGGUCUUUGAAUAAAGUCUGAGUGGGCGGC<br><br>(3' UTR with 3 miR 155-5p binding sites variant 2) |
| 184 | UGAUAAUAGACCCCUAUCACAAUUAGCAUUAAGCUGGAGCCUCGGUGGCUA<br><br>GCUUCUUGCCCCUUGGGCCUCCAUAAAGUAGGAAACACUACAUCCCCCAGC<br>CCCUCCUCCCCUUCCUGCACCCGUACCCCCACCCCUAUCACAAUUAGCAUUA<br><br>AGUGGUCUUUGAAUAAAGUCUGAGUGGGCGGC<br><br>(3' UTR with 2 miR 155-5p binding sites and 1 miR 142-3p binding site variant 2) |

Stop codon = bold
miR 142-3p binding site = underline
miR 126-3p binding site = bold underline
miR 155-5p binding site = shaded
miR 142-5p binding site = shaded and bold underline

TABLE 4B

Exemplary Preferred UTRs

| SEQ ID NO: | Seqence |
|---|---|
| 5' UTR (v1)<br>(SEQ ID NO: 3) | GGGAAAUAAGAGAGAAAAGAAGAGUAAGAAGAAAUAUAAGAGCCACC |
| 5'UTR (v1 A)<br>(SEQ ID NO: 204) | AGGAAAUAAGAGAGAAAAGAAGAGUAAGAAGAAAUAUAAGAGCCACC |
| 5' UTR (v1.1)<br>(SEQ ID NO: 39) | GGGAAAUAAGAGAGAAAAGAAGAGUAAGAAGAAAUAUAAGACCCCGGC<br>GCCGCCACC |
| 5' UTR (v1.1 A)<br>(SEQ ID NO: 205) | AGGAAAUAAGAGAGAAAAGAAGAGUAAGAAGAAAUAUAAGACCCCGGC<br>GCCGCCACC |
| 3' UTR (v1)<br>(SEQ ID NO: 150) | UGAUAAUAGGCUGGAGCCUCGGUGGCCAUGCUUCUUGCCCCUUGGGCC<br>UCCCCCCAGCCCCUCCUCCCCUUCCUGCACCCGUACCCCCGUGGUCUU<br>UGAAUAAAGUCUGAGUGGGCGGC |
| 3' UTR (v1.1)<br>(SEQ ID NO: 175) | UGAUAAUAGGCUGGAGCCUCGGUGGCCAUGCUUCUUGCCCCUUGGGCC<br>UCCCCCCAGCCCCUCCUCCCCUUCCUGCACCCGUACCCCCGUGGUCUU<br>UGAAUAAAGUCUGAGUGGGCGGC |
| 3' UTR (miR122)<br>(SEQ ID NO: 206) | UGAUAAUAGGCUGGAGCCUCGGUGGCCAUGCUUCUUGCCCCUUGGGCC<br>UCCCCCCAGCCCCUCCUCCCCUUCCUGCACCCGUACCCCCCAAACACC<br>AUUGUCACACUCCAGUGGUCUUUGAAUAAAGUCUGAGUGGGCGGC |
| 3' UTR (v1.1 miR122)<br>(SEQ ID NO: 207) | UGAUAAUAGGCUGGAGCCUCGGUGGCCAUGCUUCUUGCCCCUUGGGCC<br>UCCCCCCAGCCCCUCCUCCCCUUCCUGCACCCGUACCCCCCAAACACC<br>AUUGUCACACUCCAGUGGUCUUUGAAUAAAGUCUGAGUGGGCGGC |
| 3' UTR (v1.1 mir142-3P)<br>(SEQ ID NO: 4) | UGAUAAUAGGCUGGAGCCUCGGUGGCCUAGCUUCUUGCCCCUUGGGCC<br>UCCCCCCAGCCCCUCCUCCCCUUCCUGCACCCGUACCCCCUCCAUAAA<br>GUAGGAAACACUACAGUGGUCUUUGAAUAAAGUCUGAGUGGGCGGC |
| 3' UTR (v1.1 mir 126-3P)<br>(SEQ ID NO: 177) | UGAUAAUAGGCUGGAGCCUCGGUGGCCUAGCUUCUUGCCCCUUGGGCC<br>UCCCCCCAGCCCCUCCUCCCCUUCCUGCACCCGUACCCCCGCAUUAU<br>UACUCACGGUACGAGUGGUCUUUGAAUAAAGUCUGAGUGGGCGGC |
| 3' UTR (mir-126, miR-142-3p)<br>(SEQ ID NO: 111) | UGAUAAUAGUCCAUAAAGUAGGAAACACUACAGCUGGAGCCUCGGUGG<br>CCAUGCUUCUUGCCCCUUGGGCCUCCCCCCAGCCCCUCCUCCCCUUCC<br>UGCACCCGUACCCCCCGCAUUAUUACUCACGGUACGAGUGGUCUUUGA<br>AUAAAGUCUGAGUGGGCGGC |
| 3' UTR (v.1.1 3x miR142-3p)<br>(SEQ ID NO: 178) | UGAUAAUAGUCCAUAAAGUAGGAAACACUACAGCUGGAGCCUCGGUGG<br>CCUAGCUUCUUGCCCCUUGGGCCUCCAUAAAGUAGGAAACACUACAUC<br>CCCCCAGCCCCUCCUCCCCUUCCUGCACCCGUACCCCCUCCAUAAAGU<br>AGGAAACACUACAGUGGUCUUUGAAUAAAGUCUGAGUGGGCGGC |

In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 116. In one embodiment, the 3' UTR of the mRNA comprising the miR-142-3p microRNA binding site comprises the sequence shown in SEQ ID NO: 134.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 121. In one embodiment, the 3' UTR of the mRNA of the invention comprising the miR-126-3p microRNA binding site comprises the sequence shown in SEQ ID NO: 149.

Non-limiting exemplary sequences for miRs to which a microRNA binding site(s) of the disclosure can bind include the following: miR-142-3p (SEQ ID NO: 115), miR-142-5p (SEQ ID NO: 117), miR-146-3p (SEQ ID NO: 135), miR-146-5p (SEQ ID NO: 136), miR-155-3p (SEQ ID NO: 137), miR-155-5p (SEQ ID NO: 138), miR-126-3p (SEQ ID NO: 120), miR-126-5p (SEQ ID NO: 122), miR-16-3p (SEQ ID NO: 139), miR-16-5p (SEQ ID NO: 140), miR-21-3p (SEQ ID NO: 141), miR-21-5p (SEQ ID NO: 142), miR-223-3p (SEQ ID NO: 143), miR-223-5p (SEQ ID NO: 144), miR-24-3p (SEQ ID NO: 145), miR-24-5p (SEQ ID NO: 146), miR-27-3p (SEQ ID NO: 147) and miR-27-5p (SEQ ID NO: 148). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA bindingsite to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA bindingsite for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3' UTR of the same sequence type.

In one embodiment, other regulatory elements and/or structural elements of the 5' UTR can influence miRNA mediated gene regulation. One example of a regulatory element and/or structural element is a structured IRES (Internal Ribosome Entry Site) in the 5' UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5' UTR in order to enhance microRNA mediated gene regulation.

At least one miRNA binding site can be engineered into the 3' UTR of a polynucleotide of the invention. In this context, at least two, at least three, at least four, at least five, at least six, at least seven, at least eight, at least nine, at least ten, or more miRNA binding sites can be engineered into a 3' UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3' UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3' UTR. As yet another non-limiting example, a miRNA binding site can be engineered near the 5' terminus of the 3' UTR and near the 3' terminus of the 3' UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment the miRNA sequence in the 5' UTR can be used to stabilize a polynucleotide of the invention described herein.

In another embodiment, a miRNA sequence in the 5' UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include miR-142-5p, miR-142-3p, miR-146a-5p, and miR-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a PAH polypeptide (e.g., the wild-type sequence, functional fragment, or variant thereof) and (ii) a miRNA binding site (e.g., a miRNA binding site that binds to miR-142) and/or a miRNA binding site that binds to miR-126.

12. 3' UTRs

In certain embodiments, a polynucleotide of the present invention (e.g., a polynucleotide comprising a nucleotide sequence encoding a PAH polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3' UTR selected from the group consisting of SEQ ID NO: 4 and 104 to 113, or any combination thereof. In certain embodiments, the 3' UTR comprises a 3' UTR selected from the group consisting of SEQ ID NO:4, SEQ ID NO:111, SEQ ID NO:150, SEQ ID NO:175, SEQ ID NO:177, SEQ ID NO:178, SEQ ID NO:206, or SEQ ID NO:207, or any combination thereof. In some embodiments, the 3' UTR comprises a nucleic acid sequence selected from the group consisting of SEQ ID NOs: 111, 112, or 113 or any combination thereof. In some embodiments, the 3' UTR comprises a nucleic acid sequence of SEQ ID NO: 111. In some embodiments, the 3' UTR comprises a nucleic acid sequence of SEQ ID NO: 112. In some embodiments, the 3' UTR comprises a nucleic acid sequences of SEQ ID NO: 113. In some embodiments, the 3' UTR comprises a nucleic acid sequence of SEQ ID NO: 4. In some embodiments, the 3' UTR comprises a nucleic acid sequence of SEQ ID NO: 111. In some embodiments, the 3' UTR comprises a nucleic acid sequence of SEQ ID NO: 150. In some embodiments, the 3' UTR comprises a nucleic acid sequences of SEQ ID NO: 175. In some embodiments, the 3' UTR comprises a nucleic acid sequence of SEQ ID NO: 177. In some embodiments, the 3' UTR comprises a nucleic acid sequences of SEQ ID NO: 178. In some embodiments, the 3' UTR comprises a nucleic acid sequence of SEQ ID NO: 206. In some embodiments, the 3' UTR comprises a nucleic acid sequences of SEQ ID NO: 207.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 4 and 104 to 113, or any combination thereof.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NO:4, SEQ ID NO:111, SEQ ID NO:150, SEQ ID NO:175, SEQ ID NO:177, SEQ ID NO:178, SEQ ID NO:206, or SEQ ID NO:207, or any combination thereof.

13. Regions Having a 5' Cap

The disclosure also includes a polynucleotide that comprises both a 5' Cap and a polynucleotide of the present invention (e.g., a polynucleotide comprising a nucleotide sequence encoding a PAH polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methylguanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a PAH polypeptide) incorporate a cap moiety.

In some embodiments, polynucleotides of the present invention (e.g., a polynucleotide comprising a nucleotide sequence encoding a PAH polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a PAH polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp(5')N1mpNp (cap 1), and 7mG(5')-ppp(5')N1mpN2mp (cap 2).

As a non-limiting example, capping chimeric polynucleotides post-manufacture can be more efficient as nearly 100% of the chimeric polynucleotides can be capped. This is in contrast to −80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

14. Poly-A Tails

In some embodiments, the polynucleotides of the present disclosure (e.g., a polynucleotide comprising a nucleotide sequence encoding a PAH polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long. In one embodiment, the poly-A tail is 100 nucleotides in length.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

15. Start Codon Region

The invention also includes a polynucleotide that comprises both a start codon region and the polynucleotide described herein (e.g., a polynucleotide comprising a nucleotide sequence encoding a PAH polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

16. Stop Codon Region

The invention also includes a polynucleotide that comprises both a stop codon region and the polynucleotide described herein (e.g., a polynucleotide comprising a nucleotide sequence encoding a PAH polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

17. Polynucleotide Comprising an mRNA Encoding a PAH Polypeptide

In certain embodiments, a polynucleotide of the present disclosure, for example a polynucleotide comprising an mRNA nucleotide sequence encoding a PAH polypeptide, comprises from 5' to 3' end:
(i) a 5' cap provided above;
(ii) a 5' UTR, such as the sequences provided above;
(iii) an open reading frame encoding a PAH polypeptide, e.g., a sequence optimized nucleic acid sequence encoding a PAH disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g., a miRNA binding site that binds to miRNA-142. In some embodiments, the 5' UTR comprises the miRNA binding site. In some embodiments, the 3' UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type human PAH (SEQ ID NO:1) or a truncated version thereof (e.g., SEQ ID NO:21).

In some embodiments, a polynucleotide of the present disclosure, for example a polynucleotide comprising an mRNA nucleotide sequence encoding a polypeptide, comprises (1) a 5' cap provided above, for example, CAP1, (2) a 5' UTR, (3) a nucleotide sequence ORF selected from the group consisting of SEQ ID NOs: 2, 5-20, and 22-38, (3) a stop codon, (4) a 3'UTR, and (5) a poly-A tail provided above, for example, a poly-A tail of about 100 residues.

Exemplary PAH nucleotide constructs are described below:

SEQ ID NO: 45 consists from 5' to 3' end: 5' UTR of SEQ ID NO: 3, PAH nucleotide ORF of SEQ ID NO: 2, and 3' UTR of SEQ ID NO: 4.

SEQ ID NO: 46 consists from 5' to 3' end: 5' UTR of SEQ ID NO: 3, PAH nucleotide ORF of SEQ ID NO: 5, and 3' UTR of SEQ ID NO: 4.

SEQ ID NO: 47 consists from 5' to 3' end: 5' UTR of SEQ ID NO: 3, PAH nucleotide ORF of SEQ ID NO: 6, and 3' UTR of SEQ ID NO: 4.

SEQ ID NO: 48 consists from 5' to 3' end: 5' UTR of SEQ ID NO: 3, PAH nucleotide ORF of SEQ ID NO: 7, and 3' UTR of SEQ ID NO: 4.

SEQ ID NO: 49 consists from 5' to 3' end: 5' UTR of SEQ ID NO: 3, PAH nucleotide ORF of SEQ ID NO: 8, and 3' UTR of SEQ ID NO: 4.

SEQ ID NO: 50 consists from 5' to 3' end: 5' UTR of SEQ ID NO: 3, PAH nucleotide ORF of SEQ ID NO: 9, and 3' UTR of SEQ ID NO: 4.

SEQ ID NO: 51 consists from 5' to 3' end: 5' UTR of SEQ ID NO: 3, PAH nucleotide ORF of SEQ ID NO: 10, and 3' UTR of SEQ ID NO: 4.

SEQ ID NO: 52 consists from 5' to 3' end: 5' UTR of SEQ ID NO: 3, PAH nucleotide ORF of SEQ ID NO: 11, and 3' UTR of SEQ ID NO: 4.

SEQ ID NO: 53 consists from 5' to 3' end: 5' UTR of SEQ ID NO: 3, PAH nucleotide ORF of SEQ ID NO: 12, and 3' UTR of SEQ ID NO: 4.

SEQ ID NO: 54 consists from 5' to 3' end: 5' UTR of SEQ ID NO: 3, PAH nucleotide ORF of SEQ ID NO: 13, and 3' UTR of SEQ ID NO: 4.

SEQ ID NO: 55 consists from 5' to 3' end: 5' UTR of SEQ ID NO: 3, PAH nucleotide ORF of SEQ ID NO: 14, and 3' UTR of SEQ ID NO: 4.

SEQ ID NO: 56 consists from 5' to 3' end: 5' UTR of SEQ ID NO: 3, PAH nucleotide ORF of SEQ ID NO: 15, and 3' UTR of SEQ ID NO: 4.

SEQ ID NO: 57 consists from 5' to 3' end: 5' UTR of SEQ ID NO: 3, PAH nucleotide ORF of SEQ ID NO: 16, and 3' UTR of SEQ ID NO: 4.

SEQ ID NO: 58 consists from 5' to 3' end: 5' UTR of SEQ ID NO: 3, PAH nucleotide ORF of SEQ ID NO: 17, and 3' UTR of SEQ ID NO: 4.

SEQ ID NO: 59 consists from 5' to 3' end: 5' UTR of SEQ ID NO: 3, PAH nucleotide ORF of SEQ ID NO: 18, and 3' UTR of SEQ ID NO: 4.

SEQ ID NO: 60 consists from 5' to 3' end: 5' UTR of SEQ ID NO: 3, PAH nucleotide ORF of SEQ ID NO: 19, and 3' UTR of SEQ ID NO: 4.

SEQ ID NO: 61 consists from 5' to 3' end: 5' UTR of SEQ ID NO: 3, PAH nucleotide ORF of SEQ ID NO: 20, and 3' UTR of SEQ ID NO: 4.

SEQ ID NO: 62 consists from 5' to 3' end: 5' UTR of SEQ ID NO: 3, PAH nucleotide ORF of SEQ ID NO: 11, and 3' UTR of SEQ ID NO: 4.

SEQ ID NO: 63 consists from 5' to 3' end: 5' UTR of SEQ ID NO: 3, PAH nucleotide ORF of SEQ ID NO: 12, and 3' UTR of SEQ ID NO: 4.

SEQ ID NO: 64 consists from 5' to 3' end: 5' UTR of SEQ ID NO: 3, PAH nucleotide ORF of SEQ ID NO: 13, and 3' UTR of SEQ ID NO: 4.

SEQ ID NO: 65 consists from 5' to 3' end: 5' UTR of SEQ ID NO: 3, PAH nucleotide ORF of SEQ ID NO: 22, and 3' UTR of SEQ ID NO: 4.

SEQ ID NO: 66 consists from 5' to 3' end: 5' UTR of SEQ ID NO: 3, PAH nucleotide ORF of SEQ ID NO: 23, and 3' UTR of SEQ ID NO: 4.

SEQ ID NO: 67 consists from 5' to 3' end: 5' UTR of SEQ ID NO: 3, PAH nucleotide ORF of SEQ ID NO: 24, and 3' UTR of SEQ ID NO: 4.

SEQ ID NO: 68 consists from 5' to 3' end: 5' UTR of SEQ ID NO: 3, PAH nucleotide ORF of SEQ ID NO: 25, and 3' UTR of SEQ ID NO: 4.

SEQ ID NO: 69 consists from 5' to 3' end: 5' UTR of SEQ ID NO: 3, PAH nucleotide ORF of SEQ ID NO: 26, and 3' UTR of SEQ ID NO: 4.

SEQ ID NO: 70 consists from 5' to 3' end: 5' UTR of SEQ ID NO: 3, PAH nucleotide ORF of SEQ ID NO: 27, and 3' UTR of SEQ ID NO: 4.

SEQ ID NO: 71 consists from 5' to 3' end: 5' UTR of SEQ ID NO: 3, PAH nucleotide ORF of SEQ ID NO: 28, and 3' UTR of SEQ ID NO: 4.

SEQ ID NO: 72 consists from 5' to 3' end: 5' UTR of SEQ ID NO: 3, PAH nucleotide ORF of SEQ ID NO: 29, and 3' UTR of SEQ ID NO: 4.

SEQ ID NO: 73 consists from 5' to 3' end: 5' UTR of SEQ ID NO: 3, PAH nucleotide ORF of SEQ ID NO: 30, and 3' UTR of SEQ ID NO: 4.

SEQ ID NO: 74 consists from 5' to 3' end: 5' UTR of SEQ ID NO: 3, PAH nucleotide ORF of SEQ ID NO: 31, and 3' UTR of SEQ ID NO: 4.

SEQ ID NO: 75 consists from 5' to 3' end: 5' UTR of SEQ ID NO: 3, PAH nucleotide ORF of SEQ ID NO: 32, and 3' UTR of SEQ ID NO: 4.

SEQ ID NO: 76 consists from 5' to 3' end: 5' UTR of SEQ ID NO: 3, PAH nucleotide ORF of SEQ ID NO: 33, and 3' UTR of SEQ ID NO: 4.

SEQ ID NO: 77 consists from 5' to 3' end: 5' UTR of SEQ ID NO: 3, PAH nucleotide ORF of SEQ ID NO: 34, and 3' UTR of SEQ ID NO: 4.

SEQ ID NO: 78 consists from 5' to 3' end: 5' UTR of SEQ ID NO: 3, PAH nucleotide ORF of SEQ ID NO: 35, and 3' UTR of SEQ ID NO: 4.

SEQ ID NO: 79 consists from 5' to 3' end: 5' UTR of SEQ ID NO: 3, PAH nucleotide ORF of SEQ ID NO: 36, and 3' UTR of SEQ ID NO: 4.

SEQ ID NO: 80 consists from 5' to 3' end: 5' UTR of SEQ ID NO: 3, PAH nucleotide ORF of SEQ ID NO: 37, and 3' UTR of SEQ ID NO: 4.

SEQ ID NO: 81 consists from 5' to 3' end: 5' UTR of SEQ ID NO: 3, PAH nucleotide ORF of SEQ ID NO: 38, and 3' UTR of SEQ ID NO: 4.

SEQ ID NO: 82 consists from 5' to 3' end: 5' UTR of SEQ ID NO: 3, PAH nucleotide ORF of SEQ ID NO: 29, and 3' UTR of SEQ ID NO: 4.

SEQ ID NO: 83 consists from 5' to 3' end: 5' UTR of SEQ ID NO: 3, PAH nucleotide ORF of SEQ ID NO: 30, and 3' UTR of SEQ ID NO: 4.

SEQ ID NO: 84 consists from 5' to 3' end: 5' UTR of SEQ ID NO: 3, PAH nucleotide ORF of SEQ ID NO: 31, and 3' UTR of SEQ ID NO: 4.

SEQ ID NO:201 consists from 5' to 3' end: 5' UTR of SEQ ID NO:3, PAH nucleotide ORF of SEQ ID NO:31, and 3' UTR of SEQ ID NO:178.

SEQ ID NO:202 consists from 5' to 3' end: 5' UTR of SEQ ID NO:3, PAH nucleotide ORF of SEQ ID NO:31, and 3' UTR of SEQ ID NO:177.

SEQ ID NO:203 consists from 5' to 3' end: 5' UTR of SEQ ID NO:3, PAH nucleotide ORF of SEQ ID NO:31, and 3' UTR of SEQ ID NO:175.

In certain embodiments, in constructs with SEQ ID NOs.: 45-54, 65-74 and 201-203, all uracils therein are replaced by N1-methylpseudouracil. In certain embodiments, in constructs with SEQ ID NOs.:55-64 and 75-84, all uracils therein are replaced by 5-methoxyuracil.

In some embodiments, a polynucleotide of the present disclosure, for example a polynucleotide comprising an mRNA nucleotide sequence encoding a PAH polypeptide, comprises (1) a 5' cap provided above, for example, CAP1, (2) a nucleotide sequence selected from the group consisting of SEQ ID NO: 45 to 84 or 201 to 203, and (3) a poly-A tail provided above, for example, a poly A tail of ~100 residues. In certain embodiments, in constructs with SEQ ID NOs.: 45-54, 65-74, and 201-203, all uracils therein are replaced by N1-methylpseudouracil. In certain embodiments, in constructs with SEQ ID NOs.:55-64 and 75-84, all uracils therein are replaced by 5-methoxyuracil.

TABLE 5

Modified mRNA constructs including ORFs encoding human PAH or a truncated version thereof (each of constructs #1 to #43 comprises a Cap1 5' terminal cap and a 3' terminal Poly A region)

| PAH mRNA construct | 5'UTR SEQ ID NO | PAH ORF Name (Chemistry) | SEQ ID NO | 3' UTR SEQ ID NO: |
|---|---|---|---|---|
| #1 (SEQ ID NO: 45) | 3 | PAH_001 (G5) | 2 | 4 |

TABLE 5-continued

Modified mRNA constructs including ORFs encoding human PAH or a truncated version thereof (each of constructs #1 to #43 comprises a Cap1 5' terminal cap and a 3' terminal Poly A region)

| PAH mRNA construct | 5'UTR SEQ ID NO | PAH ORF Name (Chemistry) | PAH ORF SEQ ID NO | 3' UTR SEQ ID NO: |
|---|---|---|---|---|
| #2 (SEQ ID NO: 46) | 3 | PAH_002 (G5) | 5 | 4 |
| #3 (SEQ ID NO: 47) | 3 | PAH_003 (G5) | 6 | 4 |
| #4 (SEQ ID NO: 48) | 3 | PAH_004 (G5) | 7 | 4 |
| #5 (SEQ ID NO: 49) | 3 | PAH_005 (G5) | 8 | 4 |
| #6 (SEQ ID NO: 50) | 3 | PAH_006 (G5) | 9 | 4 |
| #7 (SEQ ID NO: 51) | 3 | PAH_007 (G5) | 10 | 4 |
| #8 (SEQ ID NO: 52) | 3 | PAH_008 (G5) | 11 | 4 |
| #9 (SEQ ID NO: 53) | 3 | PAH_009 (G5) | 12 | 4 |
| #10 (SEQ ID NO: 54) | 3 | PAH_010 (G5) | 13 | 4 |
| #11 (SEQ ID NO: 55) | 3 | PAH011 (G6) | 14 | 4 |
| #12 (SEQ ID NO: 56) | 3 | PAH_012 (G6) | 15 | 4 |
| #13 (SEQ ID NO: 57) | 3 | PAH_013 (G6) | 16 | 4 |
| #14 (SEQ ID NO: 58) | 3 | PAH_014 (G6) | 17 | 4 |
| #15 (SEQ ID NO: 59) | 3 | PAH_015 (G6) | 18 | 4 |
| #16 (SEQ ID NO: 60) | 3 | PAH_016 (G6) | 19 | 4 |
| #17 (SEQ ID NO: 61) | 3 | PAH_017 (G6) | 20 | 4 |
| #18 (SEQ ID NO: 62) | 3 | PAH_008 (G6) | 11 | 4 |
| #19 (SEQ ID NO: 63) | 3 | PAH_009 (G6) | 12 | 4 |
| #20 (SEQ ID NO: 64) | 3 | PAH_010(G6) | 13 | 4 |
| #21 (SEQ ID NO: 65) | 3 | PAH_018 (G5) | 22 | 4 |
| #22 (SEQ ID NO: 66) | 3 | PAH_019 (G5) | 23 | 4 |
| #23 (SEQ ID NO: 67) | 3 | PAH_020 (G5) | 24 | 4 |
| #24 (SEQ ID NO: 68) | 3 | PAH_021 (G5) | 25 | 4 |
| #25 (SEQ ID NO: 69) | 3 | PAH_022 (G5) | 26 | 4 |
| #26 (SEQ ID NO: 70) | 3 | PAH_023 (G5) | 27 | 4 |
| #27 (SEQ ID NO: 71) | 3 | PAH_024 (G5) | 28 | 4 |
| #28 (SEQ ID NO: 72) | 3 | PAH_025 (G5) | 29 | 4 |
| #29 (SEQ ID NO: 73) | 3 | PAH_026 (G5) | 30 | 4 |
| #30 (SEQ ID NO: 74) | 3 | PAH_027 (G5) | 31 | 4 |
| #31 (SEQ ID NO: 75) | 3 | PAH_028 (G6) | 32 | 4 |
| #32 (SEQ ID NO: 76) | 3 | PAH_029 (G6) | 33 | 4 |
| #33 (SEQ ID NO: 77) | 3 | PAH_030 (G6) | 34 | 4 |
| #34 (SEQ ID NO: 78) | 3 | PAH_031 (G6) | 35 | 4 |
| #35 (SEQ ID NO: 79) | 3 | PAH_032 (G6) | 36 | 4 |
| #36 (SEQ ID NO: 80) | 3 | PAH_033 (G6) | 37 | 4 |
| #37 (SEQ ID NO: 81) | 3 | PAH_034 (G6) | 38 | 4 |
| #38 (SEQ ID NO: 82) | 3 | PAH_025 (G6) | 29 | 4 |
| #39 (SEQ ID NO: 83) | 3 | PAH_026 (G6) | 30 | 4 |
| #40 (SEQ ID NO: 84) | 3 | PAH_027 (G6) | 31 | 4 |
| #41 (SEQ ID NO: 201) | 3 | PAH_027 (G5) | 31 | 178 |
| #42 (SEQ ID NO: 202) | 3 | PAH_027 (G5) | 31 | 177 |
| #43 (SEQ ID NO: 203) | 3 | PAH_027 (G5) | 31 | 175 |

18. Methods of Making Polynucleotides

The present disclosure also provides methods for making a polynucleotide of the invention (e.g., a polynucleotide comprising a nucleotide sequence encoding a PAH polypeptide) or a complement thereof.

In some aspects, a polynucleotide (e.g., a RNA, e.g., an mRNA) disclosed herein, and encoding a PAH polypeptide, can be constructed using in vitro transcription (IVT). In other aspects, a polynucleotide (e.g., a RNA, e.g., an mRNA) disclosed herein, and encoding a PAH polypeptide, can be constructed by chemical synthesis using an oligonucleotide synthesizer.

In other aspects, a polynucleotide (e.g., a RNA, e.g., an mRNA) disclosed herein, and encoding a PAH polypeptide is made by using a host cell. In certain aspects, a polynucleotide (e.g., a RNA, e.g., an mRNA) disclosed herein, and encoding a PAH polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a PAH polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a PAH polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase α (pol α) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014/028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 185 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention.

For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention. Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a PAH polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857; WO2012135805, WO2013151671; U.S. Publ. No. US20130115272; or U.S. Pat. No. 8,999,380 or 8,710,200, all of which are herein incorporated by reference in their entireties.

c. Purification of Polynucleotides Encoding PAH

Purification of the polynucleotides described herein (e.g., a polynucleotide comprising a nucleotide sequence encoding a PAH polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a PAH polypeptide) removes impurities that can reduce or remove an unwanted immune response, e.g., reducing cytokine activity.

In some embodiments, the polynucleotide of the invention (e.g., a polynucleotide comprising a nucleotide sequence encoding a PAH polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a PAH polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded PAH protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a PAH polypeptide comprising one or more of the point mutations known in the art.

In some embodiments, the use of RP-HPLC purified polynucleotide increases PAH protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of PAH protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional PAH protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of PAH protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable PAH activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional PAH in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding PAH

In some embodiments, the polynucleotides of the present invention (e.g., a polynucleotide comprising a nucleotide sequence encoding a PAH polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

19. Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a PAH polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a PAH polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a PAH polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, MD, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinylpyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions is maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

20. Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:

(a) a polynucleotide comprising a nucleotide sequence encoding a PAH polypeptide; and (b) a delivery agent.

Lipid Nanoparticle Formulations

In some embodiments, nucleic acids of the invention (e.g. PAH mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Nucleic acids of the present disclosure (e.g. PAH mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

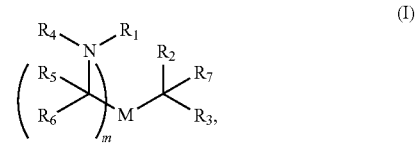

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —N(R)S(O)$_2$R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

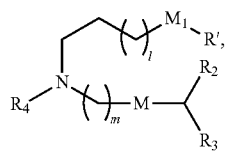

(IA)

or its N-oxide, or a salt or isomer thereof, wherein 1 is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S)$N(R)_2$, or —$NHC(O)N(R)_2$. For example, Q is —$N(R)C(O)$ R, or —$N(R)S(O)_2R$.

In certain embodiments, a subset of compounds of Formula (I) includes those of Formula (IB):

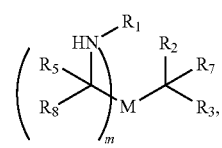

(IB)

or its N-oxide, or a salt or isomer thereof in which all variables are as defined herein. For example, m is selected from 5, 6, 7, 8, and 9; $R_4$ is hydrogen, unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)$ $R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S) $N(R)_2$, or —$NHC(O)N(R)_2$. For example, Q is —$N(R)C(O)$ R, or —$N(R)S(O)_2R$.

In certain embodiments, a subset of compounds of Formula (I) includes those of Formula (II):

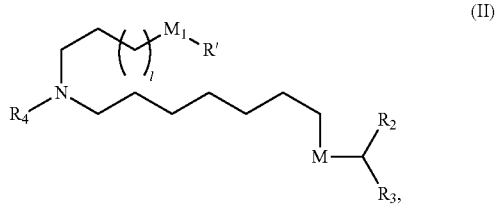

(II)

or its N-oxide, or a salt or isomer thereof, wherein 1 is selected from 1, 2, 3, 4, and 5; $M_1$ is a bond or M'; $R_4$ is hydrogen, unsubstituted $C_{1-3}$ alkyl, or —$(CH_2)_nQ$, in which n is 2, 3, or 4, and Q is OH, —$NHC(S)N(R)_2$, —$NHC(O)$ $N(R)_2$, —$N(R)C(O)R$, —$N(R)S(O)_2R$, —$N(R)R_8$, —NHC $(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In one embodiment, the compounds of Formula (I) are of Formula (IIa),

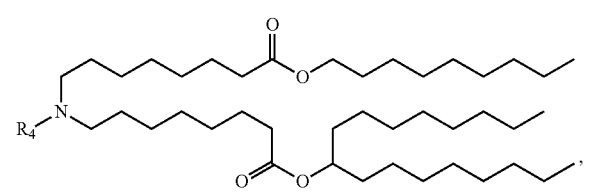

(IIa)

or their N-oxides, or salts or isomers thereof, wherein $R_4$ is as described herein.

In another embodiment, the compounds of Formula (I) are of Formula (IIb),

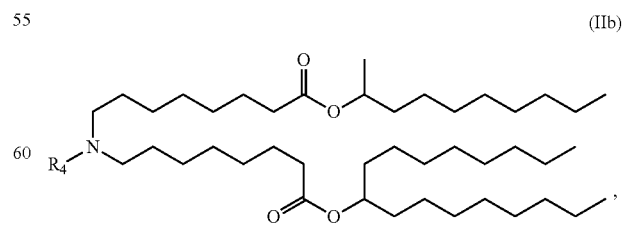

(IIb)

or their N-oxides, or salts or isomers thereof, wherein $R_4$ is as described herein.

In another embodiment, the compounds of Formula (I) are of Formula (IIc) or (IIe):

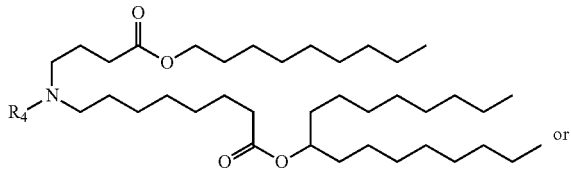
(IIc)

or

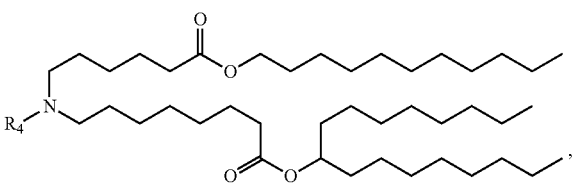
(IIe)

or their N-oxides, or salts or isomers thereof, wherein $R_4$ is as described herein.

In another embodiment, the compounds of Formula (I) are of Formula (IIf):

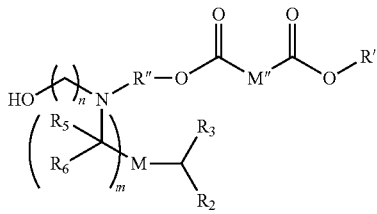
(IIf)

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (IId),

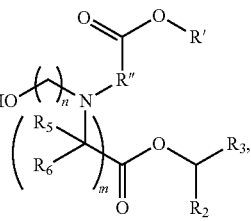
(IId)

or their N-oxides, or salts or isomers thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg),

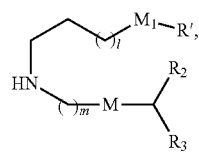
(IIg)

or their N-oxides, or salts or isomers thereof, wherein l is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

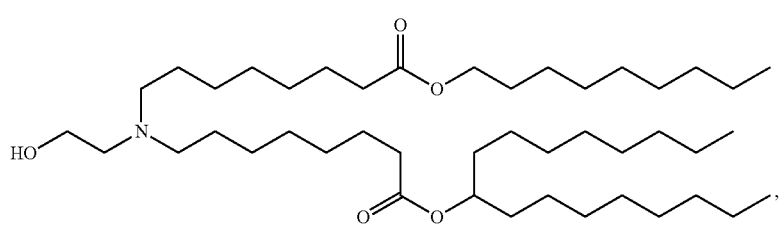
(Compound II)

or a salt thereof.

In some embodiments, the ionizable lipid is

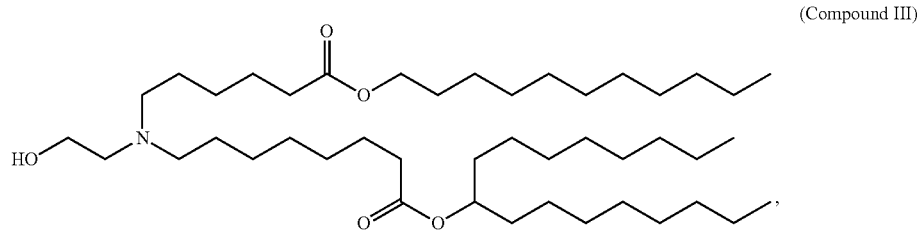 [SMILES: CCCCCCCCCCCOC(=O)CCCCCN(CCO)CCCCCCCC(=O)OC(CCCCCCCC)CCCCCCCC]

(Compound III)

or a salt thereof.

In some embodiments, the ionizable lipid is

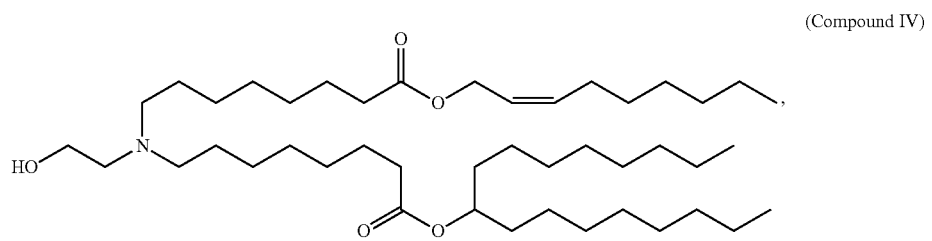 [SMILES: CCCCCC/C=C\COC(=O)CCCCCCCN(CCO)CCCCCCCC(=O)OC(CCCCCCCC)CCCCCCCC]

(Compound IV)

or a salt thereof.

In some embodiments, the ionizable lipid is

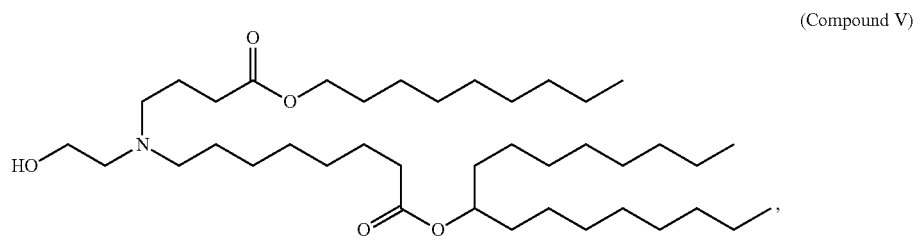 [SMILES: CCCCCCCCCOC(=O)CCCN(CCO)CCCCCCCC(=O)OC(CCCCCCCC)CCCCCCCC]

(Compound V)

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some aspects, the ionizable lipids of the present disclosure may be one or more of compounds of formula (III),

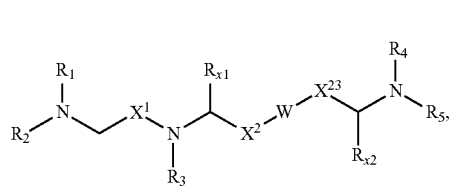

(III)

or salts or isomers thereof, wherein

W is

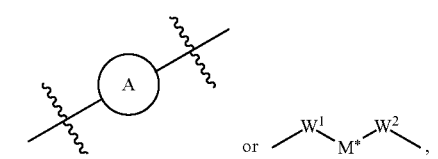

ring A is

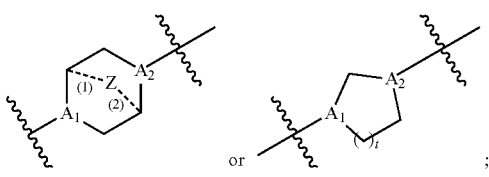

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —C(O)S—, —SC(O)—, an aryl group, and a heteroaryl group;

M* is $C_1$-$C_6$ alkyl, $W^1$ and $W^2$ are each independently selected from the group consisting of —O— and —N(R$_6$)—;

each $R_6$ is independently selected from the group consisting of H and $C_{1-5}$ alkyl;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$—C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

when ring A is

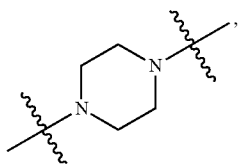 [SMILES: *N1CCN(*)CC1]

then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (IIIa1)-(IIIa8):

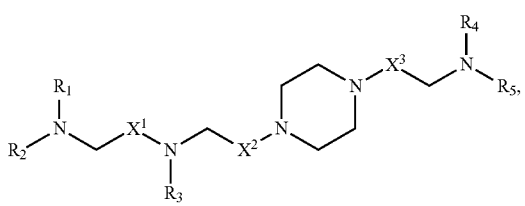

(IIIa1)

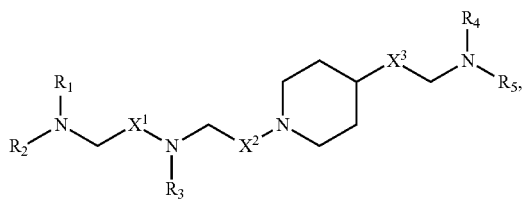

(IIIa2)

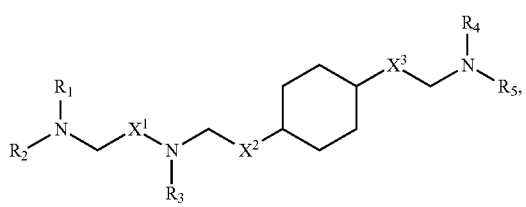

(IIIa3)

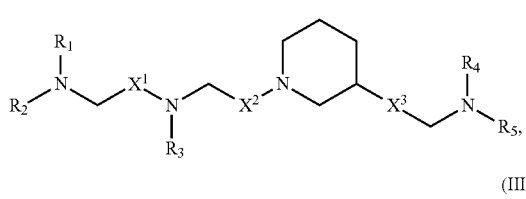

(IIIa4)

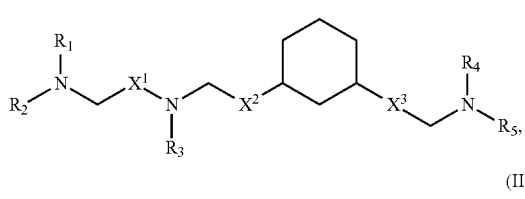

(IIIa5')

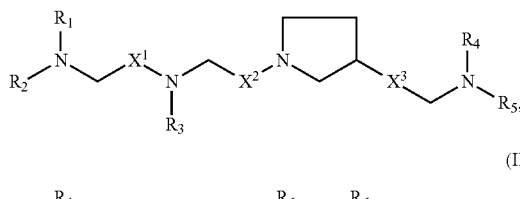

(IIIa6)

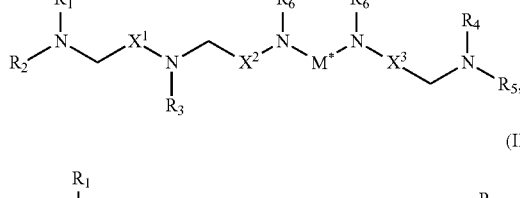

(IIIa7)

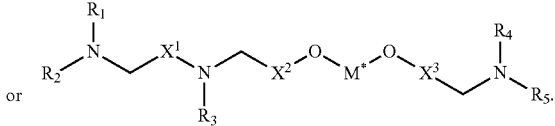

(IIIa8)

or

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is

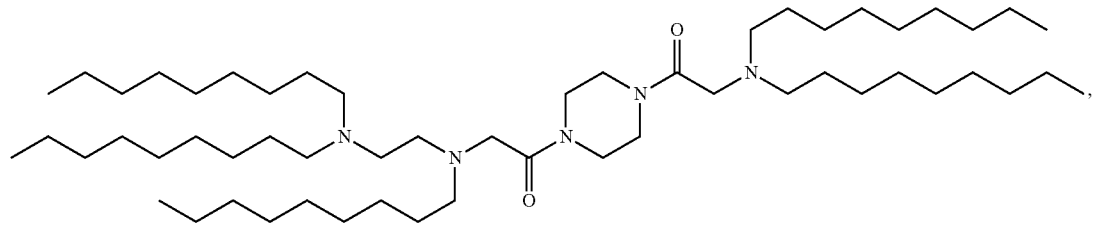

(Compound VI)

or a salt thereof.

In some embodiments, the ionizable lipid is (Compound VII), or a salt thereof.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid useful or potentially useful in the present invention is an analog or variant of DSPC. In certain embodiments, a phospholipid useful or potentially useful in the present invention is a compound of Formula (IV):

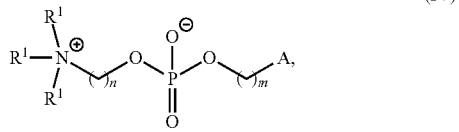

(IV)

or a salt thereof, wherein:
each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

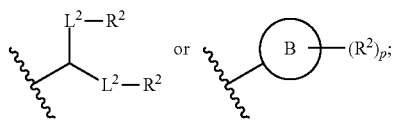

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, —$NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, —$NR^NC(O)N(R^N)$, C(O)O, OC(O), OC(O)O, $OC(O)N(R^N)$, $NR^NC(O)O$, C(O)S, SC(O), —$C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, —$S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

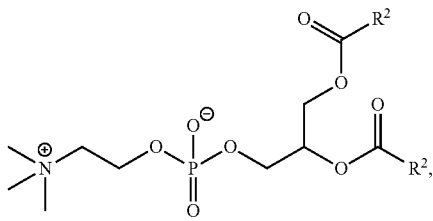

wherein each instance of $R^2$ is independently unsubstituted alkyl, unsubstituted alkenyl, or unsubstituted alkynyl.

In some embodiments, the phospholipids may be one or more of the phospholipids described in U.S. Application No. 62/520,530.

i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IV), at least one of $R^1$ is not methyl. In certain embodiments, at least one of $R^1$ is not hydrogen or methyl. In certain embodiments, the compound of Formula (IV) is of one of the following formulae:

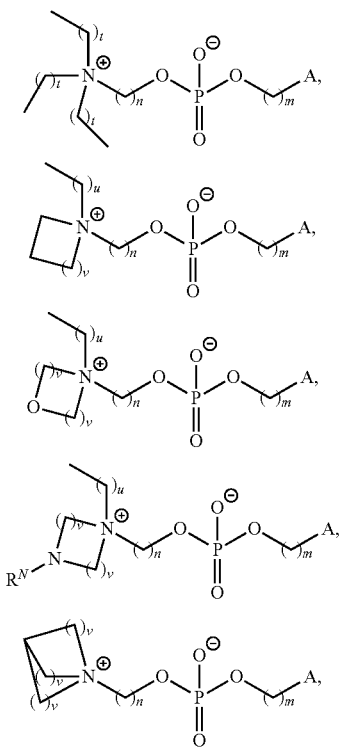

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, a compound of Formula (IV) is of Formula (IV-a):

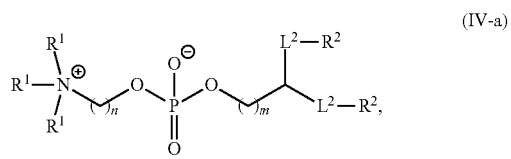

(IV-a)

or a salt thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IV) is of Formula (IV-b):

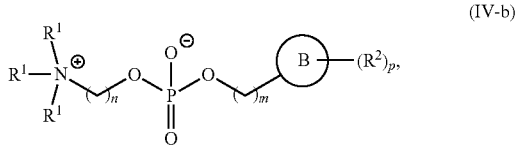

(IV-b)

or a salt thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, $N(R^N)$, O, S, —C(O), C(O)N($R^N$), $NR^NC(O)$, $NR^NC(O)N(R^N)$, C(O)O, OC(O), OC(O)O, —OC(O)N($R^N$), $NR^NC(O)O$, C(O)S, SC(O), C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, $NR^NC(S)N(R^N)$, S(O), OS(O), —S(O)O, OS(O)O, OS(O)$_2$, S(O)$_2$O, OS(O)$_2$O, N($R^N$)S(O), S(O)N($R^N$), —N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O.

In certain embodiments, the compound of Formula (IV) is of Formula (IV-c):

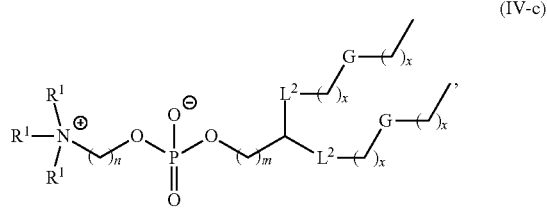

(IV-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, N($R^N$), O, S, C(O), C(O)N($R^N$), $NR^NC(O)$, —$NR^NC(O)N(R^N)$, C(O)O, OC(O), OC(O)O, OC(O)N($R^N$), $NR^NC(O)O$, C(O)S, SC(O), —C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, $NR^NC(S)N(R^N)$, S(O), OS(O), S(O)O, OS(O)O, OS(O)$_2$, S(O)$_2$O, OS(O)$_2$O, N($R^N$)S(O), —S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

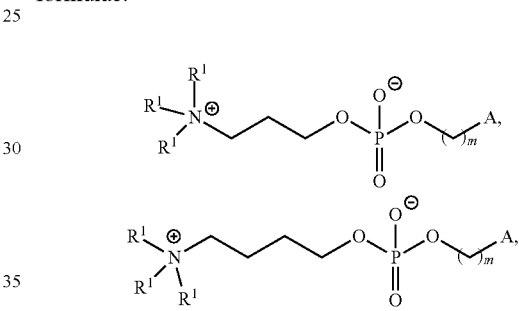

or a salt thereof.

Alternative Lipids

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful.

In certain embodiments, an alternative lipid is used in place of a phospholipid of the present disclosure.

In certain embodiments, an alternative lipid of the invention is oleic acid.

In certain embodiments, the alternative lipid is one of the following:

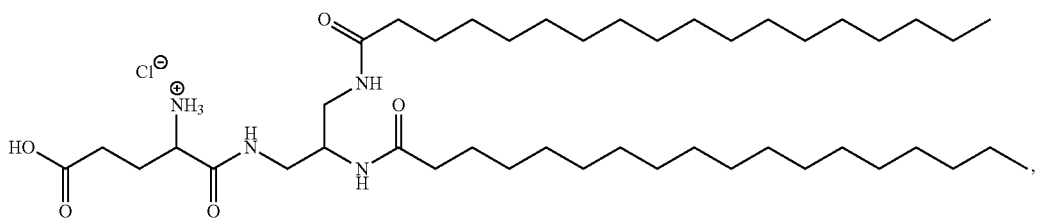

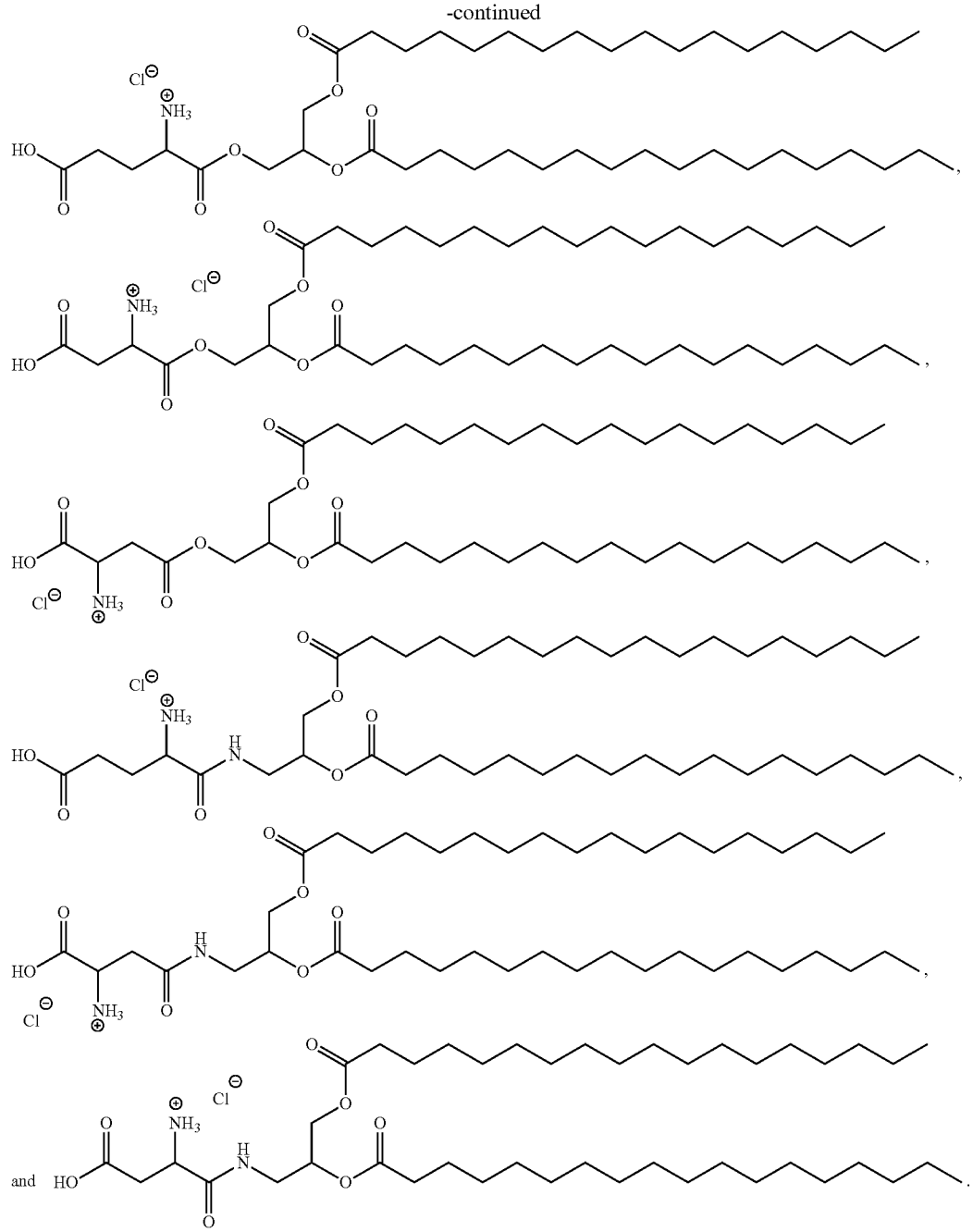

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of. Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

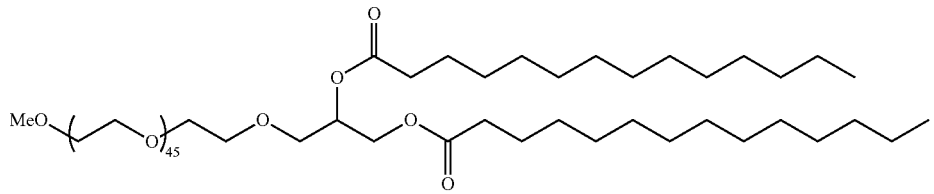

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

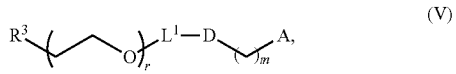
(V)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^N$), S, C(O), C(O)N($R^N$), $NR^NC(O)$, C(O)O, —OC(O), OC(O)O, OC(O)N($R^N$), $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

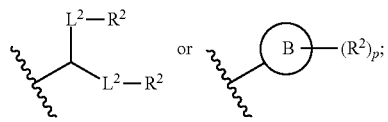

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC(O)$, C(O)O, OC(O), OC(O)O, OC(O)N($R^N$), —$NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^NC(O)$, —$NR^NC(O)N(R^N)$, C(O)O, OC(O), OC(O)O, OC(O)N($R^N$), $NR^NC(O)O$, C(O)S, SC(O), —C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, $NR^NC(S)N(R^N)$, S(O), OS(O), S(O)O, OS(O)O, OS(O)$_2$, S(O)$_2$O, OS(O)$_2$O, N($R^N$)S(O), —S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R^3$ is —$OR^O$, and $R^O$ is hydrogen). In certain embodiments, the compound of Formula (V) is of Formula (V—OH):

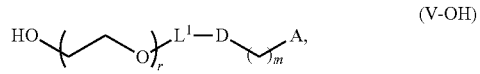
(V-OH)

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI):

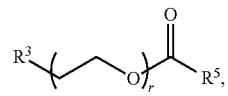
(VI)

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, N($R^N$), O, S, C(O), —C(O)N($R^N$), $NR^NC(O)$, $NR^NC(O)N(R^N)$, C(O)O, OC(O), OC(O)O, OC(O)N($R^N$), —$NR^NC(O)O$, C(O)S, SC(O), C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, $NR^NC(S)N(R^N)$, S(O), OS(O), S(O)O, OS(O)O, OS(O)$_2$, —S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O; and each instance of $R^N$ is independently hydrogen, optionally substituted alkyl, or a nitrogen protecting group.

In certain embodiments, the compound of Formula (VI) is of Formula (VI-OH):

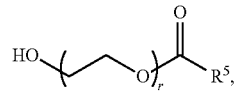
(VI-OH)

or a salt thereof. In some embodiments, r is 45.

In yet other embodiments the compound of Formula (VI) is:

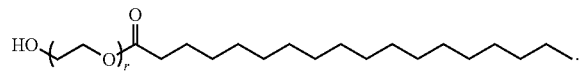

or a salt thereof.

In one embodiment, the compound of Formula (VI) is (Compound I)

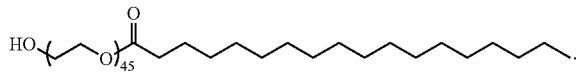

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of

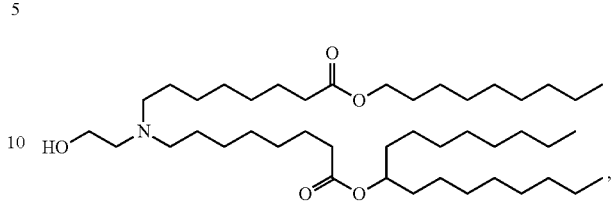

and a PEG lipid comprising Formula VI.

In some embodiments, a LNP of the invention comprises an ionizable cationic lipid of

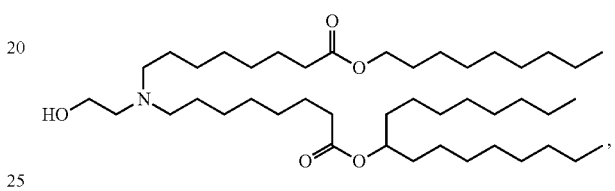

and an alternative lipid comprising oleic acid.

In some embodiments, a LNP of the invention comprises an ionizable cationic lipid of

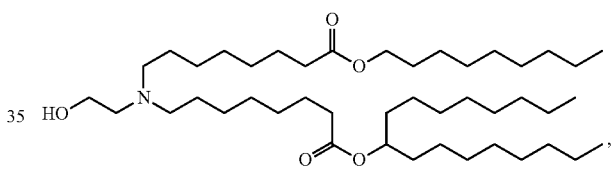

an alternative lipid comprising oleic acid, a structural lipid comprising cholesterol, and a PEG lipid comprising a compound having Formula VI.

In some embodiments, a LNP of the invention comprises an ionizable cationic lipid of

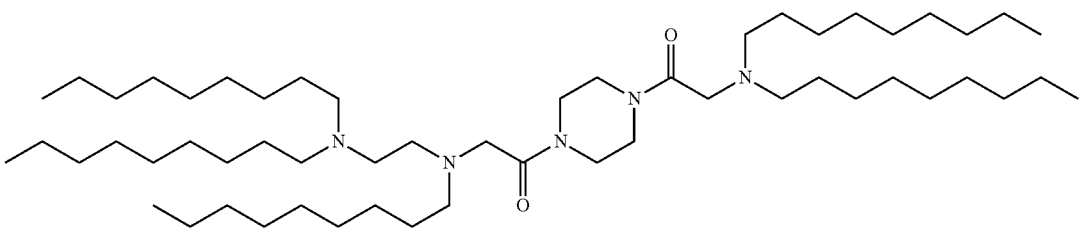 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP of the invention comprises an ionizable cationic lipid of
a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1 14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "C2-14 alkenyl" means an optionally substituted linear or branched hydrocarbon including 2 14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "C2-14 alkynyl" means an optionally substituted linear or branched hydrocarbon including 2 14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups).

Examples of carbocycles include cyclopropyl, cyclopentyl, cyclohexyl, phenyl, naphthyl, and 1,2 dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR OC(O)R), an aldehyde (e.g., C(O)H), a carbonyl (e.g., C(O)R, alternatively represented by C=O), an acyl halide (e.g., C(O)X, in which X is a halide selected from bromide, fluoride, chloride, and iodide), a carbonate (e.g., OC(O)OR), an alkoxy (e.g., OR), an acetal (e.g., C(OR)$_2$R"", in which each OR are alkoxy groups that can be the same or different and R"" is an alkyl or alkenyl group), a phosphate (e.g., P(O)43-), a thiol (e.g., SH), a sulfoxide (e.g., S(O)R), a sulfinic acid (e.g., S(O)OH), a sulfonic acid (e.g., S(O)2OH), a thial (e.g., C(S)H), a sulfate (e.g., S(O)42-), a sulfonyl (e.g., S(O)2), an amide (e.g., C(O)NR2, or N(R)C(O)R), an azido (e.g., N3), a nitro (e.g., NO2), a cyano (e.g., CN), an isocyano (e.g., NC), an acyloxy (e.g., OC(O)R), an amino (e.g., NR2, NRH, or NH2), a carbamoyl (e.g., OC(O)NR2, OC(O)NRH, or OC(O)NH2), a sulfonamide (e.g., S(O)2NR2, S(O)2NRH, S(O)2NH2, N(R)S(O)2R, N(H)S(O)2R, N(R)S(O)2H, or N(H)S(O)2H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C1 6 alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N☐O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C 6 alkyl, C1-C6 alkenyl, C1-C6 alkynyl, 3-14-membered carbocycle or 3-14-membered heterocycle) derivatives.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, poly acrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound as described herein, and (ii) a polynucleotide encoding a PAH polypeptide. In such nanoparticle composition, the lipid composition disclosed herein can encapsulate the polynucleotide encoding a PAH polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid: about 5-25% structural lipid: about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a PAH polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

21. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a PAH polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N- dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropylltetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2 S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2 S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z, 16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxyl-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1 S,25)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos.

US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin (34 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a PAH polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-SLAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a PAH polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding a PAH polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a PAH polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

f. Cations and Anions

In some embodiments, the compositions or formulations of the present disclosure comprise the polynucleotides described herein (e.g., a polynucleotide comprising a nucleotide sequence encoding a PAH polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

g. Amino Acid Lipids

In some embodiments, the compositions or formulations of the present disclosure comprise the polynucleotides described herein (e.g., a polynucleotide comprising a nucleotide sequence encoding a PAH polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

h. Interpolyelectrolyte Complexes

In some embodiments, the compositions or formulations of the present disclosure comprise the polynucleotides described herein (e.g., a polynucleotide comprising a nucleotide sequence encoding a PAH polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

i. Crystalline Polymeric Systems

In some embodiments, the compositions or formulations of the present disclosure comprise the polynucleotides described herein (e.g., a polynucleotide comprising a nucleotide sequence encoding a PAH polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

j. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a PAH polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TIS-SELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

k. Peptides and Proteins

In some embodiments, the compositions or formulations of the present disclosure comprise the polynucleotides described herein (e.g., a polynucleotide comprising a nucleotide sequence encoding a PAH polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

l. Conjugates

In some embodiments, the compositions or formulations of the present disclosure comprise the polynucleotides described herein (e.g., a polynucleotide comprising a nucleotide sequence encoding a PAH polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

22. Accelerated Blood Clearance

The disclosure provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically, by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance, many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of

B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically unregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested.

Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance, the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively, agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5-). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related pseudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

23. Methods of Use

The polynucleotides, pharmaceutical compositions and formulations described herein are used in the preparation, manufacture and therapeutic use of to treat and/or prevent PAH-related diseases, disorders or conditions. In some embodiments, the polynucleotides, compositions and formulations of the invention are used to treat and/or prevent hyperphenylalaninemia. In some embodiments, the polynucleotides, compositions and formulations of the invention are used to treat and/or prevent phenylketonuria.

In some embodiments, the polynucleotides, pharmaceutical compositions and formulations of the invention are used in methods for reducing the levels of phenylalanine in a subject in need thereof. For instance, one aspect of the invention provides a method of alleviating the symptoms of PKU in a subject comprising the administration of a composition or formulation comprising a polynucleotide encoding PAH to that subject (e.g., an mRNA encoding a PAH polypeptide).

In some embodiments, the polynucleotides, pharmaceutical compositions and formulations of the invention are used to reduce the level of phenylalanine, the method comprising administering to the subject an effective amount of a polynucleotide encoding a PAH polypeptide. In some embodiments, the administration of the polynucleotide, pharmaceutical composition or formulation of the invention results in reduction in the level of phenylalanine to less than 1,200 µM (e.g., 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175 µM), within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

In some embodiments, the administration of an effective amount of a polynucleotide, pharmaceutical composition or formulation of the invention reduces the levels of a biomarker of PKU. In some embodiments, the administration of the polynucleotide, pharmaceutical composition or formulation of the invention results in reduction in the level of one or more biomarkers of PKU, within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

Replacement therapy is a potential treatment for PKU. Thus, in certain aspects of the invention, the polynucleotides, e.g., mRNA, disclosed herein comprise one or more sequences encoding a PAH polypeptide that is suitable for use in gene replacement therapy for PKU. In some embodiments, the present disclosure treats a lack of PAH or PAH activity, or decreased or abnormal PAH activity in a subject by providing a polynucleotide, e.g., mRNA, that encodes a PAH polypeptide to the subject. In some embodiments, the polynucleotide is sequence-optimized. In some embodiments, the polynucleotide (e.g., an mRNA) comprises a nucleic acid sequence (e.g., an ORF) encoding a PAH polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142 and/or a miRNA binding site that binds miRNA-126.

In some embodiments, the administration of a composition or formulation comprising polynucleotide, pharmaceutical composition or formulation of the invention to a subject results in a decrease in phenylalanine in blood/plasma to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of PAH in cells of the subject. In some embodiments, administering the polynucleotide, pharmaceutical composition or formulation of the invention results in an increase of PAH expression and/or enzymatic activity in the subject. For example, in some embodiments, the polynucleotides of the present invention are used in methods of administering a composition or formulation comprising an mRNA encoding a PAH polypeptide to a subject, wherein the method results in an increase of PAH expression and/or enzymatic activity in at least some cells of a subject.

In some embodiments, the administration of a composition or formulation comprising an mRNA encoding a PAH polypeptide to a subject results in an increase of PAH expression and/or enzymatic activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal subject, e.g., a human not suffering from PKU.

In some embodiments, the administration of the polynucleotide, pharmaceutical composition or formulation of the invention results in expression of PAH protein in at least some of the cells of a subject that persists for a period of time sufficient to allow significant phenylalanine metabolism to occur.

In some embodiments, the expression of the encoded polypeptide is increased. In some embodiments, the polynucleotide increases PAH expression and/or enzymatic activity levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the PAH expression and/or enzymatic activity level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 2 and 5-20 or a polynucleotide selected from the group of SEQ ID NOs: 22-38, wherein the polynucleotide encodes an PAH polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotides (e.g., mRNA), pharmaceutical compositions and formulations used in the methods of the invention comprise a uracil-modified sequence encoding a PAH polypeptide disclosed herein and a miRNA binding site disclosed herein, e.g., a miRNA binding site that binds to miR-142 and/or a miRNA binding site that binds to miR-126. In some embodiments, the uracil-modified sequence encoding a PAH polypeptide comprises at least one chemically modified nucleobase, e.g., N1-methylpseudouracil or 5-methoxyuracil. In some embodiments, at least 95% of a type of nucleobase (e.g., uracil) in a uracil-modified sequence encoding a PAH polypeptide of the invention are modified nucleobases. In some embodiments, at least 95% of uracil in a uracil-modified sequence encoding a PAH polypeptide is 1-N-methylpseudouridine or 5-methoxyuridine. In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 47.5:10.5:39.0:3.0 or about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10: 38.5:3; 48.5:10.5:39:2; 48.5:10.5:38.5:2.5; 48.5:10.5:39.5: 1.5; 48.5:10.5:38.0:3; 47:10.5:39.5:3; 47:10:40.5:2.5; 47:11: 40:2; 47:10.5:39.5:3; 48:10.5:38.5:3; 48:10:39.5:2.5; 48:11: 39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 47.5:10.5:39.0:3.0 or about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

PKU is associated with an impaired ability to convert phenylalanine to tyrosine. Accordingly, PKU patients commonly show high levels of phenylalanine in their blood.

PKU is an autosomal recessive inborn error of amino acid metabolism characterized by the inability to convert phenylalanine to tyrosine. Accordingly, PKU patients can be asymptomatic carriers of the disorder or suffer from the various symptoms associated with the disease. PKU patients commonly show high levels of phenylketones (produced via alternative pathways when phenylalanine metabolism is impaired) in their plasma, serum, urine, and/or tissue (e.g., liver). Unless otherwise specified, the methods of treating PKU patients or human subjects disclosed herein include treatment of both asymptomatic carriers and those individuals with abnormal levels of biomarkers.

PAH Protein Expression Levels

Certain aspects of the invention feature measurement, determination and/or monitoring of the expression level or levels of phenylalanine hydroxylase (PAH) protein in a subject, for example, in an animal (e.g., rodents, primates, and the like) or in a human subject. Animals include normal, healthy or wildtype animals, as well as animal models for use in understanding PKU and treatments thereof. Exemplary animal models include rodent models, for example, PAH deficient mice also referred to as PAH mice.

PAH protein expression levels can be measured or determined by any art-recognized method for determining protein levels in biological samples, e.g., from blood samples or a needle biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased PAH protein expression levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy. In some embodiments, an mRNA therapy of the invention (e.g., a single intravenous dose) results in decreased phenylalanine expression levels in the blood, plasma, or liver tissue of the subject (e.g., less than 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175 or 1,200 µM) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy.

PAH Protein Activity

In PKU patients, PAH enzymatic activity is reduced compared to a normal physiological activity level. Further aspects of the invention feature measurement, determination and/or monitoring of the activity level(s) (i.e., enzymatic activity level(s)) of PAH protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample.

In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. In certain embodiments of the invention feature PAH activity described in terms of U/ml plasma or U/mg protein (tissue), where units ("U") are described in terms of nmol substrate hydrolyzed per hour (or nmol/hr).

In certain embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of PAH activity in tissue (e.g., liver) between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

PAH Biomarkers

Further aspects of the invention feature determining the level (or levels) of a biomarker determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase "elevated level" means amounts greater than normally found in a normal or wildtype preclinical animal or in a normal or healthy subject, e.g. a human subject. As used herein, the term "supraphysiologic" means amounts greater than normally found in a normal or wildtype preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference blood, serum, plasma, and/or tissue (e.g., liver) phenylalanine level, in said subject prior to administration (e.g., in a person suffering from PKU) or in a normal or healthy subject. Comparing or comparison to can also be in the context, for example, of comparing to a control value, e.g., as compared to a reference blood, serum, plasma and/or tissue (e.g., liver) Phe level in said subject prior to administration (e.g., in a person suffering from PKU) or in a normal or healthy subject.

As used herein, a "control" is preferably a sample from a subject wherein the PKU status of said subject is known. In one embodiment, a control is a sample of a healthy patient. In another embodiment, the control is a sample from at least one subject having a known PKU status, for example, a severe, mild, or healthy PKU status, e.g. a control patient. In another embodiment, the control is a sample from a subject not being treated for PKU. In a still further embodiment, the control is a sample from a single subject or a pool of samples from different subjects and/or samples taken from the subject(s) at different time points.

The term "level" or "level of a biomarker" as used herein, preferably means the mass, weight or concentration of a biomarker of the invention within a sample or a subject. It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In certain embodiments, LC-MS can be used as a means for determining the level of a biomarker according to the invention.

The term "determining the level" of a biomarker as used herein can mean methods which include quantifying an amount of at least one substance in a sample from a subject, for example, in a bodily fluid from the subject (e.g., serum, plasma, urine, lymph, etc.) or in a tissue of the subject (e.g., liver, etc.).

The term "reference level" as used herein can refer to levels (e.g., of a biomarker) in a subject prior to administration of an mRNA therapy of the invention (e.g., in a person suffering from PKU) or in a normal or healthy subject.

As used herein, the term "normal subject" or "healthy subject" refers to a subject not suffering from symptoms associated with PKU. Moreover, a subject will be considered to be normal (or healthy) if it has no mutation of the functional portions or domains of the PAH gene and/or no mutation of the PAH gene resulting in a reduction of or deficiency of the enzyme PAH or the activity thereof, resulting in symptoms associated with PKU. Said mutations will be detected if a sample from the subject is subjected to a genetic testing for such PAH mutations. In certain embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for PKU or in a subject being treated for PKU to a control level of the biomarker comprises comparing the level of the biomarker in the sample from the subject (in need of treatment or being treated for PKU) to a baseline or reference level, wherein if a level of the biomarker in the sample from the subject (in need of treatment or being treated for PKU) is elevated, increased or higher compared to the baseline or reference level, this is indicative that the subject is suffering from PKU and/or is in need of treatment; and/or wherein if a level of the biomarker in the sample from the subject (in need of treatment or being treated for PKU) is decreased or lower compared to the baseline level this is indicative that the subject is not suffering from, is successfully being treated for PKU, or is not in need of treatment for PKU. The stronger the reduction (e.g., at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, or at least 100% reduction) of the level of a biomarker, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., plasma, serum, urine, e.g., urinary sediment) or in tissue(s) in a subject (e.g., liver), within 1, 2, 3, 4, 5, 6 or more days following administration is indicative of a dose suitable for successful treatment PKU, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours post administration, in particular 24, 48, 72 or 96 hours post administration.

A sustained reduction in substrate levels (e.g., biomarkers) is particularly indicative of mRNA therapeutic dosing and/or administration regimens successful for treatment of PKU. Such sustained reduction can be referred to herein as "duration" of effect. In exemplary embodiments, a reduction of at least about 20%, at least about 30%, at least about 40%, at least about 50%, at least about 60%, at least about 65%, at least about 70%, at least about 75%, at least about 80%, at least about 85%, at least about 90%, or at least about 95% at least about 96%, at least about 97%, at least about 98%, at least about 99%, at least about 100% or more of the level of biomarker, in particular, in a bodily fluid (e.g., plasma, serum, urine, e.g., urinary sediment) or in tissue(s) in a subject (e.g., liver), within 1, 2, 3, 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in a biomarker, optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk. about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk.

24. Compositions and Formulations for Use

Certain aspects of the invention are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a PAH polypeptide (e.g., the wild-type sequence, functional fragment, or variant thereof), wherein the polynucleotide comprises at least one chemically modified nucleobase, e.g., N1-methylpseudouracil or 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are N1-methylpseudouracils or 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and (ii) a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent is a lipid nanoparticle comprising Compound II, Compound VI, a salt or a stereoisomer thereof, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

In some embodiments, the uracil or thymine content of the ORF relative to the theoretical minimum uracil or thymine content of a nucleotide sequence encoding the PAH polypeptide (% $U_{TM}$ or % $T_{TM}$), is between about 100% and about 150%.

In some embodiments, the polynucleotides, compositions or formulations above are used to treat and/or prevent PAH-related diseases, disorders or conditions, e.g., PKU.

25. Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electroosmosis, endocervical, endosinusial, endotracheal, extracorporeal, hemodialysis, infiltration, interstitial, intraabdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a PAH polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a PAH polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

26. Kits and Devices a. Kits

The invention provides a variety of kits for conveniently and/or effectively using the claimed nucleotides of the present invention. Typically, kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

27. Combination Treatment

The pharmaceutical compositions and polynucleotides described herein can be used in combination methods of treatment together with an additional agent in the treatment of PKU. Tetrahydrobiopterin ($BH_4$) is a cofactor of PAH in the degradation of phenylalanine. Tetrahydrobiopterin ($BH_4$), an analogue thereof, or a salt of tetrahydrobiopterin ($BH_4$) or an analogue thereof can be administered to a human subject concurrently, prior to, or subsequent to treatment with a pharmaceutical composition or polynucleotide described herein. Exemplary tetrahydrobiopterin ($BH_4$) analogues include sapropterin (KUVAN®; sapropterin dihydrochloride), 6-hydroxymethyl pterin (HMP), and 6-acetyl-7,7-dimethyl-7,8-dihydropterin (ADDP). Tetrahydrobiopterin ($BH_4$), an analogue thereof, or a salt of tetrahydrobiopterin ($BH_4$) or an analogue thereof can be administered by the same or a different route of administration as a pharmaceutical composition or polynucleotide described herein. For example, tetrahydrobiopterin ($BH_4$), an analogue thereof, or a salt of tetrahydrobiopterin ($BH_4$) or an analogue thereof can be administered orally and the pharmaceutical composition or polynucleotide can be administered intravenously. In another example, tetrahydrobiopterin ($BH_4$), an analogue thereof, or a salt of tetrahydrobiopterin ($BH_4$) or an analogue thereof can be administered orally and the pharmaceutical composition or polynucleotide can be administered subcutaneously.

28. Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type PAH sequence) with another amino acid residue. An amino acid can be substituted in a parent or reference sequence (e.g., a wild type PAH polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, symptoms, sequelae, or any effects causing a decrease in the quality of life of a patient of PKU are considered associated with PKU and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a PAH peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding a PAH peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a PAH polypeptide, and a second part (e.g., genetically fused to the first part) comprising a second therapeutic protein (e.g., a protein with a distinct enzymatic activity, an antigen binding moiety, or a moiety capable of extending the plasma half life of PAH, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a PAH deficiency), an effective amount of an agent is, for example, an amount of mRNA expressing sufficient PAH to ameliorate, reduce, eliminate, or prevent the symptoms associated with the PAH deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., PAH) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional PAH fragment. As used herein, a functional fragment of PAH refers to a fragment of wild type PAH (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

PAH Associated Disease: As use herein the terms "PAH-associated disease" or "PAH-associated disorder" refer to diseases or disorders, respectively, which result from aberrant PAH activity (e.g., decreased activity or increased activity). As a non-limiting example, PKU is a PAH associated disease.

The terms "PAH enzymatic activity" and "PAH activity," are used interchangeably in the present disclosure and refer to PAH's ability to convert phenylalanine to tyrosine. Accordingly, a fragment or variant retaining or having PAH enzymatic activity or PAH activity refers to a fragment or variant that has measurable enzymatic activity in catalyzing the conversion of phenylalanine to tyrosine.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI).

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (I1-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing acute disease, i.e., it is a prophylactic treatment.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-di-one. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine ($\psi$) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$) (also known as N1-methyl-pseudouridine), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, 1-methyl-3-(3-amino-3-carboxypropyl)pseudouridine ($acp^3\psi$), and 2'-O-methyl-pseudouridine ($\psi m$).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or cannot exhibit symptoms of the disease, disorder, and/or condition but harbors a propensity to develop a disease or its symptoms. In some embodiments, an individual who is susceptible to a disease, disorder, and/or condition (for example, PKU) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or a vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of:
(i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or
(ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a PAH polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence)

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., hyperphenylalaninemia, PKU. For example, "treating" PKU can refer to diminishing symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g., polymorphisms, isoforms, etc.) and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-tRNA$_i^{MEt}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108:229-241). Scanning by the PIC ends upon complementary base-pairing between nucleotides comprising the anticodon of the initiator Met-tRNA$_i^{Met}$ transfer RNA and nucleotides comprising the initiation codon of the mRNA. Productive base-pairing between the AUG codon and the Met-tRNA$_i^{Met}$ anticodon elicits a series of structural and biochemical events that culminate in the joining of the large 60S ribosomal subunit to the PIC to form an active ribosome that is competent for translation elongation.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence GCCRCC, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof (Examples of translational enhancer compositions and methods of use thereof, see U.S. Pat. No. 5,807,707 to Andrews et al., incorporated herein by reference in its entirety; U.S. Pat. No. 5,723,332 to Chernajovsky, incorporated herein by reference in its entirety; U.S. Pat. No. 5,891,665 to Wilson, incorporated herein by reference in its entirety.)

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity). Accordingly, polynucleotides of the disclosure may be comprised of one or more modifications (e.g., may include one or more chemical, structural, or functional modifications, including any combination thereof).

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Nucleic acid: As used herein, the term "nucleic acid" is used in its broadest sense and encompasses any compound and/or substance that includes a polymer of nucleotides, or derivatives or analogs thereof. These polymers are often referred to as "polynucleotides". Accordingly, as used herein the terms "nucleic acid" and "polynucleotide" are equivalent and are used interchangeably. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, mRNAs, modified mRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Pre Initiation Complex (PIC): As used herein, the term "pre-initiation complex" (alternatively "43S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term "residence time" refers to the time of occupancy of a pre-initiation complex (PIC) or a ribosome at a discrete position or location along an mRNA molecule.

Translational Regulatory Activity: As used herein, the term "translational regulatory activity" (used interchangeably with "translational regulatory function") refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning.

29. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

| | | CONSTRUCT SEQUENCES | | | | |
|---|---|---|---|---|---|---|
| | By "G5" is meant that all uracils (U) in the mRNA are replaced by N1-methylpseudouracils. | | | | | |
| | By "G6" is meant that all uracils (U) in the mRNA are replaced by 5-methoxyuracils. | | | | | |
| | mRNA Name | ORF Sequence (Amino Acid) | ORF Sequence (Nucleotide) | 5' UTR Sequence | 3' UTR Sequence | Construct Sequence |
| SEQ ID NO: | | 1 | 2 | 3 | 4 | 45 |
| | PAH_001 (hPAH.FL.G5) Cap: C1 PolyA tail: | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGUCCACCGCCGU GCUCGAGAACCCCG GCCUGGGGCGGAAA CUGAGCGACUUUGG CCAGGAAACCAGCU AUAUUGAGGACAAC UGCAACCAGACAAG CGCCAUCAGCCUGA UCUUCUCACUGAAG GAGGAGGUGGGCGC CCUGGCCAAGGUGC UCAGGCUGUUCGAG GAGAACGACGUGAA CCUGACUCAUAUCG AGAGCAGACCAUCU CGGCUGAAGAAAGA CGAGUACGAGUUCU UCACCCAUCUCGAU AAGAGAAGCCUGCC CGCACUGACCAACA UCAUAAAGAUUCUG AGGCACGACAUCGG GGCCACCGUGCACG AACUGAGUCGGGAC AAGAAGAAGGACAC UGUUCCUUGGUUCC CACGGACUAUUCAG GAGCUGGACAGAUU CGCUAACCAGAUCC UGUCCUACGGCGCC GAGCUCGACGCUGA CCACCCAGGCUUCA AGGACCCCGUGUAC CGGGCUAGAAGAAA GCAAUUCGCCGACA UCGCCUACAAUUAU AGGCACGGCCAGCC CAUUCCUAGAGUGG AGUACAUGGAGGAA GAGAAGAAGACCUG GGGCACCGUGUUCA AGACCUUAAAGAGC CUGUAUAAGACACA CGCUUGCUACGAGU ACAAUCACAUUUUC CCACUGCUGGAGAA GUACUGUGGCUUUC ACGAGGAUAAUAUA CCUCAGCUGGAAGA CGUUUCCCAGUUCC UGCAGACUUGCACC GGCUUCAGACUUAG GCCUGUGGCGGGCC UCCUGUCUUCGAGA GAUUUCCUGGGAGG GCUGGCCUUCCGCG UGUUCCACUGCACC CAGUAUAUCCGCCA CGGGAGCAAGCCCA UGUACACACCCGAG CCCGACAUUUGCCA CGAGCUGUUAGGCC | GGGAAA UAAGAG AGAAAA GAAGAG UAAGAA GAAAUA CCACC | UGAUAA UAGGCU GGAGCC UCGGUG GCCUAG CUUCUU AACCCU GCCCCU UAAGAG UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 45 consists from 5' to 3' end: 5' UTR of SEQ ID NO: 3, ORF Sequence of SEQ ID NO: 2, and 3 UTR of SEQ ID NO: 4 |

-continued

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | ACGUGCCUUUGUUC UCUGACAGGAGCUU UGCGCAGUUCAGUC AGGAAAUCGGACUG GCCAGCCUGGGUGC CCCUGACGAGUACA UCGAGAAGCUGGCC ACCAUCUACUGGUU CACUGUCGAGUUCG GUCUGUGCAAGCAG GGCGAUAGCAUCAA GGCUUACGGAGCCG GCCUUCUGAGCAGC UUCGGCGAGCUGCA AUACUGCCUGAGCG AGAAGCCUAAGCUG UUGCCUUUGGAACU CGAGAAGACAGCUA UCCAGAACUACACC GUUACCGAGUUCCA GCCUCUGUACUACG UGGCCGAGAGCUUC AACGACGCCAAGGA GAAGGUGAGAAACU UCGCGGCAACAAUU CCCAGGCCUUUUAG CGUGAGAUACGACC CCUACACUCAACGA AUCGAAGUGCUGGA UAACACCCAGCAGC UGAAGAUCCUGGCC GACAGUAUCAACAG CGAAAUUGGCAUUC UGUGCUCAGCCCUG CAGAAGAUUAAA | | | |
| SEQ ID NO: | 1 | 5 | 3 | 4 | 46 |
| PAH_002 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGUCAACCGCUGU UCUGGAGAACCCCG GCCUGGGCCGGAAG CUGUCCGAUUUCGG CCAGGAGACUAGCU ACAUCGAGGAUAAC UGCAACCAGAACGG CGCCAUCAGCCUGA UAUUUAGCCUCAAG GAAGAAGUGGGUGC UCUGGCCAAGGUCC UGGACUGUUCGAA GAGAACGACGUGAA CCUGACCCAUAUCG AAAGCGGCCCAGC CGGCUGAAGAAGGA CGAGUACGAGUUCU UUACGCACCUGGAC AAACGGAGCCUCCC CGCACUGACUAACA UUAUUAAGAUCCUG AGGCACGAUAUCGG UGCCACUGUGCACG AACUGAGCCGGGAC AAGAAGAAAGACAC UGUUCCUUGGUUUC CCAGGACGAUUCAG GAACUGGACAGAUU CGCCAUCAGAUCC UCAGCUACGGCGCC GAGCUGGACGCUGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 46 consists from 5' to 3' end: 5' UTR of SEQ ID NO: 3, ORF Sequence of SEQ ID NO: 5, and 3 UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCAUCCCGGCUUUA | | | |
| | | AGGACCCGGUGUAU | | | |
| | | CGGGCCAGACGCAA | | | |
| | | GCAGUUCGCCGAUA | | | |
| | | UUGCCUAUAACUAC | | | |
| | | AGACACGGCCAGCC | | | |
| | | UAUCCCUAGGGUGG | | | |
| | | AGUACAUGGAGGAG | | | |
| | | GAGAAGAAGACUUG | | | |
| | | GGGCACCGUUUUCA | | | |
| | | AGACCCUGAAAUCC | | | |
| | | CUCUACAAGACCCA | | | |
| | | CGCGUGCUACGAGU | | | |
| | | AUAACCAUAUCUUU | | | |
| | | CCUCUCCUGGAGAA | | | |
| | | GUACUGCGGCUUCC | | | |
| | | ACGAGGACAAUAUC | | | |
| | | CCACAGCUCGAGGA | | | |
| | | CGUGAGCCAGUUCU | | | |
| | | UGCAGACCUGCACA | | | |
| | | GGGUUCAGACUGCG | | | |
| | | CCCCGUGGCCGGUC | | | |
| | | UGCUCAGCAGUAGG | | | |
| | | GACUUCCUCGGCGG | | | |
| | | ACUGGCAUUCCGGG | | | |
| | | UGUUCCACUGUACC | | | |
| | | CAGUACAUUAGACA | | | |
| | | CGGCUCCAAGCCCA | | | |
| | | UGUACACCCCAGAA | | | |
| | | CCAGACAUCUGCCA | | | |
| | | CGAGCUGCUGGGCC | | | |
| | | ACGUGCCCUUGUUU | | | |
| | | UCAGAUAGGAGCUU | | | |
| | | CGCCCAGUUCAGCC | | | |
| | | AGGAAAUCGGGCUG | | | |
| | | GCCAGUCUGGGCGC | | | |
| | | CCCUGACGAGUAUA | | | |
| | | UCGAGAAACUGGCC | | | |
| | | ACCAUCUACUGGUU | | | |
| | | CACCGUGGAGUUCG | | | |
| | | GCCUCUGCAAGCAG | | | |
| | | GGUGACAGCAUCAA | | | |
| | | GGCAUACGGCGCAG | | | |
| | | GGCUGCUGAGCAGC | | | |
| | | UUCGGCGAGCUCCA | | | |
| | | GUAUUGCCUGUCGG | | | |
| | | AGAAGCCCAAGCUG | | | |
| | | CUGCCACUGGAGCU | | | |
| | | GGAGAAGACCGCCA | | | |
| | | UCCAGAAUUAUACC | | | |
| | | GUCACAGAGUUUCA | | | |
| | | GCCUCUGUAUUACG | | | |
| | | UGGCUGAGUCCUUU | | | |
| | | AACGACGCCAAAGA | | | |
| | | GAAGGUGAGGAACU | | | |
| | | UCGCAGCGACUAUU | | | |
| | | CCUAGACCCUUCUC | | | |
| | | CGUCCGGUACGAUC | | | |
| | | CUUACACCCAGAGG | | | |
| | | AUCGAGGUGCUGGA | | | |
| | | CAACACCCAGCAGC | | | |
| | | UCAAGAUUCUGGCC | | | |
| | | GAUUCCAUUAAUAG | | | |
| | | CGAGAUAGGCAUUC | | | |
| | | UGUGCAGCGCACUG | | | |
| | | CAGAAGAUCAAG | | | |

-continued

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 6 | 3 | 4 | 47 |
| PAH_003 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVPHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUCGAGAACCCCG GCCUGGGUAGGAAG CUGAGCGACUUCGG CCAGGAAACAAGCU ACAUCGAAGAUAAC UGCAACCAGAACGG UGCCAUCUCCCUGA UCUUUUCACUUAAG GAAGAGGUCGGAGC CUUAGCCAAGGUGC UUAGGCUGUUCGAG GAGAACGACGUCAA CCUUACCCACAUUG AGUCCAGACCCAGC AGGCUGAAGAAGGA CGAGUACGAGUUCU UCACACAUCUGGAC AAGAGAAGCUUACC CGCCCUGACCAACA UUAUUAAGAUCCUG CGACACGACAUCGG GGCCACCGUGCACG AACUGAGCAGAGAC AAGAAGAAGGAUAC UGUGCCCUGGUUCC CUAGGACAAUCCAG GAGUUGGAUCGUUU CGCCAACCAGAUCC UGUCCUACGGAGCC GAACUGGACGCUGA CCACCCCGGAUUUA AGGAUCCUGUGUAU CGGGCCCGAAGAAA GCAGUUCGCAGAUA UUGCCUAUAAUUAC AGGCACGGCCAGCC UAUCCCCAGAGUCG AGUACAUGGAAGAG GAGAAGAAGACCUG GGGUACAGUGUUCA AGACCCUCAAGAGC CUGUACAAGACCCA CGCUUGCUACGAAU ACAACCACAUCUUC CCCUUGCUUGAGAA AUACUGCGGUUUCC ACGAGGACAAUAUU CCGCAACUGGAGGA CGUGUCGCAGUUUC UGCAGACCUGUACC GGCUUUCGGCUCAG GCCUGUGGCCGGUC UGUUGUCUAGCAGA GAUUUUCUGGGCGG GCUGGCCUUCAGAG UCUUCCACUGCACC CAGUACAUCAGGCA CGGAAGCAAGCCGA UGUACACACCCGAG CCCGACAUCUGUCA CGAGCUCCUCGGCC ACGUGCCCCUGUUC AGCGACAGAAGCUU CGCCCAGUUUAGUC AGGAAAUCGGCCUG GCCAGUCUGGGCGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 47 consists from 5' to 3' end: 5' UTR of SEQ ID NO: 3, ORF Sequence of SEQ ID NO: 6, and 3 UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCUGACGAGUAUA UCGAGAAGCUGGCU ACCAUAUAUUGGUU UACCGUGGAGUUCG GACUGUGCAAGCAG GGCGACUCCAUCAA GGCUUACGGUGCCG GGCUGCUGAGCAGC UUCGGCGAGCUCCA GUAUUGCCUGAGCG AGAAGCCCAAGCUG CUGCCGCUGGAGCU GGAGAAGACCGCCA UCCAGAACUAUACC GUCACCGAGUUCCA GCCCCUGUACUACG UGGCUGAGAGCUUU AACGACGCCAAGGA GAAGGUCAGAAACU UCGCCGCUACCAUU CCCAGACCCUUCAG CGUGAGAUACGACC CUUACACACAGAGG AUAGAGGUUUUGG ACAACACCCAGCAA CUGAAGAUCUUGGC UGAUAGCAUUAACU CAGAGAUCGGCAUU CUGUGCAGCGCCCU GCAGAAGAUCAAG | | | |
| SEQ ID NO: | 1 | 7 | 3 | 4 | 48 |
| PAH_004 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVPHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACUGCCGU GUUGGAGAACCCCG GCUGGGCAGAAAG CUCAGCGACUUCGG CCAGGAAACCAGUU AUAUUGAGGACAAC UGCAACCAGAACGG CGCAAUUAGUCUUA UCUUUAGCCUGAAG GAGGAGGUAGGCGC CCUGGCCAAAGUGC UGAGACUGUUCGAA GAGAACGACGUGAA UCUGACACACAUCG AGUCCCGCCCCAGC CGGCUCAAGAAGGA CGAGUACGAGUUCU UUACCCACCUGGAU AAGCGCAGCCUUCC UGCCCUGACCAACA UCAUAAAGAUUCUC AGACACGACAUUGG CGCCACCGUUCACG AACUGAGCAGAGAC AAGAAGAAAGACAC CGUCCCCUGGUUCC CCAGGACCAUCCAG GAACUGGACCGGUU CGCUAACCAGAUCC UGUCCUACGGCGCC GAGCUGGACGCCGA CCACCCUGGCUUUA AGGACCCCGUGUAU AGGGCCAGAAGGAA GCAGUUCGCGGAUA UCGCUUACAACUAC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 48 consists from 5' to 3' end: 5' UTR of SEQ ID NO: 3, ORF Sequence of SEQ ID NO: 7, and 3 UTR of SEQ ID NO: 4 |

| | CONSTRUCT SEQUENCES | | | | |
|---|---|---|---|---|---|
| \multicolumn{6}{c}{By "G5" is meant that all uracils (U) in the mRNA are replaced by N1-methylpseudouracils.} | | | | | |
| \multicolumn{6}{c}{By "G6" is meant that all uracils (U) in the mRNA are replaced by 5-methoxyuracils.} | | | | | |
| mRNA Name | ORF Sequence (Amino Acid) | ORF Sequence (Nucleotide) | 5' UTR Sequence | 3' UTR Sequence | Construct Sequence |
| | | CGUCACGGCCAACC GAUCCCAAGGGUCG AGUACAUGGAGGAG GAGAAGAAGACCUG GGGUACAGUGUUCA AGACUCUCAAGAGU CUGUACAAGACACA CGCCUGCUACGAGU ACAACCACAUCUUC CCAUUGCUGGAGAA GUAUUGCGGCUUCC ACGAAGACAACAUU CCCCAGCUGGAGGA CGUGAGCCAGUUUC UGCAGACCUGCACC GGCUUCCGGCUGAG GCCCGUGGCGGGGC UGCUGUCUUCAAGA GACUUCCUGGGCGG ACUGGCCUUCAGGG UCUUCCACUGCACA CAGUACAUCAGACA CGGAAGCAAACCCA UGUACACCCCUGAG CCCGACAUCUGCCA CGAGCUGCUGGGCC ACGUGCCUCUGUUC AGCGACCGCAGCUU CGCCCAGUUCUCGC AGGAAAUCGGCCUG GCCAGCCUGGGCGC UCCUGACGAAUACA UUGAGAAACUCGCC ACAAUUUACUGGUU CACUGUGGAGUUCG GACUGUGCAAGCAG GGCGAUUCCAUCAA AGCGUACGGCGCAG GCCUGCUGAGCUCG UUCGGCGAACUGCA AUACUGCCUGUCCG AGAAGCCGAAACUG CUGCCUCUGGAGCU CGAGAAGACAGCCA UCCAGAAUUACACA GUGACAGAAUUCCA GCCCUUAUACUACG UGGCUGAAUCUUUC AACGACGCAAAGGA GAAGGUGCGCAACU UUGCAGCCACCAUC CCACGACCCUUCAG CGUGCGGUACGACC CGUACACCCAGAGA AUCGAGGUGCUGGA CAAUACCCAACAGC UCAAGAUCCUCGCC GAUUCAAUCAAUUC CGAGAUCGGGAUCC UGUGCAGCGCACUG CAGAAGAUAAAG | | | |
| SEQ ID NO: | 1 | 8 | 3 | 4 | 49 |
| PAH_005 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY | AUGAGCACCGCCGU GCUGGAGAACCCCG GCCUGGGCCGGAAG CUGAGCGACUUCGG CCAGGAGACAAGCU | GGGAAA UAAGAG AGAAAA GAAGAG UAAGAA | UGAUAA UAGGCU GGAGCC UCGGUG GCCUAG | SEQ ID NO: 49 consists from 5' to 3' end: 5' |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | ACAUCGAGGACAAC UGCAACCAGAACGG CGCCAUCAGCCUGA UCUUCUCCCUGAAG GAGGAGGUGGGCGC CCUGGCCAAGGUGC UGCGGCUGUUCGAG GAGAACGACGUGAA CCUGACCCACAUCG AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAGGAUAC CGUGCCCUGGUUCC CACGGACCAUCCAG GAGCUGGACCGGUU CGCCAACCAGAUCC UGAGCUACGGCGCC GAGCUGGACGCCGA CCACCCCGGCUUCA AGGACCCCGUGUAC CGGGCCCGGCGGAA GCAGUUCGCCGACA UCGCCUACAACUAC CGGCACGGCCAGCC CAUUCCUCGGGUGG AGUACAUGGAGGAG GAGAAGAAGACCUG GGGCACCGUGUUCA AGACCCUCAAGAGC CUGUACAAGACCCA CGCCUGCUACGAGU ACAACCACAUCUUC CCACUGCUGGAGAA GUACUGCGGCUUCC ACGAGGAUAACAUC CCACAGCUGGAGGA CGUGAGCCAGUUCC UGCAGACCUGCACC GGCUUCAGACUGCG GCCUGUGGCCGGCC UGCUGAGCUCCAGA GACUUCCUGGGCGG CCUGGCCUUCCGGG UGUUCCACUGCACC CAGUACAUCAGACA CGGCAGCAAGCCCA UGUACACACCUGAG CCCGACAUCUGCCA CGAACUCCUGGGCC ACGUGCCCCUGUUC AGCGACCGGAGCUU CGCCCAGUUCUCCC AGGAGAUCGGACUG GCCAGCCUUGGAGC UCCCGACGAAUACA UUGAGAAGCUGGCC ACCAUCUACUGGUU CACCGUGGAGUUCG GCCUGUGCAAGCAG GGCGACAGCAUCAA GGCCUACGGCGCCG GCCUUCUGAGCAGC UUCGGCGAGCUGCA | GAAAUA UAAGAG CCACC | CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | UTR of SEQ ID NO: 3, ORF Sequence of SEQ ID NO: 8, and 3 UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GUACUGCCUGAGCG AGAAGCCCAAGCUG CUGCCCCUGGAGCU AGAGAAGACCGCCA UCCAGAACUACACC GUGACCGAGUUCCA GCCCCUGUACUACG UGGCCGAGAGCUUC AACGACGCCAAGGA GAAGGUGCGGAACU UCGCCGCCACAAUC CCUAGACCCUUCAG CGUGCGGUACGACC CCUACACCCAGCGG AUCGAGGUGCUGGA CAAUACCCAGCAGC UGAAGAUUCUGGCC GACUCCAUCAACAG CGAAAUCGGCAUCC UGUGCAGCGCCCUG CAGAAGAUCAAG | | | |
| SEQ ID NO: | 1 | 9 | 3 | 4 | 50 |
| PAH_006 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACAAGCU ACAUCGAGGACAAC UGCAACCAGAACGG CGCCAUCAGCCUGA UCUUUUCUCUGAAG GAGGAGGUGGGCGC CCUGGCCAAGGUGC UGCGGCUGUUCGAG GAGAACGACGUGAA CCUGACCCACAUCG AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAGGACAC CGUGCCCUGGUUCC CUCGGACCAUCCAG GAGCUGGACCGGUU CGCCAACCAGAUCC UGAGCUACGGCGCC GAGCUGGACGCCGA CCACCCCGGCUUCA AGGACCCCGUGUAC CGGGCCCGGCGGAA GCAGUUCGCCGACA UCGCCUACAACUAC CGGCACGGCCAGCC CAUCCCUCGGGUGG AGUACAUGGAGGAG GAGAAGAAGACCUG GGGCACCGUGUUCA AGACCCUGAAGUCU CUGUACAAGACCCA CGCCUGCUACGAGU ACAACCACAUCUUU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 50 consists from 5' to 3' end: 5' UTR of SEQ ID NO: 3, ORF Sequence of SEQ ID NO: 9, and 3 UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCUCUCCUGGAGAA | | | |
| | | GUACUGCGGCUUCC | | | |
| | | ACGAGGACAAUAUC | | | |
| | | CCUCAGCUGGAGGA | | | |
| | | CGUGAGCCAGUUCC | | | |
| | | UGCAGACCUGCACC | | | |
| | | GGCUUCCGGCUGAG | | | |
| | | GCCUGUGGCCGGGC | | | |
| | | UGCUGAGCAGCAGA | | | |
| | | GACUUCCUGGGCGG | | | |
| | | CCUGGCCUUCCGGG | | | |
| | | UGUUCCACUGCACC | | | |
| | | CAGUACAUCAGACA | | | |
| | | CGGGAGCAAGCCCA | | | |
| | | UGUACACUCCCGAG | | | |
| | | CCCGACAUCUGCCA | | | |
| | | CGAGUUACUGGGCC | | | |
| | | ACGUGCCCUGUUC | | | |
| | | AGCGACCGGAGCUU | | | |
| | | CGCCCAGUUCUCAC | | | |
| | | AGGAGAUCGGGCUG | | | |
| | | GCAAGCCUGGGCGC | | | |
| | | UCCCGACGAGUAUA | | | |
| | | UAGAGAAGCUGGCC | | | |
| | | ACCAUCUACUGGUU | | | |
| | | CACCGUGGAGUUCG | | | |
| | | GCCUGUGCAAGCAG | | | |
| | | GGCGACAGCAUCAA | | | |
| | | GGCUUACGGAGCUG | | | |
| | | GGCUGCUUAGCUCC | | | |
| | | UUCGGCGAGCUGCA | | | |
| | | GUACUGCCUGAGCG | | | |
| | | AGAAGCCCAAGCUG | | | |
| | | CUGCCCCUUGAGCU | | | |
| | | CGAGAAGACCGCCA | | | |
| | | UCCAGAACUACACC | | | |
| | | GUGACCGAGUUCCA | | | |
| | | GCCCCUGUACUACG | | | |
| | | UGGCCGAGAGCUUC | | | |
| | | AACGACGCCAAGGA | | | |
| | | GAAGGUGCGGAACU | | | |
| | | UCGCCGCAACCAUC | | | |
| | | CCUAGGCCCUUCAG | | | |
| | | CGUGCGGUACGACC | | | |
| | | CCUACACCCAGCGG | | | |
| | | AUCGAGGUGCUGGA | | | |
| | | CAAUACCCAGCAGC | | | |
| | | UGAAGAUCUUAGCU | | | |
| | | GACUCAAUCAACAG | | | |
| | | CGAGAUUGGCAUCC | | | |
| | | UGUGCAGCGCCCUG | | | |
| | | CAGAAGAUCAAG | | | |
| SEQ ID NO: | 1 | 10 | 3 | 4 | 51 |
| PAH_007 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL | AUGAGCACCGCCGU GCUGGAGAACCCCG GCCUGGGCCGGAAG CUGAGCGACUUCGG CCAGGAGACAUCCU ACAUCGAGGACAAC UGCAACCAGAACGG CGCCAUCUCCCUCA UCUUCAGCCUGAAG GAGGAGGUCGCGC CCUGCCAAGGUCC UCGCCUCUUCGAG GAGAACGACGUCAA CCUCACCCACAUCG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC CCCCC CAGCCC CUCCUC CCCUUC CUGCAC CCGUAC | SEQ ID NO: 51 consists from 5' to 3' end: 5' UTR of SEQ ID NO: 3, ORF Sequence of SEQ ID NO: 10, and 3' UTR of |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AGUCCCGCCCCUCC CGCCUCAAGAAGGA CGAGUACGAGUUCU UCACCCACCUCGAC AAGCGCUCCCUCCC CGCCCUCACCAACA UCAUCAAGAUUCUU AGGCACGACAUCGG CGCCACCGUCCACG AGCUCUCCCGCGAC AAGAAGAAGGACAC CGUCCCCUGGUUCC CUCGCACCAUCCAG GAGCUCGACCGCUU CGCCAACCAGAUCC UCUCCUACGGCGCC GAGUUAGACGCCGA CCACCCCGGCUUCA AGGACCCCGUCUAC CGCGCCCGCCGCAA GCAGUUCGCCGACA UCGCCUACAACUAC CGCCACGGCCAGCC CAUCCCACGCGUCG AGUACAUGGAGGAG GAGAAGAAGACCUG GGGCACCGUCUUCA AGACCCUCAAGUCC CUCUACAAGACCCA CGCCUGCUACGAGU ACAACCACAUCUUU CCACUCCUCGAGAA GUACUGCGGCUUCC ACGAGGAUAACAUC CCUCAGCUCGAGGA CGUCUCCCAGUUCC UCCAGACCUGCACC GGCUUUCGCCUGCG CCCGGUGGCAGGCC UGCUGAGCUCUCGG GACUUCCUCGGCGG CCUCGCCUUCCGCG UCUUCCACUGCACC CAGUACAUCAGGCA CGGGUCCAAGCCCA UGUACACCCCAGAG CCCGACAUCUGCCA CGAACUCCUCGGCC ACGUGCCCUCUUC UCCGACCGCUCCUU CGCCCAGUUCUCCC AGGAGAUUGGCCUG GCCAGCUUGGGAGC ACCCGACGAGUACA UAGAGAAGCUCGCC ACCAUCUACUGGUU CACCGUCGAGUUCG GCCUCUGCAAGCAG GGCGACUCCAUCAA GGCCUACGGGGCCG GCUUGCUGAGUUCU UUCGGCGAGCUCCA GUACUGCCUCUCCG AGAAGCCCAAGCUC UUACCACUGGAGCU GGAGAAGACCGCCA UCCAGAACUACACC GUCACCGAGUUCCA GCCCCUCUACUACG UCGCCGAGUCCUUC AACGACGCCAAGGA | | CCCCUC CAUAAA GUAGGA AACACU ACAGUG GUCUUU GAAUAA AGUCUG AGUGGG CGGC | SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAAGGUCCGCAACU UCGCGGCAACAAUC CCUAGACCCUUCUC CGUCCGCUACGACC CCUACACCCAGCGC AUCGAGGUGCUGGA CAACACUCAGCAGC UGAAGAUCCUGGCU GAUAGCAUUAACUC CGAAAUUGGGAUCC UCUGCUCCGCCCUC CAGAAGAUCAAG | | | |
| SEQ ID NO: | 1 | 11 | 3 | 4 | 52 |
| PAH_008 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU CCUCGAGAACCCCG GCCUGGGCAGAAAG CUGAGCGACUUCGG CCAGGAAACCAGCU ACAUCGAGGACAAC UGCAACCAGAACGG CGCCAUCAGCCUGA UCUUCAGCCUGAAG GAGGAGGUGGGCGC CCUGGCCAAGGUGC UGAGACUGUUCGAG GAGAACGACGUGAA CCUGACCCACAUCG AGAGCAGACCCUCC AGACUGAAGAAGGA CGAGUACGAGUUCU UCACCCACCUGGAC AAGAGAAGCCUGCC CGCCCUGACCAACA UCAUCAAGAUCCUG AGACACGACAUCGG AGCCACCGUGCACG AGCUGAGCAGAGAC AAGAAGAAGGACAC CGUGCCCUGGUUCC CCAGAACCAUCCAG GAGCUGGACAGAUU CGCCAACCAGAUCC UGAGCUACGGUGCC GAGCUAGACGCCGA CCACCCCGGCUUCA AGGACCCCGUGUAC AGAGCCAGAAGAAA GCAGUUCGCCGACA UCGCCUACAACUAC AGACACGGGCAGCC GAUCCCCAGAGUGG AGUACAUGGAGGAG GAGAAGAAGACCUG GGGCACCGUGUUCA AGACCCUCAAGAGC CUGUACAAGACCCA CGCCUGCUACGAGU ACAACCACAUCUUC CCUCUGCUGGAGAA GUACUGCGGCUUCC ACGAGGACAACAUC CCACAGCUGGAGGA CGUGAGCCAGUUCC UGCAGACCUGCACC GGCUUCAGACUCAG GCCCGUUGCCGGAC UGCUGAGCAGAGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 52 consists from 5' to 5' end: 5' UTR of SEQ ID NO: 3, ORF Sequence of SEQ ID NO: 11, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GACUUCCUGGGCGG | | | |
| | | CCUGGCCUUCAGAG | | | |
| | | UGUUCCACUGCACC | | | |
| | | CAGUACAUCAGACA | | | |
| | | CGGCAGCAAGCCCA | | | |
| | | UGUACACACCCGAG | | | |
| | | CCCGACAUCUGCCA | | | |
| | | CGAACUGCUGGGCC | | | |
| | | ACGUGCCCCUGUUC | | | |
| | | AGCGACAGAAGCUU | | | |
| | | CGCCCAGUUCAGCC | | | |
| | | AGGAGAUCGGUCUG | | | |
| | | GCUAGCUUGGGAGC | | | |
| | | CCCAGACGAGUACA | | | |
| | | UCGAGAAGCUGGCC | | | |
| | | ACCAUCUACUGGUU | | | |
| | | CACCGUGGAGUUCG | | | |
| | | GCCUGUGCAAGCAG | | | |
| | | GGAGACAGCAUCAA | | | |
| | | GGCCUACGGAGCCG | | | |
| | | GCCUACUGAGCAGC | | | |
| | | UUCGGCGAGCUGCA | | | |
| | | GUACUGCCUGAGCG | | | |
| | | AGAAGCCCAAGCUG | | | |
| | | UUGCCUCUGGAGCU | | | |
| | | GGAGAAGACCGCCA | | | |
| | | UCCAGAACUACACC | | | |
| | | GUGACCGAGUUCCA | | | |
| | | GCCCCUGUACUACG | | | |
| | | UGGCCGAGAGCUUC | | | |
| | | AACGACGCCAAGGA | | | |
| | | GAAGGUGAGAAACU | | | |
| | | UCGCCGCCACUAUC | | | |
| | | CCCAGACCCUUCAG | | | |
| | | CGUGAGAUACGACC | | | |
| | | CCUACACCCAGAGA | | | |
| | | AUCGAGGUGCUGGA | | | |
| | | CAACACCCAGCAGC | | | |
| | | UGAAGAUUCUGGCC | | | |
| | | GAUAGCAUCAACAG | | | |
| | | CGAGAUCGGCAUCC | | | |
| | | UGUGCAGCGCCCUG | | | |
| | | CAGAAGAUCAAG | | | |

| SEQ ID NO: | 1 | 12 | 3 | 4 | 53 |
|---|---|---|---|---|---|
| PAH_009 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC | AUGAGCACCGCCGU CCUCGAGAACCCCG GCCUGGGCAGAAAG CUGAGCGACUUCGG CCAGGAAACCAGCU ACAUCGAGGACAAC UGCAACCAGAACGG CGCCAUCAGCCUGA UCUUCUCACUCAAA GAAGAAGUUGGUGC AUUGGCCAAGUAU UGCGCUUAUUUGAG GAGAACGACGUGAA CCUGACCCACAUCG AGAGCAGACCCUCC AGACUGAAGAAGGA CGAGUACGAGUUCU UCACCCACCUGGAC AAGAGAAGCCUGCC CGCCCUGACCAACA UCAUCAAGAUCCUG AGACACGACAUCGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG | SEQ ID NO: 53 consists from 5' to 3' end: 5' UTR of SEQ ID NO: 3, ORF Sequence of SEQ ID NO: 12, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AGCCACCGUGCACG AGCUGAGCAGAGAC AAGAAGAAGGACAC CGUGCCCUGGUUCC CCAGAACCAUCCAG GAGCUGGACAGAUU CGCCAACCAGAUCC UGAGCUACGGUGCC GAGCUAGACGCCGA CCACCCCGGCUUCA AGGACCCCGUGUAC AGAGCCAGAAGAAA GCAGUUCGCCGACA UCGCCUACAACUAC AGACACGGGCAGCC GAUCCCCAGAGUGG AGUACAUGGAGGAG GAGAAGAAGACCUG GGGCACCGUGUUCA AGACCCUCAAGAGC CUGUACAAGACCCA CGCCUGCUACGAGU ACAACCACAUCUUC CCUCUGCUGGAGAA GUACUGCGGCUUCC ACGAGGACAACAUC CCACAGCUGGAGGA CGUGAGCCAGUUCC UGCAGACCUGCACC GGCUUCAGACUCAG GCCCGUUGCCGGAC UGCUGAGCAGCAGA GACUUCCUGGGCGG CCUGGCCUUCAGAG UGUUCCACUGCACC CAGUACAUCAGACA CGGCAGCAAGCCCA UGUACACACCCGAG CCCGACAUCUGCCA CGAACUGCUGGGCC ACGUGCCCCUGUUC AGCGACAGAAGCUU CGCCCAGUUCAGCC AGGAGAUCGGUCUG GCUAGCUUGGGAGC CCCAGACGAGUACA UCGAGAAGCUGGCC ACCAUCUACUGGUU CACCGUGGAGUUCG GCCUGUGCAAGCAG GGAGACAGCAUCAA GGCCUACGGAGCCG GCCUACUGAGCAGC UUCGGCGAGCUGCA GUACUGCCUGAGCG AGAAGCCCAAGCUG UUGCCUCUGGAGCU GGAGAAGACCGCCA UCCAGAACUACACC GUGACCGAGUUCCA GCCCCUGUACUACG UGGCCGAGAGCUUC AACGACGCCAAGGA GAAGGUGAGAAACU UCGCCGCCACUAUC CCCAGACCCUUCAG CGUGAGAUACGACC CCUACACCCAGAGA AUCGAGGUGCUGGA CAACACCCAGCAGC UGAAGAUUCUGGCC | | AGUGGG CGGC | |

-continued

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAUAGCAUCAACAG CGAGAUCGGCAUCC UGUGCAGCGCCCUG CAGAAGAUCAAG | | | |
| SEQ ID NO: | 1 | 13 | 3 | 4 | 54 |
| PAH_010 (hPAH.FL.G5) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACCAGCU ACAUCGAGGACAAC UGCAACCAGAACGG CGCCAUCAGCCUGA UCUUCAGCCUGAAG GAGGAGGUGGGCGC CCUGGCCAAGGUGC UGCGGCUGUUCGAG GAGAACGACGUGAA CCUGACCCACAUCG AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAGGACAC CGUGCCCUGGUUCC CGCGGACCAUCCAG GAGCUGGACCGGUU CGCCAACCAGAUCC UGAGCUACGGCGCC GAGCUGGACGCCGA CCACCCCGGCUUCA AGGACCCCGUGUAC CGGGCCCGGCGGAA GCAGUUCGCCGACA UCGCCUACAACUAC CGGCACGGCCAGCC CAUCCCGCGGGUGG AGUACAUGGAGGAG GAGAAGAAGACCUG GGGCACCGUGUUCA AGACCCUGAAGAGC CUGUACAAGACCCA CGCCUGCUACGAGU ACAACCACAUCUUC CCACUGCUGGAGAA GUACUGCGGCUUCC ACGAGGACAACAUC CCACAGCUGGAGGA CGUGAGCCAGUUCC UGCAGACCUGCACC GGCUUCCGGCUGCG GCCCGUGGCCGGCC UGCUGAGCAGCCGG GACUUCCUGGGCGG CCUGGCCUUCCGGG UGUUCCACUGCACC CAGUACAUCCGGCA CGGCAGCAAGCCCA UGUACACGCCCGAG CCCGACAUCUGCCA CGAGCUGCUGGGCC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 54 consists from 5' to 3' end: 5' UTR of SEQ ID NO: 3, ORF Sequence of SEQ ID NO: 13, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | ACGUGCCCCUGUUC | | | |
| | | AGCGACCGGAGCUU | | | |
| | | CGCCCAGUUCAGCC | | | |
| | | AGGAGAUCGGCCUG | | | |
| | | GCCAGCCUGGGCGC | | | |
| | | GCCCGACGAGUACA | | | |
| | | UCGAGAAGCUGGCC | | | |
| | | ACCAUCUACUGGUU | | | |
| | | CACCGUGGAGUUCG | | | |
| | | GCCUGUGCAAGCAG | | | |
| | | GGCGACAGCAUCAA | | | |
| | | GGCCUACGGCGCCG | | | |
| | | GCCUGCUGAGCAGC | | | |
| | | UUCGGCGAGCUGCA | | | |
| | | GUACUGCCUGAGCG | | | |
| | | AGAAGCCCAAGCUG | | | |
| | | CUGCCCCUGGAGCU | | | |
| | | GGAGAAGACCGCCA | | | |
| | | UCCAGAACUACACC | | | |
| | | GUGACCGAGUUCCA | | | |
| | | GCCCCUGUACUACG | | | |
| | | UGGCCGAGAGCUUC | | | |
| | | AACGACGCCAAGGA | | | |
| | | GAAGGUGCGGAACU | | | |
| | | UCGCCGCCACCAUC | | | |
| | | CCACGGCCCUUCAG | | | |
| | | CGUGCGGUACGACC | | | |
| | | CCUACACCCAGCGG | | | |
| | | AUCGAGGUGCUGGA | | | |
| | | CAACACCCAGCAGC | | | |
| | | UGAAGAUCCUGGCC | | | |
| | | GACAGCAUCAACAG | | | |
| | | CGAGAUCGGCAUCC | | | |
| | | UGUGCAGCGCCCUG | | | |
| | | CAGAAGAUCAAG | | | |
| SEQ ID NO: | 1 | 14 | 3 | 4 | 55 |
| PAH_011 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GACUGGGAAGAAAG CUGUCCGAUUUCGG GCAGGAGACUUCCU ACAUCGAGGACAAC UGCAACCAGAACGG GGCCAUCUCCCUGA UCUUCAGCCUGAAG GAGGAGGUGGGCGC CCUGGCGAAGGUGC UCCGGCUGUUCGAG GAGAACGACGUGAA CCUGACGCACAUCG AAAGCCGGCCCAGC CGGCUGAAGAAGGA CGAGUACGAGUUCU UCACGCACCUGGAC AAGAGGAGCUUGCC CGCCCUCACCAACA UCAUCAAGAUCCUG CGGCACGACAUCGG CGCCACGGUGCACG AGCUGAGCCGCGAC AAGAAGAAGGAUAC CGUGCCCUGGUUCC CCAGGACCAUCCAG GAGCUGGACAGAUU CGCCAACCAGAUCC UGAGCUACGGCGCC GAACUGGACGCCGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 46 consists from 5' to 3' end: 5' UTR of SEQ ID NO: 3, ORF Sequence of SEQ ID NO: 14, and 3' UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCACCCCGGCUUUA AGGACCCCGUGUAC AGGGCCAGGCGGAA ACAGUUCGCCGACA UCGCCUAUAACUAC AGGCACGGGCAACC CAUCCCUAGGGUCG AGUACAUGGAGGAG GAGAAGAAGACCUG GGGCACAGUGUUCA AGACCCUCAAAUCC CUGUACAAGACACA CGCCUGCUACGAGU AUAACCACAUCUUC CCUCUCCUGGAGAA GUAUUGCGGCUUUC ACGAAGACAACAUC CCGCAGCUGGAAGA CGUGUCCCAGUUCC UGCAGACCUGUACC GGAUUCAGGUUAAG ACCUGUGGCCGGCC UGCUGAGCAGCAGG GAUUUCCUAGGCGG GCUCGCCUUCAGGG UGUUCCAUUGCACC CAGUACAUCAGACA CGGCUCCAAGCCGA UGUAUACGCCUGAG CCCGACAUCUGCCA CGAGCUGCUGGGCC ACGUGCCGCUGUUC AGCGAUAGAAGCUU CGCCCAGUUCAGCC AGGAGAUCGGCCUG GCCAGCCUGGGAGC GCCUGACGAAUAUA UCGAGAAGCUCGCC ACCAUCUACUGGUU UACCGUGGAAUUCG GCCUGUGCAAGCAG GGAGACUCCAUCAA GGCCUACGGGGCUG GGCUGCUGUCCUCC UUCGGGGAGCUCCA GUACUGUCUCUCCG AGAAGCCCAAGCUG CUGCCCCUCGAGCU GGAGAAGACCGCGA UCCAGAACUAUACC GUCACCGAAUUCCA GCCCCUGUAUUACG UGGCCGAGUCCUUU AACGACGCCAAGGA GAAGGUCCGGAAUU UCGCUGCCACCAUU CCCAGGCCCUUCAG CGUGCGGUACGAUC CCUACACCCAGCGC AUAGAGGUGCUGGA UAAUACACAGCAGC UGAAGAUCCUGGCC GACAGCAUCAAUAG CGAAAUAGGCAUCC UGUGCAGCGCCCUG CAGAAGAUCAAG | | | |

-continued

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 15 | 3 | 4 | 56 |
| PAH_012 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVPHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGUCCACCGCCGU GCUCGAGAACCCUG GCCUGGGCAGGAAG CUGAGCGACUUCGG GCAAGAGACAAGCU ACAUCGAGGAUAAC UGCAAUCAGAACGG CGCCAUCAGCCUGA UCUUCUCCCUGAAG GAGGAGGUGGGCGC CCUGGCUAAGGUGC UGAGGCUAUUCGAA GAGAACGACGUGAA UCUGACCCAUAUCG AGAGCCGCCCCAGC CGGCUCAAGAAGGA CGAGUACGAGUUCU UUACUCACCUGGAC AAGCGGUCCCUGCC CGCCCUGACAAACA UCAUCAAGAUCCUC AGGCACGAUAUCGG AGCCACCGUCCACG AGCUGAGCCGCGAC AAGAAGAAAGACAC CGUGCCCUGGUUUC CCAGGACCAUCCAG GAGCUGGAUCGGUU UGCCAACCAGAUCC UGAGCUACGGGGCC GAACUUGACGCCGA CCAUCCCGGGUUCA AGGACCCGGUGUAC CGGGCUAGGCGAAA GCAAUUCGCCGACA UUGCCUACAACUAC CGUCACGGCCAGCC CAUCCCACGGGUGG AAUACAUGGAGGAG GAGAAGAAGACCUG GGGAACAGUCUUCA AGACCCUGAAGUCA CUGUACAAGACCCA CGCCUGCUACGAGU AUAACCACAUCUUC CCACUCCUCGAGAA GUACUGCGGCUUCC ACGAGGACAACAUC CCUCAGCUGGAGGA CGUGAGCCAGUUCC UGCAGACCUGCACC GGCUUUCGUCUGCG UCCCGUGGCGGGAC UGCUGAGCAGCAGG GACUUCCUGGGCGG ACUGGCCUUCCGGG UGUUCCACUGCACA CAGUACAUCCGACA CGGCAGCAAGCCGA UGUAUACACCGGAG CCGGACAUUUGCCA CGAGCUCCUGGGCC ACGUGCCCCUGUUC AGCGACAGGAGCUU CGCCCAGUUCAGCC AGGAGAUCGGCCUG GCCAGCCUGGGUGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 56 consists from 5' to 3' end: 5' UTR of SEQ ID NO:3, ORF Sequence of SEQ ID NO: 15, and 3' UTR of SEQ ID NO: 4 |

| | CONSTRUCT SEQUENCES | | | | |
|---|---|---|---|---|---|
| | By "G5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | CCCAGACGAGUACA UAGAGAAGCUGGCG ACCAUCUACUGGUU CACGGUCGAGUUCG GCCUGUGCAAACAG GGCGACAGCAUUAA GGCCUACGGCGCCG GCCUGCUCAGCUCC UUCGGCGAGCUCCA GUAUUGCCUGAGCG AGAAGCCCAAGCUG CUGCCCCUGGAGCU CGAGAAGACUGCCA UUCAGAACUACACU GUGACCGAGUUCCA GCCCCUGUACUACG UGGCGGAGAGCUUC AACGACGCCAAGGA GAAGGUGAGGAACU UCGCCGCCACCAUC CCUCGGCCCUUCUC CGUUAGGUACGACC CCUACACCCAGAGG AUCGAGGUGCUGGA UAAUACCCAGCAGC UGAAGAUCCUGGCG GACAGCAUCAACAG CGAAAUCGGCAUCC UGUGCAGCGCCUUA CAGAAGAUCAAG | | | |
| SEQ ID NO: | 1 | 16 | 3 | 4 | 57 |
| PAH_013 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVPHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACGUCAU ACAUCGAGGAUAAC UGCAACCAGAACGG UGCCAUCUCCCUGA UCUUCAGCCUGAAG GAAGAGGUGGGCGC CCUGGCCAAGGUCC UGAGACUGUUCGAG GAGAACGACGUGAA CCUGACCCACAUCG AAAGCAGACCCAGC AGGCUGAAGAAGA CGAGUACGAAUUCU UCACCCACCUGGAC AAGCGGAGCCUGCC CGCCCUCACUAACA UCAUCAAGAUCCUU AGACACGACAUAGG CGCCACCGUCCACG AACUCAGCAGGGAC AAGAAGAAGGACAC CGUGCCCUGGUUCC CCAGGACCAUCCAG GAGCUGGACCGCUU CGCCAACCAGAUUC UGUCCUACGGAGCU GAACUCGACGCCGA CCAUCCCGGAUUCA AAGACCCCGUGUAC AGAGCCAGAAGAAA GCAGUUCGCCGACA UCGCGUACAACUAU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAG GUAGGA AACACU ACAGUG GUCUUU GAAUAA AGUCUG AGUGGG CGGC | SEQ ID NO: 57 consists from 5' to 3' end: 5' UTR of SEQ ID NO: 3, ORF Sequence of SEQ ID NO: 16, and 3' UTR of SEQ ID NO: 4 |

| | | CONSTRUCT SEQUENCES | | | |
|---|---|---|---|---|---|
| | | By "G5" is meant that all uracils (U) in the mRNA are replaced by N1-methylpseudouracils. | | | |
| | | By "G6" is meant that all uracils (U) in the mRNA are replaced by 5-methoxyuracils. | | | |
| mRNA Name | ORF Sequence (Amino Acid) | ORF Sequence (Nucleotide) | 5' UTR Sequence | 3' UTR Sequence | Construct Sequence |
| | | AGGCACGGCCAGCC GAUCCCCAGAGUCG AGUACAUGGAGGAG GAGAAGAAGACCUG GGGCACCGUGUUCA AGACCCUGAAGUCC CUGUACAAGACCCA CGCUUGCUACGAGU AUAACCACAUCUUC CCACUCCUGGAGAA GUACUGCGGCUUCC ACGAAGACAACAUU CCCCAGCUCGAGGA CGUGAGCCAAUUCC UGCAGACCUGCACC GGCUUCCGCCUGAG GCCCGUUGCCGGCC UGCUGAGCUCCAGA GAUUUCCUCGGCGG CCUGGCCUUCAGAG UGUUUCACUGCACC CAGUACAUCCGCCA CGGCUCCAAGCCAA UGUACACCCCGGAG CCCGAUAUCUGUCA CGAGCUGCUGGGCC ACGUGCCCCUCUUC AGCGACCGAAGCUU CGCCCAGUUUUCCC AAGAGAUAGGACUU GCCUCCCUCGGUGC CCCGGACGAAUAUA UUGAGAAACUCGCC ACCAUCUACUGGUU UACGGUGGAAUUCG GACUGUGCAAGCAG GGCGACAGCAUCAA AGCCUACGGGGCAG GGCUGCUGUCUAGC UUCGGGGAGCUCCA AUACUGCCUGAGCG AGAAACCCAAGCUC CUGCCUCUCGAGCU GGAGAAGACCGCUA UCCAGAAUUACACC GUGACUGAAUUCCA GCCCCUGUACUACG UCGCCGAGAGCUUU AACGACGCCAAGGA GAAAGUACGAAACU UCGCCGCUACCAUU CCCCGCCCCUUCAG CGUGAGGUACGACC CUUACACCCAGCGU AUCGAGGUGCUGGA UAAUACCCAACAGC UGAAGAUACUCGCC GACUCCAUCAACAG CGAGAUCGGCAUCC UGUGUUCCGCCCUC CAGAAGAUCAAG | | | |
| SEQ ID NO: | 1 | 17 | 3 | 4 | 58 |
| PAH_014 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY | AUGUCCACGGCCGU CCUGGAGAAUCCGG GCCUGGGGAGGAAA CUGAGCGACUUCGG GCAGGAGACAUCCU | GGGAAA UAAGAG AGAAAA GAAGAG UAAGAA | UGAUAA UAGGCU GGAGCC UCGGUG GCCUAG | SEQ ID NO: 58 consists from 5' to 3' end: 5' |

CONSTRUCT SEQUENCES

By "G5" is meant that all uracils (U) in the mRNA are replaced by N1-methylpseudouracils.

By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | ACAUCGAGGACAAC UGCAACCAGAACGG AGCCAUCAGCCUGA UCUUCAGCCUCAAA GAGGAGGUGGGCGC UCUCGCCAAGGUGC UGAGACUGUUCGAG GAGAACGACGUCAA CCUCACGCACAUCG AAUCCCGACCCAGC CGUCUGAAGAAGGA CGAGUACGAGUUCU UCACCCAUCUCGAC AAGCGGUCCCUGCC CGCCCUCACAAACA UCAUCAAGAUCCUG CGGCACGACAUCGG CGCCACCGUGCACG AGCUGUCCAGGGAC AAGAAGAAAGAUAC CGUGCCGUGGUUCC CCAGGACGAUCCAG GAGCUCGACCGGUU CGCCAACCAGAUCC UGAGCUACGGCGCC GAACUCGACGCCGA CCACCCCGGCUUUA AGGAUCCCGUGUAC AGAGCCAGGAGGAA GCAGUUUGCCGACA UCGCGUACAACUAC AGACACGGGCAGCC CAUCCCCAGGGUGG AGUACAUGGAGGAG GAGAAGAAGACCUG GGGCACCGUCUUCA AGACACUGAAGUCC CUGUACAAGACCCA CGCCUGCUACGAGU ACAACCACAUUUUC CCUCUGCUGGAGAA GUACUGCGGCUUCC ACGAAGACAACAUA CCGCAGCUCGAGGA CGUGAGCCAAUUUC UGCAGACCUGCACC GGUUUUAGACUGAG GCCCGUGGCCGGCC UGCUGAGCAGCAGG GAUUUUCUCGGUGG ACUGGCCUUCAGAG UGUUCCACUGCACC CAGUAUAUAAGACA CGGCUCCAAGCCCA UGUACACCCCAGAG CCUGACAUCUGCCA CGAACUGCUGGGUC ACGUGCCCCUCUUC AGCGACAGGUCCUU CGCCCAGUUCAGCC AGGAAAUCGGCCUG GCCUCCCUCGGCGC UCCCGACGAAUACA UCGAGAAGCUGGCC ACAAUCUACUGGUU CACCGUCGAGUUCG GCCUGUGCAAGCAG GGCGACUCCAUCAA GGCCUACGGCGCGG GGCUGCUAUCCUCC UUCGGGGAGCUCCA | GAAAUA UAAGAG CCACC | CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | UTR of SEQ ID NO: 3, ORF Sequence of SEQ ID NO: 17, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GUACUGCCUGUCCG AGAAGCCCAAGCUC CUGCCCCUGGAACU GGAGAAGACCGCCA UCCAGAACUACACC GUGACCGAGUUCCA GCCACUGUACUACG UCGCCGAGAGUUUC AACGACGCCAAAGA GAAAGUGCGGAACU UCGCCGCCACCAUC CCUAGACCUUUCUC CGUCAGAUACGACC CAUACACGCAGCGG AUCGAGGUCCUGGA CAACACUCAGCAAC UCAAGAUUCUGGCU GACAGUAUCAAUAG CGAGAUCGGGAUCC UGUGUAGCGCCCUU CAGAAGAUCAAG | | | |
| SEQ ID NO: | 1 | 18 | 3 | 4 | 59 |
| PAH_015 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACGAGCU ACAUCGAGGACAAC UGCAACCAGAACGG CGCCAUCAGCCUGA UCUUCUCCCUGAAG GAGGAGGUGGGCGC CCUGGCCAAGGUGC UGCGGCUGUUCGAG GAGAACGACGUGAA CCUGACCCACAUCG AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAAGACAC CGUGCCCUGGUUCC CACGGACCAUCCAG GAGCUGGACCGGUU CGCCAACCAGAUCC UGAGCUACGGCGCC GAGCUGGACGCCGA CCACCCCGGCUUCA AGGACCCCGUGUAC CGGGCCCGGCGGAA GCAGUUCGCCGACA UCGCCUACAACUAC CGGCACGGCCAGCC CAUCCCACGGGUGG AGUACAUGGAGGAG GAGAAGAAGACCUG GGGCACCGUGUUCA AGACCCUGAAGUCC CUGUACAAGACCCA CGCCUGCUACGAGU ACAACCACAUCUUU | GGGAAA UAAGAG AGAAAA GAAGAG UAAGAA GAAAUA UAAGAG CCACC | UGAUAA UAGGCU GGAGCC GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 59 consists from 5' to 3' end: 5' UTR of SEQ ID NO: 3, ORF Sequence of SEQ ID NO: 18, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCCUUCUGGAGAA | | | |
| | | GUACUGCGGCUUCC | | | |
| | | ACGAGGACAAUAUC | | | |
| | | CCUCAGCUGGAGGA | | | |
| | | CGUGAGCCAGUUCC | | | |
| | | UGCAGACCUGCACC | | | |
| | | GGCUUCCGCCUGAG | | | |
| | | GCCCGUGGCCGGCC | | | |
| | | UGCUGAGCUCCAGG | | | |
| | | GACUUCCUGGGCGG | | | |
| | | CCUGGCCUUCCGGG | | | |
| | | UGUUCCACUGCACC | | | |
| | | CAGUACAUCCGACA | | | |
| | | CGGCAGCAAGCCCA | | | |
| | | UGUACACGCCCGAG | | | |
| | | CCCGACAUCUGCCA | | | |
| | | CGAGCUCCUGGGCC | | | |
| | | ACGUGCCCCUGUUC | | | |
| | | AGCGACCGGAGCUU | | | |
| | | CGCCCAGUUCUCCC | | | |
| | | AGGAGAUCGGACUG | | | |
| | | GCCAGCCUGGGAGC | | | |
| | | ACCCGACGAAUACA | | | |
| | | UCGAGAAGCUGGCC | | | |
| | | ACCAUCUACUGGUU | | | |
| | | CACCGUGGAGUUCG | | | |
| | | GCCUGUGCAAGCAG | | | |
| | | GGCGACAGCAUCAA | | | |
| | | GGCCUACGGCGCCG | | | |
| | | GUCUGCUGUCCAGC | | | |
| | | UUCGGCGAGCUGCA | | | |
| | | GUACUGCCUGAGCG | | | |
| | | AGAAGCCCAAGCUG | | | |
| | | CUGCCCCUGGAACU | | | |
| | | GGAGAAGACCGCCA | | | |
| | | UCCAGAACUACACC | | | |
| | | GUGACCGAGUUCCA | | | |
| | | GCCCCUGUACUACG | | | |
| | | UGGCCGAGAGCUUC | | | |
| | | AACGACGCCAAGGA | | | |
| | | GAAGGUGCGGAACU | | | |
| | | UCGCCGCCACCAUA | | | |
| | | CCCCGCCCCUUCAG | | | |
| | | CGUGCGGUACGACC | | | |
| | | CCUACACCCAGCGG | | | |
| | | AUCGAGGUGCUGGA | | | |
| | | CAACACCCAACAGC | | | |
| | | UGAAGAUCCUGGCC | | | |
| | | GAUAGCAUCAACAG | | | |
| | | CGAGAUCGGCAUCC | | | |
| | | UGUGCAGCGCCCUG | | | |
| | | CAGAAGAUCAAG | | | |
| SEQ ID NO: | 1 | 19 | 3 | 4 | 60 |
| PAH_016 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL | AUGAGCACCGCCGU GCUGGAGAACCCCG GCCUGGGCCGGAAG CUGAGCGACUUCGG CCAGGAAACCAGCU ACAUCGAGGACAAC UGCAACCAGAACGG CGCCAUCAGCCUGA UCUUCAGCCUCAAG GAGGAGGUGGGCGC CCUGGCCAAGGUGC UGCGGCUGUUCGAG GAGAACGACGUGAA CCUGACCCACAUCG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC | SEQ ID NO: 60 consists from 5' to 3' end: 5' UTR of SEQ ID NO: 3, ORF Sequence of SEQ ID NO: 19, and 3' UTR of |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAGGAUAC CGUGCCCUGGUUCC CGCGGACCAUCCAG GAGCUGGACCGGUU CGCCAACCAGAUCC UGAGCUACGGCGCC GAGCUGGACGCCGA CCACCCCGGCUUCA AGGACCCCGUGUAC CGGGCCCGGCGGAA GCAGUUCGCCGACA UCGCCUACAACUAC CGGCACGGCCAGCC CAUCCCGCGGGUGG AGUACAUGGAGGAG GAGAAGAAGACCUG GGGCACCGUGUUCA AGACCCUGAAGUCU CUGUACAAGACCCA CGCCUGCUACGAGU ACAACCACAUCUUU CCCCUGCUCGAGAA GUACUGCGGCUUCC ACGAGGAUAACAUA CCGCAGCUGGAGGA CGUGAGCCAGUUCC UGCAGACCUGCACC GGCUUCAGAUUGAG GCCCGUCGCUGGUC UGCUGAGCUCCAGG GACUUCCUGGGCGG CCUGGCCUUCCGGG UGUUCCACUGCACC CAGUACAUCAGGCA CGGCAGCAAGCCCA UGUACACGCCCGAG CCCGACAUCUGCCA CGAGCUCCUGGGCC ACGUGCCCCUGUUC AGCGACCGGAGCUU CGCCCAGUUCAGCC AAGAGAUCGGACUG GCUAGCCUCGGCGC CCCGGACGAGUAUA UCGAGAAGCUGGCC ACCAUCUACUGGUU CACCGUGGAGUUCG GCCUGUGCAAGCAG GGCGACAGCAUCAA GGCCUACGGCGCCG GCCUCCUCAGCUCU UUCGGCGAGCUGCA GUACUGCCUGAGCG AGAAGCCCAAGCUG CUGCCCCUCGAACU GGAGAAGACCGCCA UCCAGAACUACACC GUGACCGAGUUCCA GCCCCUGUACUACG UGGCCGAGAGCUUC AACGACGCCAAGGA | | CCCCUC CAUAAA GUAGGA AACACU ACAGUG GUCUUU GAAUAA AGUCUG AGUGGG CGGC | SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAAGGUGCGGAACU UCGCCGCGACCAUC CCUAGGCCCUUCAG CGUGCGGUACGACC CCUACACCCAGCGG AUCGAGGUGCUGGA CAAUACCCAGCAGC UGAAGAUUCUCGCC GACUCGAUCAACAG CGAGAUCGGGAUCC UGUGCAGCGCCCUG CAGAAGAUCAAG | | | |
| SEQ ID NO: | 1 | 20 | 3 | 4 | 61 |
| PAH_017 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACGUCCU ACAUCGAGGACAAC UGCAACCAGAACGG CGCCAUCUCCCUCA UCUUCAGCCUGAAG GAGGAGGUCGGCGC CCUCGCCAAGGUCC UCCGCCUCUUCGAG GAGAACGACGUCAA CCUCACCCACAUCG AGUCCCGCCCCUCC CGCCUCAAGAAGGA CGAGUACGAGUUCU UCACCCACCUCGAC AAGCGCUCCCUCCC CGCCCUCACCAACA UCAUCAAGAUCCUG AGACACGACAUCGG CGCCACCGUCCACG AGCUCUCCCGCGAC AAGAAGAAGGAUAC CGUCCCCUGGUUCC CACGCACCAUCCAG GAGCUCGACCGCUU CGCCAACCAGAUCC UCUCCUACGGCGCC GAGCUGGACGCCGA CCACCCCGGCUUCA AGGACCCCGUCUAC CGCGCCCGCCGCAA GCAGUUCGCCGACA UCGCCUACAACUAC CGCCACGGCCAGCC CAUUCCCCGCGUCG AGUACAUGGAGGAG GAGAAGAAGACCUG GGGCACCGUCUUCA AGACCCUCAAGUCC CUCUACAAGACCCA CGCCUGCUACGAGU ACAACCACAUCUUU CCCCUCCUCGAGAA GUACUGCGGCUUCC ACGAGGACAAUAUC CCUCAGCUCGAGGA CGUCUCCCAGUUCC UCCAGACCUGCACC GGCUUUCGGCUGCG CCCGGUCGCCGGCC UGCUGUCCAGCAGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 61 consists from 5' to 3' end: 5' UTR of SEQ ID NO: 3, ORF Sequence of SEQ ID NO: 20, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GACUUCCUCGGCGG | | | |
| | | CCUCGCCUUCCGCG | | | |
| | | UCUUCCACUGCACC | | | |
| | | CAGUACAUUCGGCA | | | |
| | | CGGCUCCAAGCCCA | | | |
| | | UGUACACACCCGAG | | | |
| | | CCCGACAUCUGCCA | | | |
| | | CGAGCUGCUCGGCC | | | |
| | | ACGUGCCCCUCUUC | | | |
| | | UCCGACCGCUCCUU | | | |
| | | CGCCCAGUUCUCCC | | | |
| | | AGGAGAUUGGGCUG | | | |
| | | GCCUCCCUGGGAGC | | | |
| | | GCCCGACGAGUACA | | | |
| | | UUGAGAAGCUCGCC | | | |
| | | ACCAUCUACUGGUU | | | |
| | | CACCGUCGAGUUCG | | | |
| | | GCCUCUGCAAGCAG | | | |
| | | GGCGACUCCAUCAA | | | |
| | | GGCUUACGGGGCGG | | | |
| | | GGCUCCUCUCCAGC | | | |
| | | UUCGGCGAGCUCCA | | | |
| | | GUACUGCCUCUCCG | | | |
| | | AGAAGCCCAAGCUC | | | |
| | | CUCCCGCUGGAACU | | | |
| | | GGAGAAGACCGCCA | | | |
| | | UCCAGAACUACACC | | | |
| | | GUCACCGAGUUCCA | | | |
| | | GCCCCUCUACUACG | | | |
| | | UCGCCGAGUCCUUC | | | |
| | | AACGACGCCAAGGA | | | |
| | | GAAGGUCCGCAACU | | | |
| | | UCGCGGCUACCAUC | | | |
| | | CCGCGGCCCUUCUC | | | |
| | | CGUCCGCUACGACC | | | |
| | | CCUACACCCAGCGC | | | |
| | | AUCGAGGUGCUCGA | | | |
| | | CAAUACCCAACAGC | | | |
| | | UGAAGAUCCUGGCG | | | |
| | | GACAGCAUUAACUC | | | |
| | | CGAGAUCGGGAUCC | | | |
| | | UCUGCUCCGCCCUC | | | |
| | | CAGAAGAUCAAG | | | |

| SEQ ID NO: | 1 | 11 | 3 | 4 | 62 |
|---|---|---|---|---|---|
| PAH_008 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS | AUGAGCACCGCCGU CCUCGAGAACCCCG GCCUGGGCAGAAAG CUGAGCGACUUCGG CCAGGAAACCAGCU ACAUCGAGGACAAC UGCAACCAGAACGG CGCCAUCAGCCUGA UCUUCAGCCUGAAG GAGGAGGUGGGCGC CCUGGCCAAGGUGC UGAGACUGUUCGAG GAGAACGACGUGAA CCUGACCCACAUCG AGAGCAGACCCUCC AGACUGAAGAAGGA CGAGUACGAGUUCU UCACCCACCUGGAC AAGAGAAGCCUGCC CGCCCUGACCAACA UCAUCAAGAUCCUG AGACACGACAUCGG AGCCACCGUGCACG | GGGAAA UAAGAG AGAAAA GAAGAG UAAGAA GAAAUA UAAGAG CCACC | UGAUAA UAGGCU GGAGCC GCCCCU UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG | SEQ ID NO: 62 consists from 5' to 3' end: 5' UTR of SEQ ID NO: 3, ORF Sequence of SEQ ID NO: 11, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AGCUGAGCAGAGAC AAGAAGAAGGACAC CGUGCCCUGGUUCC CCAGAACCAUCCAG GAGCUGGACAGAUU CGCCAACCAGAUCC UGAGCUACGGUGCC GAGCUAGACGCCGA CCACCCCGGCUUCA AGGACCCCGUGUAC AGAGCCAGAAGAAA GCAGUUCGCCGACA UCGCCUACAACUAC AGACACGGGCAGCC GAUCCCCAGAGUGG AGUACAUGGAGGAG GAGAAGAAGACCUG GGGCACCGUGUUCA AGACCCUCAAGAGC CUGUACAAGACCCA CGCCUGCUACGAGU ACAACCACAUCUUC CCUCUGCUGGAGAA GUACUGCGGCUUCC ACGAGGACAACAUC CCACAGCUGGAGGA CGUGAGCCAGUUCC UGCAGACCUGCACC GGCUUCAGACUCAG GCCCGUUGCCGGAC UGCUGAGCAGCAGA GACUUCCUGGGCGG CCUGGCCUUCAGAG UGUUCCACUGCACC CAGUACAUCAGACA CGGCAGCAAGCCCA UGUACACACCCGAG CCCGACAUCUGCCA CGAACUGCUGGGCC ACGUGCCCCUGUUC AGCGACAGAAGCUU CGCCCAGUUCAGCC AGGAGAUCGGUCUG GCUAGCUUGGGAGC CCCAGACGAGUACA UCGAGAAGCUGGCC ACCAUCUACUGGUU CACCGUGGAGUUCG GCCUGUGCAAGCAG GGAGACAGCAUCAA GGCCUACGGAGCCG GCCUACUGAGCAGC UUCGCGAGCUGCA GUACUGCCUGAGCG AGAAGCCCAAGCUG UUGCCUCUGGAGCU GGAGAAGACCGCCA UCCAGAACUACACC GUGACCGAGUUCCA GCCCCUGUACUACG UGGCCGAGAGCUUC AACGACGCCAAGGA GAAGGUGAGAAACU UCGCCGCCACUAUC CCCAGACCCUUCAG CGUGAGAUACGACC CCUACACCCAGAGA AUCGAGGUGCUGGA CAACACCCAGCAGC UGAAGAUUCUGGCC GAUAGCAUCAACAG | | CGGC | |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CGAGAUCGGCAUCC UGUGCAGCGCCCUG CAGAAGAUCAAG | | | |
| SEQ ID NO: | 1 | 12 | 3 | 4 | 63 |
| PAH_009 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU CCUCGAGAACCCCG GCCUGGGCAGAAAG CUGAGCGACUUCGG CCAGGAAACCAGCU ACAUCGAGGACAAC UGCAACCAGAACGG CGCCAUCAGCCUGA UCUUCUCACUCAAA GAAGAAGUUGGUGC AUUGGCCAAAGUAU UGCGCUUAUUGAG GAGAACGACGUGAA CCUGACCCACAUCG AGAGCAGACCCUCC AGACUGAAGAAGGA CGAGUACGAGUUCU UCACCCACCUGGAC AAGAGAAGCCUGCC CGCCCUGACCAACA UCAUCAAGAUCCUG AGACACGACAUCGG AGCCACCGUGCACG AGCUGAGCAGAGAC AAGAAGAAGGACAC CGUGCCCUGGUUCC CCAGAACCAUCCAG GAGCUGGACAGAUU CGCCAACCAGAUCC UGAGCUACGGUGCC GAGCUAGACGCCGA CCACCCCGGCUUCA AGGACCCCGUGUAC AGAGCCAGAAGAAA GCAGUUCGCCGACA UCGCCUACAACUAC AGACACGGGCAGCC GAUCCCCAGAGUGG AGUACAUGGAGGAG GAGAAGAAGACCUG GGGCACCGUGUUCA AGACCCUCAAGAGC CUGUACAAGACCCA CGCCUGCUACGAGU ACAACCACAUCUUC CCUCUGCUGGAGAA GUACUGCGGCUUCC ACGAGGACAACAUC CCACAGCUGGAGGA CGUGAGCCAGUUCC UGCAGACCUGCACC GGCUUCAGACUCAG GCCCGUUGCCGGAC UGCUGAGCAGCAGA GACUUCCUGGGCGG CCUGGCCUUCAGAG UGUUCCACUGCACC CAGUACAUCAGACA CGGCAGCAAGCCCA UGUACACACCCGAG CCCGACAUCUGCCA CGAACUGCUGGGCC ACGUGCCCCUGUUC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 63 consists from 5' to 3' end: 5' UTR of SEQ ID NO: 3, ORF Sequence of SEQ ID NO: 12, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCGACAGAAGCUU CGCCCAGUUCAGCC AGGAGAUCGGUCUG GCUAGCUUGGGAGC CCCAGACGAGUACA UCGAGAAGCUGGCC ACCAUCUACUGGUU CACCGUGGAGUUCG GCCUGUGCAAGCAG GGAGACAGCAUCAA GGCCUACGGAGCCG GCCUACUGAGCAGC UUCGGCGAGCUGCA GUACUGCCUGAGCG AGAAGCCCAAGCUG UUGCCUCUGGAGCU GGAGAAGACCGCCA UCCAGAACUACACC GUGACCGAGUUCCA GCCCCUGUACUACG UGGCCGAGAGCUUC AACGACGCCAAGGA GAAGGUGAGAAACU UCGCCGCCACUAUC CCCAGACCCUUCAG CGUGAGAUACGACC CCUACACCCAGAGA AUCGAGGUGCUGGA CAACACCCAGCAGC UGAAGAUUCUGGCC GAUAGCAUCAACAG CGAGAUCGGCAUCC UGUGCAGCGCCCUG CAGAAGAUCAAG | | | |
| SEQ ID NO: | 1 | 13 | 3 | 4 | 64 |
| PAH_010 (hPAH.FL.G6) Cap: C1 PolyA tail: 100 nt | MSTAVLENPGLGRKL SDFGQETSYIEDNCN QNGAISLIFSLKEEVG ALAKVLRLFEENDVN LTHIESRPSRLKKDEY EFFTHLDKRSLPALT NIIKILRHDIGATVHE LSRDKKKDTVPWFPR TIQELDRFANQILSYG AELDADHPGFKDPV YRARRKQFADIAYN YRHGQPIPRVEYMEE EKKTWGTVFKTLKSL YKTHACYEYNHIFPL LEKYCGFHEDNIPQL EDVSQFLQTCTGFRL RPVAGLLSSRDFLGG LAFRVFHCTQYIRHG SKPMYTPEPDICHELL GHVPLFSDRSFAQFS QEIGLASLGAPDEYIE KLATIYWFTVEFGLC KQGDSIKAYGAGLLS SFGELQYCLSEKPKL LPLELEKTAIQNYTV TEFQPLYYVAESFND AKEKVRNFAATIPRP FSVRYDPYTQRIEVL DNTQQLKILADSINSE IGILCSALQKIK | AUGAGCACCGCCGU GCUGGAGAACCCCG GCCUGGGCCGGAAG CUGAGCGACUUCGG CCAGGAGACCAGCU ACAUCGAGGACAAC UGCAACCAGAACGG CGCCAUCAGCCUGA UCUUCAGCCUGAAG GAGGAGGUGGGCGC CCUGGCCAAGGUGC UGCGGCUGUUCGAG GAGAACGACGUGAA CCUGACCCACAUCG AGAGCCGGCCCAGC CGGCUGAAGAAGGA CGAGUACGAGUUCU UCACCCACCUGGAC AAGCGGAGCCUGCC CGCCCUGACCAACA UCAUCAAGAUCCUG CGGCACGACAUCGG CGCCACCGUGCACG AGCUGAGCCGGGAC AAGAAGAAGGACAC CGUGCCCUGGUUCC CGCGGACCAUCCAG GAGCUGGACCGGUU CGCCAACCAGAUCC UGAGCUACGGCGCC GAGCUGGACGCCGA CCACCCCGGCUUCA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC CAUAAA UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 64 consists from 5' to 3' end: 5' UTR of SEQ ID NO: 3, ORF Sequence of SEQ ID NO: 13, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGGACCCCGUGUAC | | | |
| | | CGGGCCCGGCGGAA | | | |
| | | GCAGUUCGCCGACA | | | |
| | | UCGCCUACAACUAC | | | |
| | | CGGCACGGCCAGCC | | | |
| | | CAUCCCGCGGGUGG | | | |
| | | AGUACAUGGAGGAG | | | |
| | | GAGAAGAAGACCUG | | | |
| | | GGGCACCGUGUUCA | | | |
| | | AGACCCUGAAGAGC | | | |
| | | CUGUACAAGACCCA | | | |
| | | CGCCUGCUACGAGU | | | |
| | | ACAACCACAUCUUC | | | |
| | | CCACUGCUGGAGAA | | | |
| | | GUACUGCGGCUUCC | | | |
| | | ACGAGGACAACAUC | | | |
| | | CCACAGCUGGAGGA | | | |
| | | CGUGAGCCAGUUCC | | | |
| | | UGCAGACCUGCACC | | | |
| | | GGCUUCCGGCUGCG | | | |
| | | GCCCGUGGCCGGCC | | | |
| | | UGCUGAGCAGCCGG | | | |
| | | GACUUCCUGGGCGG | | | |
| | | CCUGGCCUUCCGGG | | | |
| | | UGUUCCACUGCACC | | | |
| | | CAGUACAUCCGGCA | | | |
| | | CGGCAGCAAGCCCA | | | |
| | | UGUACACGCCCGAG | | | |
| | | CCCGACAUCUGCCA | | | |
| | | CGAGCUGCUGGGCC | | | |
| | | ACGUGCCCCUGUUC | | | |
| | | AGCGACCGGAGCUU | | | |
| | | CGCCCAGUUCAGCC | | | |
| | | AGGAGAUCGGCCUG | | | |
| | | GCCAGCCUGGGCGC | | | |
| | | GCCCGACGAGUACA | | | |
| | | UCGAGAAGCUGGCC | | | |
| | | ACCAUCUACUGGUU | | | |
| | | CACCGUGGAGUUCG | | | |
| | | GCCUGUGCAAGCAG | | | |
| | | GGCGACAGCAUCAA | | | |
| | | GGCCUACGGCGCCG | | | |
| | | GCCUGCUGAGCAGC | | | |
| | | UUCGGCGAGCUGCA | | | |
| | | GUACUGCCUGAGCG | | | |
| | | AGAAGCCCAAGCUG | | | |
| | | CUGCCCCUGGAGCU | | | |
| | | GGAGAAGACCGCCA | | | |
| | | UCCAGAACUACACC | | | |
| | | GUGACCGAGUUCCA | | | |
| | | GCCCCUGUACUACG | | | |
| | | UGGCCGAGAGCUUC | | | |
| | | AACGACGCCAAGGA | | | |
| | | GAAGGUGCGGAACU | | | |
| | | UCGCCGCCACCAUC | | | |
| | | CCACGGCCCUUCAG | | | |
| | | CGUGCGGUACGACC | | | |
| | | CCUACACCCAGCGG | | | |
| | | AUCGAGGUGCUGGA | | | |
| | | CAACACCCAGCAGC | | | |
| | | UGAAGAUCCUGGCC | | | |
| | | GACAGCAUCAACAG | | | |
| | | CGAGAUCGGCAUCC | | | |
| | | UGUGCAGCGCCCUG | | | |
| | | CAGAAGAUCAAG | | | |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 21 | 22 | 3 | 4 | 65 |
| PAH_018 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE NHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU UCCCAGAACCAUCC AGGAGCUGGACAGG UUCGCAAACCAGAU ACUCUCCUACGGCG CAGAGCUGGACGCC GACCACCCAGGCUU CAAGGACCCCGUCU ACAGGGCCAGGCGC AAGCAGUUCCAGA UAUUGCCUACAAUU AUCGACACGGUCAG CCCAUCCCUAGAGU GGAGUACAUGGAGG AAGAGAAGAAGACC UGGGGCACCGUGUU CAAGACUCUGAAGA GUCUGUACAAGACA CACGCUUGUUACGA GUAUAAUCACAUCU UCCCUCUGCUGGAG AAGUACUGCGGUUU CCACGAAGAUAACA UCCCGCAGCUCGAG GACGUGUCCCAGUU UCUGCAGACUUGCA CUGGCUUUAGACUG AGGCCCGUCGCCGG ACUGCUGUCCUCCA GAGACUUCCUGGGC GGGCUUGCUUUCAG AGUGUUUCACUGUA CACAGUAUAUUCGC CACGGGAGCAAACC CAUGUACACCCCUG AGCCCGACAUUUGU CACGAAUUGCUGGG ACACGUGCCUCUGU UUAGCGAUAGAAGC UUCGCCCAGUUCAG CCAGGAAAUCGGGC UGGCCUCACUGGGC GCCCCAGACGAGUA CAUCGAGAAGCUGG CCACCAUAUACUGG UUCACAGUGGAGUU CGGCCUGUGCAAGC AAGGCGACUCUAUC AAGGCUUACGGUGC CGGGCUGUUGAGCU CAUUCGGAGAGCUG CAAUAUUGUUUAUC AGAGAAACCUAAGC UGCUGCCCCUUGAG CUCGAGAAGACAGC CAUACAGAACUACA CCGUGACCGAGUUC CAGCCACUGUAUUA CGUGGCCGAAUCCU UCAACGACGCAAAG GAGAAGGUGAGAA ACUUUGCCGCUACC AUCCCUCGGCCCUU CUCCGUUAGAUACG ACCCCUACACCCAA CGGAUUGAGGUGCU GGACAAUACCCAGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 65 consists from 5' to 3' end: 5' UTR of SEQ ID NO: 3, ORF Sequence of SEQ ID NO: 22, and 3' UTR of SEQ ID NO: 4 |

-continued

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AAUUGAAGAUCCUU GCCGACUCGAUCAA CAGCGAGAUCGGCA UUCUGUGCAGCGCG UUGCAGAAGAUCAA G | | | |
| SEQ ID NO: | 21 | 23 | 3 | 4 | 66 |
| PAH_019 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCACGUACUAUCC AGGAGCUGGAUGA UUCGCGAACCAGAU CCUGAGCUACGGCG CCGAGCUCGACGCC GACCAUCCCGGAUU UAAGGAUCCCGUGU AUAGGGCUAGGAGG AAACAGUUCGCCGA UAUUGCCUAUAAUU AUAGACACGGGCAG CCUAUUCCAAGAGU GGAGUAUAUGGAG GAGGAGAAGAAGAC CUGGGGCACAGUGU UCAAGACCUUGAAG AGUCUGUACAAGAC ACACGCCUGUUACG AGUACAACCACAUC UUUCCCCUGCUGGA GAAGUACUGCGGCU UCCACGAGGAUAAU AUCCCACAACUGGA GGACGUGAGCCAGU UCCUGCAAACCUGC ACUGGCUUCCGUCU GCGACCCGUCGCCG GCCUCCUCAGCAGC CGGGAUUUCCUUGG CGGGCUGGCCUUUC GGGUGUUUCACUGC ACUCAGUACAUCCG GCACGGUUCUAAGC CCAUGUAUACCCCA GAGCCUGACAUCUG UCACGAGCUGCUCG GCCACGUGCCCCUG UUCAGCGACCGGUC CUUCGCCCAGUUCA GCCAGGAGAUCGGC CUGGCCUCUCUGGG CGCUCCCGACGAGU AUAUCGAGAAGCUG GCUACGAUUUACUG GUUCACCGUCGAAU UCGGCCUGUGCAAG CAAGGGGACAGCAU UAAAGCCUACGGGG CUGGAUUACUGUCA AGCUUCGGGGAACU GCAGUAUUGCCUGU CCGAGAAACCCAAA CUGCUUCCGCUGGA GCUCGAGAAGACUG CCAUCCAGAACUAC ACGGUGACCGAGUU CCAGCCCCUGUACU ACGUCGCUGAGUCA UUCAACGACGCUAA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 66 consists from 5' to 3' end: 5' UTR of SEQ ID NO: 3, ORF Sequence of SEQ ID NO: 23, and 3' UTR of SEQ ID NO: 4 |

-continued

| | CONSTRUCT SEQUENCES | | | | |
|---|---|---|---|---|---|
| | By "G5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | GGAGAAGGUGCGCA AUUUCGCUGCCACC AUCCCCAGGCCCUU UAGCGUGAGAUACG AUCCUUACACCCAG AGGAUUGAAGUGCU GGAUAACACUCAGC AACUGAAGAUCCUG GCAGACAGCAUCAA UAGCGAGAUUGGCA UCCUGUGCAGCGCC CUGCAGAAGAUUAA A | | | |
| SEQ ID NO: | 21 | 24 | 3 | 4 | 67 |
| PAH_020 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCUCGGACCAUCC AGGAGCUGGACAGA UUCGCCAACCAGAU UCUGAGCUACGGGG CCGAAUUGGACGCC GACCACCCAGGCUU UAAGGACCCUGUUU ACAGAGCUAGGAGG AAGCAGUUCGCCGA UAUUGCCUAUAACU ACAGACACGGCCAG CCUAUCCCCAGAGU GGAGUACAUGGAGG AGGAGAAGAAGACG UGGGGCACCGUGUU CAAGACUCUGAAGU CUCUUUACAAGACA CACGCUUGCUACGA GUACAAUCACAUCU UCCCACUGCUGGAG AAGUACUGUGGCUU CCACGAAGACAACA UUCCCCAGCUUGAG GACGUGAGUCAGUU CCUGCAGACCUGCA CAGGCUUCCGUCUC CGGCCUGUGGCUGG GCUGCUGAGCAGCA GAGACUUCCUGGGA GGCCUGGCUUUCCG GGUGUUUCAUUGCA CGCAGUACAUUAGA CACGGCUCCAAGCC AAUGUACACACCAG AGCCCGACAUCUGC CACGAGCUGCUGGG ACACGUGCCACUCU UCAGCGACAGAUCA UUCGCCCAGUUCUC UCAGGAGAUCGGAC UGGCUUCCCUUGGA GCACCUGACGAGUA CAUCGAGAAACUGG CCACUAUCUAUUGG UUCACAGUGGAAUU UGGCCUGUGCAAGC AGGGCGACUCUAUC AAGGCCUACGGCGC CGGACUGCUGUCCU CCUUCGGCGAACUG CAGUAUUGUCUGUC AGAGAAGCCCAAGC | GGGAAA UAAGAG AGAAAA GAAGAG UAAGAA GAAAUA UAAGAG CCACC | UGAUAA UAGGCU GGAGCC GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 67 consists from 5' to 3' end: 5' UTR of SEQ ID NO: 3, ORF Sequence of SEQ ID NO: 24, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UGCUGCCCCUAGAA CUCGAGAAGACAGC CAUACAGAAUUACA CCGUGACCGAGUUU CAGCCCCUCUACUA CGUGGCCGAAUCUU UCAACGACGCCAAG GAGAAGGUGAGGA AUUUCGCCGCCACC AUCCCUCGGCCGUU UUCCGUGCGAUACG ACCCCUAUACCCAG CGGAUCGAGGUGCU GGACAACACGCAGC AACUGAAGAUUCUG GCGGACUCAUCAA CAGCGAGAUCGGCA UCCUGUGUAGCGCA CUGCAGAAGAUUAA G | | | |

| SEQ ID NO: | | 21 | 25 | 3 | 4 | 68 |
|---|---|---|---|---|---|---|
| PAH_021 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUACCUUGGUU UCCCAGAACAAUUC AGGAACUGGACCGG UUUGCCAACCAGAU CCUUAGUUACGGCG GACCACCCCGGCUU UAAGGAUCCUGUGU AUAGAGCCAGGAGG AAGCAGUUCGCUGA UAUUGCCUACAAUU ACAGGCACGGUCAA CCCAUCCCCAGGGU GGAGUACAUGGAGG AGGAGAAGAAGACC UGGGGCACCGUCUU CAAGACCCUGAAGU CUCUAUAUAAGACU CACGCCUGCUACGA GUACAAUCACAUCU UCCCACUCCUGGAG AAGUACUGCGGCUU CCACGAGGACAACA UUCCCCAGCUGGAG GACGUGUCCCAGUU CCUGCAGACCUGCA CCGGCUUCCGGCUG CGUCCGGUCGCCGG GCUGCUGUCUUCAC GCGAUUUUCUGGGC GGAUUGGCCUUUAG GGUCUUCCACUGCA CCCAGUACAUCAGA CACGGAUCUAAGCC CAUGUACACACCCG AGCCUGAUAUUUGC CACGAACUGUUGGG ACACGUGCCUCUGU UCUCUGACAGAAGC UUCGCCCAGUUUUC CCAGGAGAUCGGCC UGGCCUCCCUCGGA GCACCCGACGAGUA CAUAGAGAAGCUGG CCACUAUAUACUGG UUCACUGUUGAGUU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 68 consists from 5' to 3' end: 5' UTR of SEQ ID NO: 3, ORF Sequence of SEQ ID NO: 25, and 3' UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UGGGCUGUGCAAGC AGGGCGAUUCUAUA AAGGCCUACGGGGC CGGACUGCUGUCCU CCUUUGGGGAGCUG CAGUACUGUCUUUC UGAGAAGCCCAAAC UUCUGCCCCUGGAG CUUGAGAAGACGGC CAUCCAGAAUUACA CCGUGACUGAGUUC CAACCACUUUAUUA CGUGGCUGAAUCCU UCAACGACGCCAAG GAGAAGGUGAGGA ACUUUGCCGCCACA AUUCCUCGCCCUUU CUCCGUGAGAUACG ACCCCUAUACCCAA CGGAUUGAAGUUCU UGACAACACCCAGC AGCUGAAGAUACUG GCCGACUCAAUAAA CUCUGAGAUCGGAA UCCUGUGCAGUGCC CUGCAGAAGAUCAA G | | | |
| SEQ ID NO: | 21 | 26 | 3 | 4 | 69 |
| PAH_022 (hPAH.ARD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU UCCCCGGACCAUCC AGGAGCUGGACCGG UUCGCCAACCAGAU CCUGAGCUACGGCG CCGAGCUGGACGCC GACCACCCCGGCUU CAAGGACCCCGUGU ACCGGGCCCGGCGG AAGCAGUUCGCCGA CAUCGCCUACAACU ACCGGCACGGCCAG CCCAUCCCGCGGGU GGAGUACAUGGAGG AGGAGAAGAAGACC UGGGGCACCGUGUU CAAGACCCUUAAGA GCCUGUACAAGACC CACGCCUGCUACGA GUACAACCACAUCU UCCCCUGCUGGAG AAGUACUGCGGCUU CCACGAGGACAACA UUCCACAGCUGGAG GACGUGAGCCAGUU CCUGCAGACCUGCA CCGGCUUCCGCCUG CGGCCUGUGGCCGG ACUGCUGAGCAGCC GGGACUUCCUGGGC GGCCUGGCCUUCCG GGUGUUCCACUGCA CCCAGUACAUCCGG CACGGCAGCAAGCC CAUGUACACACCCG AGCCCGACAUCUGC CACGAGCUGCUGGG CCACGUGCCCCUGU UCAGCGACCGGAGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 69 consists from 5' to 3' end: 5' UTR of SEQ ID NO: 3, ORF Sequence of SEQ ID NO: 26, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UUCGCCCAGUUCAG CCAGGAGAUCGGGU UAGCCAGCCUGGGC GCUCCCGACGAGUA CAUCGAGAAGCUGG CCACCAUCUACUGG UUCACCGUGGAGUU CGGCCUGUGCAAGC AGGGCGACAGCAUC AAGGCCUACGGGGC CGGGCUGCUCAGCA GCUUCGGCGAGCUG CAGUACUGCCUGAG CGAGAAGCCCAAGC UGCUGCCCCUGGAG UUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACAA UCCCCAGACCCUUC AGCGUGCGGUACGA CCCCUACACCCAGC GGAUCGAGGUGCUG GACAACACACAGCA GCUGAAGAUCCUGG CCGACUCAAUCAAC AGCGAAAUCGGCAU CCUGUGCAGCGCCC UGCAGAAGAUCAAG | | | |
| SEQ ID NO: | 21 | 27 | 3 | 4 | 70 |
| PAH_023 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU UCCCCGGACCAUCC AGGAGCUGGACCGG UUCGCCAACCAGAU CCUGAGCUACGGCG CCGAACUCGACGCC GACCACCCCGGCUU CAAGGACCCCGUGU ACCGGGCCCGGCGG AAGCAGUUCGCCGA CAUCGCCUACAACU ACCGGCACGGCCAG CCCAUUCCCGGGU GGAGUACAUGGAGG AGGAGAAGAAGACC UGGGGCACCGUGUU CAAGACCCUCAAGU CCCUGUACAAGACC CACGCCUGCUACGA GUACAACCACAUCU UCCCGCUGCUGGAG AAGUACUGCGGCUU CCACGAGGACAACA UUCCUCAGCUGGAG GACGUGAGCCAGUU CCUGCAGACCUGCA CCGGCUUCAGGCUG CGACCCGUCGCCGG CCUGCUGAGCAGCC GGGACUUCCUGGGC GGCCUGGCCUUCCG GGUGUUCCACUGCA CCCAGUACAUCCGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 70 consists from 5' to 3' end: 5' UTR of SEQ ID NO: 3, ORF Sequence of SEQ ID NO: 27, and 3' UTR of SEQ ID NO: 4 |

| | CONSTRUCT SEQUENCES | | | | |
|---|---|---|---|---|---|
| | By "G5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | CACGGCAGCAAGCC CAUGUACACGCCCG AGCCCGACAUCUGC CACGAGCUGCUGGG CCACGUGCCCCUGU UCAGCGACCGGAGC UUCGCCCAGUUCAG CCAGGAGAUCGGAC UGGCUAGCCUGGGC GCUCCAGACGAAUA CAUCGAGAAGCUGG CCACCAUCUACUGG UUCACCGUGGAGUU CGGCCUGUGCAAGC AGGGCGACAGCAUC AAGGCCUACGGAGC AGGCCUUCUGUCAA GCUUCGGCGAGCUG CAGUACUGCCUGAG CGAGAAGCCCAAGC UGCUGCCCCUGGAG UUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCUACCA UUCCCCGGCCCUUC AGCGUGCGGUACGA CCCCUACACCCAGC GGAUCGAGGUGCUG GACAACACACAGCA GCUGAAGAUCCUGG CUGACUCCAUCAAC AGCGAGAUUGGGAU CCUGUGCAGCGCCC UGCAGAAGAUCAAG | | | |
| SEQ ID NO: | 21 | 28 | 3 | 4 | 71 |
| PAH_024 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCGCGGACCAUCC AGGAGCUGGACCGG UUCGCCAACCAGAU CCUGAGCUACGGCG CCGAGCUCGACGCC GACCACCCCGGCUU CAAGGACCCCGUCU ACCGCGCCCGCCGC AAGCAGUUCGCCGA CAUCGCCUACAACU ACCGCCACGGCCAG CCCAUUCCCCGCGU CGAGUACAUGGAGG AGGAGAAGAAGACC UGGGGCACCGUCUU CAAGACCCUCAAGU CCCUCUACAAGACC CACGCCUGCUACGA GUACAACCACAUCU UUCCCCUCCUCGAG AAGUACUGCGGCUU CCACGAGGACAACA UCCCUCAGCUCGAG GACGUCUCCCAGUU CCUCCAGACCUGCA CCGGCUUCCGGCUG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 71 consists from 5' to 3' end: 5' UTR of SEQ ID NO: 3, ORF Sequence of SEQ ID NO: 28, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGGCCCGUGGCUGG ACUCCUCUCCUCCC GCGACUUCCUCGGC GGCCUCGCCUUCCG CGUCUUCCACUGCA CCCAGUACAUAAGA CACGGGUCCAAGCC CAUGUACACGCCCG AGCCCGACAUCUGC CACGAGCUCCUCGG CCACGUGCCCCUCU UCUCCGACCGCUCC UUCGCCCAGUUCUC CCAGGAGAUCGGCC UGGCCUCCCUGGGA GCGCCCGACGAGUA CAUCGAGAAGCUCG CCACCAUCUACUGG UUCACCGUCGAGUU CGGCCUCUGCAAGC AGGGCGACUCCAUC AAGGCCUACGGAGC UGGCCUGCUGUCCU CCUUCGGCGAGCUC CAGUACUGCCUCUC CGAGAAGCCCAAGC UCCUCCCACUGGAG UUGGAGAAGACCGC CAUCCAGAACUACA CCGUCACCGAGUUC CAGCCCCUCUACUA CGUCGCCGAGUCCU UCAACGACGCCAAG GAGAAGGUCCGCAA CUUCGCUGCAACCA UCCCACGGCCCUUC UCCGUCCGCUACGA CCCCUACACCCAGC GCAUCGAGGUCCUC GACAAUACGCAGCA GCUCAAGAUCCUCG CCGACUCGAUUAAC UCCGAAAUCGGCAU CCUCUGCUCCGCCC UCCAGAAGAUCAAG | | | |

| SEQ ID NO: | | 21 | 29 | 3 | 4 | 72 |
|---|---|---|---|---|---|---|
| | PAH_025 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ | AUGGUGCCCUGGUU CCCCAGAACCAUCC AGGAGCUGGACAGA UUCCGAACCAGAU CCUGAGCUACGGCG CCGAGCUCGACGCC GACCACCCCGGCUU CAAGGACCCCGUGU ACAGAGCCAGAGA AAGCAGUUCGCCGA CAUCGCCUACAACU ACAGACACGGCCAG CCCAUCCCAAGAGU GGAGUACAUGGAG AGGAGAAGAAGACC UGGGGCACCGUGUU CAAGACCCUCAAGA GCCUGUACAAGACC CACGCCUGCUACGA GUACAACCACAUCU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU | SEQ ID NO: 72 consists from 5' to 3' end: 5' UTR of SEQ ID NO: 3, ORF Sequence of SEQ ID NO: 29, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | RIEVLDNTQQLKILA DSINSEIGILCSALQKI K | UUCCCCUGCUGGAG AAGUACUGCGGCUU CCACGAGGACAACA UACCCCAGCUGGAG GACGUGAGCCAGUU CCUGCAGACCUGCA CCGGCUUCAGACUG AGGCCCGUGGCCGG CCUGCUGUCCAGUA GAGACUUCCUGGGC GGCCUGGCCUUCAG AGUGUUCCACUGCA CCCAGUACAUCAGA CACGGCAGCAAGCC CAUGUACACCCCAG AGCCCGACAUCUGC CACGAGCUGCUGGG ACACGUGCCCCUGU UCAGCGACAGAAGC UUCGCCCAGUUCUC CCAGGAAAUCGGCC UCGCCAGUCUGGGC GCCCCGGACGAGUA CAUCGAGAAGCUGG CCACCAUCUACUGG UUCACCGUGGAGUU CGGCCUGUGCAAGC AAGGGGACUCCAUC AAGGCCUACGGAGC CGGACUGCUGAGCA GCUUCGGCGAGCUG CAGUACUGCCUGAG CGAGAAGCCCAAGC UGCUGCCCUUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGAGAA ACUUCGCCGCCACC AUCCCCAGACCCUU CAGCGUGAGAUACG ACCCCUACACCCAG AGAAUCGAGGUGCU GGACAACACCCAGC AGCUGAAGAUCCUG GCCGACAGCAUCAA CAGCGAGAUCGGCA UCCUGUGCAGCGCC CUGCAGAAGAUCAA G | | GAAUAA AGUCUG AGUGGG CGGC | |
| SEQ ID NO: | 21 | 30 | 3 | 4 | 73 |
| PAH_026 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG | CCCCAGAACCAUCC AGGAGCUGGACAGA UUCGCCAACCAGAU AUGGUGCCCUGGUU CCUGAGCUACGGCG CCGAGCUGGACGCC GACCACCCCGGCUU CAAGGACCCCGUGU ACAGAGCCAGAAGA AAGCAGUUCGCCGA CAUCGCCUACAACU ACAGACACGGCCAG CCCAUCCCCAGAGU | GGGAAA UAAGAG AGAAAA GAAGAG UAAGAA GAAAUA CCACC | UGAUAA UAGGCU GGAGCC UCGGUG GCCUAG CUUCUU GCCCCU UAAGAG GCCCCU UGGGCC UCCCCC CAGCCC CUCCUC CCCUUC CUGCAC | SEQ ID NO: 73 consists from 5' to 3' end: 5' UTR of SEQ ID NO: 3, ORF Sequence of SEQ ID NO: 30, and 3' |

| CONSTRUCT SEQUENCES |||||
|---|---|---|---|---|
| By "G5" is meant that all uracils (U) in the mRNA are replaced by N1-methylpseudouracils. |||||
| By "G6" is meant that all uracils (U) in the mRNA are replaced by 5-methoxyuracils. |||||

| mRNA Name | ORF Sequence (Amino Acid) | ORF Sequence (Nucleotide) | 5' UTR Sequence | 3' UTR Sequence | Construct Sequence |
|---|---|---|---|---|---|
| | APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | GGAGUACAUGGAGG AGGAGAAGAAGACC UGGGGCACCGUGUU CAAGACCCUUAAGA GCCUGUACAAGACC CACGCCUGCUACGA GUACAACCACAUCU UCCCACUGCUGGAG AAGUACUGCGGCUU CCACGAGGACAACA UUCCGCAGCUGGAG GACGUGAGCCAGUU CCUGCAGACCUGCA CCGGCUUCAGACUU CGCCCCGUGGCCGG CCUGCUGAGCAGCA GAGACUUCCUGGGC GGCCUGGCCUUCAG AGUGUUCCACUGCA CCCAGUACAUCAGA CACGGCAGCAAGCC CAUGUACACACCUG AGCCCGACAUCUGC CACGAGCUGCUGGG CCACGUGCCCCUGU UCAGCGACAGAAGC UUCGCCCAGUUCAG CCAGGAGAUCGGCC UGGCAAGUCUGGGC GCUCCUGACGAGUA CAUCGAGAAGCUGG CCACCAUCUACUGG UUCACCGUGGAGUU CGGCCUGUGCAAGC AGGGCGACAGCAUC AAGGCCUACGGCGC UGGCCUGCUGUCCA GUUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGAGAA ACUUCGCCGCCACC AUCCCCAGACCCUU CAGCGUGAGAUACG ACCCCUACACCCAG AGAAUCGAGGUGCU GGACAACACCCAGC AGCUGAAGAUCCUG GCCGAUAGCAUCAA CAGCGAGAUCGGCA UCCUGUGCAGCGCC CUGCAGAAGAUCAA G | | CCGUAC CCCCUC CAUAAA GUAGGA AACACU ACAGUG GUCUUU GAAUAA AGUCUG AGUGGG CGGC | UTR of SEQ ID NO: 4 |
| SEQ ID NO: | 21 | 31 | 3 | 4 | 74 |
| PAH_027 (hPAH.ΔRD.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV | AUGGUGCCCUGGUU CCCACGGACCAUCC AGGAGCUGGACCGG UUCGCCAACCAGAU CCUGAGCUACGGCG | GGGAAA UAAGAG AGAAAA GAAGAG UAAGAA | UGAUAA UAGGCU GGAGCC UCGGUG GCCUAG | SEQ ID NO: 74 consists from 5' to 3' end: 5' |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | CCGAGCUGGACGCC GACCACCCCGGCUU CAAGGACCCCGUGU ACCGGGCCCGGCGG AAGCAGUUCGCCGA CAUCGCCUACAACU ACCGGCACGGCCAG CCCAUCCCGCGGGU GGAGUACAUGGAGG AGGAGAAGAAGACC UGGGGCACCGUGUU CAAGACCCUGAAGA GCCUGUACAAGACC CACGCCUGCUACGA GUACAACCACAUCU UCCCUCUGCUGGAG AAGUACUGCGGCUU CCACGAGGACAACA UCCCGCAGCUGGAG GACGUGAGCCAGUU CCUGCAGACCUGCA CCGGCUUCCGGCUG CGGCCCGUGGCCGG CCUGCUGAGCAGCC GGGACUUCCUGGGC GGCCUGGCCUUCCG GGUGUUCCACUGCA CCCAGUACAUCCGG CACGGCAGCAAGCC CAUGUACACGCCCG AGCCCGACAUCUGC CACGAGCUGCUGGG CCACGUGCCCCUGU UCAGCGACCGGAGC UUCGCCCAGUUCAG CCAGGAGAUCGGCC UGGCCAGCCUGGGC GCGCCCGACGAGUA CAUCGAGAAGCUGG CCACCAUCUACUGG UUCACCGUGGAGUU CGGCCUGUGCAAGC AGGGCGACAGCAUC AAGGCCUACGGCGC CGGCCUGCUGAGCA GCUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACCA UCCCUCGGCCCUUC AGCGUGCGGUACGA CCCCUACACCCAGC GGAUCGAGGUGCUG GACAACACCCAGCA GCUGAAGAUCCUGG CCGACAGCAUCAAC AGCGAGAUCGGCAU CCUGUGCAGCGCCC UGCAGAAGAUCAAG | GAAAUA UAAGAG CCACC | CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | UTR of SEQ ID NO:3, ORF Sequence of SEQ ID NO: 31, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 21 | 32 | 3 | 4 | 75 |
| PAH_028 (hPAH.ΔRD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCCAGGACCAUUC AGGAGCUGGACAGG UUCGCCAACCAAAU CCUCUCCUACGGCG CCGAGCUCGACGCU GACCACCCCGGCUU CAAGGACCCCGUGU ACCGGGCCAGGAGG AAGCAGUUCGCCGA UAUCGCCUACAACU ACAGGCACGGCCAG CCCAUCCCGAGGGU GGAGUACAUGGAGG AGGAGAAGAAGACC UGGGGAACCGUGUU CAAGACCCUCAAGU CCCUGUACAAGACC CACGCCUGCUACGA GUACAACCACAUCU UCCCCUGCUCGAG AAGUACUGCGGUUU CCACGAGGACAACA UCCCGCAGCUGGAG GACGUGUCGCAGUU CCUGCAGACUUGUA CCGGAUUCCGGCUG CGGCCCGUGGCAGG ACUGCUGAGCAGCC GGGACUUCCUGGGC GGUCUGGCCUUUCG UGUGUUCCACUGCA CCCAGUACAUCCGG CACGGCUCCAAGCC CAUGUACACCCCUG AGCCCGACAUCUGC CACGAGCUGCUGGG CCACGUGCCCCUGU UUAGCGACAGGAGC UUCGCCCAGUUUAG CCAGGAGAUCGGCU UGGCCAGCCUGGGU GCCCCAGACGAGUA UAUCGAGAAGCUGG CCACCAUCUACUGG UUUACGGUGGAGUU CGGCCUGUGCAAGC AGGGAGACAGCAUC AAGGCGUACGGAGC CGGCCUGCUCAGCU CCUUCGGCGAGCUG CAAUACUGCCUGAG CGAGAAGCCUAAGC UCCUGCCUCUGGAA CUGGAGAAGACUGC CAUCCAGAACUACA CAGUCACCGAGUUC CAGCCGCUCUAUUA CGUGGCCGAGAGCU UCAACGACGCGAAG GAGAAGGUGAGAA AUUUCGCGGCAACC AUCCCCAGACCCUU CAGCGUGCGCUACG ACCCCUAUACCCAG CGGAUCGAGGUGCU AGAUAACACCCAGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 75 consists from 5' to 3' end: 5' UTR of SEQ ID NO: 3, ORF Sequence of SEQ ID NO: 32, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCUGAAGAUCCUG GCCGACUCGAUUAA CUCAGAGAUCGGAA UCCUGUGCAGCGCC CUGCAGAAGAUCAA G | | | |
| SEQ ID NO: | 21 | 33 | 3 | 4 | 76 |
| PAH_029 (hPAH.ΔRD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUUCCCUGGUU CCCCAGAACCAUUC AGGAGCUGGAUCGG UUCGCCAACCAAAU CCUCUCCUACGGGG CCGAGCUGGACGCA GACCACCCAGGCUU CAAAGAUCCUGUGU ACCGGGCCCGCCGC AAGCAGUUCGCCGA CAUCGCCUACAACU CCCAUCCCGCGCGU GGAGUACAUGGAGG AGGAGAAGAAGACC UGGGGCACGGUCUU CAAGACCCUGAAGU CUCUCUACAAGACG CACGCGUGCUACGA GUACAAUCACAUCU UUCCGCUGCUGGAG AAGUACUGCGGCUU CCACGAGGACAACA UACCCCAGCUGGAG GACGUGAGCCAGUU CCUCCAGACCUGUA CGGGCUUCAGACUG CGCCCAGUGGCUGG UCUGCUGAGCAGCA GGGACUUUCUGGGC GGGCUCGCCUUCCG GGUGUUUCAUUGCA CCCAGUACAUCCGG CACGGCAGCAAGCC UAUGUACACUCCCG AGCCCGACAUCUGC CACGAGCUGCUGGG CCACGUGCCGCUGU UCUCCGACAGGAGC UUCGCCCAGUUCAG CCAGGAGAUCGGCC UCGCCAGCCUCGGA GCACCCGACGAGUA UAUUGAGAAGCUGG CCACCAUCUACUGG UUCACCGUGGAGUU CGGACUGUGCAAGC AGGGCGACAGCAUA AAGGCCUACGGCGC CGGCCUCCUGUCCA GCUUCGGCGAGCUC CAGUACUGCCUCUC CGAGAAGCCCAAGC UGCUGCCCCUGGAG CUCGAGAAGACCGC CAUCCAGAAUUACA CCGUGACCGAGUUC CAACCCCUGUACUA CGUGGCCGAGUCCU UCAACGACGCCAAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UAAGCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 76 consists from 5' to 3' end: 5' UTR of SEQ ID NO: 3, ORF Sequence of SEQ ID NO: 33, and 3' UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAGAAGGUGCGGAA CUUUGCCGCCACAA UUCCUCGACCAUUC UCGGUGCGCUACGA CCCGUACACCCAGC GAAUCGAGGUACUG GACAACACACAGCA GCUGAAGAUCCUGG CCGAUUCCAUCAAC UCCGAAAUCGGCAU CCUGUGCAGCGCCC UGCAGAAGAUCAAG | | | |
| SEQ ID NO: | 21 | 34 | 3 | 4 | 77 |
| PAH_030 (hPAH.ΔRD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCGCGGACGAUCC AAGAGCUGGACAGG UUCGCCAACCAGAU CCUGAGCUACGGGG CCGAGCUCGACGCC GACCACCCCGGCUU CAAGGACCCUGUCU ACAGAGCCAGGCGG AAACAGUUCGCCGA UAUCGCCUAUAACU ACAGGCACGGCCAG CCCAUCCCCAGAGU CGAGUACAUGGAGG AAGAGAAGAAGACC UGGGGCACCGUCUU CAAGACCCUCAAAU CGCUGUACAAGACC CACGCCUGCUACGA GUACAACCACAUCU UCCCACUCCUGGAG AAGUACUGUGGCUU CCACGAGGAUAACA UUCCCCAGCUGGAA GACGUGAGCCAAUU CCUGCAGACCUGCA CCGGAUUCAGACUG CGCCCCGUGGCCGG ACUGCUGUCAUCCA GAGAUUUCCUGGGC GGGCUGGCCUUUCG AGUUUUCCACUGCA CCCAGUACAUCCGU CACGGGAGCAAGCC CAUGUAUACACCGG AGCCCGAUAUCUGC CACGAGCUGCUCGG ACACGUGCCCCUGU UCAGUGACAGAAGU UUUGCCCAAUUUAG CCAAGAGAUCGGCC UGGCCUCCCUGGGA GCCCCUGACGAGUA CAUCGAGAAGCUGG CCACCAUCUACUGG UUCACCGUGGAGUU CGGGUUGUGCAAGC AGGGCGACUCCAUC AAAGCCUACGGCGC CGGCCUGCUGUCCU CCUUCGGCGAGCUG CAAUACUGCCUGUC CGAGAAGCCCAAGC UGCUGCCCCUUGAA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 77 consists from 5' to 5' end: 5' UTR of SEQ ID NO: 3, ORF Sequence of SEQ ID NO: 34, and 3' UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CUGGAGAAGACCGC<br>CAUCCAGAACUAUA<br>CCGUGACCGAGUUC<br>CAACCCCUGUACUA<br>CGUGGCCGAGAGCU<br>UCAACGACGCCAAG<br>GAGAAGGUCCGCAA<br>UUUUGCCGCCACUA<br>UCCCACGGCCCUUC<br>UCCGUGCGGUACGA<br>UCCCUACACCCAGC<br>GUAUCGAGGUGCUC<br>GACAAUACCCAGCA<br>ACUGAAGAUCCUCG<br>CCGACAGCAUCAAC<br>AGCGAGAUAGGAAU<br>CCUGUGUAGCGCCC<br>UGCAGAAGAUUAAA | | | |
| SEQ ID NO: | 21 | 35 | 3 | 4 | 78 |
| PAH_031<br>(hPAH.ΔRD.G6)<br>Cap: C1<br>PolyA tail:<br>100 nt | MVPWFPRTIQELDRF<br>ANQILSYGAELDADH<br>PGFKDPVYRARRKQF<br>ADIAYNYRHGQPIPR<br>VEYMEEEKKTWGTV<br>FKTLKSLYKTHACYE<br>YNHIFPLLEKYCGFH<br>EDNIPQLEDVSQFLQ<br>TCTGFRLRPVAGLLS<br>SRDFLGGLAFRVFHC<br>TQYIRHGSKPMYTPE<br>PDICHELLGHVPLFSD<br>RSFAQFSQEIGLASLG<br>APDEYIEKLATIYWF<br>TVEFGLCKQGDSIKA<br>YGAGLLSSFGELQYC<br>LSEKPKLLPLELEKTA<br>IQNYTVTEFQPLYYV<br>AESFNDAKEKVRNFA<br>ATIPRPFSVRYDPYTQ<br>RIEVLDNTQQLKILA<br>DSINSEIGILCSALQKI<br>K | AUGGUGCCCUGGUU<br>UCCACGGACCAUCC<br>AGGAGCUGGACAGA<br>UUCGCCAACCAGAU<br>UCUGAGCUACGGGG<br>CCGAGCUCGACGCC<br>GACCACCCCGGCUU<br>CAAGGACCCCGUGU<br>ACAGGGCCAGGAGG<br>AAGCAGUUCGCCGA<br>CAUCGCCUAUAACU<br>ACCGGCACGGACAG<br>CCCAUCCCACGGGU<br>GGAGUAUAUGGAG<br>GAGGAGAAGAAGAC<br>CUGGGGCACCGUG<br>UUAAGACCCUCAAG<br>AGCCUUUACAAGAC<br>ACACGCCUGCUACG<br>AGUACAACCAUAUC<br>UUUCCCCUGCUAGA<br>GAAGUACUGCGGGU<br>UCCACGAAGAUAAU<br>AUACCCCAGCUGGA<br>AGACGUCUCCCAGU<br>UCCUGCAGACCUGC<br>ACCGGCUUCCGCCU<br>CAGACCCGUGGCGG<br>GUCUGCUGAGCAGC<br>CGGGACUUCCUCGG<br>CGGACUGGCCUUUA<br>GAGUGUUCCAUUGC<br>ACCCAGUACAUCCG<br>CCACGGCUCCAAGC<br>CCAUGUACACCCCG<br>GAGCCCGAUAUCUG<br>CCACGAGCUCCUCG<br>GACACGUGCCCCUG<br>UUUUCCGACCGGUC<br>CUUCGCCCAGUUCA<br>GCCAGGAAAUCGGG<br>CUUGCAAGCCUGGG<br>AGCUCCCGACGAGU<br>AUAUCGAGAAGCUG<br>GCCACAAUCUACUG<br>GUUCACGGUGGAGU<br>UCGGCCUGUGCAAA<br>CAGGGAGAUAGCAU | GGGAAA<br>UAAGAG<br>AGAAAA<br>GGAGCC<br>UAAGAA<br>GAAAUA<br>UAAGAG<br>CCACC | UGAUAA<br>UAGGCU<br>GGAGCC<br>UCGGUG<br>GCCUAG<br>CUUCUU<br>GCCCCU<br>UGGGCC<br>UCCCCC<br>CAGCCC<br>CUCCUC<br>CCCUUC<br>CUGCAC<br>CCGUAC<br>CCCCUC<br>CAUAAA<br>GUAGGA<br>AACACU<br>ACAGUG<br>GUCUUU<br>GAAUAA<br>AGUCUG<br>AGUGGG<br>CGGC | SEQ ID NO: 78 consists from 5' to 3' end: 5' UTR of SEQ ID NO: 3, ORF Sequence of SEQ ID NO: 35, and 3' UTR of SEQ ID NO: 4 |

| | CONSTRUCT SEQUENCES | | | | |
|---|---|---|---|---|---|
| | By "G5" is meant that all uracils (U) in the mRNA are replaced by N1-methylpseudouracils. | | | | |
| | By "G6" is meant that all uracils (U) in the mRNA are replaced by 5-methoxyuracils. | | | | |
| mRNA Name | ORF Sequence (Amino Acid) | ORF Sequence (Nucleotide) | 5' UTR Sequence | 3' UTR Sequence | Construct Sequence |
| | | CAAGGCCUACGGCG CCGGCCUGCUCAGC AGCUUUGGGGAGCU GCAGUACUGCCUCA GCGAGAAGCCCAAG CUGCUGCCCCUCGA GCUGGAGAAGACCG CCAUCCAGAACUAC ACCGUGACCGAGUU CCAGCCCCUGUAUU ACGUUGCCGAGAGC UUCAACGACGCCAA GGAGAAGGUCCGAA AUUUCGCCGCGACC AUCCCCAGGCCCUU CUCCGUGAGGUACG ACCCUUACACCCAG CGGAUCGAGGUGCU GGACAAUACCCAGC AGCUGAAGAUCCUG GCGGAUAGCAUAAA CAGCGAAAUCGGAA UCCUCUGCAGCGCC CUGCAGAAGAUCAA A | | | |

| SEQ ID NO: | 21 | 36 | 3 | 4 | 79 |
|---|---|---|---|---|---|
| PAH_032 (hPAH.ARD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQKILA DSINSEIGILCSALQKI K | AUGGUGCCCUGGUU UCCCCGGACCAUCC AGGAGCUGGACCGG UUCGCCAACCAGAU CCUGAGCUACGGCG GACCACCCCGGCUU CAAGGACCCCGUGU ACCGGGCCCGGCGG AAGCAGUUCGCCGA CAUCGCCUACAACU ACCGGCACGGCCAG CCCAUCCCCUCGGGU GGAGUACAUGGAGG AGGAGAAGAAGACC UGGGGCACCGUGUU CAAGACCCUGAAGU CCCUGUACAAGACC CACGCCUGCUACGA GUACAACCACAUCU UCCCCUGCUGGAG AAGUACUGCGGCUU CCACGAGGACAACA UCCCGCAGCUGGAG GACGUGAGCCAGUU CCUGCAGACCUGCA CCGGCUUCCGGCUG CGGCCCGUGGCCGG CCUGCUGAGCAGCC GGGACUUCCUGGGC GGCCUGGCCUUCCG GGUGUUCCACUGCA CCCAGUACAUCCGC CACGGCAGCAAGCC CAUGUACACCCCAG AGCCCGACAUCUGC CACGAGCUGCUGGG CCACGUGCCCCUGU UCAGCGACCGGAGC UUCGCCCAGUUCAG CCAGGAGAUCGGCC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 79 consists from 5' to 3' end: 5' UTR of SEQ ID NO: 3, ORF Sequence of SEQ ID NO: 36, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UGGCCUCUCUGGGC | | | |
| | | GCCCCUGACGAGUA | | | |
| | | UAUCGAGAAGCUGG | | | |
| | | CCACCAUCUACUGG | | | |
| | | UUCACCGUGGAGUU | | | |
| | | CGGCCUGUGCAAGC | | | |
| | | AGGGCGACAGCAUC | | | |
| | | AAGGCCUACGGCGC | | | |
| | | CGGGCUGCUGUCCU | | | |
| | | CCUUCGGCGAGCUG | | | |
| | | CAGUACUGCCUGAG | | | |
| | | CGAGAAGCCCAAGC | | | |
| | | UGCUGCCCCUGGAA | | | |
| | | CUCGAGAAGACCGC | | | |
| | | CAUCCAGAACUACA | | | |
| | | CCGUGACCGAGUUC | | | |
| | | CAGCCCCUGUACUA | | | |
| | | CGUGGCCGAGAGCU | | | |
| | | UCAACGACGCCAAG | | | |
| | | GAGAAGGUGCGGAA | | | |
| | | CUUCGCCGCCACCA | | | |
| | | UACCCAGGCCCUUC | | | |
| | | AGCGUGCGGUACGA | | | |
| | | CCCCUACACCCAGC | | | |
| | | GGAUCGAGGUGCUG | | | |
| | | GACAAUACCCAGCA | | | |
| | | GCUGAAGAUCCUGG | | | |
| | | CCGACUCCAUCAAC | | | |
| | | AGCGAGAUCGGAAU | | | |
| | | CCUGUGCAGCGCCC | | | |
| | | UGCAGAAGAUCAAG | | | |
| SEQ ID NO: | 21 | 37 | 3 | 4 | 80 |
| PAH_033 (hPAH.RD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU UCCCCGGACCAUCC AGGAGCUGGACCGG UUCGCCAACCAGAU CCUGAGCUACGGCG CCGAGCUGGACGCC GACCACCCCGGCUU CAAGGACCCCGUGU ACCGGGCCCGGCGG AAGCAGUUCGCCGA CAUCGCCUACAACU ACCGGCACGGCCAG CCCAUCCCACGGGU GGAGUACAUGGAGG AGGAGAAGAAGACC UGGGGCACCGUGUU CAAGACCCUGAAGU CUCUGUACAAGACC CACGCCUGCUACGA GUACAACCACAUCU UCCCGCUGCUGGAG AAGUACUGCGGCUU CCACGAGGACAACA UCCCGCAGCUGGAG GACGUGAGCCAGUU CCUGCAGACCUGCA CCGGCUUCCGCCUG CGACCCGUGGCGGG CCUGCUGAGCAGCC GGGACUUCCUGGGC GGCCUGGCCUUCCG GGUGUUCCACUGCA CCCAGUACAUCCGC CACGGGAGCAAGCC CAUGUACACCCCUG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 80 consists from 5' to 3' end: 5' UTR of SEQ ID NO: 3, ORF Sequence of SEQ ID NO: 37, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGCCCGACAUCUGC CACGAGCUGCUGGG CCACGUGCCCCUGU UCAGCGACCGGAGC UUCGCCCAGUUCAG CCAGGAGAUCGGCC UGGCCAGCCUGGGA GCCCCGGACGAGUA UAUCGAGAAGCUGG CCACCAUCUACUGG UUCACCGUGGAGUU CGGCCUGUGCAAGC AGGGCGACAGCAUC AAGGCCUACGGGGC CGGGCUGCUGUCCA GCUUCGGCGAGCUG CAGUACUGCCUGAG CGAGAAGCCCAAGC UGCUGCCCCUCGAG CUCGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACAA UCCCCAGGCCCUUC AGCGUGCGGUACGA CCCCUACACCCAGC GGAUCGAGGUGCUG GACAAUACCCAGCA GCUGAAGAUCCUGG CGGACUCCAUCAAC AGCGAGAUCGGAAU CCUGUGCAGCGCCC UGCAGAAGAUCAAG | | | |
| SEQ ID NO: | 21 | 38 | 3 | 4 | 81 |
| PAH_034 (hPAH.ΔRD*G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCGCGGACCAUCC AGGAGCUGGACCGG UUCGCCAACCAGAU CCUGAGCUACGGCG CCGAGCUCGACGCC GACCACCCCGGCUU CAAGGACCCCGUCU ACCGCGCCCGCCGC AAGCAGUUCGCCGA CAUCGCCUACAACU ACCGCCACGGCCAG CCCAUCCCGCGCGU CGAGUACAUGGAGG AGGAGAAGAAGACC UGGGGCACCGUCUU CAAGACCCUCAAGU CCCUCUACAAGACC CACGCCUGCUACGA GUACAACCACAUCU UCCCGCUCCUCGAG AAGUACUGCGGCUU CCACGAGGACAACA UCCCGCAGCUCGAG GACGUCUCCCAGUU CCUCCAGACCUGCA CCGGCUUUAGACUG CGGCCCGUGGCCGG ACUCCUCUCCUCCC | GGGAAA UAAGAG AGAAAA GAAGAG UAAGAA GCCUAG GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 81 consists from 5' to 3' end: 5' UTR of SEQ ID NO: 3, ORF Sequence of SEQ ID NO: 38, and 3' UTR of SEQ ID NO: 4 |

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GCGACUUCCUCGGC<br>GGCCUCGCCUUCCG<br>CGUCUUCCACUGCA<br>CCCAGUACAUUAGA<br>CACGGGUCCAAGCC<br>CAUGUACACGCCCG<br>AGCCCGACAUCUGC<br>CACGAGCUCCUCGG<br>CCACGUGCCCCUCU<br>UCUCCGACCGCUCC<br>UUCGCCCAGUUCUC<br>CCAGGAGAUCGGCC<br>UGGCCUCACUGGGC<br>GCCCCUGACGAAUA<br>CAUCGAGAAGCUCG<br>CCACCAUCUACUGG<br>UUCACCGUCGAGUU<br>CGGCCUCUGCAAGC<br>AGGGCGACUCCAUC<br>AAGGCAUACGGCGC<br>UGGCCUGCUGAGCA<br>GCUUCGGCGAGCUC<br>CAGUACUGCCUCUC<br>CGAGAAGCCCAAGC<br>UCCUGCCCCUAGAA<br>CUGGAGAAGACCGC<br>CAUCCAGAACUACA<br>CCGUCACCGAGUUC<br>CAGCCCCUCUACUA<br>CGUCGCCGAGUCCU<br>UCAACGACGCCAAG<br>GAGAAGGUCCGCAA<br>CUUCGCCGCCACGA<br>UCCCGCGGCCCUUC<br>UCCGUCCGCUACGA<br>CCCCUACACCCAGC<br>GCAUCGAGGUCCUC<br>GACAAUACGCAGCA<br>GCUCAAGAUCCUCG<br>CCGACUCGAUCAAC<br>UCCGAGAUUGGGAU<br>CCUCUGCUCCGCCC<br>UCCAGAAGAUCAAG | | | |
| SEQ ID NO: | 21 | 29 | 3 | 4 | 82 |
| PAH_025<br>(hPAH.ARD.G6)<br>Cap: C1<br>PolyA tail:<br>100 nt | MVPWFPRTIQELDRF<br>ANQILSYGAELDADH<br>PGFKDPVYRARRKQF<br>ADIAYNYRHGQPIPR<br>VEYMEEEKKTWGTV<br>FKTLKSLYKTHACYE<br>YNHIFPLLEKYCGFH<br>EDNIPQLEDVSQFLQ<br>TCTGFRLRPVAGLLS<br>SRDFLGGLAFRVFHC<br>TQYIRHGSKPMYTPE<br>PDICHELLGHVPLFSD<br>RSFAQFSQEIGLASLG<br>APDEYIEKLATIYWF<br>TVEFGLCKQGDSIKA<br>YGAGLLSSFGELQYC<br>LSEKPKLLPLELEKTA<br>IQNYTVTEFQPLYYV<br>AESFNDAKEKVRNFA<br>ATIPRPFSVRYDPYTQ<br>RIEVLDNTQQLKILA | AUGGUGCCCUGGUU<br>CCCCAGAACCAUCC<br>AGGAGCUGGACAGA<br>UUCGCCAACCAGAU<br>CCUGAGCUACGGCG<br>CCGAGCUCGACGCC<br>GACCACCCCGGCUU<br>CAAGGACCCCGUGU<br>ACAGAGCCAGAAGA<br>AAGCAGUUCGCCGA<br>CAUCGCCUACAACU<br>ACAGACACGGCCAG<br>CCCAUCCCAAGAGU<br>GGAGUACAUGGAGG<br>AGGAGAAGAAGACC<br>UGGGGCACCGUGUU<br>CAAGACCCUCAAGA<br>GCCUGUACAAGACC<br>CACGCCUGCUACGA<br>GUACAACCACAUCU<br>UCCCCUGCUGGAG | GGGAAA<br>UAAGAG<br>AGAAAA<br>GAAGAG<br>UAAGAA<br>GAAAUA<br>UAAGAG<br>CCACC | UGAUAA<br>UAGGCU<br>GGAGCC<br>UCGGUG<br>GCCUAG<br>CUUCUU<br>GCCCCU<br>UGGGCC<br>UCCCCC<br>CAGCCC<br>CUCCUC<br>CCCUUC<br>CUGCAC<br>CCGUAC<br>CCCCUC<br>CAUAAA<br>GUAGGA<br>AACACU<br>ACAGUG<br>GUCUUU<br>GAAUAA | SEQ ID<br>NO: 82<br>consists<br>from 5' to<br>3' end: 5'<br>UTR of<br>SEQ ID<br>NO: 3,<br>ORF<br>Sequence<br>of SEQ ID<br>NO: 29,<br>and 3'<br>UTR of<br>SEQ ID<br>NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | DSINSEIGILCSALQKIK | AAGUACUGCGGCUUCCACGAGGACAACAUACCCCAGCUGGAGGACGUGAGCCAGUUCCUGCAGACCUGCACCGGCUUCAGACUGAGGCCCGUGGCCGGCCUGCUGUCCAGUAGAGACUUCCUGGGCGGCCUGGCCUUCAGAGUGUUCCACUGCACCCAGUACAUCAGACACGGCAGCAAGCCCAUGUACACCCCAGAGCCCGACAUCUGCCACGAGCUGCUGGGACACGUGCCCCUGUCAGCGACAGAAGCUUCGCCCAGUUCUCCCAGGAAAUCGGCCUCGCCAGUCUGGGCGCCCCGGACGAGUACAUCGAGAAGCUGGCCACCAUCUACUGGUUCACCGUGGAGUUCGGCCUGUGCAAGCAAGGGGACUCCAUCAAGGCCUACGGAGCCGGACUGCUGAGCAGCUUCGGCGAGCUGCAGUACUGCCUGAGCGAGAAGCCCAAGCUGCUGCCCUUGGAGCUGGAGAAGACCGCCAUCCAGAACUACACCGUGACCGAGUUCCAGCCCCUGUACUACGUGGCCGAGAGCUUCAACGACGCCAAGGAGAAGGUGAGAAACUUCGCCGCCACCAUCCCCAGACCCUUCAGCGUGAGAUACGACCCCUACACCCAGAGAAUCGAGGUGCUGGACAACACCCAGCAGCUGAAGAUCCUGGCCGACAGCAUCAACAGCGAGAUCGGCAUCCUGUGCAGCGCCCUGCAGAAGAUCAAG | | AGUCUGAGUGGGCGGC | |
| SEQ ID NO: | 21 | 30 | 3 | 4 | 83 |
| PAH_026 (hPAH.ΔRD.G6) Cap: C1 PolyA tail: 100 nt | MVPWFPRTIQELDRFANQILSYGAELDADHPGFKDPVYRARRKQFADIAYNYRHGQPIPRVEYMEEEKKTWGTVFKTLKSLYKTHACYEYNHIFPLLEKYCGFHEDNIPQLEDVSQFLQTCTGFRLRPVAGLLSSRDFLGGLAFRVFHCTQYIRHGSKMYTPEPDICHELLGHVPLFSDRSFAQFSQEIGLASLG | AUGGUGCCCUGGUUCCCCAGAACCAUCCAGGAGCUGGACAGAUUCGCCAACCAGAUCCUGAGCUACGGCGCCGAGCUGGACGCCGACCACCCCGGCUUCAAGGACCCCGUGUACAGAGCCAGAAGAAAGCAGUUCGCCGACAUCGCCUACAACUACAGACACGGCCAGCCCAUCCCCAGAGU | GGGAAAUAAGAGAGAAAAGAAGAGUAAGAAGAAAUACCACC | UGAUAAUAGGCUGGAGCCUCGGUGGCCUAGCUUCUUGCCCCUUAAGGCCCCUUGGGCCUCCCCUCCUCCCCUUCUGCAC | SEQ ID NO: 83 consists from 5' to 3' end: 5' UTR of SEQ ID NO: 3, ORF Sequence of SEQ ID NO: 30, and 3' |

| CONSTRUCT SEQUENCES |||||
|---|---|---|---|---|
colspan=5 | By "G5" is meant that all uracils (U) in the mRNA are replaced by N1-methylpseudouracils.
By "G6" is meant that all uracils (U) in the mRNA are replaced by 5-methoxyuracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | GGAGUACAUGGAGG AGGAGAAGAAGACC UGGGGCACCGUGUU CAAGACCCUUAAGA GCCUGUACAAGACC CACGCCUGCUACGA GUACAACCACAUCU UCCCACUGCUGGAG AAGUACUGCGGCUU CCACGAGGACAACA UUCCGCAGCUGGAG GACGUGAGCCAGUU CCUGCAGACCUGCA CCGGCUUCAGACUU CGCCCCGUGGCCGG CCUGCUGAGCAGCA GAGACUUCCUGGGC GGCCUGGCCUUCAG AGUGUUCCACUGCA CCCAGUACAUCAGA CACGGCAGCAAGCC CAUGUACACACCUG AGCCCGACAUCUGC CACGAGCUGCUGGG CCACGUGCCCCUGU UCAGCGACAGAAGC UUCGCCCAGUUCAG CCAGGAGAUCGGCC UGGCAAGUCUGGGC GCUCCUGACGAGUA CAUCGAGAAGCUGG CCACCAUCUACUGG UUCACCGUGGAGUU CGGCCUGUGCAAGC AGGGCGACAGCAUC AAGGCCUACGGCGC UGGCCUGCUGUCCA GUUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGAGAA ACUUCGCCGCCACC AUCCCCAGACCCUU CAGCGUGAGAUACG ACCCCUACACCCAG AGAAUCGAGGUGCU GGACAACACCCAGC AGCUGAAGAUCCUG GCCAUAGCAUCAA CAGCGAGAUCGGCA UCCUGUGCAGCGCC CUGCAGAAGAUCAA G | | CCGUAC CCCCUC CAUAAA GUAGGA AACACU ACAGUG GUCUUU GAAUAA AGUCUG AGUGGG CGGC | UTR of SEQ ID NO: 4 |
| SEQ ID NO: | 21 | 31 | 3 | 4 | 84 |
| PAH_027 (hPAH.ΔRD.G6) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV | AUGGUGCCCUGGUU CCCCACGGACCAUCC AGGAGCUGGACCGG UUCGCCAACCAGAU CCUGAGCUACGGCG | GGGAAA UAAGAG AGAAAA GAAGAG UAAGAA | UGAUAA UAGGCU GGAGCC UCGGUG GCCUAG | SEQ ID NO: 84 consists from 5' to 3' end: 5' |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | CCGAGCUGGACGCC GACCACCCCGGCUU CAAGGACCCCGUGU ACCGGGCCCGGCGG AAGCAGUUCGCCGA CAUCGCCUACAACU ACCGGCACGGCCAG CCCAUCCCGCGGGU GGAGUACAUGGAGG AGGAGAAGAAGACC UGGGGCACCGUGUU CAAGACCCUGAAGA GCCUGUACAAGACC CACGCCUGCUACGA GUACAACCACAUCU UCCCUCUGCUGGAG AAGUACUGCGGCUU CCACGAGGACAACA UCCCGCAGCUGGAG GACGUGAGCCAGUU CCUGCAGACCUGCA CCGGCUUCCGGCUG CGGCCCGUGGCCGG CCUGCUGAGCAGCC GGGACUUCCUGGGC GGCCUGGCCUUCCG GGUGUUCCACUGCA CCCAGUACAUCCGG CACGGCAGCAAGCC CAUGUACACGCCCG AGCCCGACAUCUGC CACGAGCUGCUGGG CCACGUGCCCCUGU UCAGCGACCGGAGC UUCGCCCAGUUCAG CCAGGAGAUCGGCC UGGCCAGCCUGGGC GCGCCCGACGAGUA CAUCGAGAAGCUGG CCACCAUCUACUGG UUCACCGUGGAGUU CGGCCUGUGCAAGC AGGGCGACAGCAUC AAGGCCUACGGCGC CGGCCUGCUGAGCA GCUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACCA UCCCUCGGCCCUUC AGCGUGCGGUACGA CCCCUACACCCAGC GGAUCGAGGUGCUG GACAACACCCAGCA GCUGAAGAUCCUGG CCGACAGCAUCAAC AGCGAGAUCGGCAU CCUGUGCAGCGCCC UGCAGAAGAUCAAG | GAAAUA UAAGAG CCACC | CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | UTR of SEQ ID NO: 3, ORF Sequence of SEQ ID NO:31, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 195 | 196 | 3 | 4 | 199 |
| PAH_035 (hPAH.FL.G5) FLAG tag Cap: C1 PolyA tail: 100 nt | MDYKDDDDKSTAVL ENPGLGRKLSDFGQE TSYIEDNCNQNGAISL IFSLKEEVGALAKVL RLFEENDVNLTHIESR PSRLKKDEYEFFTHL DKRSLPALTNIIKILR HDIGATVHELSRDKK KDTVPWFPRTIQELD RFANQILSYGAELDA DHPGFKDPVYRARR KQFADIAYNYRHGQP IPRVEYMEEEKKTWG TVFKTLKSLYKTHAC YEYNHIFPLLEKYCG FHEDNIPQLEDVSQFL QTCTGFRLRPVAGLL SSRDFLGGLAFRVFH CTQYIRHGSKPMYTP EPDICHELLGHVPLFS DRSFAQFSQEIGLASL GAPDEYIEKLATIYW FTVEFGLCKQGDSIK AYGAGLLSSFGELQY CLSEKPKLLPLELEKT AIQNYTVTEFQPLYY VAESFNDAKEKVRNF AATIPRPFSVRYDPYT QRIEVLDNTQQLKIL ADSINSEIGILCSALQ KIK | AUGGACUACAAGGA CGACGACGACAAGA GCACCGCCGUGCUG GAGAACCCCGGCCU GGGCCGGAAGCUGA GCGACUUCGGCCAG GAGACAAGCUACAU CGAGGACAACUGCA ACCAGAACGGCGCC AUCAGCCUGAUCUU UUCUCUGAAGGAGG AGGUGGGCGCCCUG GCCAAGGUGCUGCG GCUGUUCGAGGAGA ACGACGUGAACCUG ACCCACAUCGAGAG CCGGCCCAGCCGGC UGAAGAAGGACGAG UACGAGUUCUUCAC CCACCUGGACAAGC GGAGCCUGCCCGCC CUGACCAACAUCAU CAAGAUCCUGCGGC ACGACAUCGGCGCC ACCGUGCACGAGCU GAGCCGGGACAAGA AGAAGGACACCGUG CCCUGGUUCCCUCG GACCAUCCAGGAGC UGGACCGGUUCGCC AACCAGAUCCUGAG CUACGGCGCCGAGC UGGACGCCGACCAC CCCGGCUUCAAGGA CCCCGUGUACCGGG CCCGGCGGAAGCAG UUCGCCGACAUCGC CUACAACUACCGGC ACGGCCAGCCCAUC CCUCGGGUGGAGUA CAUGGAGGAGGAGA AGAAGACCUGGGGC ACCGUGUUCAAGAC CCUGAAGUCUCUGU ACAAGACCCACGCC UGCUACGAGUACAA CCACAUCUUUCCUC UCCUGGAGAAGUAC UGCGGCUUCCACGA GGACAAUAUCCCUC AGCUGGAGGACGUG AGCCAGUUCCUGCA GACCUGCACCGGCU UCCGGCUGAGGCCU GUGGCCGGGCUGCU GAGCAGCAGAGACU UCCUGGGCGGCCUG GCCUUCCGGGUGUU CCACUGCACCCAGU ACAUCAGACACGGG AGCAAGCCCAUGUA CACUCCCGAGCCCG ACAUCUGCCACGAG UUACUGGGCCACGU GCCCCUGUUCAGCG ACCGGAGCUUCGCC CAGUUCUCACAGGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 199 consists from 5' to 3' end: 5' UTR of SEQ ID NO: 3, ORF Sequence of SEQ ID NO:196, and 3' UTR of SEQ ID NO: 4 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAUCGGGCUGGCAA | | | |
| | | GCCUGGGCGCUCCC | | | |
| | | GACGAGUAUAUAGA | | | |
| | | GAAGCUGGCCACCA | | | |
| | | UCUACUGGUUCACC | | | |
| | | GUGGAGUUCGGCCU | | | |
| | | GUGCAAGCAGGGCG | | | |
| | | ACAGCAUCAAGGCU | | | |
| | | UACGGAGCUGGGCU | | | |
| | | GCUUAGCUCCUUCG | | | |
| | | GCGAGCUGCAGUAC | | | |
| | | UGCCUGAGCGAGAA | | | |
| | | GCCCAAGCUGCUGC | | | |
| | | CCCUUGAGCUCGAG | | | |
| | | AAGACCGCCAUCCA | | | |
| | | GAACUACACCGUGA | | | |
| | | CCGAGUUCCAGCCC | | | |
| | | CUGUACUACGUGGC | | | |
| | | CGAGAGCUUCAACG | | | |
| | | ACGCCAAGGAGAAG | | | |
| | | GUGCGGAACUUCGC | | | |
| | | CGCAACCAUCCCUA | | | |
| | | GGCCCUUCAGCGUG | | | |
| | | CGGUACGACCCCUA | | | |
| | | CACCCAGCGGAUCG | | | |
| | | AGGUGCUGGACAAU | | | |
| | | ACCCAGCAGCUGAA | | | |
| | | GAUCUUAGCUGACU | | | |
| | | CAAUCAACAGCGAG | | | |
| | | AUUGGCAUCCUGUG | | | |
| | | CAGCGCCCUGCAGA | | | |
| | | AGAUCAAG | | | |

| SEQ ID NO: | 197 | 198 | 3 | 4 | 200 |
|---|---|---|---|---|---|
| PAH_036 (hPAH.ARD.G5) FLAG tag PolyA tail: 100 nt | MDYKDDDDKVPWFP RTIQELDRFANQILSY GAELDADHPGFKDP VYRARRKQFADIAY NYRHGQPIPRVEYME EEKKTWGTVFKTLKS LYKTHACYEYNHIFP LLEKYCGFHEDNIPQ LEDVSQFLQTCTGFR LRPVAGLLSSRDFLG GLAFRVFHCTQYIRH GSKPMYTPEPDICHE LLGHVPLFSDRSFAQ FSQEIGLASLGAPDEY IEKLATIYWFTVEFGL CKQGDSIKAYGAGLL SSFGELQYCLSEKPK LLPLELEKTAIQNYT VTEFQPLYYVAESFN DAKEKVRNFAATIPR PFSVRYDPYTQRIEVL DNTQQLKILADSINSE IGILCSALQKIK | AUGGACUACAAGGA CGACGACGACAAGG UGCCCUGGUUCCCA CGGACCAUCCAGGA GCUGGACCGGUUCG CCAACCAGAUCCUG AGCUACGGCGCCGA GCUGGACGCCGACC ACCCCGGCUUCAAG GACCCCGUGUACCG GGCCCGGCGGAAGC AGUUCGCCGACAUC GCCUACAACUACCG GCACGGCCAGCCCA UCCCGGGUGGAG UACAUGGAGGAGGA GAAGAAGACCUGGG GCACCGUGUUCAAG ACCCUGAAGAGCCU GUACAAGACCCACG CCUGCUACGAGUAC AACCACAUCUUCCC UCUGCUGGAGAAGU ACUGCGGCUUCCAC GAGGACAACAUCCC GCAGCUGGAGGACG UGAGCCAGUUCCUG CAGACCUGCACCGG CUUCCGGCUGCGGC CCGUGGCCGGCCUG CUGAGCAGCCGGGA CUUCCUGGGCGGCC UGGCCUUCCGGGUG UUCCACUGCACCCA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 200 consists from 5' to 3' end: 5' UTR of SEQ ID NO:3, ORF Sequence of SEQ ID NO: 198, and 3' UTR of SEQ ID NO: 4 |

-continued

CONSTRUCT SEQUENCES
By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GUACAUCCGGCACG GCAGCAAGCCCAUG UACACGCCCGAGCC CGACAUCUGCCACG AGCUGCUGGGCCAC GUGCCCCUGUUCAG CGACCGGAGCUUCG CCCAGUUCAGCCAG GAGAUCGGCCUGGC CAGCCUGGGCGCGC CCGACGAGUACAUC GAGAAGCUGGCCAC CAUCUACUGGUUCA CCGUGGAGUUCGGC CUGUGCAAGCAGGG CGACAGCAUCAAGG CCUACGGCGCCGGC CUGCUGAGCAGCUU CGGCGAGCUGCAGU ACUGCCUGAGCGAG AAGCCCAAGCUGCU GCCCCUGGAGCUGG AGAAGACCGCCAUC CAGAACUACACCGU GACCGAGUUCCAGC CCCUGUACUACGUG GCCGAGAGCUUCAA CGACGCCAAGGAGA AGGUGCGGAACUUC GCCGCCACCAUCCC UCGGCCCUUCAGCG UGCGGUACGACCCC UACACCCAGCGGAU CGAGGUGCUGGACA ACACCCAGCAGCUG AAGAUCCUGGCCGA CAGCAUCAACAGCG AGAUCGGCAUCCUG UGCAGCGCCCUGCA GAAGAUCAAG | | | |

| SEQ ID NO: | | 21 | 31 | 3 | 178 | 201 |
|---|---|---|---|---|---|---|
| PAH_027 (PAHARD. 3XmiR142.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AUGGUGCCCUGGUU CCCACGGACCAUCC AGGAGCUGGACCGG UUCGCCAACCAGAU CCUGAGCUACGGCG CCGAGCUGGACGCC GACCACCCCGGCUU CAAGGACCCCGUGU ACCGGGCCCGGCGG AAGCAGUUCGCCGA CAUCGCCUACAACU ACCGGCACGGCCAG CCCAUCCCGCGGGU GGAGUACAUGGAGG AGGAGAAGAAGACC UGGGGCACCGUGUU CAAGACCCUGAAGA GCCUGUACAAGACC CACGCCUGCUACGA GUACAACCACAUCU UCCCUCUGCUGGAG AAGUACUGCGGCUU CCACGAGGACAACA UCCCGCAGCUGGAG GACGUGAGCCAGUU CCUGCAGACCUGCA | GGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC | SEQ ID NO: 201 consists from 5' to 3' end: 5' UTR of SEQ ID NO: 3, ORF Sequence of SEQ ID NO: 31, and 3' UTR of SEQ ID NO: 178 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCGGCUUCCGGCUG | | AGUGGU | |
| | | CGGCCCGUGGCCGG | | CUUUGA | |
| | | CCUGCUGAGCAGCC | | AUAAAG | |
| | | GGGACUUCCUGGGC | | UCUGAG | |
| | | GGCCUGGCCUUCCG | | UGGGCG | |
| | | GGUGUUCCACUGCA | | GC | |
| | | CCCAGUACAUCCGG | | | |
| | | CACGGCAGCAAGCC | | | |
| | | CAUGUACACGCCCG | | | |
| | | AGCCCGACAUCUGC | | | |
| | | CACGAGCUGCUGGG | | | |
| | | CCACGUGCCCUGU | | | |
| | | UCAGCGACCGGAGC | | | |
| | | UUCGCCCAGUUCAG | | | |
| | | CCAGGAGAUCGGCC | | | |
| | | UGGCCAGCCUGGGC | | | |
| | | GCGCCCGACGAGUA | | | |
| | | CAUCGAGAAGCUGG | | | |
| | | CCACCAUCUACUGG | | | |
| | | UUCACCGUGGAGUU | | | |
| | | CGGCCUGUGCAAGC | | | |
| | | AGGGCGACAGCAUC | | | |
| | | AAGGCCUACGGCGC | | | |
| | | CGGCCUGCUGAGCA | | | |
| | | GCUUCGGCGAGCUG | | | |
| | | CAGUACUGCCUGAG | | | |
| | | CGAGAAGCCCAAGC | | | |
| | | UGCUGCCCCUGGAG | | | |
| | | CUGGAGAAGACCGC | | | |
| | | CAUCCAGAACUACA | | | |
| | | CCGUGACCGAGUUC | | | |
| | | CAGCCCCUGUACUA | | | |
| | | CGUGGCCGAGAGCU | | | |
| | | UCAACGACGCCAAG | | | |
| | | GAGAAGGUGCGGAA | | | |
| | | CUUCGCCGCCACCA | | | |
| | | UCCCUCGGCCCUUC | | | |
| | | AGCGUGCGGUACGA | | | |
| | | CCCCUACACCCAGC | | | |
| | | GGAUCGAGGUGCUG | | | |
| | | GACAACACCCAGCA | | | |
| | | GCUGAAGAUCCUGG | | | |
| | | CCGACAGCAUCAAC | | | |
| | | AGCGAGAUCGGCAU | | | |
| | | CCUGUGCAGCGCCC | | | |
| | | UGCAGAAGAUCAAG | | | |
| SEQ ID NO: | 21 | 31 | 3 | 177 | 202 |
| PAH_027 (PAHΔRD.miR126.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ | AUGGUGCCCUGGUU CCCACGGACCAUCC AGGAGCUGGACCGG UUCGCCAACCAGAU CCUGAGCUACGGCG CCGAGCUGGACGCC GACCACCCCGGCUU CAAGGACCCCGUGU ACCGGGCCCGGCGC AAGCAGUUCGCCGA CAUCGCCUACAACU ACCGGCACGGCCAG CCCAUCCCGCGGGU GGAGUACAUGGAGG AGGAGAAGAAGACC UGGGGCACCGUGUU CAAGACCCUGAAGA GCCUGUACAAGACC CACGCCUGCUACGA GUACAACCACAUCU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCCG CAUUAU UACUCA CGGUAC GAGUGG UCUUUG | SEQ ID NO: 202 consists from 5' to 3' end: 5' UTR of SEQ ID NO: 3, ORF Sequence of SEQ ID NO: 31, and 3' UTR of SEQ ID NO: 177 |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | RIEVLDNTQQLKILA DSINSEIGILCSALQKI K | UCCCUCUGCUGGAG AAGUACUGCGGCUU CCACGAGGACAACA UCCCGCAGCUGGAG GACGUGAGCCAGUU CCUGCAGACCUGCA CCGGCUUCCGGCUG CGGCCCGUGGCCGG CCUGCUGAGCAGCC GGGACUUCCUGGGC GGCCUGGCCUUCCG GGUGUUCCACUGCA CCCAGUACAUCCGG CACGGCAGCAAGCC CAUGUACACGCCCG AGCCCGACAUCUGC CACGAGCUGCUGGG CCACGUGCCCCUGU UCAGCGACCGGAGC UUCGCCCAGUUCAG CCAGGAGAUCGGCC UGGCCAGCCUGGGC GCGCCCGACGAGUA CAUCGAGAAGCUGG CCACCAUCUACUGG UUCACCGUGGAGUU CGGCCUGUGCAAGC AGGGCGACAGCAUC AAGGCCUACGGCGC CGGCCUGCUGAGCA GCUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACCA UCCCUCGGCCCUUC AGCGUGCGGUACGA CCCCUACACCCAGC GGAUCGAGGUGCUG GACAACACCCAGCA GCUGAAGAUCCUGG CCGACAGCAUCAAC AGCGAGAUCGGCAU CCUGUGCAGCGCCC UGCAGAAGAUCAAG | | AAUAAA GUCUGA GUGGGC GGC | |
| SEQ ID NO: | 21 | 31 | 3 | 175 | 203 |
| PAH_027 (PAHΔRD miRless.G5) Cap: C1 PolyA tail: 100 nt | MVPWFPRTIQELDRF ANQILSYGAELDADH PGFKDPVYRARRKQF ADIAYNYRHGQPIPR VEYMEEEKKTWGTV FKTLKSLYKTHACYE YNHIFPLLEKYCGFH EDNIPQLEDVSQFLQ TCTGFRLRPVAGLLS SRDFLGGLAFRVFHC TQYIRHGSKPMYTPE PDICHELLGHVPLFSD RSFAQFSQEIGLASLG APDEYIEKLATIYWF | AUGGUGCCCUGGUU CCCACGGACCAUCC AGGAGCUGGACCGG UUCGCCAACCAGAU CCUGAGCUACGGCG CCGAGCUGGACGCC GACCACCCCGGCUU CAAGGACCCCGUGU ACCGGGCCCGGCGC AAGCAGUUCGCCGA CAUCGCCUACAACU ACCGGCACGGCCAG CCCAUCCCGCGGGU GGAGUACAUGGAGG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC | SEQ ID NO: 203 consists from 5' to 3' end: 5' UTR of SEQ ID NO: 3, ORF Sequence of SEQ ID NO: 31, and 3' UTR of |

CONSTRUCT SEQUENCES

By "G5" is meant that all uracils (U) in the mRNA are replaced by N1-methylpseudouracils.
By "G6" is meant that all uracils (U) in the mRNA are replaced by 5-methoxyuracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | TVEFGLCKQGDSIKA YGAGLLSSFGELQYC LSEKPKLLPLELEKTA IQNYTVTEFQPLYYV AESFNDAKEKVRNFA ATIPRPFSVRYDPYTQ RIEVLDNTQQLKILA DSINSEIGILCSALQKI K | AGGAGAAGAAGACC UGGGGCACCGUGUU CAAGACCCUGAAGA GCCUGUACAAGACC CACGCCUGCUACGA GUACAACCACAUCU UCCCUCUGCUGGAG AAGUACUGCGGCUU CCACGAGGACAACA UCCCGCAGCUGGAG GACGUGAGCCAGUU CCUGCAGACCUGCA CCGGCUUCCGGCUG CGGCCCGUGGCCGG CCUGCUGAGCAGCC GGGACUUCCUGGGC GGCCUGGCCUUCCG GGUGUUCCACUGCA CCCAGUACAUCCGG CACGGCAGCAAGCC CAUGUACACGCCCG AGCCCGACAUCUGC CACGAGCUGCUGGG CCACGUGCCCCUGU UCAGCGACCGGAGC UUCGCCCAGUUCAG CCAGGAGAUCGGCC UGGCCAGCCUGGGC GCGCCCGACGAGUA CAUCGAGAAGCUGG CCACCAUCUACUGG UUCACCGUGGAGUU CGGCCUGUGCAAGC AGGGCGACAGCAUC AAGGCCUACGGCGC CGGCCUGCUGAGCA GCUUCGGCGAGCUG CAGUACUGCCUGAG CGAGAAGCCCAAGC UGCUGCCCCUGGAG CUGGAGAAGACCGC CAUCCAGAACUACA CCGUGACCGAGUUC CAGCCCCUGUACUA CGUGGCCGAGAGCU UCAACGACGCCAAG GAGAAGGUGCGGAA CUUCGCCGCCACCA UCCCUCGGCCCUUC AGCGUGCGGUACGA CCCCUACACCCAGC GGAUCGAGGUGCUG GACAACACCCAGCA GCUGAAGAUCCUGG CCGACAGCAUCAAC AGCGAGAUCGGCAU CCUGUGCAGCGCCC UGCAGAAGAUCAAG | | CCCCGU GGUCUU UGAAUA AAGUCU GAGUGG GCGGC | SEQ ID NO: 175 |

EXAMPLES

Example 1: Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:

(a) Capped and protected 5' segment comprising a normal 3'OH (SEG. 1)

(b) 5' triphosphate segment which can include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG.2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5' UTR (SEG. 1), open reading frame or ORF (SEG. 2) and 3' UTR+PolyA (SEG. 3).

The yields of each step can be as much as 90-95%.

Example 2: PCR for cDNA Production

PCR procedures for the preparation of cDNA can be performed using 2×KAPA HIFI™ HotStart ReadyMix by Kapa Biosystems (Woburn, MA). This system includes 2×KAPA ReadyMix12.5 µl; Forward Primer (10 µM) 0.75 µl; Reverse Primer (10 µM) 0.75 µl; Template cDNA –100 ng; and dH$_2$0 diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T$_{120}$ for a poly-A$_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3: In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:
1 Template cDNA—1.0
2 10× transcription buffer (400 mM Tris-HCl pH 8.0, 190 mM MgCl$_2$, 50 mM DTT, 10 mM Spermidine)—2.0 µl
3 Custom NTPs (25 mM each)—7.2 µl
4 RNase Inhibitor—20 U
5 T7 RNA polymerase—3000 U
6 dH$_2$0—Up to 20.0 µl. and
7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 µg of RNA. Following the cleanup, the RNA can be quantified using the NanoDrop and analyzed by agarose gel electrophoresis to confirm the RNA is the proper size and that no degradation of the RNA has occurred.

Example 4: Enzymatic Capping

Capping of a polynucleotide can be performed with a mixture includes: IVT RNA 60 µg-180 µg and dH$_2$0 up to 72 µl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$0 (Up to 28 µl); and incubation at 37° C. for 30 minutes for 60 µg RNA or up to 2 hours for 180 µg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5: PolyA Tailing Reaction

Without a poly-T in the cDNA, a poly-A tailing reaction must be performed before cleaning the final product. This can be done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$) (12.0 µl); 20 mM ATP (6.0 µl); Poly-A Polymerase (20 U); dH$_2$0 up to 123.5 µl and incubating at 37° C. for 30 min. If the poly-A tail is already in the transcript, then the tailing reaction can be skipped and proceed directly to cleanup with Ambion's MEGA-CLEAR™ kit (Austin, TX) (up to 500 µg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6: Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5') ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England Bio-Labs, Ipswich, MA). Cap 1 structure can be generated using both Vaccinia Virus Capping Enzyme and a 2'-O methyltransferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7: Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8: Agarose Gel Electrophoresis of Modified RNA or RT PCR Products

Individual polynucleotides (200-400 ng in a 20 µl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9: Nanodrop Modified RNA Quantification and UV Spectral Data

Modified polynucleotides in TE buffer (1 µl) can be used for Nanodrop UV absorbance readings to quantitate the yield of each polynucleotide from a chemical synthesis or in vitro transcription reaction.

Example 10: Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11: Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12: Synthesis of mRNA Encoding PAH

Sequence optimized polynucleotides encoding PAH polypeptides are synthesized and characterized as described in Examples 1 to 11. mRNA's encoding both human PAH and a truncated version thereof comprising the PAH catalytic and tertramerization domains were prepared for the Examples described below, and were synthesized and characterized as described in Examples 1 to 11.

An mRNA encoding human PAH or a truncated version thereof can be constructed, e.g., by using the ORF sequence (amino acid) provided in SEQ ID NO: 1 or 21, respectively. The mRNA sequence includes both 5' and 3' UTR regions flanking the ORF sequence (nucleotide). In an exemplary construct, the 5' UTR and 3' UTR sequences are SEQ ID NO: 3 and SEQ ID NO: 4, respectively (see Construct Sequences Table).

5'UTR:
(SEQ ID NO: 3)
GGGAAAUAAGAGAGAAAAGAAGAGUAAGAAGAAAUAUAAGAGCCACC

3'UTR:
(SEQ ID NO: 4)
UGAUAAUAGGCUGGAGCCUCGGUGGCCUAGCUUCUUGCCCCUUGGGCCUC
CCCCCAGCCCCUCCUCCCCUUCCUGCACCCGUACCCCCUCCAUAAAGUAG
GAAACACUACAGUGGUCUUUGAAUAAAGUCUGAGUGGGCGGC

In another exemplary construct, the 5' UTR and 3' UTR sequences are SEQ ID NOs.: 3 and 175, respectively (see below):

5'UTR:
(SEQ ID NO: 3)
GGGAAAUAAGAGAGAAAAGAAGAGUAAGAAGAAAUAUAAGAGCCACC

3'UTR:
(SEQ ID NO: 175)
UGAUAAUAGGCUGGAGCCUCGGUGGCCUAGCUUCUUGCCCCUUGGGCCUC
CCCCCAGCCCCUCCUCCCCUUCCUGCACCCGUACCCCGUGGUCUUUGAA
UAAAGUCUGAGUGGGCGGC

In another exemplary construct, the 5' UTR and 3' UTR sequences are SEQ ID NOs.: 3 and 177, respectively (see below):

5'UTR:
(SEQ ID NO: 3)
GGGAAAUAAGAGAGAAAAGAAGAGUAAGAAGAAAUAUAAGAGCCACC

3'UTR:
(SEQ ID NO: 177)
UGAUAAUAGGCUGGAGCCUCGGUGGCCUAGCUUCUUGCCCCUUGGGCCUC
CCCCCAGCCCCUCCUCCCCUUCCUGCACCCGUACCCCCGCAUUAUUACU
CACGGUACGAGUGGUCUUUGAAUAAAGUCUGAGUGGGCGGC

In another exemplary construct, the 5' UTR and 3' UTR sequences are SEQ ID NOs.: 3 and 178, respectively (see below):

5'UTR:
(SEQ ID NO: 3)
GGGAAAUAAGAGAGAAAAGAAGAGUAAGAAGAAAUAUAAGAGCCACC

3'UTR:
(SEQ ID NO: 178)
UGAUAAUAGUCCAUAAAGUAGGAAACACUACAGCUGGAGCCUCGGUGGCCU
AGCUUCUUGCCCCUUGGGCCUCCAUAAAGUAGGAAACACUACAUCCCCCA
GCCCCUCCUCCCCUUCCUGCACCCGUACCCCCUCCAUAAAGUAGGAAACAC
UACAGUGGUCUUUGAAUAAAGUCUGAGUGGGCGGC

In another exemplary construct, the 5' UTR and 3' UTR sequences are SEQ ID NOs.: 88 and 150, respectively (see below):

5'UTR:
(SEQ ID NO: 88)
UCAAGCUUUUGGACCCUCGUACAGAAGCUAAUACGACUCACUAUAGGGAAA
UAAGAGAGAAAAGAAGAGUAAGAAGAAAUAUAAGAGCCACC

3'UTR:
(SEQ ID NO: 150)
UGAUAAUAGGCUGGAGCCUCGGUGGCCAUGCUUCUUGCCCCUUGGGCCUCC
CCCCAGCCCCUCCUCCCCUUCCUGCACCCGUACCCCCGUGGUCUUUGAAUA
AAGUCUGAGUGGGCGGC

The PAH mRNA sequence is prepared as modified mRNA. Specifically, during in vitro transcription, modified mRNA can be generated using N1-methylpseudouridine-5'-Triphosphate to ensure that the mRNAs contain 100% N1-methylpseudouridine instead of uridine. Further, PAH-mRNA can be synthesized with a primer that introduces a polyA-tail, and a Cap 1 structure is generated on both mRNAs using Vaccinia Virus Capping Enzyme and a 2'-O methyl-transferase to generate: m7G(5')ppp(5')G-2'-O-methyl.

Example 13: Detecting Endogenous PAH Expression In Vitro

PAH expression is characterized in a variety of cell lines derived from both mice and human sources. Cell are cultured in standard conditions and cell extracts are obtained by placing the cells in lysis buffer. For comparison purposes, appropriate controls are also prepared. To analyze PAH expression, lysate samples are prepared from the tested cells and mixed with lithium dodecyl sulfate sample loading buffer and subjected to standard Western blot analysis. For detection of PAH, the antibody used is a commercial anti-PAH antibody. For detection of a load control, the antibody used is an anti-Glyceraldehyde-3-phosphate dehydrogenase (GAPDH) antibody.

Endogenous PAH expression can be used as a base line to determine changes in PAH expression resulting from transfection with mRNAs comprising nucleic acids encoding PAH.

Example 14: In Vitro Expression of PAH in SNU-423 Cells

To measure in vitro expression of human PAH or a truncated human PAH (PAH-ΔRD) in a human liver cell line, SNU-423 cells (ATCC® CRL2238™), were seeded on 6-well plates (BD Biosciences, San Jose, USA) one day prior to transfection. mRNA formulations encoding wild type PAH (with an N-terminal FLAG tag), sequence optimized human full-length PAH, sequence optimized truncated PAH (PAH-ΔRD), or GFP control were transfected into cells using 2 μg mRNA and 6 μL Lipofectamine MessengerMAX in 250 μL OPTI-MEM per well and incubated. The sequence optimized full-length PAH mRNA constructs included PAH-001 (SEQ ID NO:45), PAH-002 (SEQ ID NO:46), PAH-003 (SEQ ID NO:47), PAH-004 (SEQ ID NO:48), PAH-005 (SEQ ID NO:49), PAH-006 (SEQ ID NO:50), PAH-007 (SEQ ID NO:51), PAH-008 (SEQ ID NO:52), and PAH-010 (SEQ ID NO:54). The sequence optimized truncated PAH mRNA constructs included PAH-018 (SEQ ID NO:4565), PAH-020 (SEQ ID NO:67), PAH-021 (SEQ ID NO:68), PAH-022 (SEQ ID NO:69), PAH-023 (SEQ ID NO:70), PAH-024 (SEQ ID NO:71), PAH-026 (SEQ ID NO:73), and PAH-027 (SEQ ID NO:74). The sequences of the PAH constructs used in these experiments are described in the Construct Sequences Table.

After 24 hours, the cells in each well were lysed using a consistent amount of lysis buffer. Protein concentrations of each were determined. To analyze PAH expression, equal loads of each lysate (20 μg) were prepared in a loading buffer and subjected to standard Western blot analysis. GAPDH was used as a control. For detection of PAH and GAPDH, commercial antibodies were used [mouse monoclonal antibody to FLAG epitope for PAH detection—Sigma F3165; and rabbit monoclonal antibody to GAPDH—Abcam ab9485)] according to the manufacturer's instructions.

Figure 3:
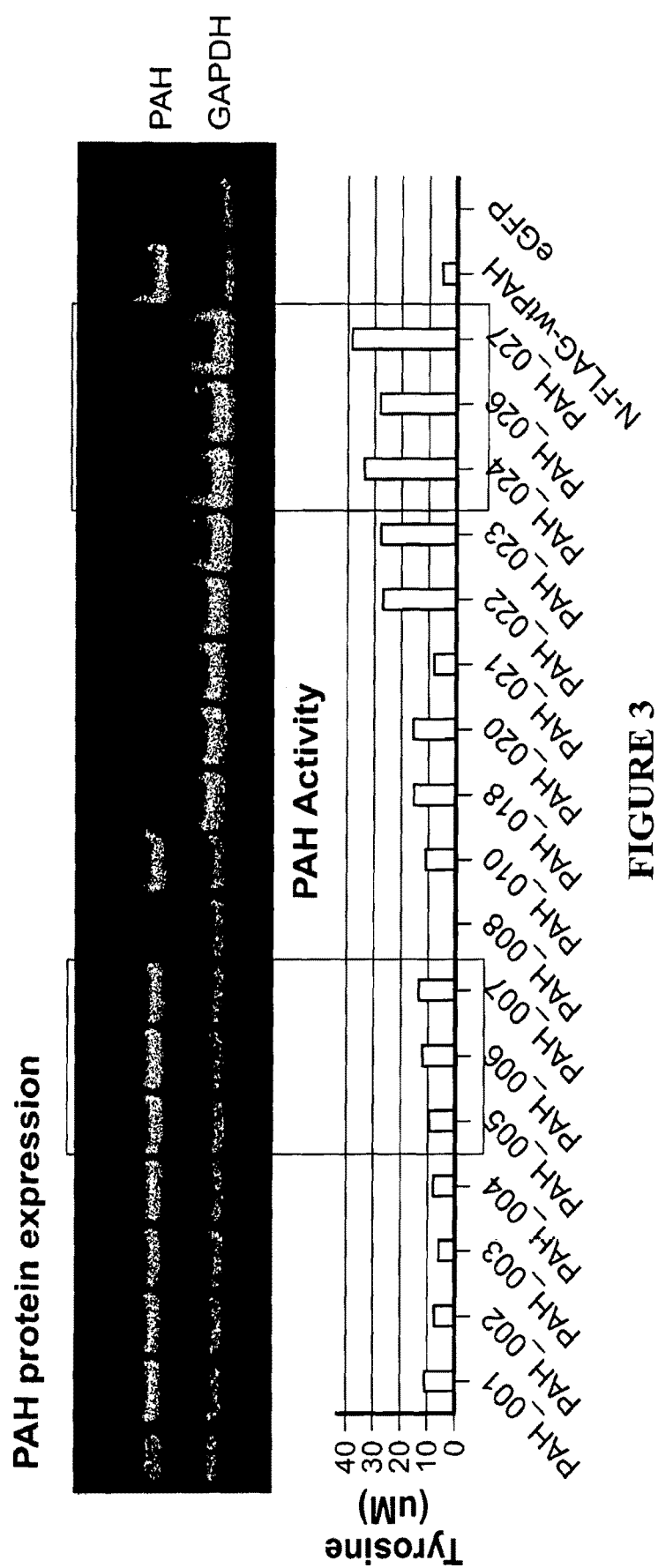
FIG. 3 includes a Western blot showing the expression of human PAH and truncated human PAH (PAH-ΔRD) constructs in SNU-423 cells 24 hours post transfection, as well as the activity of these enzymes. GAPDH was used as a loading control.

FIG. 3 top panel shows the expression level of the full length human PAH and truncated human PAH proteins.

Example 15: In Vitro PAH Activity in SNU-423 Cells

An in vitro PAH activity assay was performed to determine whether PAH exogenously-expressed after introduction of mRNA comprising a PAH sequence is active.
A. Expression Assay
SNU-423 cells were transfected with mRNA formulations comprising human PAH, truncated human PAH, or a GFP control. Cells were transfected with Lipofectamin 2000 and lysed as described in Example 14 above.
B. Activity Assay
To assess whether exogenous PAH shown in FIG. 3 top panel can function, an in vitro activity assay was performed using transfected SNU-423 cell lysates as the source of enzymatic activity. The enzymatic assay was conducted in a solution containing 4 mM EDTA, 6 mM DTT, 2 mM Phenylalanine (PAH substrate), and 3, 200 units per mL of catalase, in a volume of 50 μl. The assay mixture was incubated at 25° C. for 3 minutes and then the lysate was added. After 2 minutes, the reaction was initiated by the addition of 150 μM tetrahydrobiopterin. Tyrosine formation was monitored using HPLC by recording tyrosine fluorescence at 304 nm at 40° C.

The PAH activity assay results are shown in the bottom panel of FIG. 3 (using lysates 24 hours after transfection).

The expression and activity experiment provided in Example 14 was repeated using selected mRNA constructs to further determine whether mRNA encoding full-length and truncated PAH can express functional PAH protein in vitro. SNU-423 human hepatocellular carcinoma cells (0.5× $10^6$) were transfected with the mRNA constructs encoding wild type full-length PAH (PAH-005, PAH-006, or PAH-007; SEQ ID NOs:49-51, respectively) or with the mRNA constructs encoding truncated PAH (with its regulatory domain deleted (ΔrdPAH)) (PAH-024, PAH-026, or PAH-027; SEQ ID NOs:71, 73, and 74, respectively) described in Example 14 by lipofection using Lipofectamine™. Control cells were transfected with mRNA encoding GFP. 2 μg of mRNA was used in transfections. Cells were lysed at 24, 48, and 72-hours following transfection, and the protein was extracted and evaluated for PAH protein concentration and enzymatic activity. Lysates from transfected cells were evaluated by Western blot analysis to demonstrate protein expression. The expression levels were quantified and normalized to endoplasmic reticulum resident protein 72 (ERP72) levels. A high-performance liquid chromatography (HPLC) assay, which detects tyrosine formation from phenylalanine (Tyr activity) in the presence of PAH and cofactor $BH_4$, was used to determine activity.

Figure 4A:
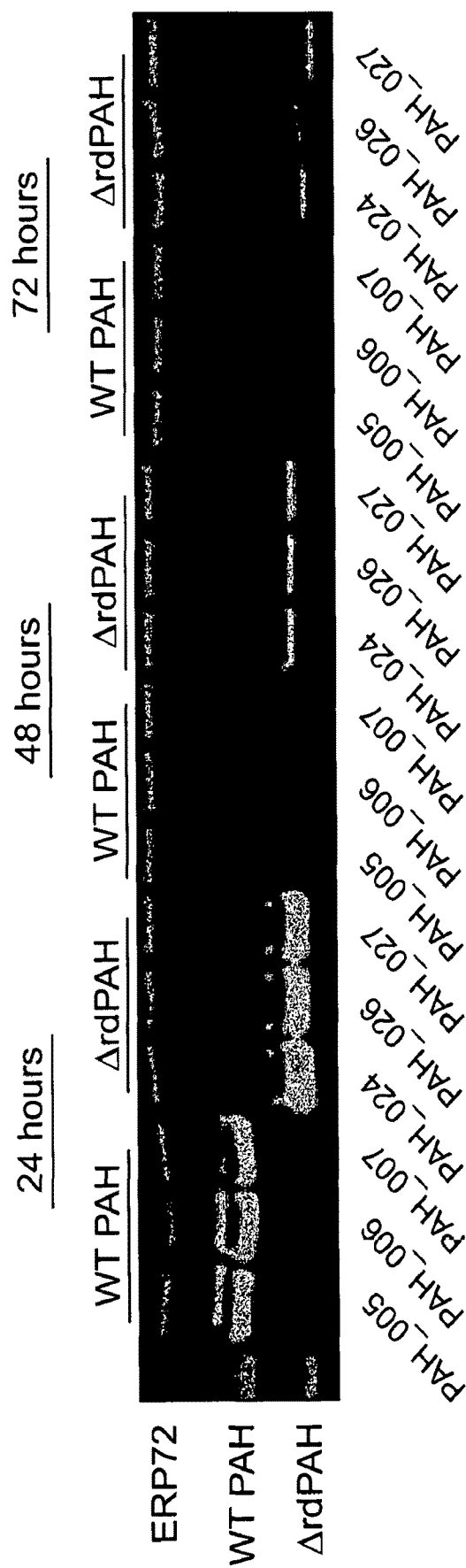
FIG. 4A shows a Western blot showing the expression of human PAH and truncated human PAH (PAH-ΔRD or ΔrdPAH) constructs in SNU-423 cells 24, 48 and 72 hours post transfection. ERP72 was used as a loading control.
Figure 4B:
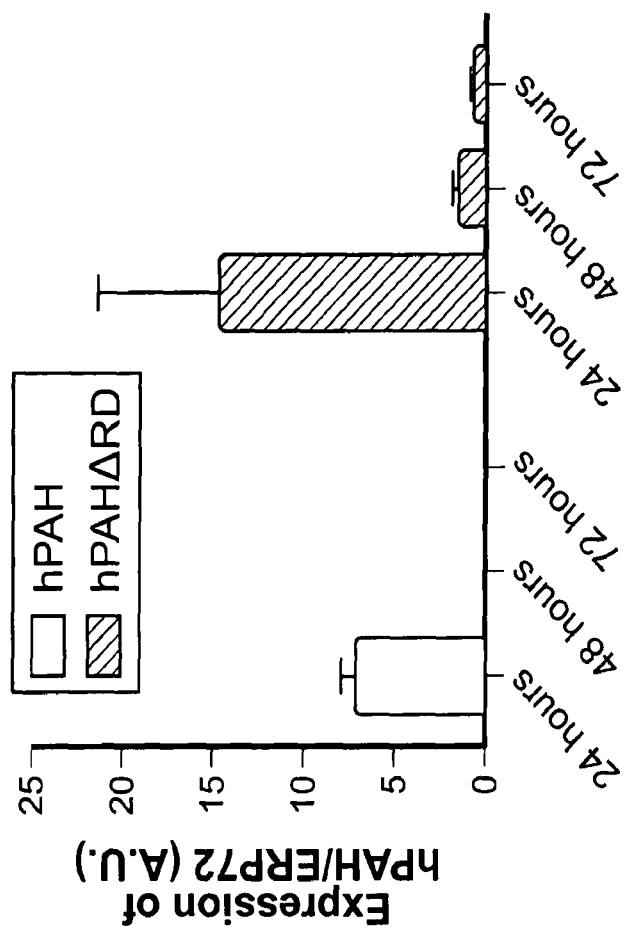
FIG. 4B is a bar graph showing the quantified expression levels of the human PAH and truncated human PAH (PAH-ΔRD or ΔrdPAH) enzymes shown in FIG. 4A at 24, 24, and 72 hours post-transfection.

FIG. 4A provides Western blot results showing that the expression of the full-length and truncated PAH proteins from the mRNA constructs were detectable at 24 hours following transfection, but only the mRNA-expressed truncated proteins could be detected in lysates through 72 hours post-transfection. In contrast, full-length PAH was undetectable at 48-hours and 72-hours following transfection. FIG. 4B shows the quantified expression levels of the mRNA constructs depicted in FIG. 4A at 24, 48, and 72 hours post-transfection. The expression levels in cells transfected with truncated PAH mRNA were approximately two times greater than the expression levels in cells transfected with full-length PAH mRNA, when normalized to ERP72. Data are presented as mean±standard deviation (SD).

Figure 5A:
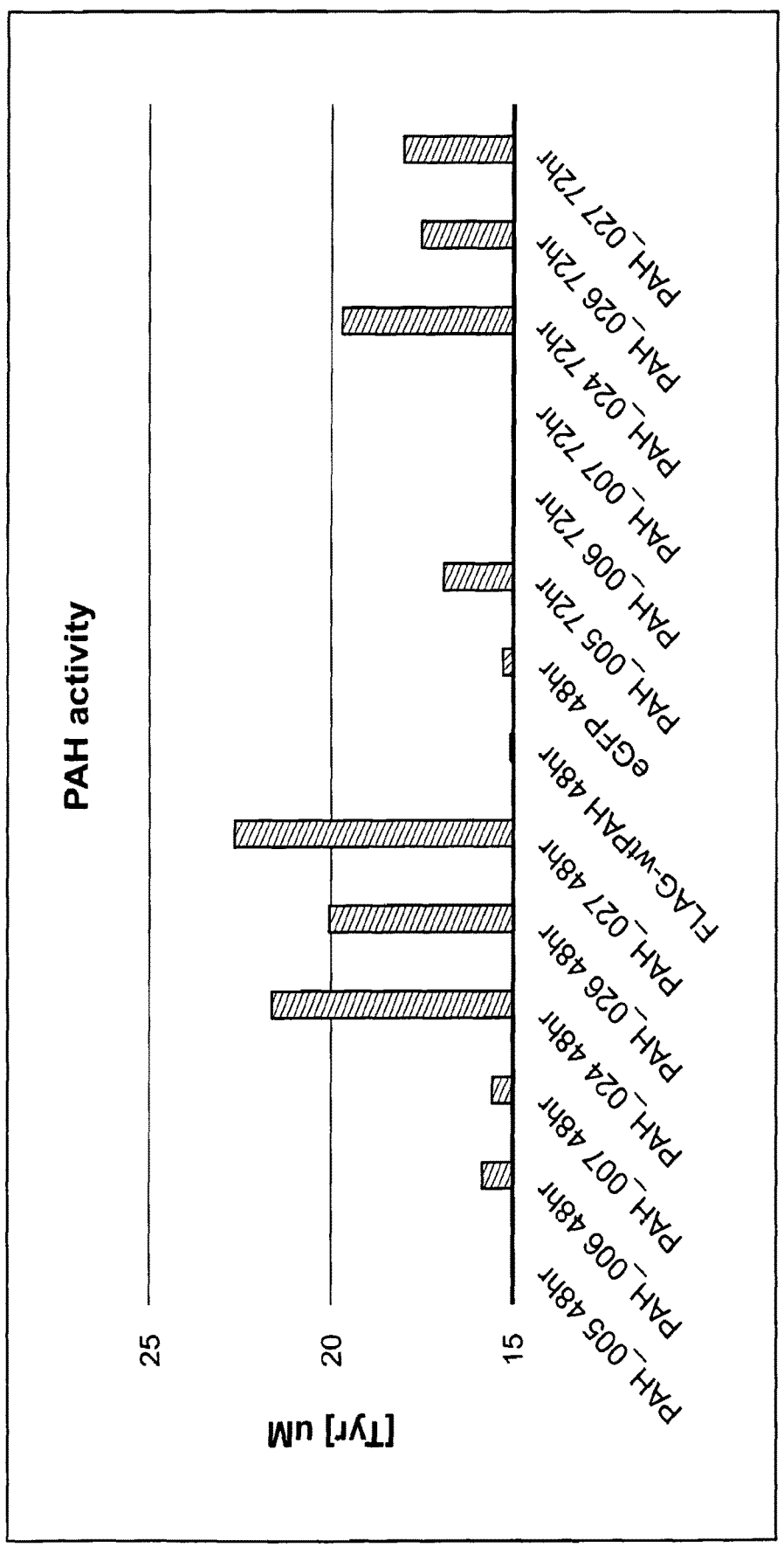
FIG. 5A is a bar graph showing the individual activity of the enzymes shown in FIG. 4A.
Figure 5B:
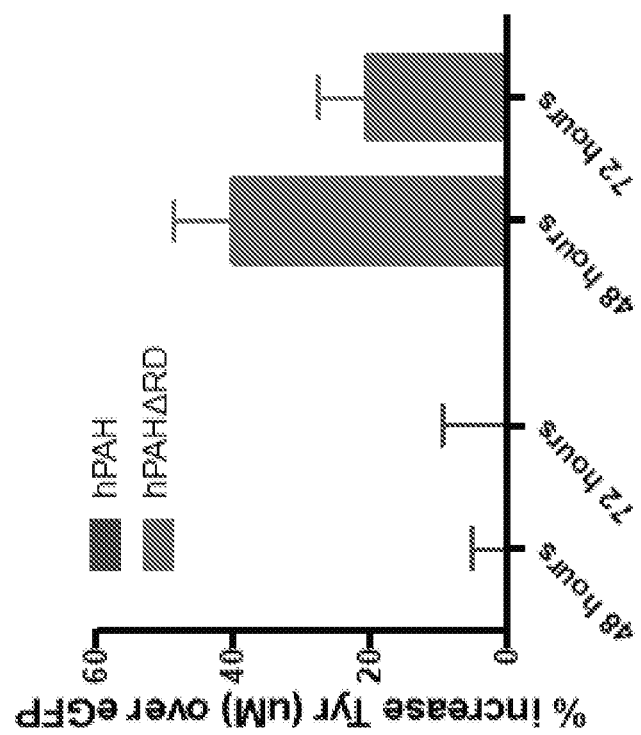
FIG. 5B is a bar graph showing the average activity of the human PAH enzymes and the average activity of the truncated human PAH (PAH-ΔRD or ΔrdPAH) enzymes shown in FIG. 5A.

FIG. 5A shows the activity levels of each of the full-length and truncated constructs at 48 and 72 hours post-transfection. FIG. 5B shows the average activity of the full-length and truncated PAH enzymes depicted in FIG. 5A at 24, 48, and 72 hours post-transfection. Data are presented as mean±standard deviation (SD). The activity data indicates that both the full-length and truncated mRNA-expressed proteins have activity, although enzymatic activity is higher in cells transfected with mRNA encoding the truncated PAH protein at all time points that were evaluated following transfection. Taken together, the results of FIGS. 4A-B and FIGS. 5A-B show that truncated human PAHARD (PAH_024, PAH_026, PAH_027) is more stable and active than wild-type human PAH (PAH_005, PAH_006, PAH_007) in deficient human epithelial cells (SNU-423 cells).

Example 16: Assessing the Addition of PAH Cofactors on PAH Activity in SNU-423 Cells The PAH enzyme requires the activity of the cofactor tetrahydrobiopterin ($BH_4$) in order to convert Phe to tyrosine (Tyr). To test whether the addition of $BH_4$ can improve the expression and activity of mRNA-expressed human truncated PAH (PAHΔRD) in human hepatocellular carcinoma cells, SNU-423 cells were seeded (3.75×10$^5$) on 6-well plates (BD Biosciences, San Jose, USA) and transfected the next day with mRNA construct PAH-027 (SEQ ID NO:202) or a control mRNA encoding eGFP. Cells were transfected using 2 µg mRNA, as described in Example 14, by lipofection using Lipofectamine™ MessengerMAX (LMRNA015; Thermo Fisher Scientific [Waltham, MA]), either with or without 100 µM of BH$_4$. The BH$_4$ was added at transfection, and again at 16, 24, and 48 hours post-transfection. Cells were lysed at 18, 24, 48, and 72-hours following transfection, and the protein was extracted and evaluated for PAH protein concentration and enzymatic activity. Lysates from transfected cells were evaluated by Western blot analysis to demonstrate protein expression. The expression levels were quantified and normalized to endoplasmic reticulum resident protein 72 (ERP72) levels. A high-performance liquid chromatography (HPLC) assay, which detects tyrosine formation from phenylalanine (Tyr activity) in the presence of PAH and cofactor BH$_4$, was used to determine activity.

Figure 6A:
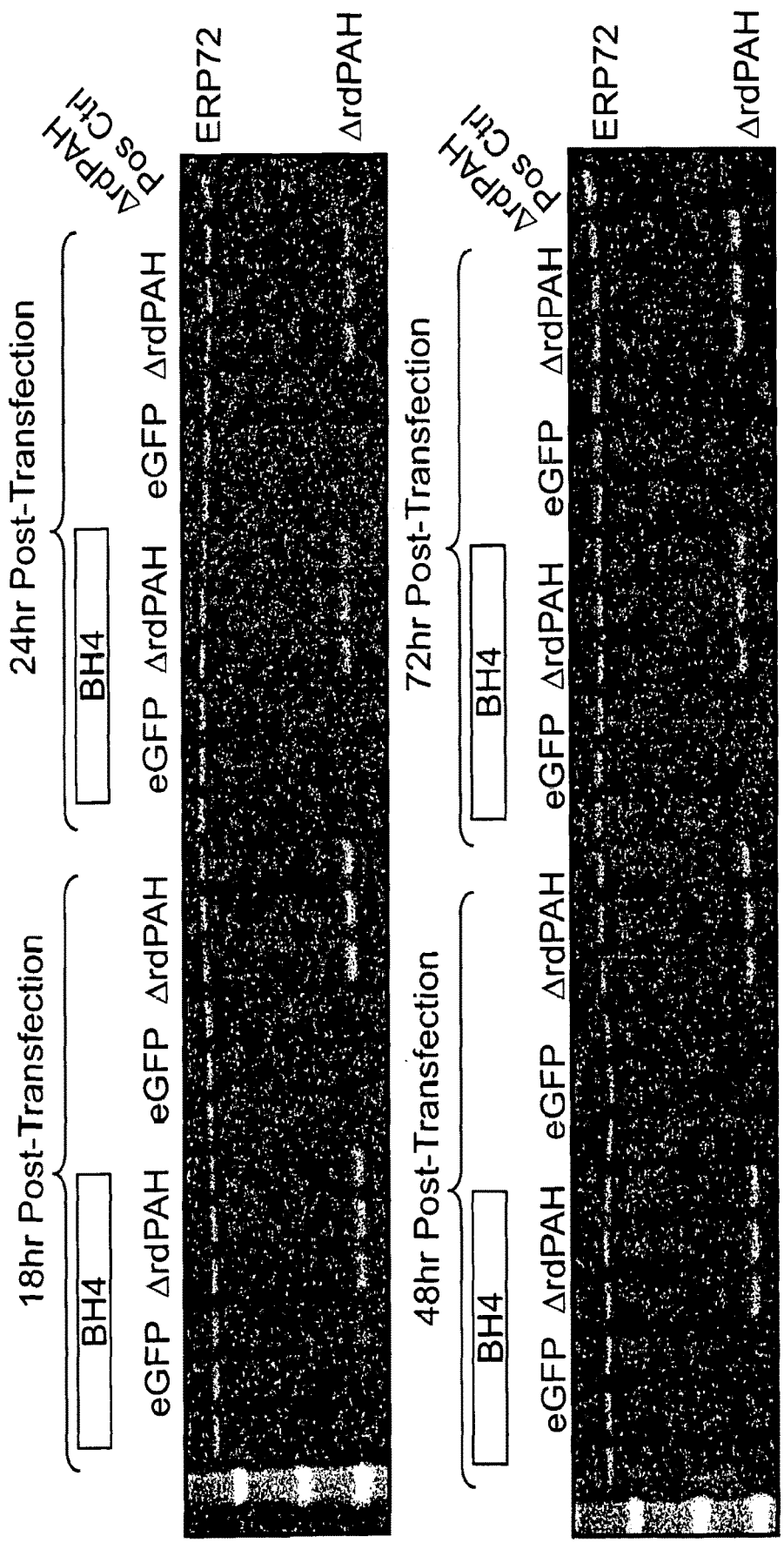
FIG. 6A shows a Western blot showing the expression of a truncated human PAH (PAH-ΔRD or ΔrdPAH) construct, or a control eGFP construct, in SNU-423 cells 24, 48 and 72 hours post transfection, with or without cofactor tetrahydrobiopterin ($BH_4$) added to the cells. ERP72 was used as a loading control.
Figure 6B:
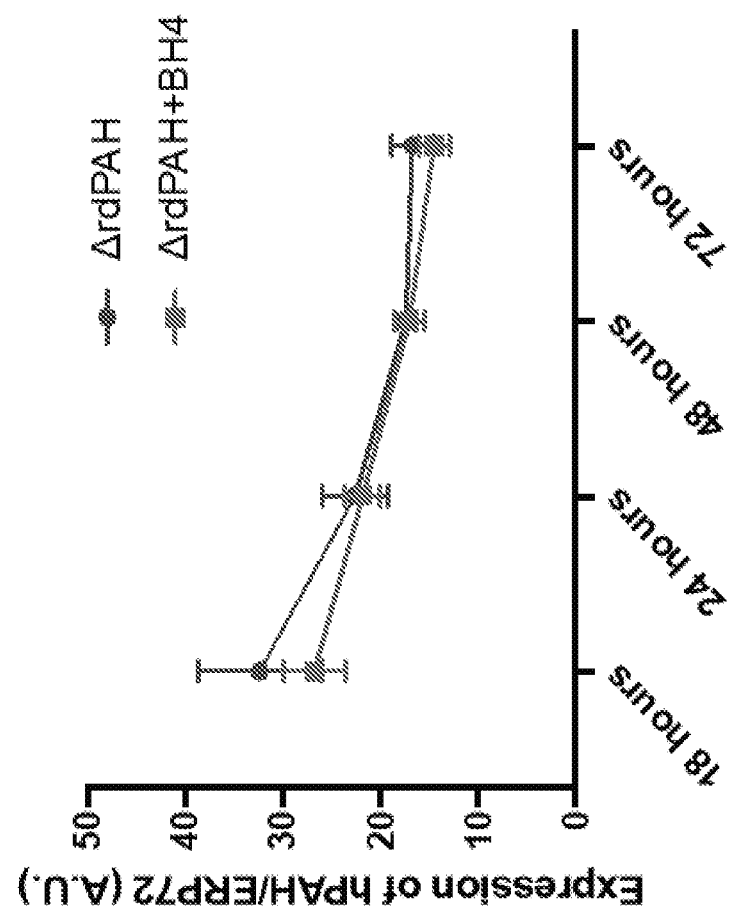
FIG. 6B is a bar graph showing the quantified expression levels of the truncated human PAH (PAH-ΔRD or ΔrdPAH) enzyme shown in FIG. 4A at 24, 24, and 72 hours post-transfection, with and without cofactor $BH_4$.
Figure 6C:
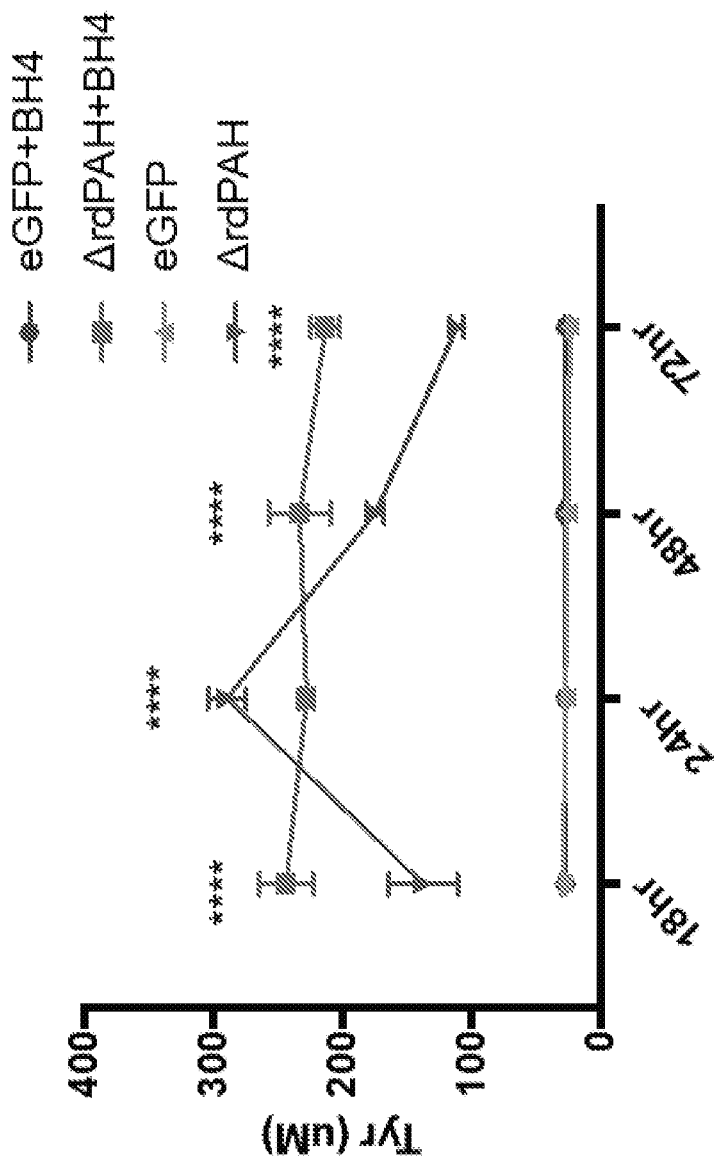
FIG. 6C is a bar graph showing the activity of the enzyme shown in FIG. 6A and FIG. 6B, and the eGFP control, without and without cofactor $BH_4$.

FIG. 6A provides Western blot results showing that mRNA expresses the PAHΔRD protein at 18, 24, 48, and 72 hours after mRNA transfection, with and without the presence of BH$_4$. No expression was detected in the control cells that received eGFP mRNA. Compared with eGFP mRNA transfected cells, cells transfected with PAHΔRD mRNA showed supraphysiologic PAH protein levels that were sustained out to 72 hours. Human PAH protein levels were similar in PAHΔRD mRNA-transfected cells in the presence or absence of BH$_4$. FIG. 6B shows that the PAHΔRD protein expression levels were similar at each time point, whether or not BH$_4$ is administered. FIG. 6C shows that there was a significant increase in Tyr production in SNU-423 cells transfected with PAHΔRD mRNA compared with SNU-423 cells transfected with eGFP mRNA. In addition, there was a significant and sustained increase in Tyr production in SNU 423 cells transfected with PAHΔRD mRNA in the presence of BH$_4$ compared with PAHΔRD mRNA-transfected cells without BH$_4$ supplementation. Overall, the results demonstrate that PAHΔRD mRNA transfection of SNU-423 cells expressed functional human PAH enzyme, regardless of the presence or absence of BH$_4$; however, the addition of BH$_4$ to transfected cells enhanced PAH enzyme activity in this study.

Example 17: Human PAH Mutant and Chimeric Constructs

A polynucleotide of the present invention can comprise at least a first region of linked nucleosides encoding human PAH or human PAHΔRD, which can be constructed, expressed, and characterized according to the examples above. Similarly, the polynucleotide sequence can contain one or more mutations that results in the expression of a human PAH or human PAHΔRD with increased or decreased activity. Furthermore, the polynucleotide sequence encoding PAH can be part of a construct encoding a chimeric fusion protein.

Example 18: Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound II or a lipid according to Formula (III) such as Compound VI, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 µm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the Table 6 below. The term "Compound" refers to an ionizable lipid such as MC3, Compound II, or Compound VI. "Phospholipid" can be DSPC or DOPE. "PEG-lipid" can be PEG-DMG or Compound I.

TABLE 6

Exemplary Formulations of Nanoparticles

| Composition (mol %) | Components |
| --- | --- |
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 19: In Vivo PAH Expression in Animal Models

To assess the ability of PAH-coding mRNAs to facilitate PAH expression in vivo, mRNA encoding human PAH or a truncated version thereof is introduced into an animal model of PKU.

A frequently used genetic mouse model of PKU is the BTBR-PAH$^{enu2}$ mouse (Shedlovsky et al., Genetics, 1205-1210, 1993). PAH$^{enu2}$ mice, created by the germline ethylnitrosourea (ENU) mutagenesis, are characterized by a biochemical phenotype that closely resembles untreated human PKU, being characterized by reduced PAH activity, phenylalanine plasma levels 10-20 times greater than those of normal littermates and deficits of biogenic amines. Homozygous mutant mice show severe hyperphenylalaninemia, and the mice exhibit neurologic dysfunction, and catecholaminergic defects. They are hypopigmented unless maintained on a low phenylalanine diet. Reduction of blood phenylalanine increases the ability of the mutant mouse to produce pigment. This yields an easily visible coat-color gauge, indicating therapeutic levels of gene expression.

To model different degrees of hyperphenylalaninemia, one can use the following: for mild hyperphenylalaninemia: heterozygous PAH$^{enu2}$ mice; for mild-PKU: homozygous PAH$^{enu2}$ mice maintained with a phenylalanine-free diet and receiving phenylalanine in drinking water (e.g., 2 grams per liter), or BTBR-PAH$^{enu1}$, or BTBR-PAH$^{enu2}$/BTBR-PAH$^{enu1}$ compound heterozygotes; and for classical PKU: homozygous PAH$^{enu2}$ mice (Sarkissian et al., Mol. Genet. Metabol., 69:188-194 (2000); Pascucci et al., PLOS ONE, 8(12):E84697 (2013)).

The model mice are injected intravenously with 0.5 mg/kg of either control mRNA (green fluorescent protein (GFP) mRNA) or human PAH mRNA. The mRNA is formulated in lipid nanoparticles for delivery into the mice. Mice are sacrificed after 24 or 48 hrs and PAH protein levels in liver lysates are determined by capillary electrophoresis (CE). GAPDH expression is examined for use as a load control. For control GFP injections, 4 mice are tested for each time point. For human PAH mRNA injections, 6 mice are tested for each time point. Treatment with mRNA encoding PAH is expected to reliably induce expression of PAH. Blood phenylalanine levels are measured as a PD marker.

Example 20: Wild Type Rat or Mouse as a Surrogate System for Assessing PAH

To determine if wild type animals (mouse/rat) can be used to assess PAH activity, a study was conducted to determine baseline phenylalanine exposure following either intraperitoneal (IP) or oral (PO) administration of phenylalanine or aspartame (phenylalanine dipeptide).

Wild type animals such as rats and mice, usually maintain phenylalanine levels under 100 μM. Therefore, overexpression of PAH via, e.g., the mRNAs disclosed herein in these animals is unlikely to change the baseline phenylalanine levels. Therefore, it was planned to increase the phenylalanine levels in these animals and overexpress PAH through the mRNAs described herein and test the efficacy.

To test this idea, it was first evaluated if the baseline phenylalanine levels in these animals could be increased by dosing them with phenylalanine or aspartame and measuring the phenylalanine levels at different time points post dose. FIGS. 7A-B show that systemic exposure of phenylalanine was observed for 60-90 minutes in rats (FIG. 7A) and less than 40 minutes in mice (FIG. 7B) following administration of aspartame, irrespective of delivery route. Thus, these data show that there is a 40 minute window in mice and a 60-90 minute window in rats during which PAH efficacy can be evaluated.

Thus, these wild type animal models can be used to measure a change in phenylalanine exposure following administration of PAH-mRNA constructs.

Example 21: Evaluating PAH in Wild Type Rat

Rats are dosed i.v. with 0.5 mg/kg PAH. Wt, PAHΔRD, and control (eGFP) mRNAs. 8 hours post dose, the rats are challenged with aspartame at 1000 mg/kg via oral gavage. Blood is collected at 0 min, 20 min, 40 min, 60 min, 90 min, and 120 min post challenge. Blood phenylalanine levels are measured. The animals are sacrificed after the last bleed and expression of PAH proteins in the liver is determined.

Figure 8:
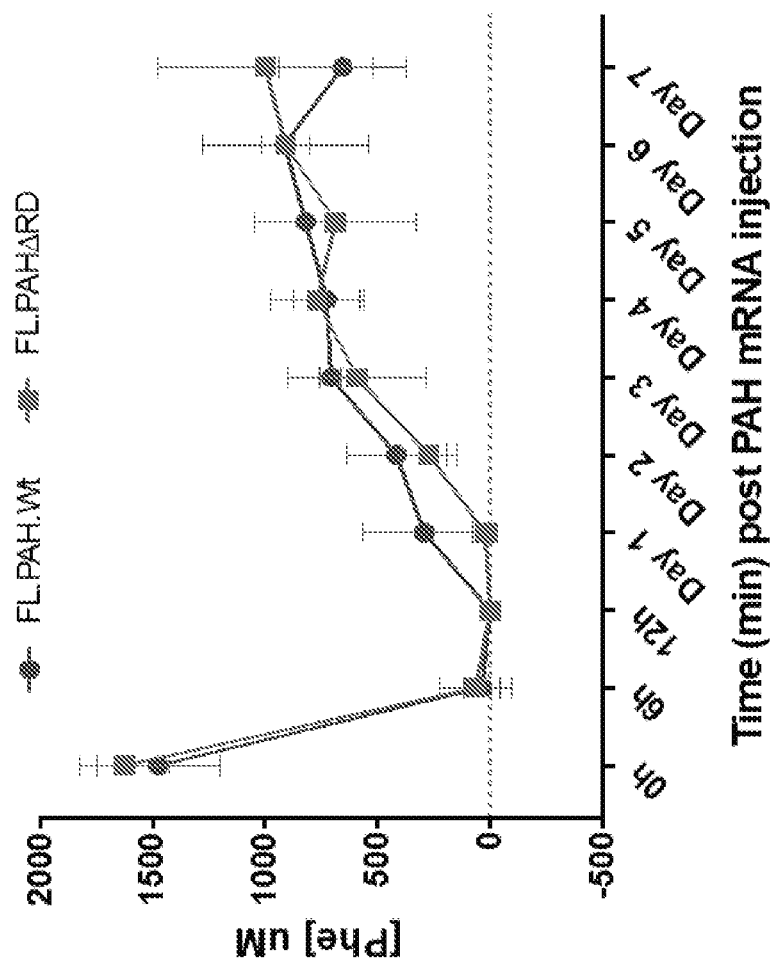
FIG. 8 is a graph showing the activity of human PAH and truncated human PAH (PAH-ΔRD) in homozygous $PAH^{enu2}$ mice following injection of a single dose of mRNA, as measured in blood phenylalanine levels over time.

Example 22: Assessing Duration of PAH Activity and Dose Response in a PKU Mouse Model—Single Dose Studies To test the ability of 1-methyl-pseudouridine modified mRNA constructs to express PAH in vivo, and to assess the activity of mRNA-expressed PAH, a single 0.5 mg/kg dose of mRNA encoding human PAH (SEQ ID NO:199) or human PAHΔRD (SEQ ID NO:200) was IV administered to homozygous PAH$^{enu2}$ mice (n=5-6 per construct) via tail vein injection. The mRNA was formulated in lipid nanoparticles (Compound II) for delivery into mice. Blood was drawn from mice prior to mRNA injection (0 hours) and 6 hours, 12 hours, 1 day, 2, days, 3 days, 4 days, 5 days, 6 days, and 7 days following mRNA injection. Blood phenylalanine levels were measured at each time point using LC-MS/MS on Dried Blood Spots (DBS) as a marker for PAH activity. FIG. 8 shows that PAH activity increased at 6 hours following injection of mRNA constructs encoding human PAH or human PAHΔRD, as exhibited by a significant drop in blood phenylalanine levels. The circulating phenylalanine levels in PKU mice were reduced to normal (wild-type) levels within 6 hours following a single mRNA dose. Phenylalanine levels rose during the course of 7 days following injection, but were still lower than phenylalanine levels prior to mRNA injection.

Figure 9:
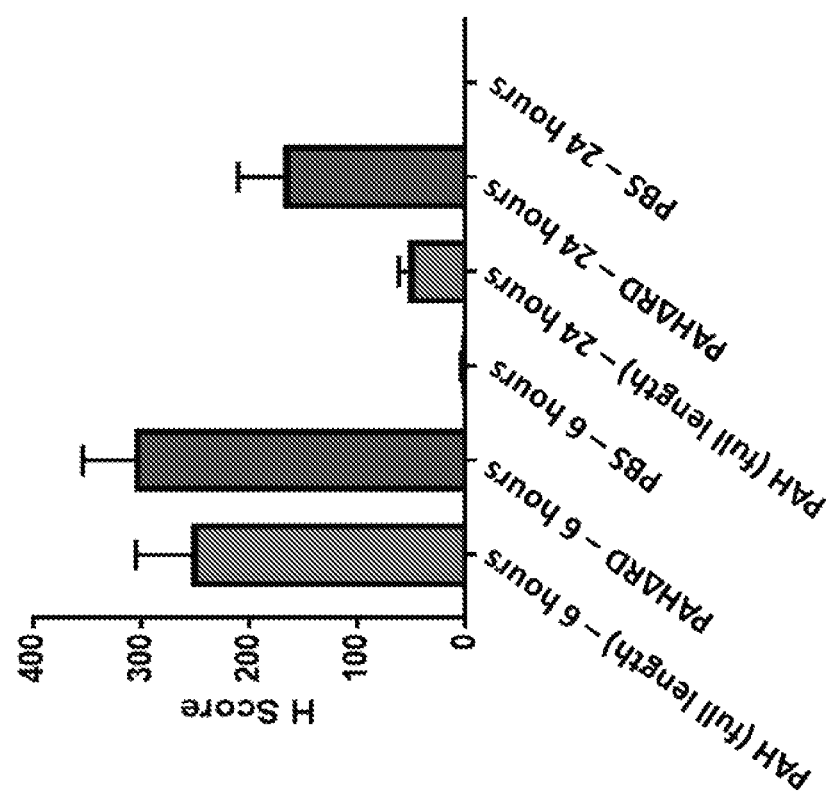
FIG. 9 is a bar graph showing the H scores from in situ hybridization of mRNA encoding human PAH and truncated human PAH (PAH-ΔRD) in liver cells from mRNA-injected homozygous $PAH^{enu2}$ mice.
Figure 10A:
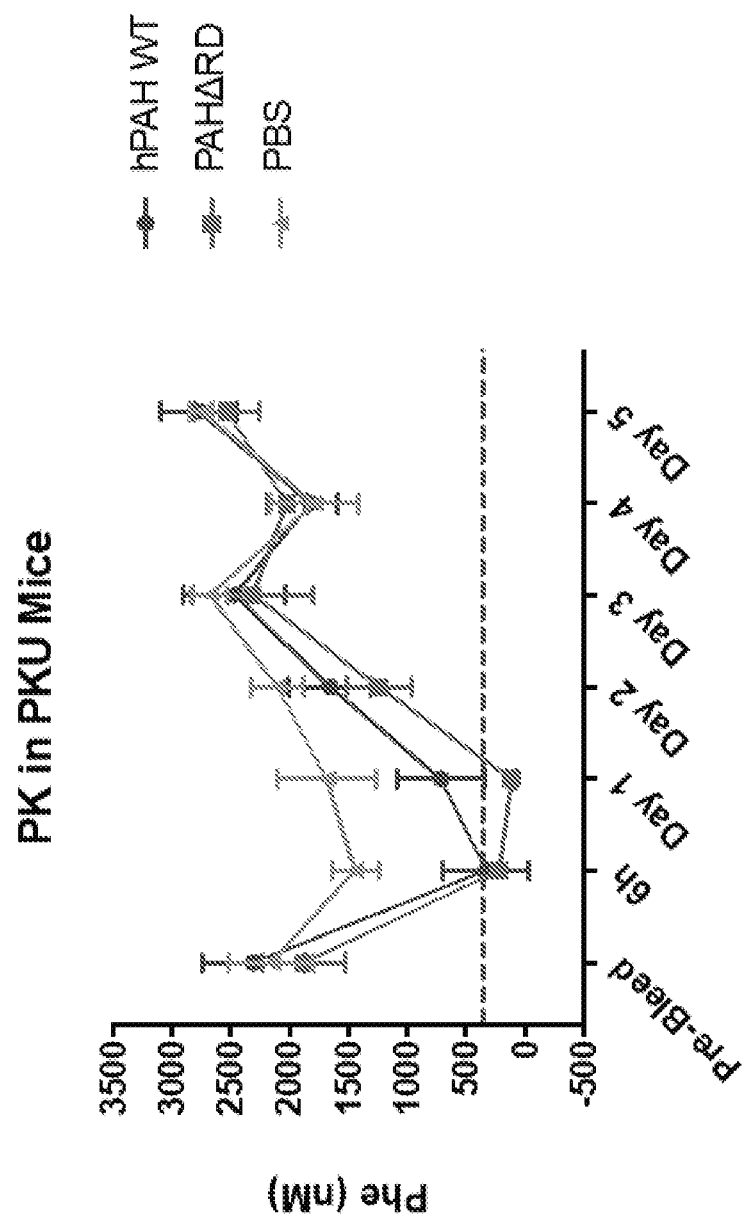
FIG. 10A is a graph showing the activity of human PAH and truncated human PAH (PAH-ΔRD) in homozygous $PAH^{enu2}$ mice following injection of a single dose of mRNAs encoding PAH, compared to activity in control animals injected with PBS, as measured in blood phenylalanine levels over time.
Figure 10B:
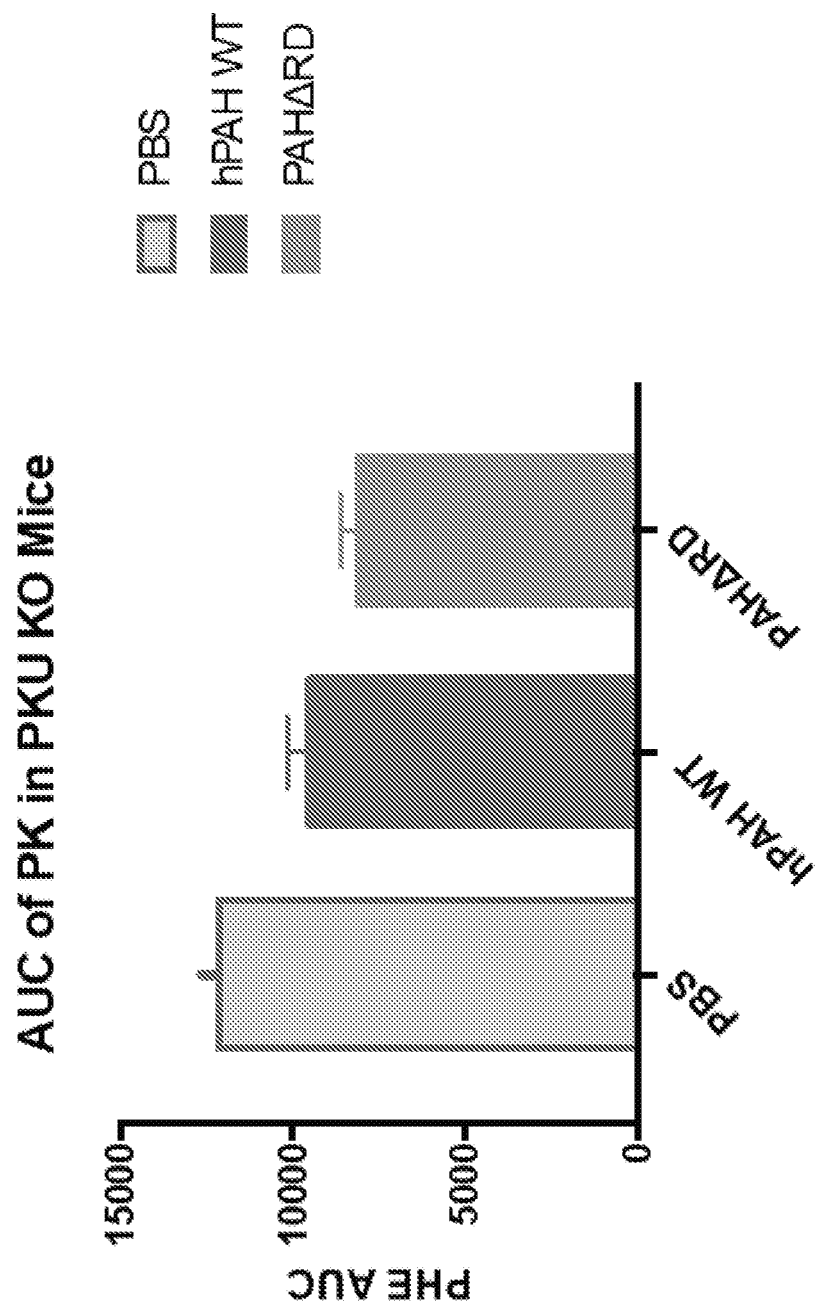
FIG. 10B is a bar graph showing the area under the curve (AUC) values for human PAH and truncated human PAH (PAH-ΔRD) in homozygous $PAH^{enu2}$ mice.

To further test the duration of PAH activity following administration of mRNA encoding human PAH (SEQ ID NO:199) or human PAHΔRD (SEQ ID NO:202) in vivo, homozygous PAH$^{enu2}$ mice were injected with a single 0.5 mg/kg dose of mRNA via tail vein injection. The mRNA was formulated in lipid nanoparticles (Compound II) for delivery into mice. Control mice were injected with PBS. Blood was drawn from mice prior to mRNA injection (pre-bleed) and 6 hours, 1 day, 2 days, 3 days, 4 days, and 5 days following mRNA injection. Phenylalanine levels were measured in plasma at each time point using LC-MS/MS as a marker for PAH activity. PAH mRNA, protein, and protein activity levels were assayed in tissues (liver, spleen, and brain) collected at each time point (data not shown). In situ hybridization was used to assay the levels and location of PAH mRNA. FIG. 9 shows that more mRNA encoding PAHΔRD was taken up by hepatocytes than mRNA encoding the full-length PAH protein. FIG. 10A shows that plasma phenylalanine levels decreased following a single injection of mRNA encoding human PAH or human PAHΔRD, relative to pre-bleed levels of phenylalanine, indicating an increase in PAH activity compared to control mice injected with PBS. Plasma phenylalanine levels gradually rose to about pre-bleed levels by about 3 days following injection mRNA injection. FIG. 10B shows the area under the curve (AUC) values for plasma phenylalanine in mice injected with mRNA encoding human PAH or human PAHΔRD or in mice injected with PBS. Plasma phenylalanine concentrations were lower in mice injected with mRNA encoding human PAHΔRD.

In another experiment to test the dose-response and duration of action of mRNA encoding human PAH in homozygous PAH$^{enu2}$ mice, eight groups of the homozygous mutant mice (n=5 per group) were administered 0.2 mg/kg, 0.5 mg/kg, 1.0 mg/kg, 2.0 mg/kg, 2.0 mg/kg, 3.0 mg/kg, or 5 mg/kg of human PAHΔRD mRNA (SEQ ID NO:202) by tail vein IV injection. In addition, one group of homozygous PAH$^{enu2}$ mice was administered 5 mg/kg of the PAHΔRD mRNA (SEQ ID NO:202) and received 20 mg/kg of BH$_4$ (a co-factor required for PAH activity) twice daily for the duration of the study. The mRNA was formulated in lipid nanoparticles (Compound II/Compound I) prior to injection. Blood samples were collected from mice prior to mRNA dosing (pre-bleed) and 1, 2, 3, and 4 days post-dose and analyzed for blood Phe concentrations using LC-MS/MS on dried blood spots. Circulating Tyr levels were also determined by LC-MS/MS on dried blood spots, which detects tyrosine formation from phenylalanine (Tyr activity) in the presence of PAH and cofactor BH$_4$.

Figure 11:
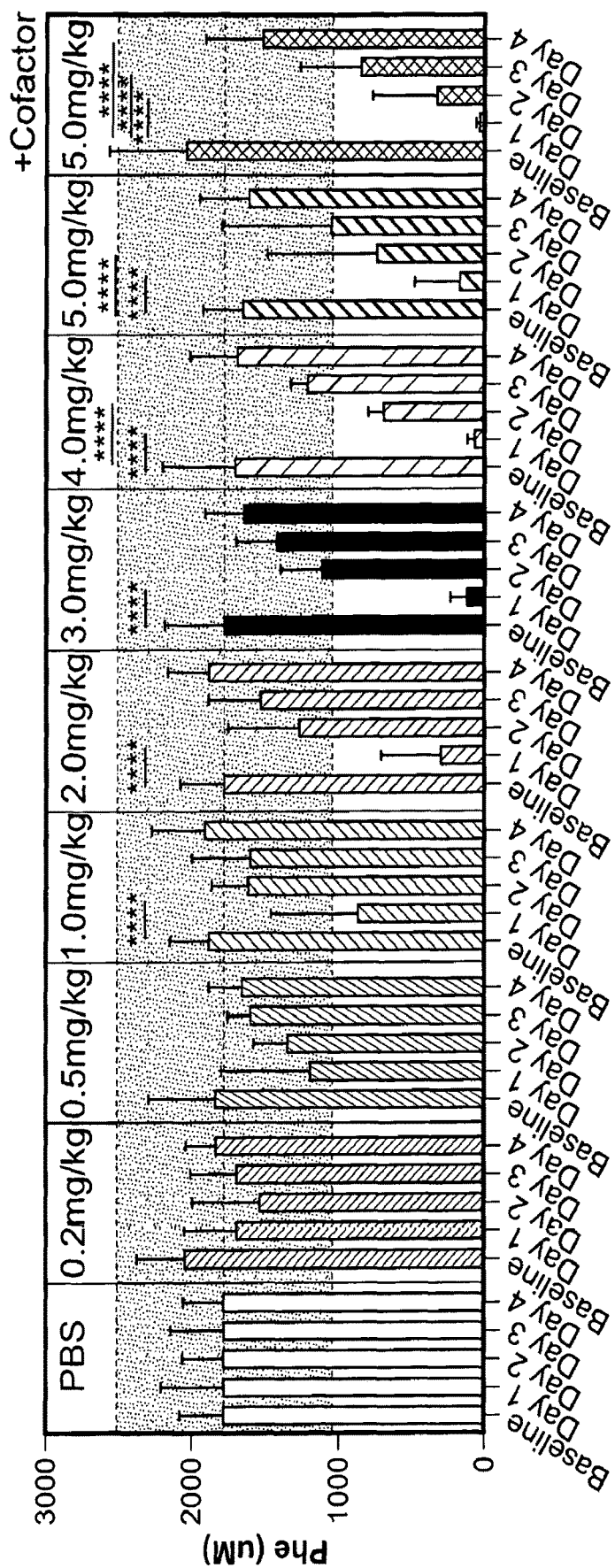
FIG. 11 is a bar graph showing the activity of truncated human PAH (PAH-ΔRD) in homozygous $PAH^{enu2}$ mice following injection of a single dose of 0.2 mg/kg, 0.5 mg/kg, 1.0 mg/kg, 2.0 mg/kg, 3.0 mg/kg, 4.0 mg/kg, or 5.0 mg/kg of mRNA, or a single 5.0 mg/kg dose of mRNA with cofactor $BH_4$, as measured in blood phenylalanine (Phe) levels at 1, 2, 3, and 4 days after mRNA injection, compared to the blood Phe level in the homozygous $PAH^{enu2}$ mice prior to injection of mRNA or PBS control (baseline).

FIG. 11 shows the blood Phe levels in the homozygous PAH$^{enu2}$ mice at each dose level of PAHΔRD mRNA over the course of the four days following mRNA administration, compared to Phe levels over four days in control PAH$^{enu2}$ mice administered PBS, and compared to the Phe levels in the mice prior to injection of mRNA or PBS control (baseline). A significant reduction in blood Phe levels was observed in the mice that received 1.0 mg/kg or more of the PAHΔRD mRNA at 24 hours following intravenous administration. The magnitude of blood Phe reduction was dose responsive, achieving approximately 50%, 80%, and 90% reduction from baseline in mice that received 1.0 mg/kg, 2.0 mg/kg and ≥3 mg/kg of PAHΔRD mRNA respectively (see Table 7). In addition, the duration of reduction in blood Phe levels following PAHΔRD mRNA injection was also dose responsive. The PAH$^{enu2}$ mice that received 1.0 mg/kg of the PAHΔRD mRNA had rebounded to 95% of circulating baseline Phe levels at 2 days following mRNA injection, but the mutant mice that received either 2.0 mg/kg or 3 mg/kg of the PAHΔRD mRNA rebounded to approximately 78% and 76% of baseline Phe values, respectively, at 2 days following mRNA administration. A longer duration of action effect was observed in animals that received 4 mg/kg or 5 mg/kg of PAHΔRD mRNA, achieving 48% and 55% of the baseline Phe levels at 2 days following mRNA administration. The circulating blood Phe levels in all dose groups were above baseline levels by day 4 following mRNA (see FIG. 11 and Table 1).

TABLE 1

Percent of baseline Phe levels over time following administration of PAHΔRD mRNA (single injection)

|  | 0.2 mg/kg | 0.5 mg/kg | 1.0 mg/kg | 2.0 mg/kg | 3.0 mg/kg | 4.0 mg/kg | 5.0 mg/kg | 5.0 mg/kg + BH$_4$ |
|---|---|---|---|---|---|---|---|---|
| PreBleed | 100% | 100% | 100% | 100% | 100% | 100%% | 100% | 100% |
| Day 1 | 90% | 73% | 51% | 21% | 10% | 6% | 13% | 12% |
| Day 2 | 83% | 80% | 95% | 78% | 76% | 48% | 55% | 20% |
| Day 3 | 88% | 91% | 91% | 91% | 90% | 81% | 69% | 49% |
| Day 4 | 145% | 143% | 164% | 170% | 153% | 163% | 162% | 131% |

FIG. 11 also shows that the amount of circulating Phe levels at 1 day following mRNA injection were similar in homozygous PAH$^{enu2}$ mice that received BH$_4$ and 5 mg/kg of PAHΔRD mRNA and the homozygous PAH$^{enu2}$ mice that received 5 mg/kg of PAHΔRD mRNA alone (i.e., no BH$_4$) (12% versus 13% of baseline Phe levels, respectively). However, co-administration of BH$_4$ with mRNA had an effect on the duration of action of mRNA. Administration of 20 mg/kg of BH$_4$ (twice daily) with 5 mg/kg of PAHΔRD mRNA led to lower circulating Phe levels at 2 and 3 days following mRNA injection (20% and 50% of baseline control Phe levels) compared to administration of 5 mg/kg of PAHΔRD mRNA alone (55% and 69% of baseline control Phe levels at 2 and 3 days post-injection, respectively).

Table 8 shows that the activity of the mRNA-expressed PAH enzyme increased, as determined by circulating Tyr levels, in the days following mRNA injection relative to the levels prior to injection (baseline). PAH enzyme activity levels increased particular during Days 1 and 2 following injection of 1.0 to 5.0 mg/kg of mRNA. The addition of BH with 5 mg/kg of mRNA increased activity.

TABLE 8

Percent of baseline Tyr levels over time following administration of PAHΔRD mRNA (single injection)

| Study | Time Post-dose | mRNA-3283 Dose (mg/kg) | | | | | | | |
|---|---|---|---|---|---|---|---|---|---|
| Day | (h) | 0.2 | 0.5 | 1.0 | 2.0 | 3.0 | 4.0 | 5.0 | 5.0 + BH4 |
| Baseline | NA | 100% | 100% | 100% | 100% | 100% | 100% | 100% | 100% |
| Day 1 | 24 | 110% | 111% | 130% | 103% | 133% | 142% | 145% | 150% |
| Day 2 | 48 | 92% | 56% | 124% | 86% | 151% | 107% | 122% | 166% |
| Day 3 | 72 | 74% | 78% | 76% | 74% | 75% | 103% | 82% | 68% |
| Day 4 | 96 | 125% | 94% | 132% | 103% | 80% | 127% | 74% | 60% |

These data show that administering mRNA encoding truncated PAH enzyme reduces circulating Phe levels and increases enzyme activity in a dose dependent manner. Administering BH$_4$ appears to improve the duration of effect of the 5 mg/kg dose of PAHΔRD mRNA when compared to an equivalent dose of mRNA alone.

Example 23: Assessing Duration of PAH Activity and Dose Response in a PKU Mouse Model—Multiple Dose Study To test the duration of PAH activity over time in response to multiple doses of mRNA encoding human PAH (SEQ ID NO:199) or human PAHΔRD (SEQ ID NO:200) in vivo, homozygous PAH$^{enu2}$ mice were injected with six single 0.5 mg/kg doses of mRNA via tail vein injection. The doses were administered once every 7 days (at days 0, 7, 14, 21, 28, and 35). The mRNA was formulated in lipid nanoparticles (Compound II/DMG) for delivery into mice. Control mice were injected with mRNA encoding luciferase. mRNA encoding human PAHΔRD and control mRNA encoding luciferase were also administered into heterozygous PAH$^{enu2}$ mice and in wild-type mice. Blood was drawn from mice prior to the first mRNA injection (pre-bleed) and at 1, 3, and 7 days following each mRNA injection. Phenylalanine levels were measured in plasma at each time point using LC-MS/MS as a marker for PAH activity. Data analysis for circulating Phe levels was performed utilizing 2 way analysis of variance (ANOVA) with Dunnett's multiple comparison test to baseline levels. Changes in circulating Phe levels were calculated as the concentration in pre-dose sample (Day 2, baseline measurement) minus the concentration in all subsequent samples post-treatment (Days 1, 3, and 7). Statistical significant reduction of circulating Phe was qualified as an adjusted p value≤0.05. Tolerability was assessed by measuring clinical chemistry (AST and ALT levels) in mice following the last dose of mRNA.

Figure 12:
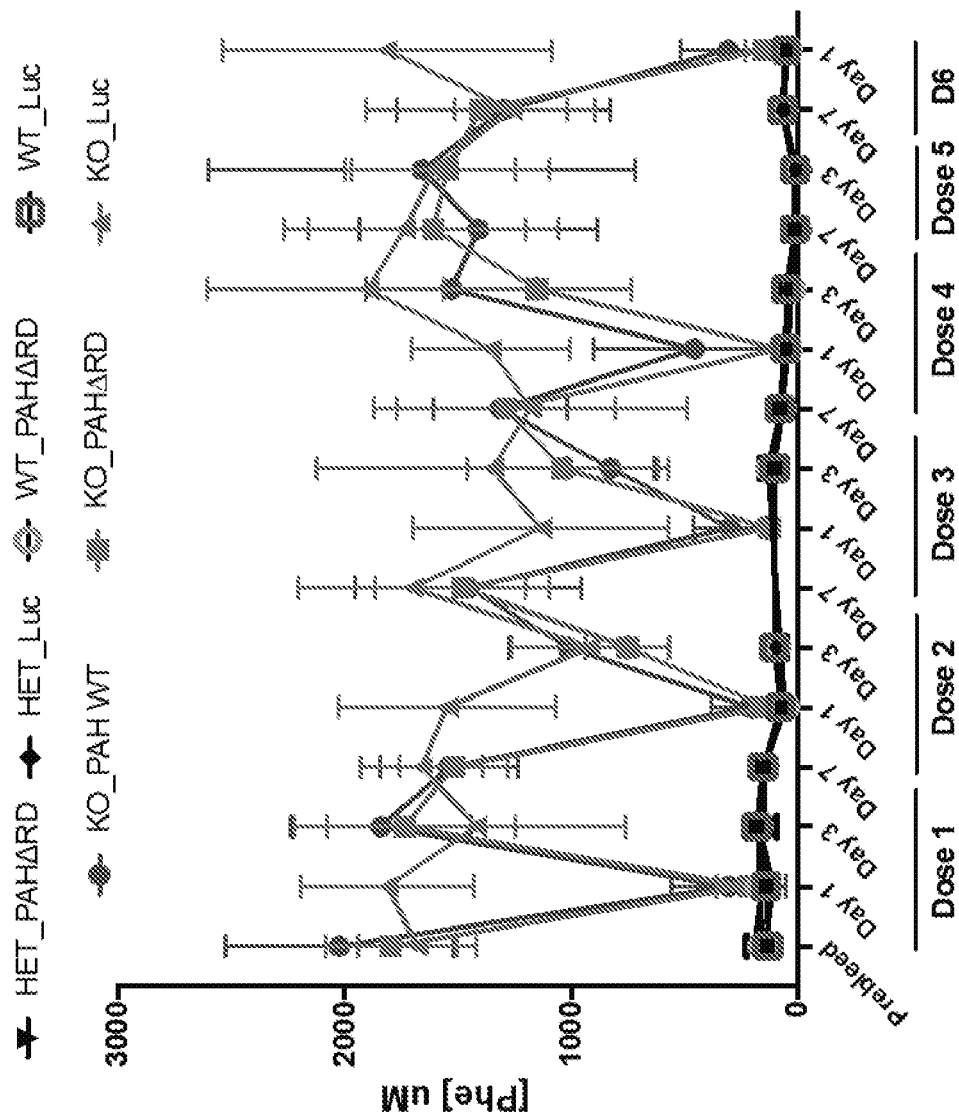
FIG. 12 is a graph showing the activity of human PAH, truncated human PAH (PAH-ΔRD), or luciferase control in homozygous $PAH^{enu2}$ mice, heterozygous $pAH^{enu2}$ mice, or in wild-type mice following injection of multiple doses of mRNAs encoding PAH, as measured in blood phenylalanine levels at 1, 3, and 7 days after each mRNA injection.

FIG. 12 shows that plasma phenylalanine levels decreased substantially each time mRNA encoding human full-length PAH or human PAHΔRD was administered into homozygous PAH$^{enu2}$ mice (and compared to the pre-bleed or baseline levels in these mice and compared to control mice administered luciferase mRNA), indicating that PAH activity increased immediately in response to each injection of mRNA. The mean circulating Phe levels in homozygous PAH$^{enu2}$ mice administered 0.5 mg/kg doses of full-length PAH or human PAHΔRD mRNA weekly were significantly reduced 24 hours (Day 1) after each dose compared with baseline levels, and were similar to levels measured in the wild-type and heterozygous mice. The greatest reduction in mean circulating Phe levels was observed in homozygous PAH$^{enu2}$ mice administered PAHΔRD mRNA, where after the first dose, Day 1 mean circulating Phe levels were reduced to 12% of baseline levels. After repeated administration, Day 1 mean circulating Phe levels steadily decreased to 8%, 7%, and 4% of baseline levels after the second, third, and fourth dose, respectively. In animals administered full-length (WT) PAH mRNA, the greatest reduction in mean circulating Phe levels was observed on Day 1 after the second dose, and increased slightly on Day 1 after the third, fourth, and sixth doses. Mean circulating Phe rebounded to baseline levels between Day 3 and Day 7 after each dose of full-length PAH or PAHΔRD mRNA. As expected, wild-type mice and heterozygous PAH$^{enu2}$ mice injected with mRNA exhibited consistently low levels of plasma phenylalanine. Overall, these results indicate that administration of full-length (WT) PAH or PAHΔRD mRNA to homozygous PAH$^{enu2}$ mice produces functional PAH proteins, as evidenced by significantly decreased mean circulating Phe levels 24 hours after each dose, reaching levels similar to those observed in wild-type mice. However, the effect was relatively short lived, with circulating Phe levels returning to pre-dose levels between Day 3 and Day 7 after each dose.

A repeat dose study using a range of mRNA doses was conducted to better understand the duration of action and to determine whether there is a dose response effect when multiple doses of human PAHΔRD mRNA are administered to homozygous PAH$^{enu2}$ mice. The PAH$^{enu2}$ mice were administered six single doses of 0.5 mg/kg, 1 mg/kg, or 2 mg/kg of human PAHΔRD mRNA (SEQ ID NO:202), or PBS as a control, via tail vein injection (n=8 mice per group). Doses were administered every 3 days (Day 0, Day 3, Day 6, Day 9, Day 12, and Day 15). The mRNA was formulated in lipid nanoparticles (Compound II/Compound I) for delivery into mice. Blood was drawn from mice prior to the first mRNA injection (pre-bleed) and at 24 hours following each mRNA dose, and then at 24, 72, and 120 hours after the final sixth dose. Phenylalanine levels were measured in the plasma at each time point using LC-MS/MS as a marker for PAH activity. Circulating Tyr levels were also determined by LC-MS/MS on dried blood spots, which detects tyrosine from phenylalanine (Tyr activity) in the presence of PAH and cofactor BH$_4$.

Figure 13A:
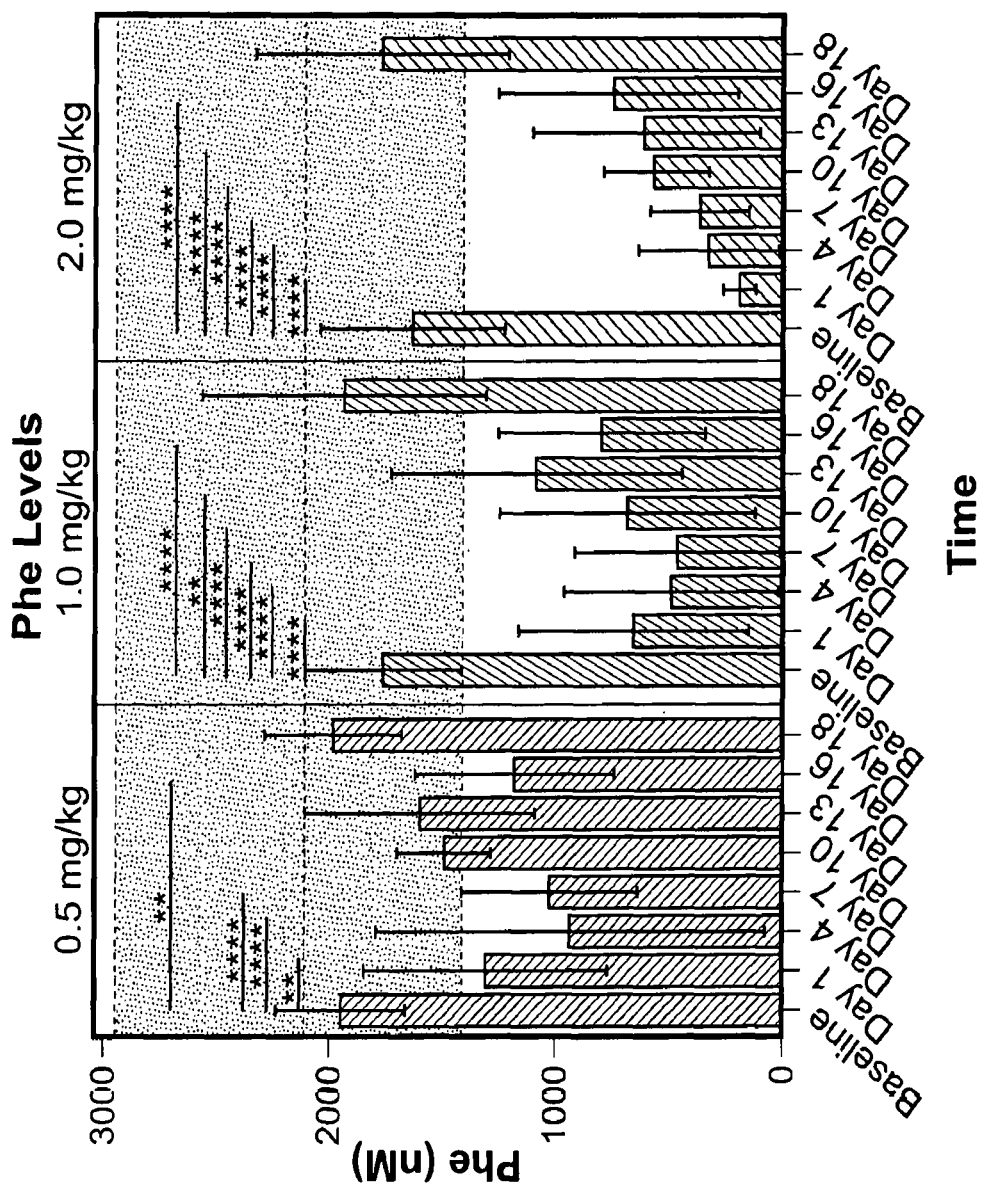
FIG. 13A is a bar graph depicting the activity of truncated human PAH (PAH-ΔRD or ΔrdPAH) in homozygous $PAH^{enu2}$ mice following injection of multiple doses of 0.5 mg/kg, 1 mg/kg, or 2.0 mg/kg of mRNA encoding PAH (at days 0, 3, 6, 9, 12, and 15), as measured in blood phenylalanine (Phe) levels, compared to the pre-dose levels of Phe in the blood of the homozygous $PAH^{enu2}$ mice prior to injection (baseline).

FIG. 13A and Table 9 show the results of the plasma Phe levels in mice injected with PAHΔRD mRNA after each injection relative to the baseline plasma Phe levels. There was a substantial decline in Phe levels following each injection of mRNA compared to the baseline levels, regardless of the size of the dose. However, there was a dose effect, wherein Phe levels were reduced to a greater extent throughout the study when 1 mg/kg or 2 mg/kg of mRNA was administered, and injecting 2 mg/kg of mRNA resulted in the greatest drop in Phe levels at most time points.

TABLE 9

Percent of baseline Phe levels over time following administration of PAHΔRD mRNA (multiple injections)

| Study Day | Time Post-dose (h) | mRNA Dose (mg/kg) | | |
|---|---|---|---|---|
| | | 0.5 | 1.0 | 2.0 |
| Baseline | NA | 100% | 100% | 100% |
| Day 1 | 24 | 66% | 35% | 11% |
| Day 4 | 24 | 46% | 27% | 18% |
| Day 7 | 24 | 53% | 28% | 23% |
| Day 10 | 24 | 77% | 40% | 36% |
| Day 13 | 24 | 82% | 63% | 41% |
| Day 16 | 24 | 60% | 46% | 44% |
| Day 18 | 72 | 103% | 109% | 112% |

Figure 13B:
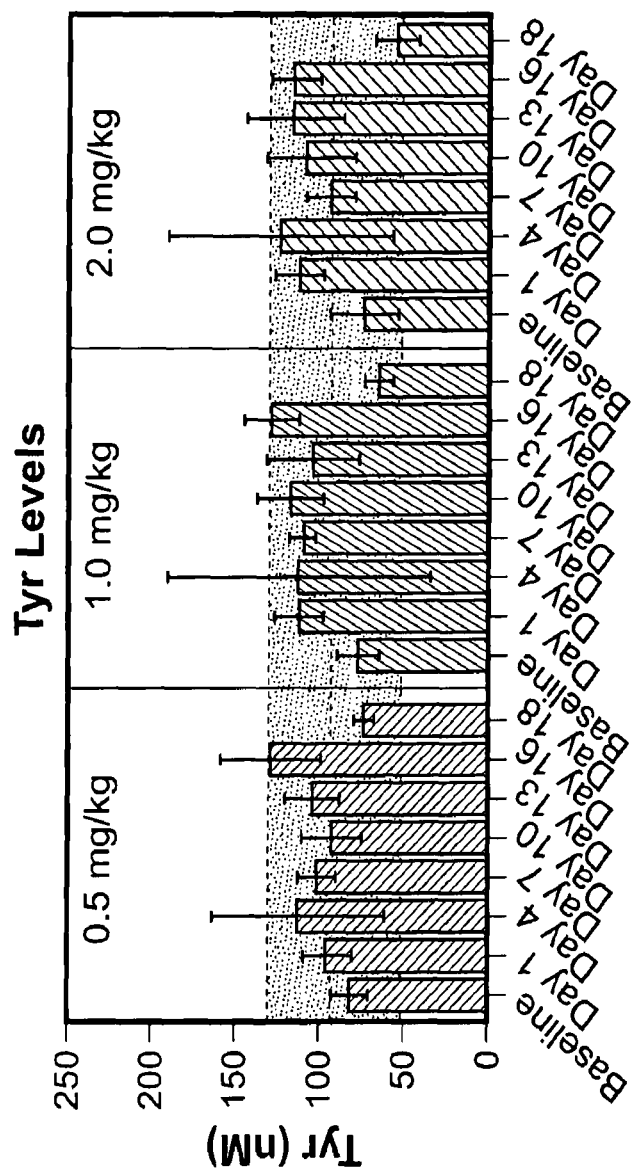
FIG. 13B is a bar graph depicting the activity of truncated human PAH (PAH-ΔRD or ΔrdPAH) in homozygous $PAH^{enu2}$ mice following injection of multiple doses of 0.5 mg/kg, 1 mg/kg, or 2.0 mg/kg of mRNA encoding PAH (at days 0, 3, 6, 9, 12, and 15), as measured in circulating Tyr levels, compared to the pre-dose levels of Tyr in the blood of the homozygous $PAH^{enu2}$ mice prior to injection (baseline).

FIG. 13B and Table 10 show the results of the Tyr levels in mice injected with PAHΔRD mRNA after each injection relative to the baseline plasma Tyr levels. The mRNA-expressed PAHΔRD protein exhibits activity, as Tyr levels were higher following injection of 0.5 mg/kg, 1.0 mg/kg, and 2.0 mg/kg of mRNA compared to the baseline Tyr levels in mice through 16 days of the study. There appeared to be a dose effect, as the 1 mg/kg and 2 mg/kg doses of mRNA resulted in relatively higher Tyr levels.

TABLE 10

Percent of baseline Tyr levels over time following administration of PAHΔRD mRNA (multiple injections)

| Study Day | Time Post-dose (h) | mRNA Dose (mg/kg) | | |
|---|---|---|---|---|
| | | 0.5 | 1.0 | 2.0 |
| Baseline | NA | 100% | 100% | 100% |
| Day 1 | 24 | 120% | 152% | 163% |
| Day 4 | 24 | 138% | 144% | 175% |
| Day 7 | 24 | 128% | 147% | 140% |
| Day 10 | 24 | 116% | 158% | 153% |
| Day 13 | 24 | 131% | 141% | 166% |
| Day 16 | 24 | 161% | 170% | 166% |
| Day 18 | 72 | 91% | 85% | 80% |

Example 24: Assessing Dose Range and the Effects of miR Binding Sites on PAH Activity in a PKU Mouse Model To determine whether different mRNA miR binding sites can affect the activity of mRNA-expressed PAH, a single dose of mRNA encoding human PAHΔRD having a miR126 binding site (SEQ ID NO:202), mRNA encoding human PAHΔRD having three miR142 binding sites (SEQ ID NO:201), or mRNA encoding human PAHΔRD without a miR binding site (SEQ ID NO:203; miRless mRNA) was injected into homozygous PAH$^{enu2}$ mice via tail vein injection. Different doses were tested for each mRNA (1.0 mg/kg, 0.5 mg/kg, or 0.2 mg/kg of mRNA having miR126 or miR142 binding sites; 1.0 mg/kg or 0.5 mg/kg for mRNA with no miR binding site). The mRNAs were formulated in lipid nanoparticles (Compound II/Compound I) for delivery into mice. Control PAH$^{enu2}$ mice were injected with 0.5 mg/kg of mRNA encoding GFP. Blood was drawn from mice prior to the first mRNA injection (pre-bleed) and at 6 hours, 1 day, 2 days, 3 days, and 7 days following each mRNA injection. Phenylalanine levels were measured in plasma at each time point using LC-MS/MS as a marker for PAH activity.

Figure 14:
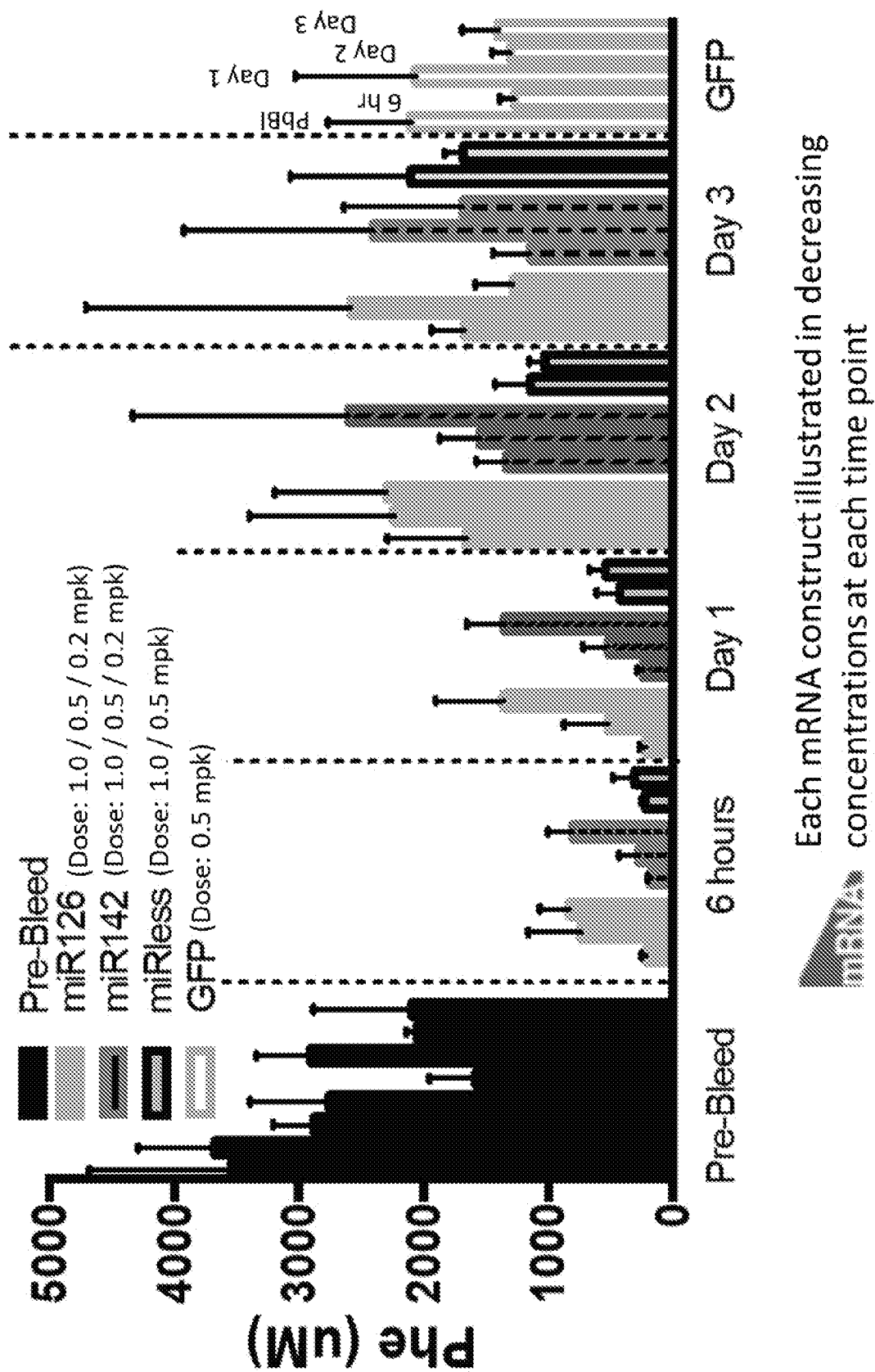
FIG. 14 is a bar graph showing the activity of truncated human PAH (PAH-ΔRD) in homozygous $PAH^{enu2}$ mice following injection of different doses of mRNAs having different miR binding sites that encode PAH, as measured in blood phenylalanine levels over time.

FIG. 14 shows that a single administration of each of the mRNA constructs encoding human PAHΔRD caused a decrease in plasma phenylalanine levels, particularly evident at 6 hours and 1 day post-injection, relative to the pre-bleed phenylalanine levels in the mice and the phenylalanine levels in control mice administered a GFP mRNA. A reduction in phenylalanine levels was observed regardless of whether the mRNA construct had a miR126 binding site, three miR142 binding sites, or did not have a miR binding site. There was a dose dependent effect associated with single administration of each of the mRNAs encoding human PAHΔRD, regardless of the presence or identity of miR binding sites, and particularly at 6 hours and 1 day post-injection, such that higher doses of mRNA resulted in larger decreases in plasma phenylalanine levels.

Example 25: Assessing Duration of PAH Protein Expression in Wild-Type Mice

To test the ability of 1-methyl-pseudouridine modified mRNA constructs to express PAH in vivo, a single 0.5 mg/kg dose of mRNA encoding human PAH (SEQ ID NO:199) or human PAHΔRD (SEQ ID NO:200) was IV administered to wild-type CD-1 mice via tail vein injection. The mRNA constructs encode a FLAG tag fused to PAH to allow detection of the protein using an anti-FLAG antibody. The mRNA was formulated in lipid nanoparticles (Compound II) for delivery into mice. Control mice were left untreated. Animals were sacrificed and about 100 mg of liver was collected at 3 hours, 6 hours, 1 day, 2 days, 3 days, 4 days, and 7 days post-injection. PAH expression was determined by protein blot on the collected liver samples.

Full-length PAH was detectable through 96 hours, although the expression levels decreased with time (data not shown). PAHΔRD protein was strongly detectable through 24 hours, with the expression decreasing with time (data not shown). Protein expressed from the PAH-006 (full-length PAH) and PAH-027 (PAHΔRD) mRNA constructs were used as loading controls to size the full-length and truncated PAH proteins.

Figure 15:
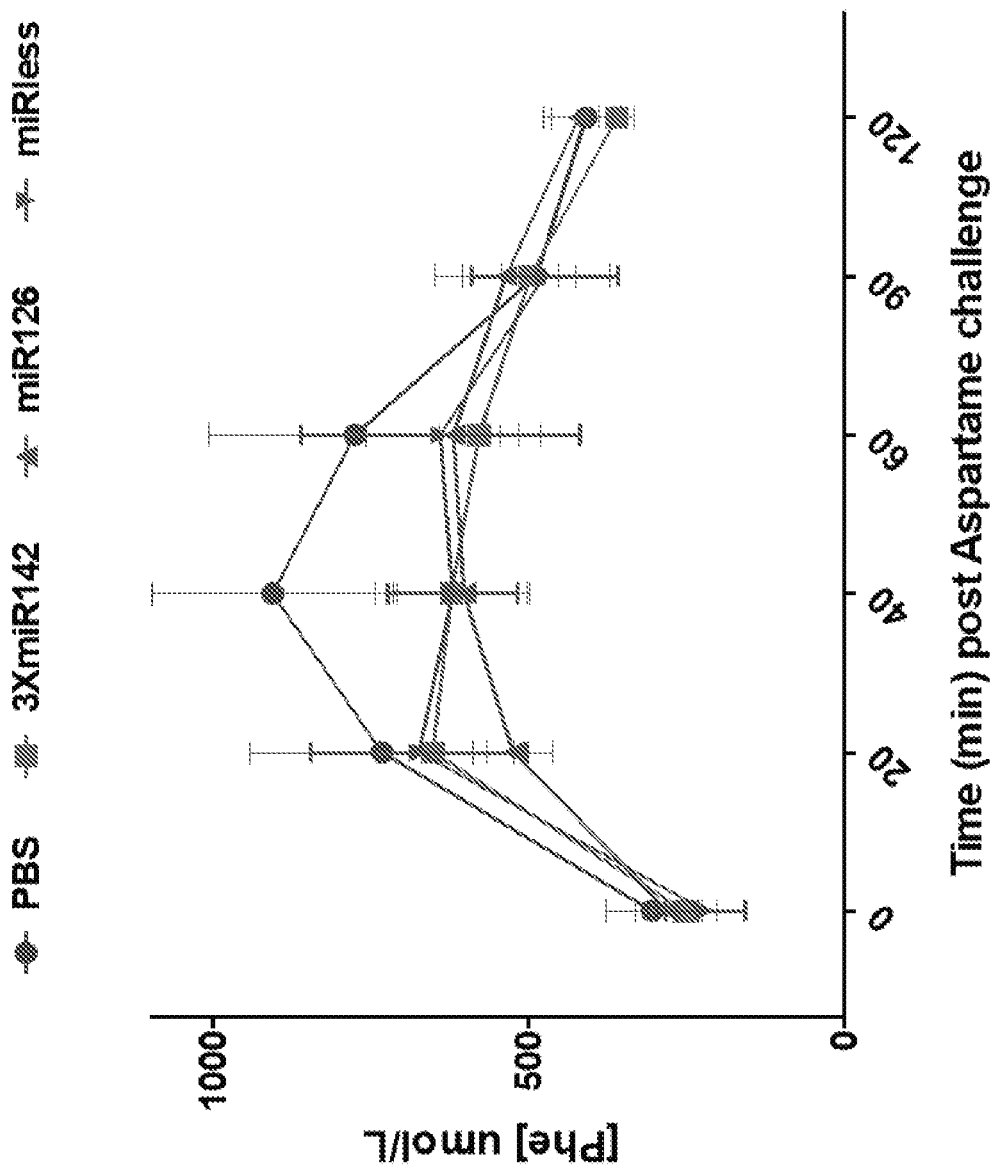
FIG. 15 is a graph showing the activity of truncated human PAH (PAH-ΔRD) in wild-type rats injected with an mRNA constructs encoding PAH-ΔRD with 3 miR142 binding sites (3×miR142), a miR126 binding site (miR126), or no miR binding site (miRless), following the administration of aspartame.
Figure 16B:
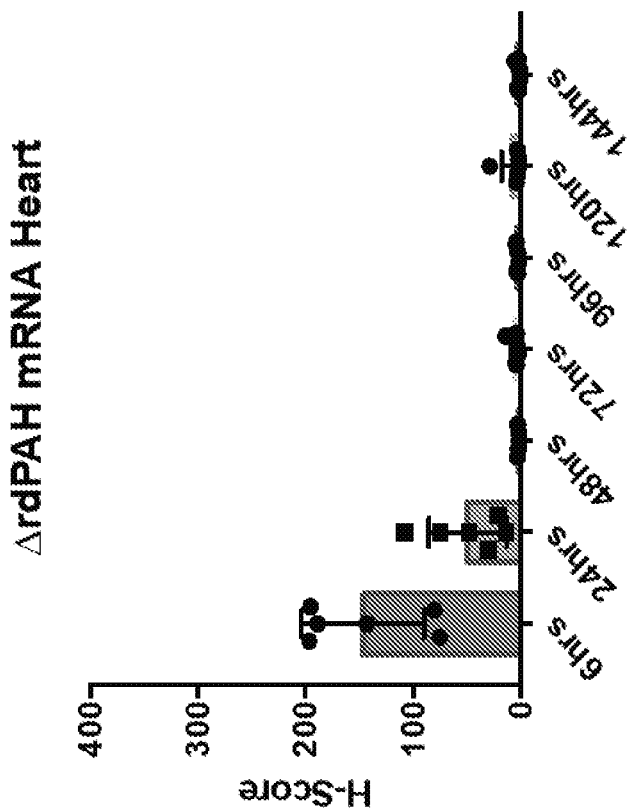
FIGS. 16A-16D are bar graphs showing the levels (H scores) of truncated human mRNA (PAH-ΔRD) in the kidneys, hearts, livers, and spleens, respectively, of wild-type rats at 6, 24, 48, 72, 96, 120, and 144 hours following mRNA injection.
Figure 16A:
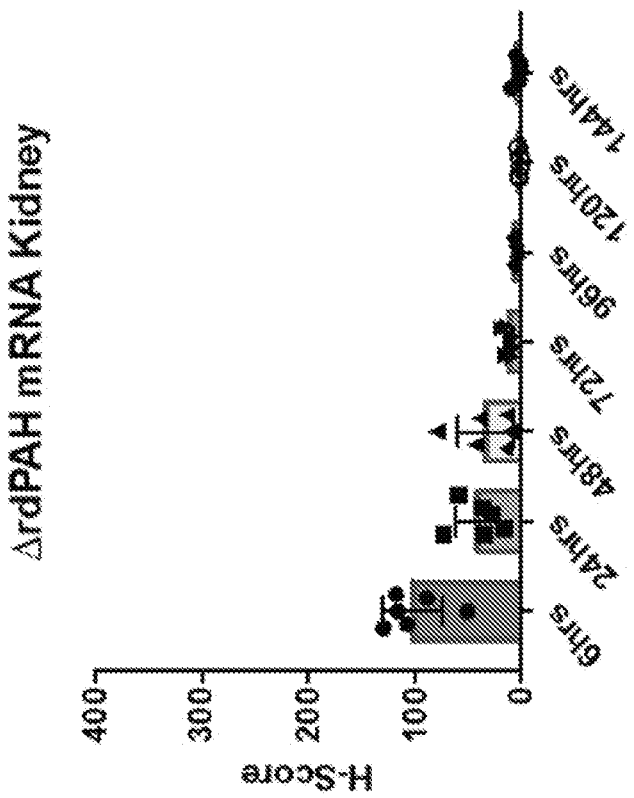
Figure 16C:
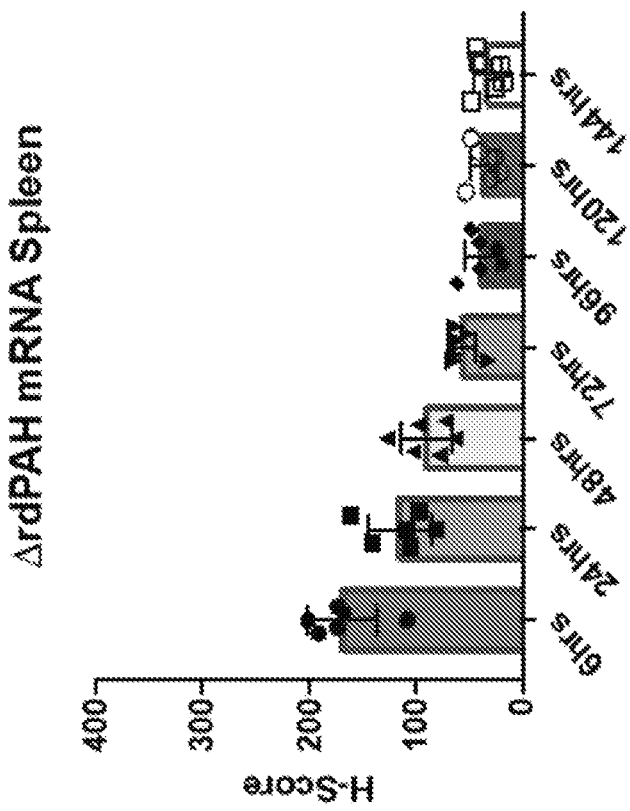
Figure 16D:
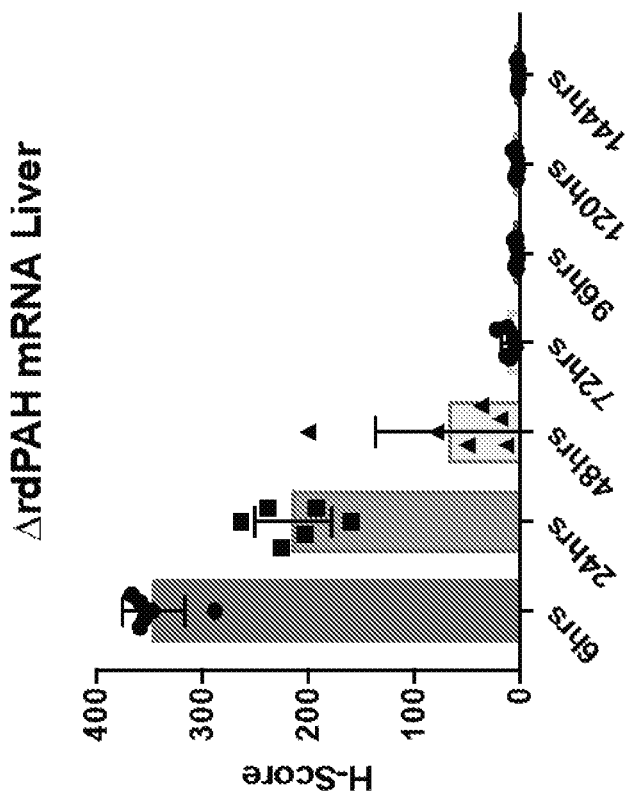
Figure 16E:
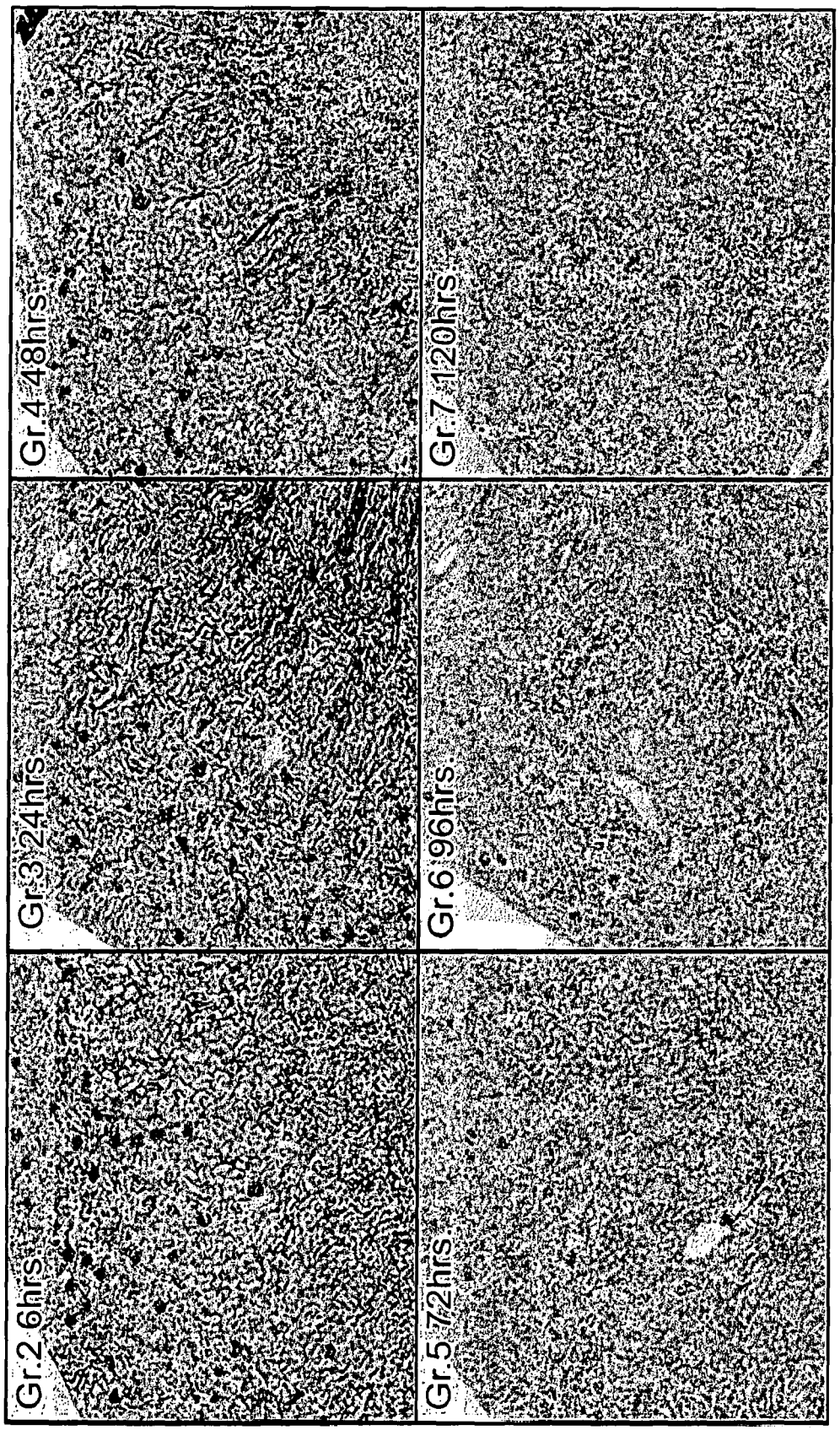
FIGS. 16E-16H show the distribution of PAHARD mRNA in the kidney, heart, liver, and spleen, respectively, at various time point following mRNA injection using in situ hybridization. The top panels in FIGS. 16F and 16G are lower magnification images of the lower panels in the figures.
Figure 16F:
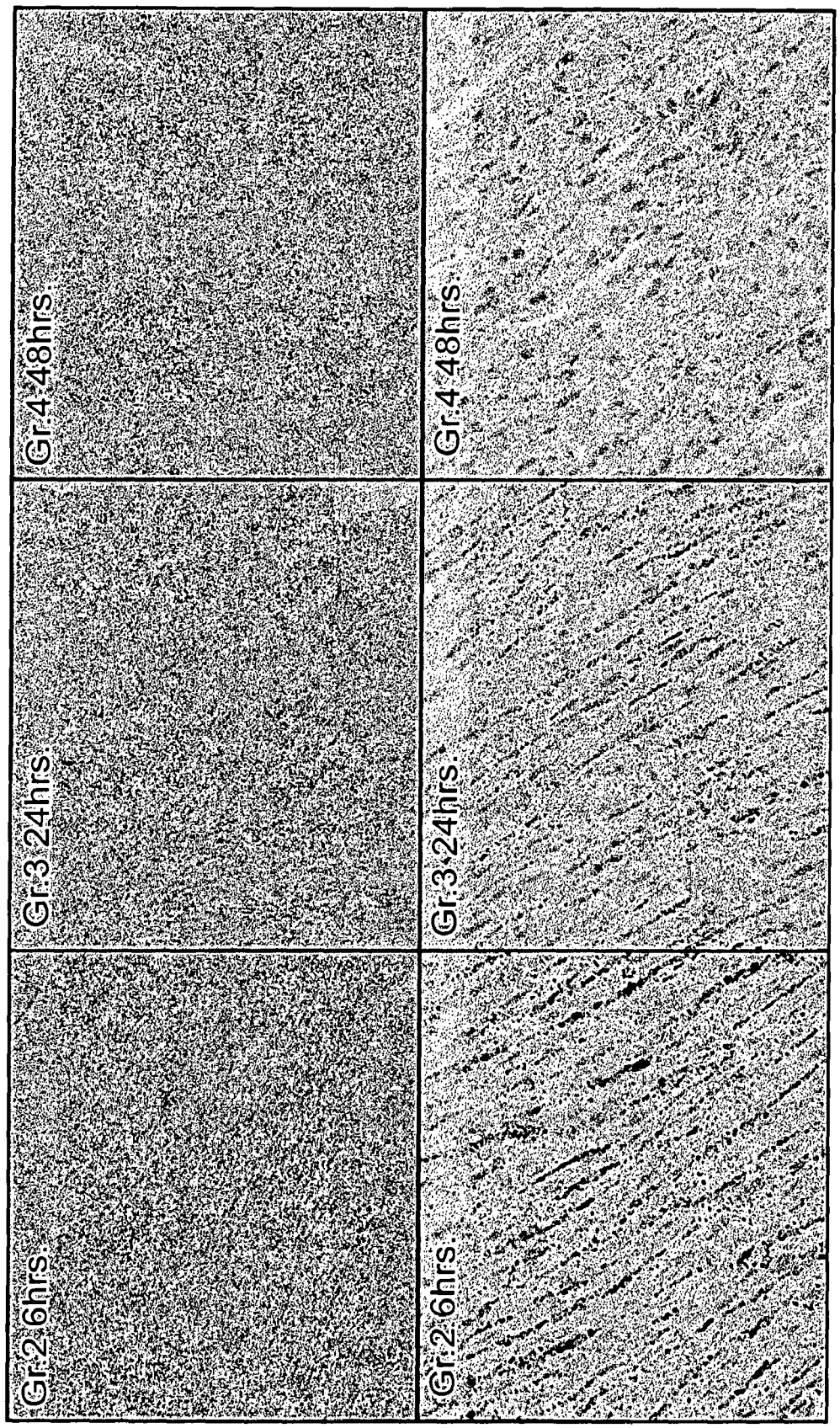
Figure 16G:
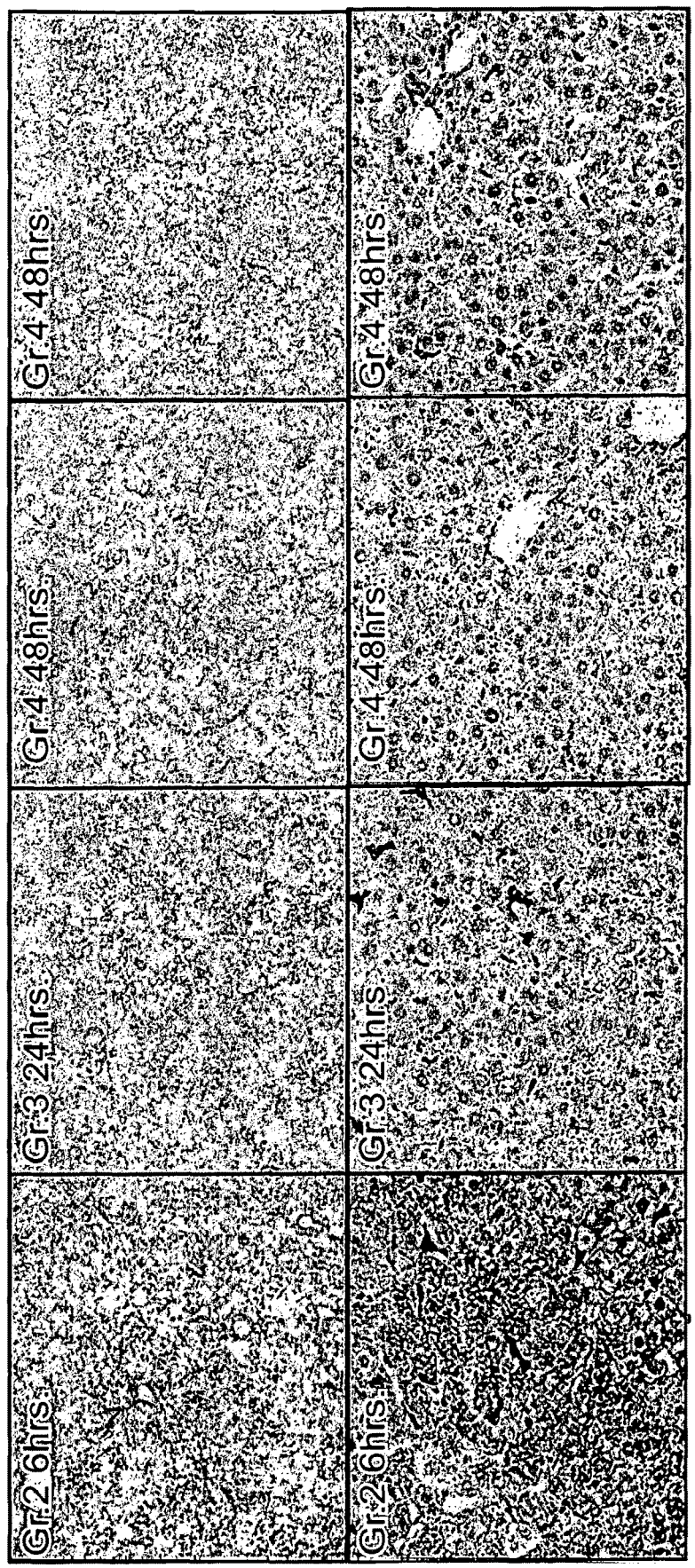
Figure 16H:
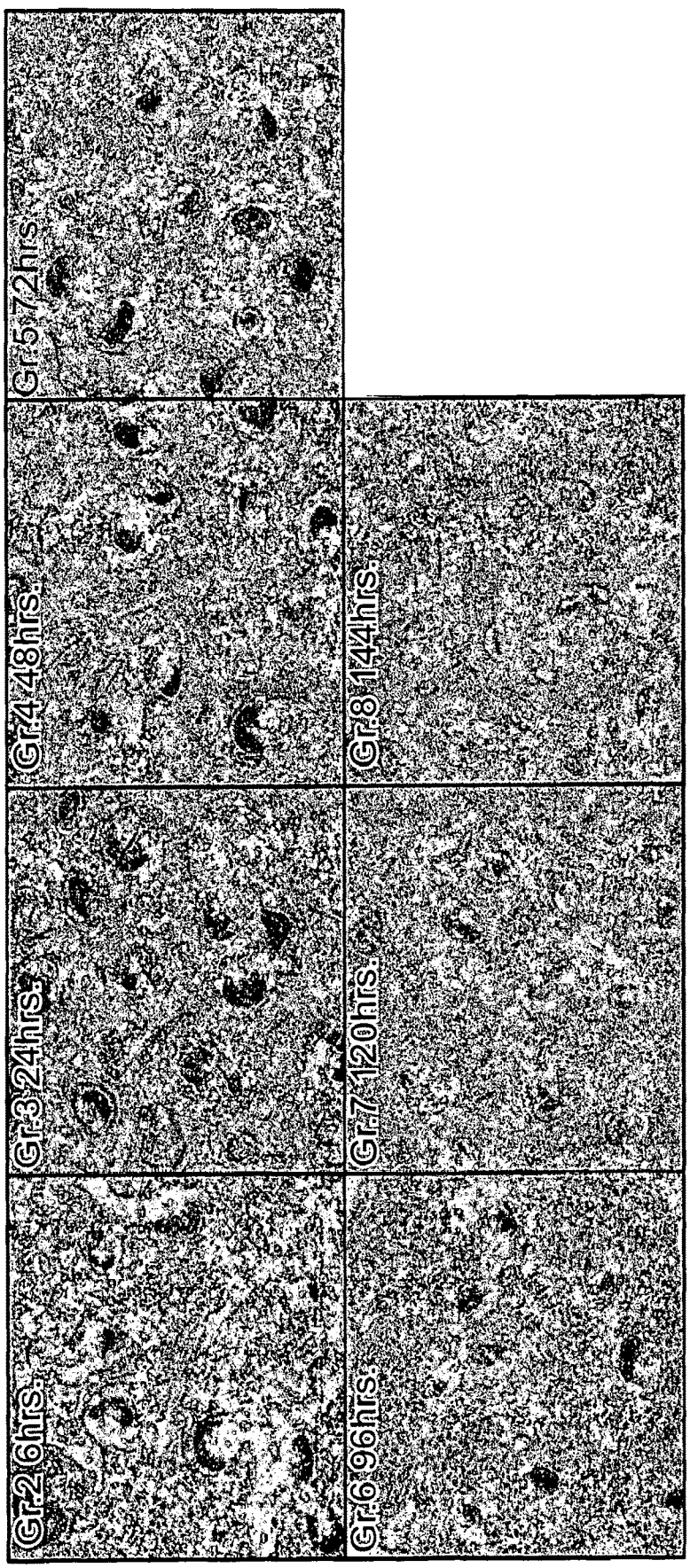

Example 26: Assessing PAH Activity in a Wild-Type Rat Surrogate System for Disease To test whether the activity of mRNA-expressed PAH can be assessed in a wild-type rat surrogate system for PKU disease, as described in Example 20 Sprague Dawley rats were administered a single 0.5 mg/kg dose of an mRNA encoding human PAHΔRD by IV tail vein injection, wherein the mRNA has a miR126 binding site (SEQ ID NO:202), three miR142 binding sites (SEQ ID NO:201), or no miR binding sites (SEQ ID NO:203). Rats were then challenged with 1 g/kg body weight of aspartame at 8 hours and 24 hours following mRNA injection. The mRNAs were formulated in lipid nanoparticles (Compound II/Compound I) for delivery into rats. Control rats were injected with PBS. Blood was drawn from rats prior to the first mRNA injection (pre-bleed) and at 20, 40, 60, 90, and 120 minutes following administration of aspartame. Phenylalanine levels were measured in plasma at each time point using LC-MS/MS as a marker for PAH activity. FIG. 15 shows that administration of 1 mg/kg of aspartame to wild-type rats causes a temporary increase in plasma phenylalanine levels. Administration of any of the mRNA constructs, having miR142 or miR126 binding sites or no miR binding sites, resulted in a decrease in plasma phenylalanine levels compared to control rats administered PBS.

Example 27: Assessing PAH Expression in Wild-Type Rats

PAH mRNA levels and distribution were determined in the plasma and tissues (liver, spleen, kidney, and heart) of wild-type Sprague Dawley rats administered 1 mg/kg of 1-methyl-pseudouridine modified mRNA encoding human PAHΔRD (SEQ ID NO:202), or with 1 mg/kg of mRNA encoding luciferase as a control, by a single IV tail vein injection. The mRNA was formulated in lipid nanoparticles (Compound II/Compound I) for delivery into rats. Rats were sacrificed at 6 hours, and 1, 2, 3, 4, 5, and 6 days following mRNA injection (n=6 rats per time point), and the tissues were harvested. In situ hybridization was used to detect amount of mRNA in the tissues at each time point following mRNA injection, and to detect the location of the mRNA within the tissues. For in situ hybridization, tissues were collected, trimmed and fixed in 10% NBF (neutral buffered formalin) for 48 hours. Samples were then transferred to PBS to maintain consistent fixation time amongst groups. Samples underwent routine paraffin processing, embedding, and sectioning. Tissue sections were cut at 5um. In situ hybridization was performed using the Leica Bond RX autostainer (Leica Microsystems, Buffalo Grove, IL), sections were baked and deparaffinized on the instrument, followed by the RNAscope 2.5 LSx DAB ISH protocol using the RNAscope 2.5 LS reagent kit-brown (cat #322100) in which the target probe signal is visualized by chromogenic diaminobenzidine. The ISH Probes included RNAscope® LS Positive Control Probe RnPPIB (cat #313928), RNAscope® 2.5 LS Negative Control Probe-_dapB (cat #312038), and a probe to the PAH construct. All images were captured with the Panoramic 250 Flash II (3DHISTECH, Budapest, Hungary) digital slide scanner. All images (low magnification 2×, high magnification 16×) were taken using the HALO software and image analysis was performed using an algorithm through HALO software. H-scores were assigned to samples based on the number of cells with the same range of positive dots per cell, while taking the total number of cells into account. All analysis results were compiled and graphed using graph pad prism.

The serum levels of mRNA encoding PAHΔRD were assayed at 15 minutes and 1, 2, 4, 6, 8, 12, and 24 hours following injection of rats using a bDNA assay (as described in Cell Reports, 2017, 21:3548-58, which is herein incorporated by reference in its entirety). Western blot and capillary electrophoresis (CE) was used to detect the levels of human PAHΔRD protein expression in the tissues at each time point following injection (using antibodies for liver (Millipore, MABN754), and spleen, kidney, and heart (Genetex, GTX54563, for each). For the protein expression results by CE, GAPDH was used as a loading control for liver (Abcam, ab8245 antibody); ERP72 was used as a loading control for spleen and liver Western blots (Cell Signaling technology, D70D12 antibody); and Vinculin was used as a loading control in kidney and heart (Abcam antibody).

FIG. 16A-16D shows the mRNA levels in kidney, heart, liver, and spleen at each time point following PAHΔRD mRNA injection. The mRNA was detected over the course of about 3 days (72 hours) in kidney, about 1 day (24 hours) in heart, 3 days (72 hours) in liver, and 6 days (144 hours) in spleen, before decreasing to levels that were more difficult to detect. The mRNA was present in liver was very high at 6 hours and 24 hours in liver before rapidly tapering off, but the mRNA was more consistently present over the course of 6 days in spleen. FIGS. 16E-16H show the distribution of PAHΔRD mRNA in kidney, heart, liver, and spleen, respectively, at various time point following mRNA injection.

Figure 17:
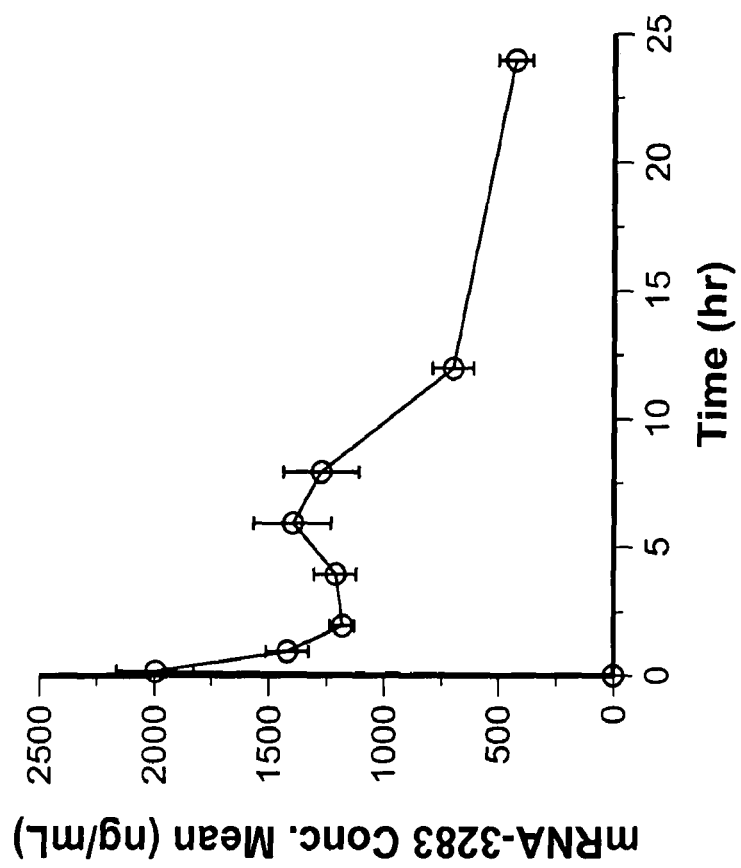
FIG. 17 is a graph showing the plasma concentration of PAHARD mRNA over 24 hours in wild-type rats following injection of mRNA encoding truncated human PAH (PAH-ΔRD), using a bDNA assay.

FIG. 17 shows the results of the bDNA assay to detect the concentration of PAHΔRD mRNA in plasma over time following mRNA injection. mRNA concentration declines following mRNA administration to rats, falling to a concentration of approximately 500 ng/mL at 24 hours post-injection.

Figure 18A:
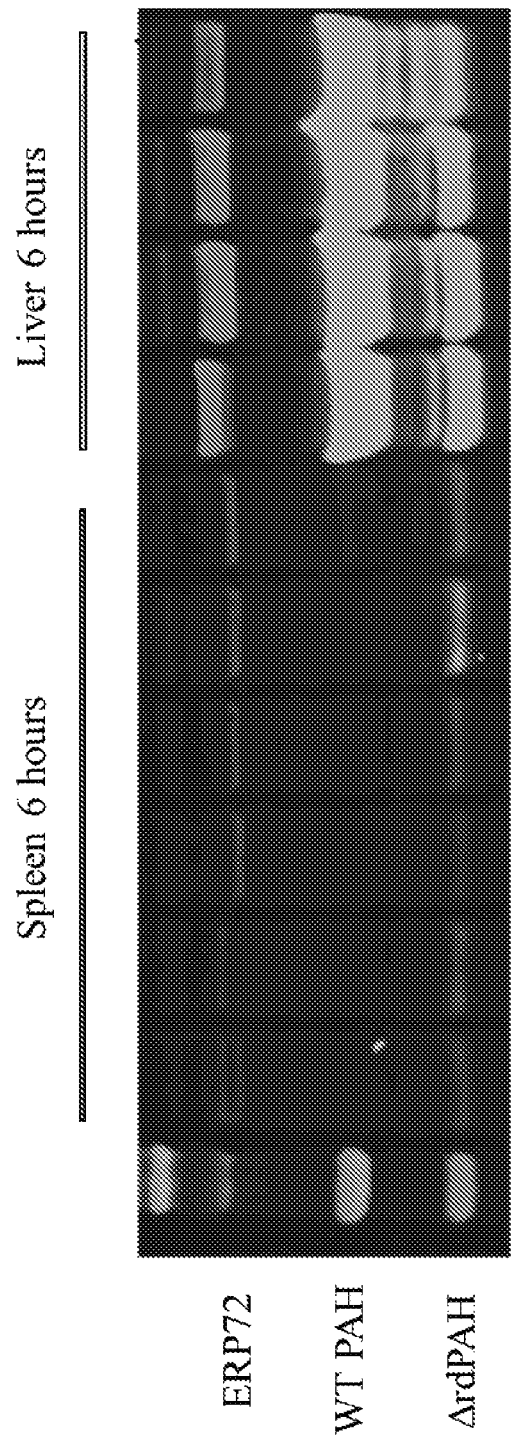
FIG. 18A is a Western blot showing the expression of a truncated human PAH (PAH-ΔRD or ΔrdPAH) in the spleen and liver of wild-type rats at 6 hours following injection of mRNA encoding the PAHARD protein. ERP72 was used as a loading control.
Figure 18B:
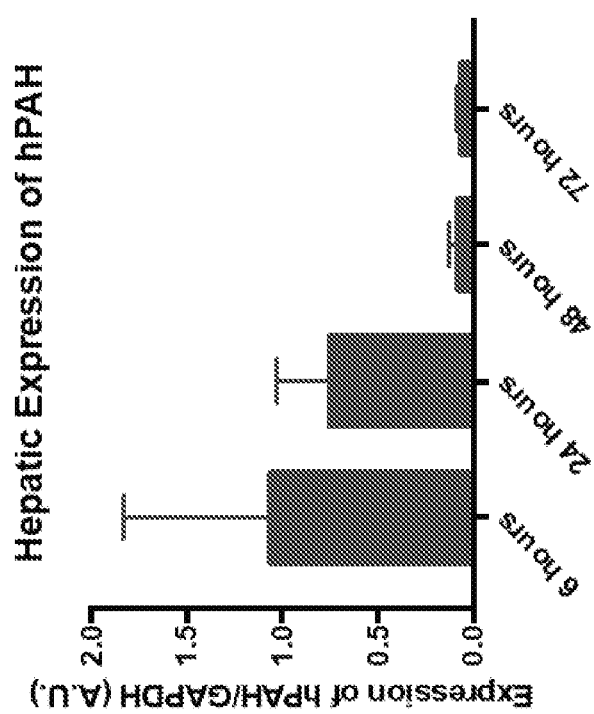
FIG. 18B is a bar graph showing the quantified expression of truncated human PAH (PAH-ΔRD or ΔrdPAH) in the liver of wild-type rats at 6, 24, 48, and 72 hours following injection of mRNA encoding the PAHARD protein.

FIG. 18A shows the Western blot results of PAHΔRD protein expression in spleen and liver at 6 hours following mRNA injection into rats. PAHΔRD protein levels were easily detected in liver at 6 hours post-injection, but detected at lower levels in spleen. PAHΔRD protein expression was undetectable in kidney and heart (data not shown). FIG. 18B is a bar graph showing the protein expression results in liver for 72 hours following mRNA administration. Protein expression levels were highest shortly after mRNA injection (at 6 hours), and are detectable, but much reduced, by 48 hours post-injection.

Example 28 Assessing Subcutaneous Administration of mRNA

To test the efficacy and dose response of subcutaneous injection of mRNA encoding PAH protein in vivo, a single dose of 0.5 mg/kg, 1 mg/kg, or 2 mg·kg of 1-methyl-pseudouridine modified mRNA construct encoding PAHΔRD (SEQ ID NO:202) was subcutaneously administered to homozygous PAH$^{enu2}$ mice (n=5 mice per group). In another group of homozygous PAH$^{enu2}$ mice, 2.0 mg/kg of the modified mRNA construct encoding PAHΔRD (SEQ ID NO:202) was subcutaneously injected into the mice two times: an initial dose (day 0) followed by a second dose 1 day later (day 1). The mRNA was formulated in lipid nanoparticles (Compound II/Compound I) for delivery into mice. Control homozygous PAH$^{enu2}$ mice were subcutaneously injected with PBS. Blood was drawn from mice at 1 day, 2, days, 3 days, and 4 days following the single subcutaneously administered dose of mRNA, or following the first subcutaneous dose of mRNA for those mice given 2 mRNA doses. Blood phenylalanine levels were measured at each time point using LC-MS/MS on Dried Blood Spots (DBS) as a marker for PAH activity.

Figure 19:
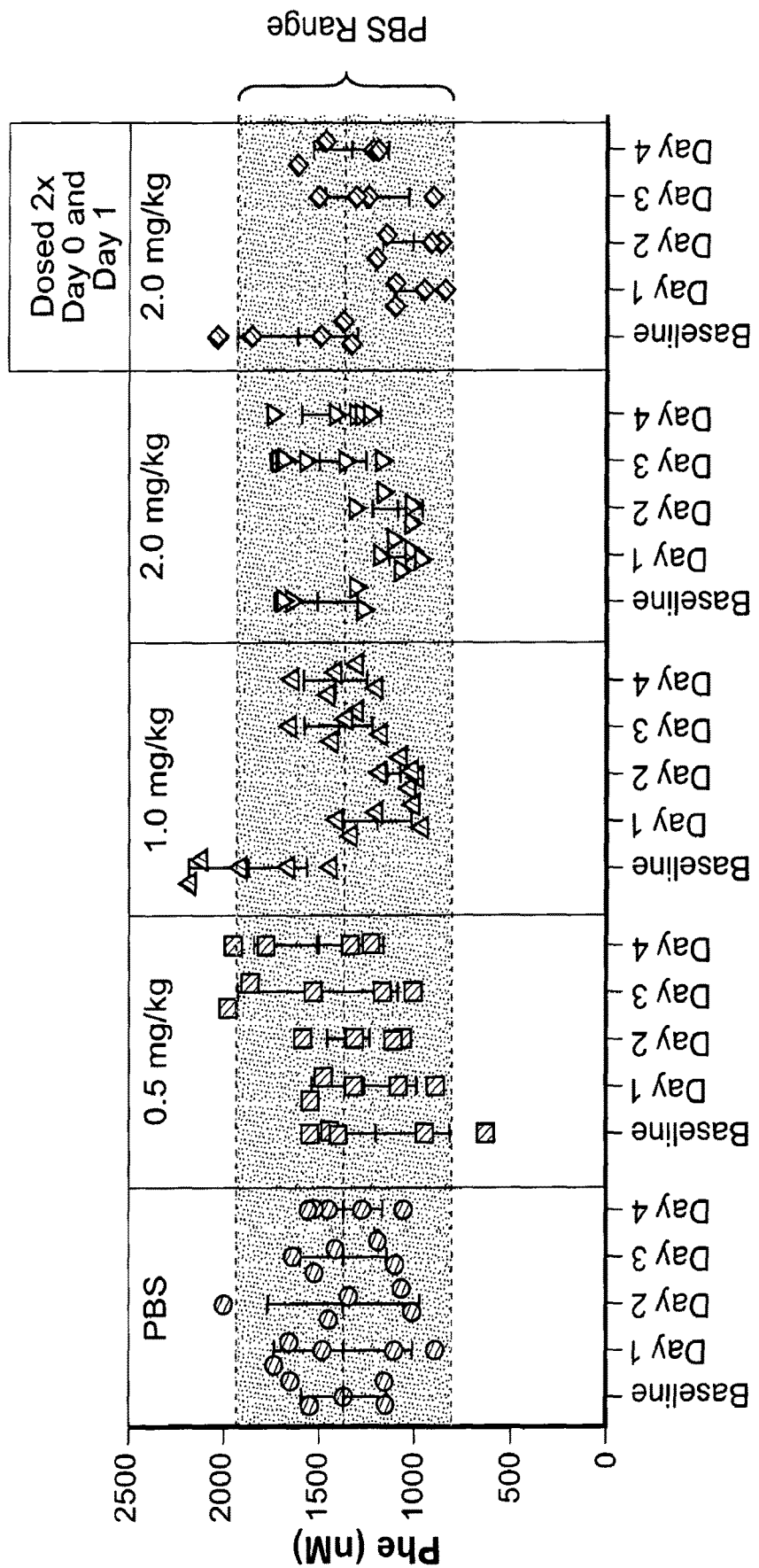
FIG. 19 is a graph showing the blood Phe levels in homozygous $PAH^{enu2}$ mice subcutaneously injected with a single dose of 0.5 mg/kg, 1.0 mg/kg, or 2.0 mg/kg of mRNA encoding truncated human PAH (PAH-ΔRD or ΔrdPAH), two doses of 2.0 mg/kg of mRNA encoding truncated human PAH (PAH-ΔRD or ΔrdPAH) (injected at days 0 and 1), or PBS as a control, compared to the blood Phe levels in the mice prior to injection of mRNA or PBS control (the baseline levels).

FIG. 19 shows that PAH activity increased following subcutaneous injection of a single 1 mg/kg or 2 mg/kg dose of the mRNA construct encoding human PAHΔRD since there was a drop in Phe levels at most time point relative to the baseline Phe levels in control mice injected with PBS. There was a significant difference ($p<0.05$) in Phe levels from the baseline levels, but the reduction in Phe was not outside the range (Mean±SD) of the PBS samples. The effect exhibited some dose dependence, as the single 0.5 mg/kg mRNA dose did not reduce Phe levels in the mice. Subcutaneously injecting two doses of 2 mg/kg of mRNA further reduced Phe levels throughout the study as compared to injecting a single 2 mg/kg dose of mRNA. Table 11 also summarizes the results of this study.

TABLE 11

Percent of baseline Phe levels over time following subcutaneous administration of PAHΔRD mRNA (single and multiple injections)

| Study Day | mRNA Dose (mg/kg) | | | 2.0 (2 doses) |
|---|---|---|---|---|
| | 0.5 | 1.0 | 2.0 | |
| Baseline | 100% | 100% | 100% | 100% |
| 24 hours | 113% | 65% | 71% | 60% |
| 48 hours | 116% | 59% | 73% | 63% |
| 72 hours | 145% | 76% | 100% | 78% |
| 96 hours | 141% | 78% | 93% | 83% |

Example 29 Assessing PAH Activity in a Wild-Type Nonhuman Primate Surrogate System for Disease To test whether the activity of mRNA-expressed PAH can be assessed in a wild-type nonhuman primate surrogate system for PKU disease, Cynomolgus moneys were IV administered (60 min infusion) weekly 0.5 mg/kg doses of a 1-methyl-pseudouridine modified mRNA construct encoding PAHΔRD, for a total of 5 weeks (5 doses in total, administered on Days 1, 8, 15, 22, and 29). Three different mRNA constructs were each tested in monkeys: an mRNA construct with an miR126 binding site (SEQ ID NO:202), an mRNA construct with three miR142 binding sites (SEQ ID NO:201), and an mRNA construct with no miR binding sites (SEQ ID NO:203)(n=5 monkeys per group). Monkeys were then challenged with 0.5 mmol/kg of phenylalanine by IV bolus(at 0 hours), and then at 8 hours or 48 hours after mRNA injection. The mRNAs were formulated in lipid nanoparticles (Compound II/Compound I) for delivery into monkeys. Blood was drawn from monkeys prior to administration of each Phe challenge (i.e., prior to the Phe challenges at 8 hours and 48 hours following mRNA injection) and at 2, 10, 30, 45, 60, 120, 180, and 240 minutes following administration of each Phe challenge. Phenylalanine levels were measured in plasma at each time point using LC-MS/MS as a marker for PAH activity.

Figure 20A:
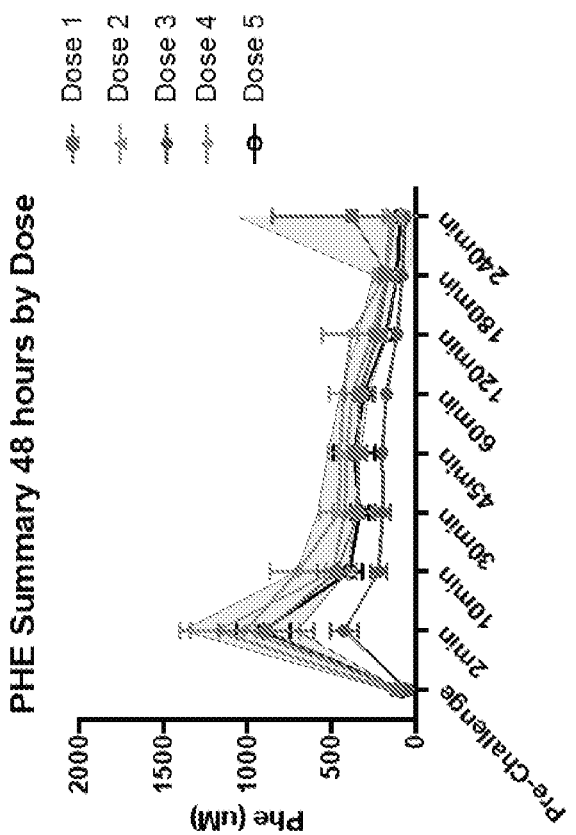
FIGS. 20A-20B are graphs showing the blood phenylalanine (Phe) levels in cynomolgus monkeys injected with multiple doses of mRNA encoding PAHARD (Doses 1-5) and administered phenylalanine at 8 hours and 48 hours after mRNA injection, at various times before and after Phe administration.
Figure 20B:
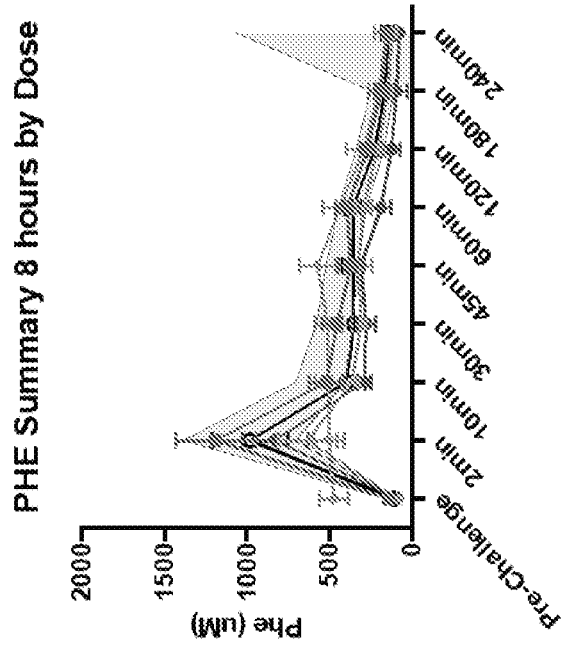
Figure 20D:
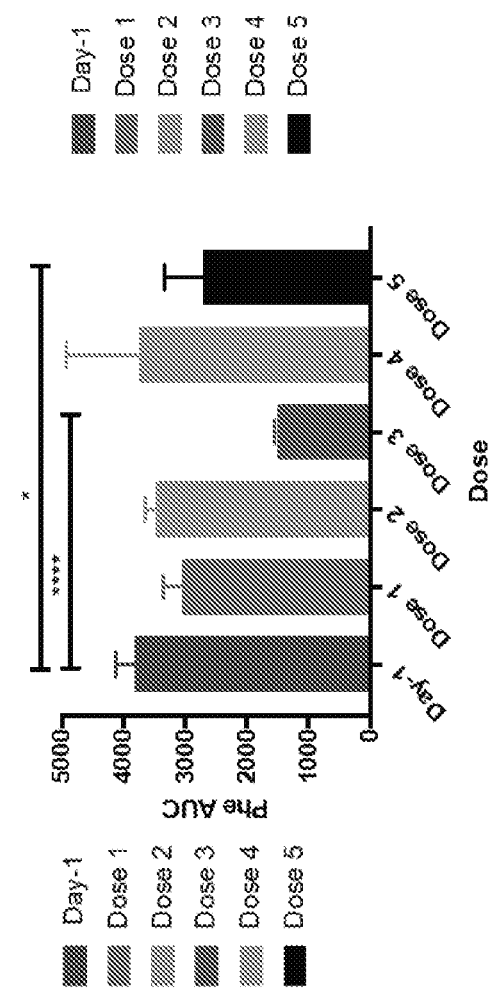
FIGS. 20C-20D show the area under the curve (AUC) values for the experimental results of FIGS. 19A-B.
Figure 20C:
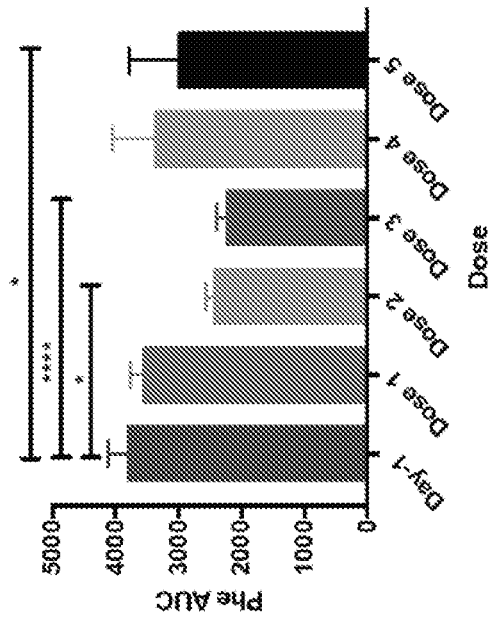

FIGS. 20A and 20B show the average plasma Phe levels following each dose of mRNA and following the Phe challenge at 8 hours after the mRNA dose (FIG. 20A) and the Phe challenge at 48 hours after the mRNA dose (FIG. 20B). After the administration of Phe challenge, circulating Phe levels increased one order of magnitude in 2 minutes and returned to baseline by 240 minutes. Significant decreases in circulating Phe were observed 2 minutes after a 8-hour Phe challenge following mRNA dosing on Days 8, 15, 22, and 29 (doses 2, 3, 4, and 5) in all dose groups compared to baseline (Two-way ANOVA; Dunnett's multiple comparison, alpha 0.05). At the forty-eight-hour challenge there was a significant decrease of circulating Phe at 2 minutes post Phe challenge after dosing on Days 1, 15, 22, and 29 (doses 1, 3, 4, and 5). FIGS. 20C and 20D show the area under the curve (AUC) values for the experimental results of FIGS. 20A-B.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A method of treating phenylketonuria in a human subject that has phenylketonuria, comprising administering to the human subject an effective amount of a pharmaceutical composition comprising a lipid nanoparticle comprising (Compound II)

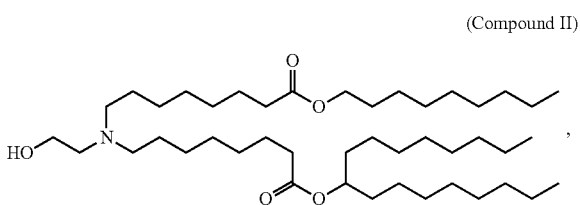 [SMILES: CCCCCCCCCOC(=O)CCCCCCCN(CCO)CCCCCCCC(=O)OC(CCCCCCCC)CCCCCCCC]

or a salt thereof, wherein the pharmaceutical composition comprises an mRNA comprising an open reading frame encoding a phenylalanine hydroxylase polypeptide.

2. The method of claim 1, wherein the lipid nanoparticle further comprises a phospholipid, a structural lipid, and a PEG-modified lipid.

3. The method of claim 1, wherein the administration to the human subject is about once a week, about once every two weeks, or about once a month.

4. The method of claim 1, wherein the pharmaceutical composition is administered intravenously.

5. The method of claim 1, wherein the pharmaceutical composition is administered subcutaneously.

6. The method of claim 2, wherein the phospholipid is 1,2-distearoyl-sn-glycero-3-phosphocholine (DSPC) or 1,2-dioleoyl-sn-glycero-3-phosphoethanolamine (DOPE), wherein the structural lipid is cholesterol, and wherein the PEG-modified lipid is PEG-DMG or (Compound I)

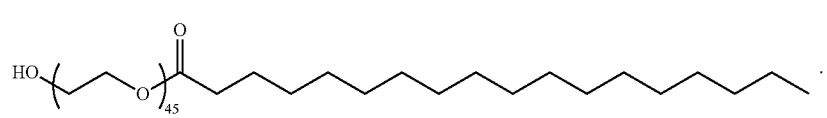

7. The method of claim 2, wherein the phospholipid is DSPC, wherein the structural lipid is cholesterol, and wherein the PEG-modified lipid is Compound I.

8. The method of claim 6, wherein the administration to the human subject is about once a week, about once every two weeks, or about once a month.

9. The method of claim 6, wherein the pharmaceutical composition is administered intravenously.

10. The method of claim 6, wherein the pharmaceutical composition is administered subcutaneously.

11. The method of claim 3, wherein the pharmaceutical composition is administered intravenously.

12. The method of claim 3, wherein the pharmaceutical composition is administered subcutaneously.

13. The method of claim 8, wherein the pharmaceutical composition is administered intravenously.

14. The method of claim 8, wherein the pharmaceutical composition is administered subcutaneously.

15. The method of claim 7, wherein the administration to the human subject is about once a week, about once every two weeks, or about once a month.

16. The method of claim 7, wherein the pharmaceutical composition is administered intravenously.

17. The method of claim 7, wherein the pharmaceutical composition is administered subcutaneously.

18. The method of claim 15, wherein the pharmaceutical composition is administered intravenously.

19. The method of claim 15, wherein the pharmaceutical composition is administered subcutaneously.

* * * * *

UNITED STATES PATENT AND TRADEMARK OFFICE
CERTIFICATE OF CORRECTION

| | | |
|---|---|---|
| PATENT NO. | : 11,939,601 B2 | Page 1 of 1 |
| APPLICATION NO. | : 16/765656 | |
| DATED | : March 26, 2024 | |
| INVENTOR(S) | : Rajendran et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this
Twelfth Day of August, 2025

Coke Morgan Stewart
*Acting Director of the United States Patent and Trademark Office*